United States Patent
Andrews et al.

(10) Patent No.: US 10,208,024 B2
(45) Date of Patent: Feb. 19, 2019

(54) 2-ARYL- AND 2-HETEROARYL-SUBSTITUTED 2-PYRIDAZIN-3(2H)-ONE COMPOUNDS AS INHIBITORS OF FGFR TYROSINE KINASES

(71) Applicant: Array BioPharma, Inc., Boulder, CO (US)

(72) Inventors: Steven W. Andrews, Boulder, CO (US); James F. Blake, Boulder, CO (US); Adam Cook, Boulder, CO (US); Indrani W. Gunawardana, Boulder, CO (US); Kevin W. Hunt, Longmont, CO (US); Andrew T. Metcalf, Boulder, CO (US); David Moreno, Boulder, CO (US); Li Ren, Boulder, CO (US); Tony P. Tang, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

(21) Appl. No.: 15/333,148

(22) Filed: Oct. 24, 2016

(65) Prior Publication Data
US 2017/0260168 A1    Sep. 14, 2017

Related U.S. Application Data

(60) Provisional application No. 62/245,956, filed on Oct. 23, 2015.

(51) Int. Cl.
| | | |
|---|---|---|
| C07D 403/14 | (2006.01) | |
| C07D 401/14 | (2006.01) | |
| C07D 413/14 | (2006.01) | |
| A61K 31/501 | (2006.01) | |
| A61K 31/5377 | (2006.01) | |
| C12Q 1/68 | (2018.01) | |
| A61K 45/06 | (2006.01) | |
| C12Q 1/6886 | (2018.01) | |
| G01N 33/574 | (2006.01) | |

(52) U.S. Cl.
CPC .......... C07D 403/14 (2013.01); A61K 31/501 (2013.01); A61K 31/5377 (2013.01); A61K 45/06 (2013.01); C07D 401/14 (2013.01); C07D 413/14 (2013.01); C12Q 1/6886 (2013.01); G01N 33/574 (2013.01)

(58) Field of Classification Search
CPC .. A61K 31/501; A61K 31/5377; A61K 45/06; C07D 403/14; C07D 401/14; C07D 413/14; G01N 33/574
See application file for complete search history.

(56) References Cited

U.S. PATENT DOCUMENTS

| | | | |
|---|---|---|---|
| 4,304,777 A | 12/1981 | Lesher et al. | |
| 4,305,943 A | 12/1981 | Lesher et al. | |
| 4,826,835 A | 5/1989 | Kuhla et al. | |
| 5,455,348 A | 10/1995 | Austel et al. | |
| 7,265,120 B2 | 9/2007 | Tsutsumi et al. | |
| 7,696,352 B2 | 4/2010 | Zhu et al. | |
| 8,163,749 B2 | 4/2012 | Corte | |
| 8,426,424 B2 | 4/2013 | Blomgren et al. | |
| 8,445,489 B2 | 5/2013 | Stieber et al. | |
| 8,598,174 B2 | 12/2013 | Barbosa, Jr. et al. | |
| 8,669,251 B2 | 3/2014 | Crawford et al. | |
| 8,716,274 B2 | 5/2014 | Crawford et al. | |
| 8,889,682 B2 | 11/2014 | Brotherton-Pleiss et al. | |
| 8,940,891 B2 | 1/2015 | Tran et al. | |
| 9,242,969 B2 | 1/2016 | Barsanti et al. | |
| 9,254,288 B2 | 2/2016 | Pollock | |
| 9,260,415 B2 | 2/2016 | Crawford et al. | |
| 9,267,176 B2 | 2/2016 | Futami et al. | |
| 9,326,985 B2 | 5/2016 | Crawford et al. | |

(Continued)

FOREIGN PATENT DOCUMENTS

| | | |
|---|---|---|
| CN | 102741256 | 10/2012 |
| EP | 2203449 | 7/2010 |

(Continued)

OTHER PUBLICATIONS

Liu et al. Org. Biomol. Chem., 2015, 13, 7643-7654.*
"Certificate of Analysis Alexa Fluor® 647-Poly GT, 10 nmol," Life Technologies, Jun. 4, 2012, 1 page.
"Certificate of Analysis FGFR2, 100 µg: Recombinant Human Fibroblast Growth Factor Receptor 2, Histidine-tagged," Life Technologies, Feb. 24, 2012, 2 pages.

(Continued)

Primary Examiner — Alexander R Pagano
Assistant Examiner — Ebenezer O Sackey
(74) Attorney, Agent, or Firm — Fish & Richardson P.C.

(57) ABSTRACT

Provided herein are compounds of the general Formula I:

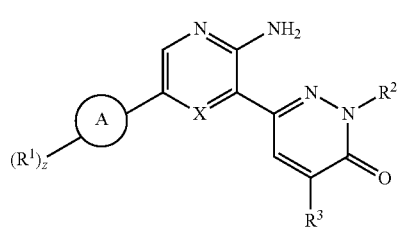

and stereoisomers and pharmaceutically acceptable salts or solvates thereof, in which X, $R^1$, $R^2$, $R^3$, Ring A and z have the meanings given in the specification, which are inhibitors of FGFR1, FGFR2, FGFR3 and/or FGFR4 and are useful in the treatment and prevention of diseases which can be treated with an FGFR inhibitor, including diseases or disorders mediated by FGFR1, FGFR2, FGFR3 and/or FGFR4.

27 Claims, No Drawings
Specification includes a Sequence Listing.

(56) References Cited

U.S. PATENT DOCUMENTS

| | | |
|---|---|---|
| 9,447,098 B2 | 9/2016 | Saxty et al. |
| 2004/0067955 A1 | 4/2004 | Tabuchi et al. |
| 2008/0090827 A1 | 4/2008 | Taylor et al. |
| 2011/0008347 A1 | 1/2011 | Ullrich et al. |
| 2011/0098269 A1 | 4/2011 | Becknell et al. |
| 2013/0012485 A1 | 1/2013 | Bäschlin et al. |
| 2015/0158873 A1 | 6/2015 | Bogdan et al. |
| 2015/0366866 A1 | 12/2015 | Ali et al. |
| 2015/0376167 A1 | 12/2015 | Jorand-Lebrun et al. |
| 2016/0215350 A1 | 7/2016 | Rabizadeh et al. |
| 2016/0235744 A1 | 8/2016 | Berdini et al. |

FOREIGN PATENT DOCUMENTS

| | | |
|---|---|---|
| EP | 3023101 | 5/2016 |
| JP | 2010-013369 | 1/2010 |
| JP | 05868992 | 2/2016 |
| WO | WO 1989/008108 | 9/1989 |
| WO | WO 2009/047522 | 4/2009 |
| WO | WO 2010/069504 | 6/2010 |
| WO | WO 2012/073017 | 6/2012 |
| WO | WO 2013/130976 | 9/2013 |
| WO | WO 2014/011900 | 1/2014 |
| WO | WO 2014/071419 | 5/2014 |
| WO | WO 2015/089333 | 6/2015 |
| WO | WO 2015/099127 | 7/2015 |
| WO | WO 2015/106717 | 7/2015 |
| WO | WO 2015/120094 | 8/2015 |
| WO | WO 2015/144804 | 10/2015 |
| WO | WO 2015/150900 | 10/2015 |
| WO | WO 2015/160634 | 10/2015 |
| WO | WO 2015/160636 | 10/2015 |
| WO | WO 2016/030509 | 3/2016 |
| WO | WO 2016/038582 | 3/2016 |
| WO | WO 2016/084883 | 6/2016 |
| WO | WO 2016/105503 | 6/2016 |
| WO | WO 2016/139227 | 9/2016 |

OTHER PUBLICATIONS

"Certificate of Analysis FGF-R3 wt, fibroblast growth factor receptor 3: Recombinant Active Protein Kinase," ProQinase, retreived from https://www.proqinase.com/sites/default/files/public/FGFR3_wt_Lot005_V2.pdf on Jan. 31, 2017, 2 pages.

"Certificate of Analysis LanthaScreen® Eu-PY20 Antibody, 25 µg," Life Technologies, Apr. 4, 2014, 1 page.

"Certificate of Analysis FGFR1, 100µg: Recombinant Human Fibroblast Growth Factor Receptor1, Histidine-tagged," Life Technologies, Feb. 25, 2014, 2 pages.

Baroy et al., "Genome Analysis of Osteosarcoma Progression Samples Identifies FGFR1 Overexpression as a Potential Treatment Target and CHM as a Candidate Tumor Suppressor Gene," PLoS One. Sep. 29, 2016;11(9):e0163859. doi: 10.1371/journal.pone.0163859.

Becker et al., "KIAA1549: BRAF Gene Fusion and FGFR1 Hotspot Mutations Are Prognostic Factors in Pilocytic Astrocytomas," J. Neuropathol. Exp. Neurol., Jul. 2015, 74(7):743-754.

Beenken et al.,"The FGF family: biology, pathophysiology and therapy," Nat. Rev. Drug Discov., Mar. 2009, 8:235-253.

Bennett et al., "Mosaic Activating Mutations in FGFR1 Cause Encephalocraniocutaneous Lipomatosis," Am J Hum Genet. Mar. 3, 2016;98(3):579-87. doi: 10.1016/j.ajhg.2016.02.006.

Birrer et al., "Whole Genome Oligonucleotide-Based Array Comparative Genomic Hybridization Analysis Identified Fibroblast Growth Factor 1 As a Prognostic Marker for Advanced-Stage Serous Ovarian Adenocarcinomas," J Clin Oncol. Jun. 1, 2007;25(16):2281-7.

Brooks et al., "Molecular Pathways: Fibroblast Growth Factor Signaling: A New Therapeutic Opportunity in Cancer," Clin Cancer Res. Apr. 1, 2012;18(7):1855-62. doi: 10.1158/1078-0432.CCR-11-0699. Epub Mar. 2, 2012.

Bunney et al., "The Effect of Mutations on Drug Sensitivity and Kinase Activity of Fibroblast Growth Factor Receptors: A Combined Experimental and Theoretical Study," EBioMedicine. Mar. 1, 2015;2(3):194-204.

Byron et al., "FGFR2 point mutations in 466 endometrioid endometrial tumors: relationship with MSI, KRAS, PIK3CA, CTNNB1 mutations and clinicopathological features," PLoS One. 2012;7(2):e30801. doi: 10.1371/journal.pone.0030801. Epub Feb. 23, 2012.

Byron et al., "The N550K/H mutations in FGFR2 confer differential resistance to PD173074, dovitinib, and ponatinib ATP-competitive inhibitors," Neoplasia. Aug. 2013;15(8):975-88.

Cazier et al., "Whole-genome sequencing of bladder cancers reveals somatic CDKN1A mutations and clinicopathological associations with mutation burden," Nat Commun. Apr. 29, 2014;5:3756. doi: 10.1038/ncomms4756.

Chang et al., "Prognostic value of FGFR gene amplification in patients with different types of cancer: a systematic review and meta-analysis," PLoS One. Aug. 29, 2014;9(8):e105524. doi: 10.1371/journal.pone.0105524. eCollection 2014.

Chellaiah et al., "Fibroblast growth factor receptor (FGFR) 3. Alternative splicing in immunoglobin-like domain III creates a receptor highly specific for acidic FGF/FGF-1," J Biol Chem. Apr. 15, 1994;269(15):11620-7.

Cheon et al., "High-affinity binding sites for related fibroblast growth factor ligands reside within different receptor immunoglobulin-like domains," Proc Natl Acad Sci U S A. Feb. 1, 1994;91(3):989-93.

Chesi M, et al., "Frequent translocation t(4;14)(p16.3;q32.3) in multiple myeloma is associated with increased expression and activating mutations of fibroblast growth factor receptor 3," Nat Genet. Jul. 1997;16(3):260-4.

Davies et al., "Somatic mutations of the protein kinase gene family in human lung cancer," Cancer Res. Sep. 1, 2005;65(17):7591-5.

Dieci et al., "Fibroblast growth factor receptor inhibitors as a cancer treatment: from a biologic rationale to medical perspectives," Cancer Discov. Mar. 2013;3(3):264-79. doi: 10.1158/2159-8290.CD-12-0362. Epub Feb. 15, 2013.

Dienstmann et al., "Genomic aberrations in the FGFR pathway: opportunities for targeted therapies in solid tumors," Ann Oncol. Mar. 2014;25(3):552-63. doi: 10.1093/annonc/mdt419. Epub Nov. 20, 2013.

Dutt et al., "Drug-sensitive FGFR2 mutations in endometrial carcinoma," Proc Natl Acad Sci U S A. Jun. 24, 2008;105(25):8713-7. doi: 10.1073/pnas.0803379105. Epub Jun. 13, 2008.

Dutt et al., "Inhibitor-sensitive FGFR1 amplification in human non-small cell lung cancer," PLoS One. 2011;6(6):e20351. doi:10.1371/journal.pone.0020351. Epub Jun. 7, 2011.

Gallo et al., "Functions of Fibroblast Growth Factor Receptors in cancer defined by novel translocations and mutations," Cytokine Growth Factor Rev. Aug. 2015;26(4):425-49. doi: 10.1016/j.cytogfr.2015.03.003. Epub Apr. 20, 2015.

Gauglhofer et al., "Up-regulation of the fibroblast growth factor 8 subfamily in human hepatocellular carcinoma for cell survival and neoangiogenesis," Hepatology. Mar. 2011;53(3):854-64. doi: 10.1002/hep.24099. Epub Feb. 11, 2011.

Goncalves et al., "Novel FGFR1 mutations in Kallmann syndrome and normosmic idiopathic hypogonadotropic hypogonadism: evidence for the involvement of an alternatively spliced isoform," Fertil Steril. Nov. 2015;104(5):1261-7.e1. doi: 10.1016/j.fertnstert.2015.07.1142. Epub Aug. 12, 2015.

Hanada et al., "Identification of fibroblast growth factor-5 as an overexpressed antigen in multiple human adenocarcinomas," Cancer Res. Jul. 15, 2001;61(14):5511-6.

Hart et al., "Transformation and Stat activation by derivatives of FGFR1, FGFR3, and FGFR4," Oncogene. Jul. 6, 2000;19(29):3309-20.

Helsten et al., "The FGFR Landscape in Cancer: Analysis of 4,853 Tumors by Next-Generation Sequencing," Clin Cancer Res. Jan. 1, 2016;22(1):259-67. doi: 10.1158/1078-0432.CCR-14-3212. Epub Sep. 15, 2015.

(56) References Cited

OTHER PUBLICATIONS

Hu MC, et al., "FGF-18, a novel member of the fibroblast growth factor family, stimulates hepatic and intestinal proliferation," Mol Cell Biol. Oct. 1998;18(10):6063-74.
International Preliminary Report on Patentability in the International Application No. PCT/US2016/058549, dated May 3, 2018, 7 pages.
International Search Report and Written Opinion in the International Application No. PCT/US2016/058549, dated Jan. 20, 2017, 11 pages.
Johnson et al., "The human fibroblast growth factor receptor genes: a common structural arrangement underlies the mechanisms for generating receptor forms that differ in their third immunoglobulin domain," Mol Cell Biol. Sep. 1991;11(9):4627-34.
Kasaian et al., "The genomic and transcriptomic landscape of anaplastic thyroid cancer: implications for therapy," BMC Cancer. Dec. 18, 2015;15:984. doi: 10.1186/s12885-015-1955-9.
Kelleher et al., "Fibroblast growth factor receptors, developmental corruption and malignant disease," Carcinogenesis. Oct. 2013;34(10):2198-205. doi: 10.1093/carcin/bgt254. Epub Jul. 23, 2013.
Kore et al.,"The role of fibroblast growth factors in tumor growth," Curr Cancer Drug Targets. Aug. 2009;9(5):639-51. Epub Aug. 1, 2009.
Krstevska-Konstantinova et al., "Favorable Growth Hormone Treatment Response in a Young Boy with Achondroplasia," Med Arch. Apr. 2016;70(2):148-50. doi: 10.5455/medarh.2016.70.148-150. Epub Apr. 1, 2016.
Kuentz et al., "Mosaic-activating FGFR2 mutation in two fetuses with papillomatous pedunculated sebaceous naevus," Br J Dermatol. Jan. 2017;176(1):204-208. doi: 10.1111/bjd.14681. Epub Oct. 2, 2016.
Kunii et al., "FGFR2-amplified gastric cancer cell lines require FGFR2 and Erbb3 signaling for growth and survival," Cancer Res. Apr. 1, 2008;68(7):2340-8. doi: 10.1158/0008-5472.CAN-07-5229.
Laitinen et al., "Reversible congenital hypogonadotropic hypogonadism in patients with CHD7, FGFR1 or GNRHR mutations," PLoS One. 2012;7(6):e39450. doi: 10.1371/journal.pone.0039450. Epub Jun. 19, 2012.
Lewin, et al, "Development of Fibroblast Growth Factor Receptor Inhibitors: Kissing Frogs to Find a Prince?," J Clin Oncol. Oct. 20, 2015;33(30)3372-4. doi: 10.1200/JCO.2015.62.7380. Epub Aug. 31, 2015.
Liao et al., "Inhibitor-sensitive FGFR2 and FGFR3 mutations in lung squamous cell carcinoma," Cancer Res. Aug. 15, 2013;73(16):5195-205. doi: 10.1158/0008-5472.CAN-12-3950. Epub Jun. 20, 2013.
Lin et al., "Modeling genomic diversity and tumor dependency in malignant melanoma," Cancer Res. Feb. 1, 2008;68(3):664-73. doi: 10.1158/0008-5472.CAN-07-2615.
Lin et al., "Molecular analysis of FGFR 2 and associated clinical observations in two Chinese families with Crouzon syndrome," Mol Med Rep. Sep. 2016;14(3):1941-6. doi: 10.3892/mmr.2016.5497. Epub Jul. 11, 2016.
Liu et al., "Clinical significance of fibroblast growth factor receptor-3 mutations in bladder cancer: a systematic review and meta-analysis," Genet Mol Res. Feb. 20, 2014;13(1):1109-20. doi: 10.4238/2014.Feb.20.12.
Lo Iacono et al., "Retrospective study testing next generation sequencing of selected cancer-associated genes in resected prostate cancer," Oncotarget. Mar. 22, 2016;7(12):14394-404. doi: 10.18632/oncotarget.7343.
Marchwicka et al., "Restored expression of vitamin D receptor and sensitivity to 1,25-dihydroxyvitamin D3 in response to disrupted fusion FOP2-FGFR1 gene in acute myeloid leukemia cells," Cell Biosci. Feb. 2, 2016;6:7. doi: 10.1186/s13578-016-0075-9. eCollection 2016.
Marek et al., "Fibroblast growth factor (FGF) and FGF receptor-mediated autocrine signaling in non-small-cell lung cancer cells," Mol Pharmacol. Jan. 2009;75(1):196-207. doi: 10.1124/mol.108.049544. Epub Oct. 10, 2008.
Martincorena et al., "Tumor evolution. High burden and pervasive positive selection of somatic mutations in normal human skin," Science. May 22, 2015;348(6237):880-6. doi:.10.1126/science.aaa6806.
Mazen et al., "Homozygous Mutation of the FGFR1 Gene Associated with Congenital Heart Disease and 46,XY Disorder of Sex Development," Sex Dev. 2016;10(1):16-22. doi: 10.1159/000444948. Epub Apr. 8, 2016.
Miki et al., "Determination of ligand-binding specificity by alternative splicing: two distinct growth factor receptors encoded by a single gene," Proc Natl Acad Sci U S A. Jan. 1, 1992;89(1):246-50.
Moeini et al., "Molecular Pathogenesis and Targeted Therapies for Intrahepatic Cholangiocarcinoma," Clin Cancer Res. Jan. 15, 2016;22(2):291-300. doi: 10.1158/1078-0432.CCR-14-3296. Epub Sep. 24, 2015.
Nagahara et al., "A Japanese familial case of hypochondroplasia with a novel mutation in FGFR3," Clin Pediatr Endocrinol. Jul. 2016;25(3):103-6. doi: 10.1297/cpe.25.103. Epub Jul. 20, 2016.
Nicholes et al., "A mouse model of hepatocellular carcinoma: ectopic expression of fibroblast growth factor 19 in skeletal muscle of transgenic mice," Am J Pathol. Jun. 2002;160(6):2295-307.
Ohishi et al., "Mutation analysis of FGFR1-3 in 11 Japanese patients with syndromic craniosynostoses," Am J Med Genet A. Jan. 2017;173(1):157-162. doi: 10.1002/ajmg.a.37992. Epub Sep. 28, 2016.
Pardo et al., "FGF-2 protects small cell lung cancer cells from apoptosis through a complex involving PKCepsilon, B-Raf and S6K2," EMBO J. Jul. 12, 2006;25(13):3078-88. Epub Jun. 29, 2006.
Presta M, et al., "Fibroblast growth factor/fibroblast growth factor receptor system in angiogenesis," Cytokine Growth Factor Rev. Apr. 2005;16(2):159-78. Epub Feb. 2, 2005.
Qian et al., "N-cadherin/FGFR promotes metastasis through epithelial-to-mesenchymal transition and stem/progenitor cell-like properties," Oncogene. Jun. 26, 2014;33(26):3411-21. doi: 10.1038/onc.2013.310. Epub Aug. 26, 2013.
Qing et al., "Antibody-based targeting of FGFR3 in bladder carcinoma and t(4;14)-positive multiple myeloma in mice," J Clin Invest. May 2009;119(5):1216-29. doi: 10.1172/JCI38017. Epub Apr. 20, 2009.
Rivera et al., "Germline and somatic FGFR1 abnormalities in dysembryoplastic neuroepithelial tumors," Acta Neuropathol. Jun. 2016;131(6):847-63. doi: 10.1007/s00401-016-1549-x. Epub Feb. 26, 2016.
Ron et al., "A Case of Beare-Stevenson Syndrome with Unusual Manifestations," Am J Case Rep. Apr. 15, 2016;17:254-8.
Rosseau et al., "Mutations in the gene encoding fibroblast growth factor receptor-3 in achondroplasia," Nature. Sep. 15, 1994;371(6494):252-4.
Ruotsalainen et al., "High pretreatment serum concentration of basic fibroblast growth factor is a predictor of poor prognosis in small cell lung cancer," Cancer Epidemiol Biomarkers Prev. Nov. 2002;11(11):1492-5.
Sawey et al., "Identification of a therapeutic strategy targeting amplified FGF19 in liver cancer by Oncogenomic screening," Cancer Cell. Mar. 8, 2011;19(3):347-58. doi: 10.1016/j.ccr.2011.01.040.
Shiang et al., "Mutations in the transmembrane domain of FGFR3 cause the most common genetic form of dwarfism, achondroplasia," Cell. Jul. 29, 1994;78(2):335-42.
Taylor et al., "Identification of FGFR4-activating mutations in human rhabdomyosarcomas that promote metastasis in xenotransplanted models," J Clin Invest. Nov. 2009;119(11):3395-407. doi: 10.1172/JCI39703. Epub Oct. 5, 2009.
Thussbas et al., "FGFR4 Arg388 allele is associated with resistance to adjuvant therapy in primary breast cancer," J Clin Oncol. Aug. 10, 2006;24(23):3747-55. Epub Jul. 5, 2006.
Ueda et al., "Deletion of the carboxyl-terminal exons of K-sam/FGFR2 by short homology-mediated recombination, generating preferential expression of specific messenger RNAs," Cancer Res. Dec. 15, 1999;59(24):6080-6.

(56) References Cited

OTHER PUBLICATIONS

Van Rhijn et al., "Novel fibroblast growth factor receptor 3 (FGFR3) mutations in bladder cancer previously identified in non-lethal skeletal disorders," Eur J Hum Genet. Dec. 2002;10(12):819-24.

Weiss et al., "Frequent and focal FGFR1 amplification associates with therapeutically tractable FGFR1 dependency in squamous cell lung cancer," Sci Transl Med. Dec. 15, 2010;2(62):62ra93. doi: 10.1126/scitranslmed.3001451.

Welm et al., "Inducible dimerization of FGFR1: development of a mouse model to analyze progressive transformation of the mammary gland," J Cell Biol. May 13, 2002;157(4):703-14. Epub May 13, 2002.

Wesche et al., "Fibroblast growth factors and their receptors in cancer," Biochem J. Jul. 15, 2011;437(2):199-213. doi: 10.1042/BJ20101603.

Wilkie et al., "Functions of fibroblast growth factors and their receptors," Curr Biol. May 1, 1995;5(5):500-7.

Wu et al., "Identification of targetable FGFR gene fusions in diverse cancers," Cancer Discov. Jun. 2013;3(6):636-47. doi: 10.1158/2159-8290.CD-13-0050. Epub Apr. 4, 2013.

Zhang et al., "Receptor specificity of the fibroblast growth factor family. The complete mammalian FGF family," J Biol Chem. Jun. 9, 2006;281(23):15694-700. Epub Apr. 4, 2006.

Zhao et al., "Monoclonal antibodies to fibroblast growth factor receptor 2 effectively inhibit growth of gastric tumor xenografts," Clin Cancer Res. Dec. 1, 2010;16(23):5750-8. doi: 10.1158/1078-0432.CCR-10-0531. Epub Jul. 29, 2010.

Zhao et al., "Whole-exome sequencing and whole genome re-sequencing for prenatal diagnosis of achondroplasia," Int J Clin Exp Med. Oct. 15, 2015;8(10):19241-9. eCollection 2015.

Zhao G, et al., "A novel, selective inhibitor of fibroblast growth factor receptors that shows a potent broad spectrum of antitumor activity in several tumor xenograft models," Mol Cancer Ther. Nov. 2011;10(11):2200-10. doi: 10.1158/1535-7163.MCT-11-0306. Epub Sep. 7, 2011.

Zhou et al., "A Pro250Arg substitution in mouse Fgfr1 causes increased expression of Cbfa1 and premature fusion of calvarial sutures," Hum Mol Genet. Aug. 12, 2000;9(13):2001-8.

Zimmer et al., "Multiple structural elements determine ligand binding of fibroblast growth factor receptors. Evidence that both Ig domain 2 and 3 define receptor specificity," J Biol Chem. Apr. 15, 1993;268(11):7899-903.

* cited by examiner

2-ARYL- AND 2-HETEROARYL-SUBSTITUTED 2-PYRIDAZIN-3(2H)-ONE COMPOUNDS AS INHIBITORS OF FGFR TYROSINE KINASES

CROSS REFERENCE TO RELATED APPLICATIONS

This application claims the benefit of U.S. Provisional Application No. 62/245,956, filed on Oct. 23, 2015, which is incorporated herein by reference in its entirety.

BACKGROUND

The present disclosure relates to novel compounds which exhibit inhibition of fibroblast growth factor receptor tyrosine kinases (FGFRs), in particular FGFR1, FGFR2, FGFR3 and/or FGFR4, pharmaceutical compositions comprising the compounds, to processes for making the compounds, and the use of the compounds in therapy. More particularly, it relates to 2-aryl- and 2-heteroaryl-substituted 2-pyridazin-3(2H)-one compounds useful in the treatment or prevention of diseases which can be treated with an FGFR inhibitor, including diseases mediated by FGFR tyrosine kinases.

Fibroblast growth factors (FGFs) and their receptors (FGFRs) regulate a wide range of physiologic cellular processes, such as embryonic development, differentiation, proliferation, survival, migration, and angiogenesis.

The FGF family comprises 18 secreted ligands (FGFs) which are readily sequestered to the extracellular matrix by heparin sulfate proteoglycans (HPSGs). For signal propagation, FGFs are released from the extracellular matrix by proteases or specific FGF-binding proteins, with the liberated FGFs subsequently binding to a cell surface FGF-receptor (FGFR) in a ternary complex consisting of FGF, FGFR and HPSG (Beenken, A., Nat. Rev. Drug Discov. 2009; 8:235-253).

There are five FGFRs, of which four (FGFRs 1-4) are highly conserved single-pass transmembrane tyrosine kinase receptors (Eswarakumar, V. P., Cytokine Growth Factor Rev., 2005; 16:139-149). The binding of an FGF to an FGFR leads to receptor dimerization and transphosphorylation of tyrosine kinase domains (Dieci, M. V., et al., Cancer Discov. 2013; 3:264-279; Korc, N., and Friesel, R. E., Curr. Cancer Drug Targets 2009; 5:639-651). Activation of downstream signaling occurs via the intracellular receptor substrate FGFR substrate 2 (FRS2) and phospholipase Cγ (PLC-γ), leading to subsequent upregulation of RAS/mitogen-activated protein kinase (MAPK) and phosphoinositide 3-kinase (PI3K)/AKT signaling pathways. Other pathways can be activated, including STAT-dependent signaling (Turner, N., Grose, R., Nat. Ref. Cancer 2010; 10:116-129; Brooks, N. S., et al., Clin Cancer Res. 2012; 18:1855-1862; Dienstmann, R., et al., Ann. Oncol. 2014; 25:552-563).

FGFR signaling components are frequently altered in human cancer, and several preclinical models have provided compelling evidence for the oncogenic potential of aberrant FGFR signaling in carcinogenesis, thereby validating FGFR signaling as an attractive target for cancer treatment.

The mechanisms by which FGFR signaling is dysregulated and drive cancer are better understood in recent years, and include activating mutations, FGFR gene amplification, chromosomal translocations, autocrine and paracrine signaling, and altered FGFR splicing.

SUMMARY OF THE INVENTION

It has now been found that 2-aryl- and 2-heteroaryl-substituted 2-pyridazin-3(2H)-one compounds are inhibitors of FGFR1, FGFR2, FGFR3 and/or FGFR4, which are useful in the treatment or prevention of diseases which can be treated with an inhibitor of FGFR1, FGFR2, FGFR3 and/or FGFR4, including diseases mediated by FGFR1, FGFR2, FGFR3 and/or FGFR4.

Accordingly, provided herein is a compound of the general Formula I:

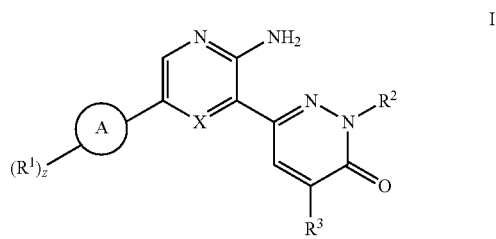

or pharmaceutically acceptable salt or solvate thereof, wherein X, Ring A, z, $R^1$, $R^2$ and $R^3$ are as defined herein.

Also provided herein is a pharmaceutical composition comprising a compound of Formula I or a pharmaceutically acceptable salt or solvate thereof, in admixture with a pharmaceutically acceptable diluent or carrier.

Also provided herein is a method of inhibiting cell proliferation, in vitro or in vivo, the method comprising contacting a cell with an effective amount of a compound of Formula I or a pharmaceutically acceptable salt or solvate thereof, or a pharmaceutical composition thereof as defined herein.

Also provided herein is a method of treating an FGFR-associated disease or disorder in a patient in need of such treatment, the method comprising administering to the patient a therapeutically effective amount of a compound of Formula I or a pharmaceutically acceptable salt or solvate thereof, or a pharmaceutical composition thereof as defined herein.

Also provided herein is a method of treating cancer and/or inhibiting metastasis associated with a particular cancer in a patient in need of such treatment, the method comprising administering to the patient a therapeutically effective amount of a compound of Formula I or a pharmaceutically acceptable salt or solvate thereof or a pharmaceutical composition thereof as defined herein.

Also provided herein is a compound of Formula I or a pharmaceutically acceptable salt or solvate thereof, or a pharmaceutical composition thereof as defined herein for use in therapy.

Also provided herein is a compound of Formula I or a pharmaceutically acceptable salt or solvate thereof or a pharmaceutical composition thereof as defined herein for use in the treatment of cancer and/or inhibiting metastasis associated with a particular cancer.

Also provided herein is a compound of Formula I or a pharmaceutically acceptable salt or solvate thereof for use in the inhibition of FGFR1, FGFR2, FGFR3 and/or FGFR4.

Also provided herein is a compound of Formula I or a pharmaceutically acceptable salt or solvate thereof or a pharmaceutical composition thereof as defined herein, for use in the treatment of an FGFR-associated disease or disorder.

Also provided herein is the use of a compound of Formula I or a pharmaceutically acceptable salt or solvate thereof, as defined herein in the manufacture of a medicament for the treatment of cancer and/or inhibiting metastasis associated with a particular cancer.

Also provided herein is a use of a compound of Formula I or a pharmaceutically acceptable salt or solvate thereof, as defined herein in the manufacture of a medicament for the inhibition of activity of FGFR1, FGFR2 FGFR3 and/or FGFR4.

Also provided herein is the use of a compound of Formula I or a pharmaceutically acceptable salt or solvate thereof, as defined herein, in the manufacture of a medicament for the treatment of an FGFR-associated disease or disorder.

Also provided herein is a method for treating cancer in a patient in need thereof, the method comprising (a) determining if the cancer is associated with a dysregulation of an FGFR gene, a fibroblast growth factor receptor, or expression or activity or level of any of the same (e.g., an FGFR-associated cancer); and (b) if the cancer is determined to be associated with a dysregulation of an FGFR gene, a fibroblast growth factor receptor, or expression or activity or level of any of the same (e.g., an FGFR-associated cancer), administering to the patient a therapeutically effective amount of a compound of Formula I or a pharmaceutically acceptable salt or solvate thereof, or a pharmaceutical composition thereof.

Also provided herein is a method for reversing or preventing acquired resistance to an anticancer drug, comprising administering a therapeutically effective amount of a compound of Formula I or a pharmaceutically acceptable salt or solvate thereof, to a patient at risk for developing or having acquired resistance to an anticancer drug. In some embodiments, the patient is administered a dose of the anticancer drug (e.g., at substantially the same time as a dose of a compound of Formula I or a pharmaceutically acceptable salt or solvate thereof is administered to the patient).

Also provided herein is a method of delaying and/or preventing development of cancer resistant to an anticancer drug in an individual, comprising concomitantly administering to the individual (a) an effective amount of a compound of Formula I and (b) an effective amount of the anticancer drug.

Also provided herein is a method of treating an individual with cancer who has increased likelihood of developing resistance to an anticancer drug, comprising concomitantly administering to the individual (a) an effective amount of a compound of Formula I and (b) an effective amount of the anticancer drug.

Also provided herein is a method for treating a disease involving angiogenesis and/or neovascularization, comprising administering to a subject in need thereof, a therapeutically effective amount of a compound of Formula I.

Also provided herein is a method for inhibiting angiogenesis in a tumor, which comprises contacting the tumor with a compound of Formula I.

Also provided herein is a pharmaceutical combination for treating cancer in a patient in need thereof, which comprises (a) a compound of Formula I or a pharmaceutically acceptable salt or solvate thereof, (b) an additional therapeutic agent, and (c) optionally at least one pharmaceutically acceptable carrier, for simultaneous, separate or sequential use for the treatment of cancer, wherein the amounts of the compound of Formula I or pharmaceutically acceptable salt or solvate thereof and of the additional therapeutic agent are together effective in treating the cancer. Also provided herein is a pharmaceutical composition comprising such a combination. Also provided herein is the use of such a combination for the preparation of a medicament for the treatment of cancer. Also provided herein is a commercial package or product comprising such a combination as a combined preparation for simultaneous, separate or sequential use; and to a method of treatment of cancer a patient in need thereof.

Also provided herein is a process for preparing a compound of Formula I or a pharmaceutically acceptable salt or solvate thereof.

Also provided herein is a compound of Formula I or a pharmaceutically acceptable salt or solvate thereof obtained by a process of preparing the compound as defined herein.

In some embodiments, a compound of Formula I or a pharmaceutically acceptable salt or solvate thereof exhibits potent and selective FGFR inhibition. In some embodiments, said inhibition occurs with relative sparing of FGFR1 inhibition. In certain embodiments, a compound of Formula I or a pharmaceutically acceptable salt or solvate thereof exhibits a relatively high potency for FGFR2 and FGFR3 (e.g., FGFR3, e.g., FGFR3-TACC3 fusion). In certain embodiments, a compound of Formula I or a pharmaceutically acceptable salt or solvate thereof provides dose-dependent inhibition of tumor growth in RT 112/84 FGFR3-TACC3 xenografts. In certain embodiments, a compound of Formula I or a pharmaceutically acceptable salt or solvate thereof exhibits (independently) greater selectivity for FGFR2 and/or FGFR3 (e.g., FGFR3) as compared to FGFR1 (e.g., exhibits greater selectivity for FGFR3 over FGFR1 in enzyme and cell-based assays e.g., exhibit greater cytotoxicity for FGFR2/3 than FGFR1 mutant cells). See Lewin, et al, *Journal of Clinical Oncology,* 2015, 22, 3372.

In some embodiments, administration of a compound of Formula I or a pharmaceutically acceptable salt or solvate thereof results in less hyperphosphatemia than administration of a pan-FGFR inhibitor (e.g., a pan-FGFR inhibitor, which when compared with the Formula I compounds described herein, exhibits less selectivity for FGFR2 and/or FGFR3 (e.g., FGFR3) as compared to FGFR1; e.g., a pan-FGFR inhibitor that is less sparing of FGFR1 inhibition than the Formula I compounds described herein). In view of the foregoing and while not wishing to be bound by theory, it is believed that a compound of Formula I or a pharmaceutically acceptable salt or solvate thereof can provide greater dosing/regimen flexibility and/or efficacy than, for example, a pan-FGFR inhibitor (e.g., a pan-FGFR inhibitor, which when compared with the Formula I compounds described herein, exhibits less selectivity for FGFR2 and/or FGFR3 (e.g., FGFR3) as compared to FGFR1; e.g., a pan-FGFR inhibitor that is less sparing of FGFR1 inhibition than the Formula I compounds described herein). By way of example, and as the skilled person will appreciate, the compounds described herein can be administered at higher doses and/or with increased frequencies, thereby providing higher drug exposure/target coverage, and done so with reduced risk of causing unwanted (e.g., abnormal) increases in blood phosphate levels, which in some instances can necessitate administration of phosphate binders and/or temporary (e.g., drug holidays) or permanent cessation of therapy to allow phosphate levels to return to normal.

Accordingly, also provided are methods of treating a FGFR-associated cancer in a patient, which include: (a) administering to a patient identified or diagnosed as having an FGFR-associated cancer one or more doses of a first FGFR inhibitor over a treatment period; (b) determining the level of phosphate in a biological sample comprising blood, serum, or plasma obtained from the patient after the treatment period; (c) selecting a patient having an elevated level of phosphate in the biological sample as compared to a reference level of phosphate; and (d) ceasing administration of the first FGFR inhibitor and initiating administration of a therapeutically effective amount of a compound as described herein or a pharmaceutically acceptable salt or solvate thereof, or a pharmaceutical composition containing the same, to the selected patient. In certain embodiments, the treatment period is at least 7 days. In other embodiments, the treatment period is at least 21 days. In certain embodiments, the first FGFR inhibitor is JNJ-42756493 or BGJ398. By way of example, the first FGFR inhibitor can be JNJ-42756493 and a daily dose of 6 mg to 12 mg of the first FGFR inhibitor is administered to the patient over the treatment period (e.g., 7 days). As another example, the first FGFR inhibitor can be BGJ398 and a daily dose of 50 mg to 125 mg of the first FGFR inhibitor is administered to the patient over the treatment period (e.g., 21 days). In certain embodiments, the patient is administered a therapeutically effective amount of a phosphate binder over the treatment period. In certain embodiments, step (d) further comprises ceasing administration of the phosphate binder to the selected patient. In certain embodiments, step (d) further includes administering a decreased dose of the phosphate binder to the selected patient relative to the dose of the phosphate binder administered to the patient over the treatment period. JNJ-42756493 (erdafitinib) is also known as JNJ-493 and has the following systematic name, N1-(3,5-dimethoxyphenyl)-N2-isopropyl-N1-(3-(1-methyl-1H-pyrazol-4-yl)quinoxalin-6-yl)ethane-1,2-diamine, and the following structure:

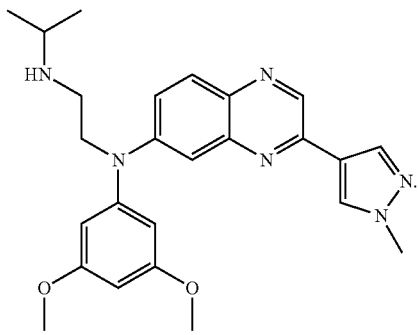 [SMILES: COc1cc(OC)cc(N(CCNC(C)C)c2ccc3ncc(-c4cnn(C)c4)nc3c2)c1]

BGJ398 (infigratinib) has the following systematic name, 3-(2,6-dichloro-3,5-dimethoxyphenyl)-1-(6-((4-(4-ethylpiperazin-1-yl)phenyl)amino)pyrimidin-4-yl)-1-methylurea, and the following chemical structure:

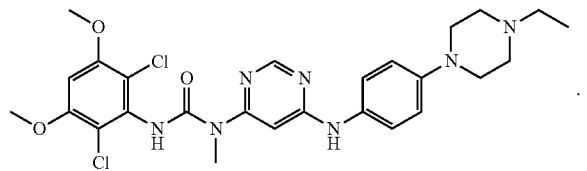 [SMILES: CCN1CCN(c2ccc(Nc3cc(N(C)C(=O)Nc4c(Cl)c(OC)cc(OC)c4Cl)ncn3)cc2)CC1]

Also provided herein are methods of treating a FGFR-associated cancer in a patient, the method comprising administering a therapeutically effective dose of a compound as described herein or a pharmaceutically acceptable salt or solvate thereof, or a pharmaceutical composition containing the same to a patient identified or diagnosed as having an FGFR-associated cancer over a treatment period of at least 8 days, wherein the patient is determined to have about the same or a decreased level of phosphate in one or more biological sample(s) comprising blood, serum, or plasma obtained from the patient over the treatment period as compared to a reference level of phosphate.

Also provided herein are methods of treating a FGFR-associated cancer in a patient, the method comprising administering a therapeutically effective dose of a compound as described herein or a pharmaceutically acceptable salt or solvate thereof, or a pharmaceutical composition containing the same to a patient identified or diagnosed as having an FGFR-associated cancer over a treatment period, wherein the patient is not administered a phosphate binder over the treatment period.

Also provided herein are methods of treating a FGFR-associated cancer in a patient, the method comprising administering a therapeutically effective dose of a compound as described herein or a pharmaceutically acceptable salt or solvate thereof, or a pharmaceutical composition containing the same to a patient identified or diagnosed as having an FGFR-associated cancer over a treatment period, wherein the patient is further administered a low dose of a phosphate binder over the treatment period.

Also provided herein are methods of treating a patient having a FGFR-associated cancer, the method comprising administering a therapeutically effective dose of a compound as described herein or a pharmaceutically acceptable salt or solvate thereof, or a pharmaceutical composition containing the same to a patient identified or diagnosed as having an FGFR-associated cancer over a treatment period, wherein the patient does not experience or is less likely to experience one or more of soft tissue calcification, stomatitis, dry mouth, nail changes, fatigue, asthenia, anorexia, malaise, and muscle aches over the treatment period.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description, and from the claims.

DETAILED DESCRIPTION OF THE INVENTION

Provided herein is a compound of the general Formula I:

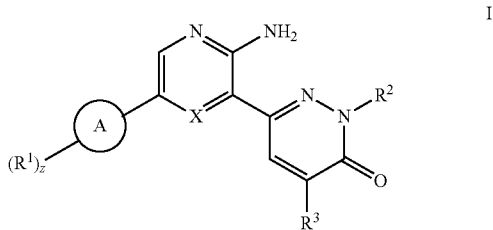

or a pharmaceutically acceptable salt or solvate thereof, wherein:
X is N or CH;
Ring A is a 5-membered heteroaryl ring having 1-2 ring nitrogen atoms;
z is 1, 2 or 3;

each R¹ is independently selected from the group consisting of:
(a) hydrogen,
(b) C1-C6 alkyl (optionally substituted with 1-3 fluoros),
(c) hydroxy(C1-C6 alkyl)- (optionally substituted with 1-3 fluoros),
(d) dihydroxy(C1-C6 alkyl)- (optionally substituted with 1-3 fluoros),
(e) cyano(C1-C6 alkyl)-,
(f) $R^aR^bN$(C1-C6 alkyl)-,
(g) (C1-C3 alkoxy)C1-C6 alkyl- (optionally substituted with 1-3 fluoros),
(h) (C3-C6 cycloalkyl)$(CH_2)_n$— where n is 0-3 and said cycloalkyl is optionally substituted with CN, OH, $R^aR^bN$—, (1-3C)alkyl or (1-3C)alkoxy,
(i) $hetCyc^1(CH_2)_m$— where m is 0-3,
(j) $hetCyc^2(CH_2)_p$— where p is 0 or 1,
(k) $hetAr^1(CH_2)_q$— where q is 1 or 2,
(l) halogen, and
(m) $hetCyc^1$C(=O)CH$_2$—;

hetCyc¹ is a 4-7 membered saturated heterocyclic ring having 1-2 ring heteroatoms independently selected from N and O, wherein said heterocyclic ring is optionally substituted with one or more substituents independently selected from the group consisting of fluoro, HO, C1-C6 alkyl (optionally substituted with 1-3 fluoros), (C1-C6 alkoxy)C1-C6 alkyl- (optionally substituted with 1-3 fluoros), (C3-C6 cycloalkoxy)C1-C6 alkyl-, hydroxy(C1-C6 alkyl)-, $R^cR^dN$— and (C1-C6 alkyl)C(=O)—;

hetCyc² is a 7-10 membered heterospirocyclic ring having 1-2 ring heteroatoms independently selected from N and O, wherein said heterospirocyclic ring is optionally substituted with one or more substituents independently selected from the group consisting of C1-C6 alkyl (optionally substituted with 1-3 fluoros), (C1-C6 alkoxy)C1-C6 alkyl- (optionally substituted with 1-3 fluoros), (C3-C6 cycloalkoxy)C1-C6 alkyl-, hydroxy(C1-C6 alkyl)-, $R^cR^dN$— and (C1-C6 alkyl)C(=O)—;

hetAr¹ is a 6-membered heteroaryl ring having 1-2 ring nitrogen atoms, wherein said ring is optionally substituted with one or more substituents independently selected from C1-C6 alkyl and halogen;

R² is Ar¹ or hetAr²;

Ar¹ is phenyl substituted with one or more groups independently selected from halogen, cyano, C1-C3 alkyl, C1-C3 alkoxy, (C1-C3 alkyl)NHC(=O)—, (C1-C3 alkyl)C(=O)NH—, (cyclopropyl)C(=O)NH— and (cyclopropyl)NHC(=O)—, wherein each of said C1-C3 alkyl and C1-C3 alkoxy portions is optionally substituted with 1-3 fluoros;

hetAr² is a 6-10 membered heteroaryl ring having 1-2 ring nitrogen atoms, wherein said heteroaryl ring is optionally substituted with one or more groups independently selected from halogen, C1-C3 alkyl, C1-C3 alkoxy, (C1-C3 alkyl)NHC(=O)—, (C1-C3 alkyl)C(=O)NH—, (C3-C4 cycloalkyl)C(=O)NH— and (C3-C4 cycloalkyl)NHC(=O)—, wherein each of said C1-C3 alkyl and C1-C3 alkoxy portions is optionally substituted with 1-3 fluoros;

R³ is hydrogen, C1-C4 alkyl or (C3-C4)cycloalkyl; and $R^a$, $R^b$, $R^c$ and $R^d$ are independently hydrogen or C1-C6 alkyl optionally substituted with F, OH or C1-C6 alkoxy.

In some embodiments of general formula (I):
X is N or CH;
Ring A is a 5-membered heteroaryl ring having 1-2 ring nitrogen atoms;
z is 1, 2 or 3;

each R¹ is independently selected from the group consisting of:
(a) hydrogen,
(b) C1-C6 alkyl (optionally substituted with 1-3 fluoros),
(c) hydroxy(C1-C6 alkyl)- (optionally substituted with 1-3 fluoros),
(d) dihydroxy(C1-C6 alkyl)- (optionally substituted with 1-3 fluoros),
(e) cyano(C1-C6 alkyl)-,
(f) $R^aR^bN$(C1-C6 alkyl)-,
(g) (C1-C3 alkoxy)C1-C6 alkyl- (optionally substituted with 1-3 fluoros),
(h) (C3-C6 cycloalkyl)$(CH_2)_n$— where n is 0-3 and said cycloalkyl is optionally substituted with CN, OH, $R^aR^bN$—, (1-3C)alkyl or (1-3C)alkoxy,
(i) $hetCyc^1(CH_2)_m$— where m is 0-3,
(j) $hetCyc^2(CH_2)_p$— where p is 0 or 1,
(k) $hetAr^1(CH_2)_q$— where q is 1 or 2, and
(l) halogen;

hetCyc¹ is a 4-7 membered saturated heterocyclic ring having 1-2 ring heteroatoms independently selected from N and O, wherein said heterocyclic ring is optionally substituted with one or more substituents independently selected from the group consisting of fluoro, HO, C1-C6 alkyl (optionally substituted with 1-3 fluoros), (C1-C6 alkoxy)C1-C6 alkyl- (optionally substituted with 1-3 fluoros), (C3-C6 cycloalkoxy)C1-C6 alkyl-, hydroxy(C1-C6 alkyl)-, $R^cR^dN$— and (C1-C6 alkyl)C(=O)—;

hetCyc² is a 7-10 membered heterospirocyclic ring having 1-2 ring heteroatoms independently selected from N and O, wherein said heterospirocyclic ring is optionally substituted with one or more substituents independently selected from the group consisting of C1-C6 alkyl (optionally substituted with 1-3 fluoros), (C1-C6 alkoxy)C1-C6 alkyl- (optionally substituted with 1-3 fluoros), (C3-C6 cycloalkoxy)C1-C6 alkyl-, hydroxy(C1-C6 alkyl)-, $R^cR^dN$— and (C1-C6 alkyl)C(=O)—;

hetAr¹ is a 6-membered heteroaryl ring having 1-2 ring nitrogen atoms, wherein said ring is optionally substituted with one or more substituents independently selected from C1-C6 alkyl and halogen;

R² is Ar¹ or hetAr²;

Ar¹ is phenyl substituted with one or more groups independently selected from halogen, cyano, C1-C3 alkyl, C1-C3 alkoxy, (C1-C3 alkyl)NHC(=O)—, (C1-C3 alkyl)C(=O)NH—, (cyclopropyl)C(=O)NH— and (cyclopropyl)NHC(=O)—, wherein each of said C1-C3 alkyl and C1-C3 alkoxy portions is optionally substituted with 1-3 fluoros;

hetAr² is a 6 membered heteroaryl ring having 1-2 ring nitrogen atoms, wherein said heteroaryl ring is optionally substituted with one or more groups independently selected from halogen, C1-C3 alkyl, C1-C3 alkoxy, (C1-C3 alkyl)NHC(=O)—, (C1-C3 alkyl)C(=O)NH—, (C3-C4 cycloalkyl)C(=O)NH— and (C3-C4 cycloalkyl)NHC(=O)—, wherein each of said C1-C3 alkyl and C1-C3 alkoxy portions is optionally substituted with 1-3 fluoros;

R³ is hydrogen, C1-C4 alkyl or (C3-C4)cycloalkyl; and $R^a$, $R^b$, $R^c$ and $R^d$ are independently hydrogen or C1-C6 alkyl optionally substituted with F, OH or C1-C6 alkoxy.

For complex chemical names employed herein, the substituent group is named before the group to which it attaches. For example, methoxyethyl comprises an ethyl backbone with a methoxy substituent.

The term "halogen" as used herein means —F (sometimes referred to herein as "fluoro" or fluoros"), —Cl, —Br and —I.

The terms "C1-C3 alkyl" and "C1-C6 alkyl" as used herein refer to a monovalent, saturated linear or branched hydrocarbon chains having from one to three and one to six carbon atoms, respectively. Examples include, but are not limited to, methyl, ethyl, 1-propyl, isopropyl, 1-butyl, isobutyl, sec-butyl, tert-butyl, 2-methyl-2-propyl, pentyl, pentan-3-yl and hexyl.

The term "hydroxy(C1-C6 alkyl)-" as used herein refers to a monovalent, saturated linear or branched hydrocarbon chain having from one to six carbon atoms, wherein any one of the carbon atoms is substituted with a hydroxy (—OH) group.

The terms "dihydroxy(C1-C6 alkyl)-" and "dihydroxy (C3-C6 alkyl)-" as used herein refers to a monovalent, saturated linear or branched hydrocarbon chain having from one to six carbon atoms or three to six carbon atoms, respectively, wherein any two of the carbon atoms are each substituted with a hydroxy group, provided that both hydroxy groups are not attached to the same carbon atom.

The term "cyano(C1-C6 alkyl)-" as used herein refers to a monovalent, saturated linear or branched hydrocarbon chain having from one to six carbon atoms, wherein any one of the carbon atoms is substituted with a cyano (—CN) group.

The terms "C1-C3 alkoxy" and "C1-C6 alkoxy" as used herein refer to groups that have the formula, —OR, wherein R is "C1-C3 alkyl" and "C1-C6 alkyl", respectively, as defined herein. Illustrative examples include, but are not limited to, methoxy, ethoxy, propoxy, 2-propoxy, butoxy, tert-butoxy, pentyloxy, and hexyloxy.

The term "(C1-C6 alkoxy)(C1-C6 alkyl)-" as used herein refers to a monovalent, saturated linear or branched hydrocarbon chain having from one to six carbon atoms, wherein any one of the carbon atoms is substituted with a C1-C6 alkoxy group as defined herein.

The term "C3-C6 cycloalkyl" refers to a monovalent, monocyclic, saturated hydrocarbon ring having from three to six ring atoms. Illustrative examples include, but are not limited to, cyclopropyl and cyclobutyl.

The term "C3-C6 cycloalkoxy" as used herein refers to a group having the formula, —OR', wherein R' is "C3-C6 cycloalkyl" as defined herein.

The term "(C3-C6 cycloalkoxy)C1-C6 alkyl-" as used herein refers to a monovalent, saturated linear or branched hydrocarbon chain having from one to six carbon atoms, wherein any one of the carbon atoms is substituted with a C3-C6 cycloalkoxy group as defined herein.

The term "heterocyclic" refers to a saturated, monovalent, monocyclic ring having the indicated number of total ring atoms, in which at least one of the ring atoms is a heteroatom (e.g., N or O).

The term "heterospirocyclic ring" as used herein refers to a bicyclic, saturated, spiro-C-fused (i.e., the two rings share a common carbon atom) heterocyclic ring system having from seven to ten total ring atoms, wherein from one to two of the ring atoms is a heteroatom independently selected from the group consisting of N and O, provided that the heteroatoms are not adjacent to one another. Each ring independently contains from 3 to 7 ring atoms, and when two of the ring atoms are heteroatoms, each of the heteroatoms can be present in the same ring, or each can be present in a different ring. Examples include 7-oxa-4-azaspiro[2.5]octane, 2-azaspiro[3.3]heptane, 2,6-diazaspiro[3.3]heptane, 2,5-diazaspiro[3.4]octane, 2,6-diazaspiro[3.4]octane, 1,6-diazaspiro[3.4]octane, 1,7-diazaspiro[4.4]nonane, 2,7-diazaspiro[4.4]nonane, 2,7-diazaspiro[3.5]nonane, 2,6-diazaspiro[3.5]nonane, 2,5-diazaspiro[3.5]nonane, 1,7-diazaspiro[3.5]nonane, 1,6-diazaspiro[3.5]nonane, 2,8-diazaspiro[4.5]decane, 1,8-diazaspiro[4.5]decane, 1,7-diazaspiro[4.5]decane, 2,7-diazaspiro[4.5]decane, 2,6-diazaspiro[4.5]decane, 3,9-diazaspiro[5.5]undecane, 2,9-diazaspiro[5.5]undecane, 7-azaspiro[3.5]nonane, 6-oxa-2-azaspiro[3.4]octane, 2-oxa-7-azaspiro[4.4]nonane, 7-oxa-2-azaspiro[3.5]nonane and 7-oxa-2-azaspiro[4.5]decane. For purposes of clarification, the chemical structures of two exemplary heterospirocyclic rings are provided:

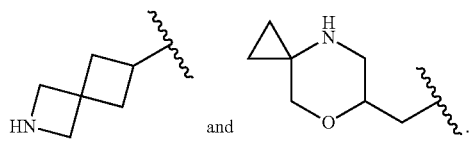

The term "(C3-C4)cycloalkyl" as used herein refers collectively to the cyclopropyl and cyclobutyl rings.

The term "heteroaryl" refers to an aromatic, monovalent or divalent, monocyclic or bicyclic ring having the indicated number of total ring atoms, in which at least one of the ring atoms is a heteroatom (e.g., N or O).

The term "compound," as used herein is meant to include all stereoisomers, geometric isomers, tautomers, and isotopically enriched variants of the structures depicted. Compounds herein identified by name or structure as one particular tautomeric form are intended to include other tautomeric forms unless otherwise specified.

The term "tautomer" as used herein refers to compounds whose structures differ markedly in arrangement of atoms, but which exist in easy and rapid equilibrium, and it is to be understood that compounds of the present invention may be depicted as different tautomers, and when compounds have tautomeric forms, all tautomeric forms are intended to be within the scope of the invention, and the naming of the compounds does not exclude any tautomer.

In certain embodiments of Formula I, X is N.

In certain embodiments of Formula I, X is CH.

In certain embodiments of Formula I, Ring A is pyrazolyl optionally substituted with one to three $R^1$ groups, wherein each $R^1$ group is independently selected from the group consisting of (a) hydrogen, (b) C1-C6 alkyl (optionally substituted with 1-3 fluoros), (c) hydroxy(C1-C6 alkyl)-(optionally substituted with 1-3 fluoros), (d) dihydroxy(C1-C6 alkyl)-(optionally substituted with 1-3 fluoros), (e) cyano (C1-C6 alkyl)-, (f) $R^aR^bN$(C1-C6 alkyl)-, (g) (C1-C3 alkoxy)C1-C6 alkyl- (optionally substituted with 1-3 fluoros), (h) (C3-C6 cycloalkyl)$(CH_2)_n$— where n is 0-3 and said cycloalkyl is optionally substituted with CN, OH, $R^aR^bN$—, (1-3C)alkyl or (1-3C)alkoxy, (i) hetCyc$^1$ $(CH_2)_m$— where m is 0-3, (j) hetCyc$^2(CH_2)_p$— where p is 0 or 1, (k) hetAr$^1(CH_2)_q$— where q is 1 or 2, (l) halogen and (m) hetCyc$^1$C(=O)$CH_2$—. In certain embodiments, z is 1.

In certain embodiments of Formula I, Ring A is pyrazolyl optionally substituted with one to three $R^1$ groups, wherein each $R^1$ group is independently selected from the group consisting of (a) hydrogen, (b) C1-C6 alkyl (optionally substituted with 1-3 fluoros), (c) hydroxy(C1-C6 alkyl)-(optionally substituted with 1-3 fluoros), (e) cyano(C1-C6 alkyl)-, (g) (C1-C3 alkoxy)C1-C6 alkyl- (optionally substituted with 1-3 fluoros), (h) (C3-C6 cycloalkyl)$(CH_2)_n$— where n is 0-3 and said cycloalkyl is optionally substituted with CN, OH, $R^aR^bN$—, (1-3C)alkyl or (1-3C)alkoxy, (i)

hetCyc¹(CH₂)ₘ— where m is 0-3, (j) hetCyc²(CH₂)ₚ where p is 0 or 1, (l) halogen and (m) hetCyc¹C(=O)CH₂—. In certain embodiments, z is 1.

In certain embodiments of Formula I, R¹ is hydrogen. In one embodiment of Formula I, R¹ is hydrogen and z is 1, 2 or 3.

In certain embodiments of Formula I, R¹ is C1-C6 alkyl optionally substituted with 1-3 fluoros. Non-limiting examples of R¹ include methyl, isopropyl, isobutyl, pentan-3-yl, 2,2-difluoroethyl, and 3,3,3-trifluoroethyl.

In certain embodiments of Formula I, R¹ is C1-C6 alkyl optionally substituted with 1-3 fluoros and z is 1, 2 or 3. In certain embodiments, z is 1. In certain embodiments of Formula I, Ring A is substituted with one to two R¹ groups independently selected from C1-C6 alkyl optionally substituted with 1-3 fluoros. In certain embodiments of Formula I, Ring A is substituted with one or two methyl groups. In certain embodiments of Formula I, Ring A is substituted with two or three groups independently selected from methyl and trifluoromethyl.

In certain embodiments of Formula I, R¹ is hydroxy(C1-C6 alkyl)- optionally substituted with 1-3 fluoros, and z is 1, 2 or 3. In certain embodiments of Formula I, R¹ is hydroxy(C3-C6 alkyl)- optionally substituted with 1-3 fluoros. In certain embodiments of Formula I, R¹ is hydroxy(C1-C6 alkyl) optionally substituted with 1-3 fluoros and z is 1. Non-limiting examples of R¹ include the structures:

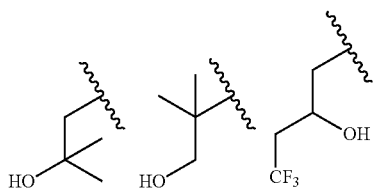

In certain embodiments of Formula I, R¹ is dihydroxy (C1-C6 alkyl)- optionally substituted with 1-3 fluoros, and z is 1, 2 or 3. In certain embodiments of Formula I, R¹ is dihydroxy(C1-C6 alkyl)- optionally substituted with 1-3 fluoros and z is 1. In certain embodiments, R¹ is dihydroxy (C3-C6 alkyl)-. Non-limiting examples of R¹ include the structures:

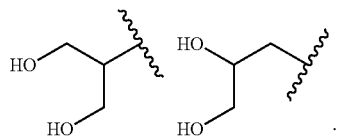

In certain embodiments of Formula I, R¹ is cyano(C1-C6 alkyl)-, and z is 1, 2 or 3. In certain embodiments of Formula I, R¹ is cyano(C1-C6 alkyl)- and z is 1. A non-limiting example of R¹ includes the structure:

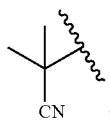

In certain embodiments of Formula I, R¹ is $R^aR^bN$(C1-C6 alkyl)-, where $R^a$ and $R^b$ are independently hydrogen or C1-C6 alkyl optionally substituted with F, OH or C1-C6 alkoxy, and z is 1, 2 or 3. In certain embodiments of Formula I, R¹ is $R^aR^bN$(C1-C6 alkyl)- and z is 1. Non-limiting examples of R¹ include the structures:

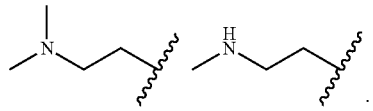

In certain embodiments of Formula I, R¹ is (C1-C3 alkoxy)C1-C6 alkyl- optionally substituted with 1-3 fluoros, and z is 1, 2 or 3. In certain embodiments of Formula I, R¹ is (C1-C3 alkoxy)C1-C6 alkyl- optionally substituted with 1-3 fluoros and z is 1. Non-limiting examples of R¹ include the structures:

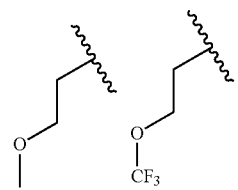

In certain embodiments of Formula I, R¹ is (C3-C6 cycloalkyl)(CH₂)ₙ— where n is 0-3 and said cycloalkyl is optionally substituted with CN, OH, $R^aR^bN$—, (1-3C)alkyl, or (1-3C)alkoxy, and z is 1, 2 or 3. In certain embodiments of Formula I, R¹ is (C3-C6 cycloalkyl)(CH₂)ₙ— where n is 0-3 and said cycloalkyl is optionally substituted with CN. In certain embodiments, n is 0 or 1. In certain embodiments of Formula I, R¹ is (C3-C6 cycloalkyl)(CH₂)ₙ— and z is 1. Non-limiting examples of R¹ include the structures:

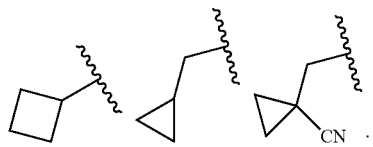

In certain embodiments of Formula I, R¹ is hetCyc¹ (CH₂)ₘ—, and z is 1, 2 or 3, where m is 0-3, and hetCyc¹ is a 4-7 membered saturated heterocyclic ring having 1-2 ring heteroatoms independently selected from N and O, wherein said heterocyclic ring is optionally substituted with one or more substituents independently selected from the group consisting of fluoro, HO, C1-C6 alkyl (optionally substituted with 1-3 fluoros), (C1-C6 alkoxy)C1-C6 alkyl- (optionally substituted with 1-3 fluoros), (C3-C6 cycloalkoxy)C1-C6 alkyl-, hydroxy(C1-C6 alkyl)-, $R^cR^dN$— and (C1-C6 alkyl)C(=O)—.

In certain embodiments of Formula I, R¹ is hetCyc¹ (CH₂)ₘ and z is 1, 2 or 3, where m is 0-3, and hetCyc¹ is azetidinyl, piperidinyl or morpholinyl optionally substituted with one or more substituents independently selected from the group consisting of fluoro, HO, C1-C6 alkyl (optionally substituted with 1-3 fluoros), (C1-C6 alkoxy)C1-C6 alkyl- (optionally substituted with 1-3 fluoros), (C3-C6 cycloalkoxy)C1-C6 alkyl-, hydroxy(C1-C6 alkyl), $R^cR^dN$— and (C1-C6 alkyl)C(=O)—.

In certain embodiments of Formula I, $R^1$ is hetCyc$^1$(CH$_2$)$_m$—, where m is 0-3, and hetCyc$^1$ is azetidinyl, piperidinyl or morpholinyl optionally substituted with one or more substituents independently selected from the group consisting of C1-C6 alkyl (optionally substituted with 1-3 fluoros) and (C1-C6 alkoxy)C1-C6 alkyl- (optionally substituted with 1-3 fluoros). In certain embodiments, z is 1.

In certain embodiments of Formula I, $R^1$ is hetCyc$_1$(CH$_2$)$_m$ and z is 1. In one embodiment, m is 0, 1 or 2. In one embodiment, m is 0. In one embodiment, m is 1. In one embodiment, m is 2.

Non-limiting examples of $R^1$ when represented by hetCyc$_1$(CH$_2$)$_m$— include the structures:

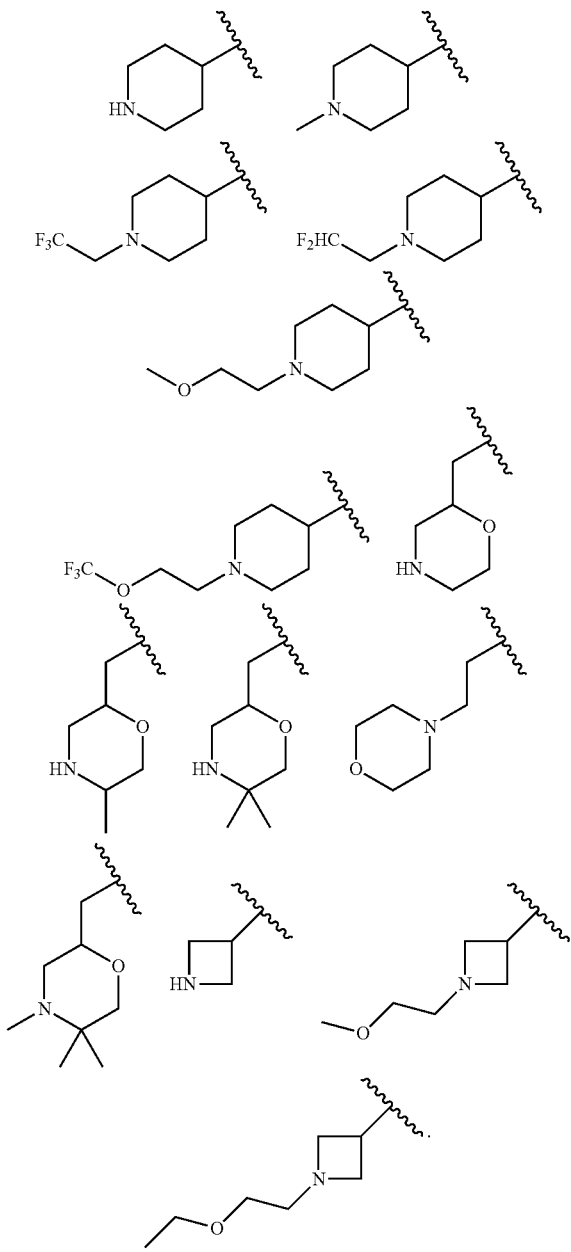

In certain embodiments of Formula I, $R^1$ is hetCyc$^2$(CH$_2$)$_p$— where p is 0 or 1, and hetCyc$^2$ is a 7-10 membered heterospirocyclic ring having 1-2 ring heteroatoms independently selected from N and O, wherein said heterospirocyclic ring is optionally substituted with one or more substituents independently selected from the group consisting of C1-C6 alkyl (optionally substituted with 1-3 fluoros), (C1-C6 alkoxy)C1-C6 alkyl- (optionally substituted with 1-3 fluoros), (C3-C6 cycloalkoxy)C1-C6 alkyl-, hydroxy(C1-C6 alkyl)-, R$^c$R$^d$N— and (C1-C6 alkyl)C(=O)—, and z is 1, 2 or 3.

In certain embodiments of Formula I, $R^1$ is hetCyc$^2$(CH$_2$)$_p$— where p is 0 or 1, and hetCyc$^2$ is a 7-10 membered heterospirocyclic ring having 1-2 ring heteroatoms independently selected from N and O, wherein said heterospirocyclic ring is unsubstituted.

In certain embodiments of Formula I, $R^1$ is hetCyc$^2$(CH$_2$)$_p$— and z is 1.

Non-limiting examples when $R^1$ is represented by hetCyc$^2$(CH$_2$)$_p$— include the structures:

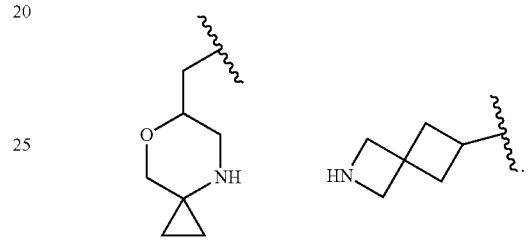

In certain embodiments of Formula I, $R^1$ is hetAr$^1$(CH$_2$)$_q$— where q is 1 or 2 and hetAr$^1$ is a 6-membered heteroaryl ring having 1-2 ring nitrogen atoms, wherein said ring is optionally substituted with one or more substituents independently selected from C1-C6 alkyl and halogen, and z is 1, 2 or 3.

In certain embodiments of Formula I, $R^1$ is hetAr$^1$(CH$_2$)$_q$— and z is 1.

Non-limiting examples when $R^1$ is represented by hetAr$^1$(CH$_2$)$_q$— include the structures:

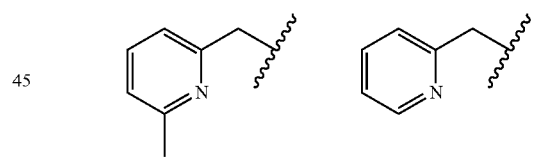

In certain embodiments of Formula I, $R^1$ is halogen. In certain embodiments when $R^1$ is halogen, z is 1, 2 or 3. Non-limiting examples of $R^1$ include F, Cl and Br. In one embodiment of Formula I, $R^1$ is F and z is 1 or 2. In one embodiment, z is 1.

In certain embodiments of Formula I, $R^1$ is hetCyc$^1$C(=O)CH$_2$—, and z is 1, 2 or 3, where m is 0-3, and hetCyc$^1$ is a 4-7 membered saturated heterocyclic ring having 1-2 ring heteroatoms independently selected from N and O, wherein said heterocyclic ring is optionally substituted with one or more substituents independently selected from the group consisting of fluoro, HO, C1-C6 alkyl (optionally substituted with 1-3 fluoros), (C1-C6 alkoxy)C1-C6 alkyl- (optionally substituted with 1-3 fluoros), (C3-C6 cycloalkoxy)C1-C6 alkyl-, hydroxy(C1-C6 alkyl)-, R$^c$R$^d$N— and (C1-C6 alkyl)C(=O)—. In one embodiment, hetCyc$^1$ is piperidinyl or morpholinyl optionally substituted with one or more substituents independently selected from the group consisting of fluoro, HO, C1-C6 alkyl (optionally substituted with 1-3 fluoros), (C1-C6 alkoxy)C1-C6 alkyl- (optionally substituted with 1-3 fluoros), (C3-C6 cycloalkoxy)C1-C6 alkyl-, hydroxy(C1-C6 alkyl), $R^cR^dN$— and (C1-C6 alkyl)C(=O)—. In certain embodiments, hetCyc$^1$ is piperidinyl or morpholinyl optionally substituted with one or more substituents independently selected from the group consisting of C1-C6 alkyl (optionally substituted with 1-3 fluoros) and (C1-C6 alkoxy)C1-C6 alkyl- (optionally substituted with 1-3 fluoros). In certain embodiments, z is 1. A non-limiting example of hetCyc$^1$C(=O)CH$_2$— is the structure:

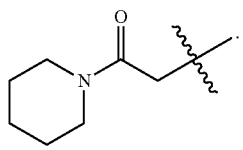 [SMILES: *CC(=O)N1CCCCC1]

In certain embodiments of Formula I, Ring A is pyrazolyl optionally substituted with one to three $R^1$ groups (that is, z is 1, 2 or 3), wherein $R^1$ is selected from the group consisting of (b) C1-C6 alkyl (optionally substituted with 1-3 fluoros), (c) hydroxy(C1-C6 alkyl)-(optionally substituted with 1-3 fluoros), (e) cyano(C1-C6 alkyl)-, (f) $R^aR^bN$(C1-C6 alkyl)-, (h) (C3-C6 cycloalkyl)(CH$_2$)$_n$— where n is 0-3 and said cycloalkyl is optionally substituted with CN, OH, $R^aR^bN$—, (1-3C)alkyl or (1-3C)alkoxy, (i) hetCyc$^1$(CH$_2$)$_m$— where m is 0-3, (j) hetCyc$^2$(CH$_2$)$_p$— where p is 0 or 1, and (m) hetCyc$^1$C(=O)CH$_2$—. In certain embodiments, z is 1

In certain embodiments of Formula I, Ring A is pyrazolyl optionally substituted with two or three $R^1$ groups (that is, z is 2 or 3), wherein each $R^1$ is independently selected from hydrogen and C1-C6 alkyl (optionally substituted with 1-3 fluoros).

In certain embodiments of Formula I, z is 1 and Ring A is pyrazolyl, which may be represented by the structure:

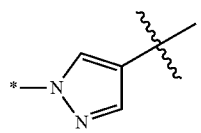

wherein the wavy line indicates the point of attachment to the 6-membered ring comprising X and the asterisk indicates the point of attachment to $R^1$, wherein $R^1$ is selected from (a) hydrogen, (b) C1-C6 alkyl (optionally substituted with 1-3 fluoros), (c) hydroxy(C1-C6 alkyl)- (optionally substituted with 1-3 fluoros), (e) cyano(C1-C6 alkyl), (g) (C1-C3 alkoxy)C1-C6 alkyl- (optionally substituted with 1-3 fluoros), (h) (C3-C6 cycloalkyl)(CH$_2$)$_n$— where n is 0-3 and said cycloalkyl is optionally substituted with CN, OH, $R^aR^bN$—, (1-3C)alkyl or (1-3C)alkoxy, (i) hetCyc$^1$(CH$_2$)$_m$— where m is 0-3, (j) hetCyc$^2$(CH$_2$)$_p$ where p is 0 or 1, (l) halogen and (m) hetCyc$^1$C(=O)CH$_2$—. In one embodiment, $R^1$ is selected from (b) C1-C6 alkyl (optionally substituted with 1-3 fluoros), (c) hydroxy(C1-C6 alkyl)- (optionally substituted with 1-3 fluoros), (e) cyano(C1-C6 alkyl)-, (f) $R^aR^bN$(C1-C6 alkyl)-, (h) (C3-C6 cycloalkyl)(CH$_2$)$_n$— where n is 0-3 and said cycloalkyl is optionally substituted with CN, OH, $R^aR^bN$—, (1-3C)alkyl or (1-3C)alkoxy, (i) hetCyc$^1$(CH$_2$)$_m$— where m is 0-3, (j) hetCyc$^2$(CH$_2$)$_p$— where p is 0 or 1, and (m) hetCyc$^1$C(=O)CH$_2$—.

In certain embodiments of Formula I, Ring A is pyrazolyl and z is 1, wherein Ring A and $R^1$ together may be represented by the structure:

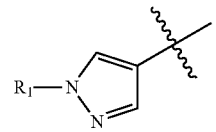

wherein the wavy line indicates the point of attachment to the 6-membered ring comprising X, wherein z is 1 and $R^1$ is selected from (a) hydrogen, (b) C1-C6 alkyl (optionally substituted with 1-3 fluoros), (c) hydroxy(C1-C6 alkyl)- (optionally substituted with 1-3 fluoros), (e) cyano(C1-C6 alkyl)-, (g) (C1-C3 alkoxy)C1-C6 alkyl- (optionally substituted with 1-3 fluoros), (h) (C3-C6 cycloalkyl)(CH$_2$)$_n$— where n is 0-3 and said cycloalkyl is optionally substituted with CN, OH, $R^aR^bN$—, (1-3C)alkyl or (1-3C)alkoxy, (i) hetCyc$_1$(CH$_2$)$_m$— where m is 0-3, (j) hetCyc$^2$(CH$_2$)$_p$— where p is 0 or 1, (l) halogen and (m) hetCyc$^1$C(=O) CH$_2$—. In one embodiment, $R^1$ is selected from (b) C1-C6 alkyl (optionally substituted with 1-3 fluoros), (c) hydroxy (C1-C6 alkyl)- (optionally substituted with 1-3 fluoros), (e) cyano(C1-C6 alkyl)-, (f) $R^aR^bN$(C1-C6 alkyl)-, (h) (C3-C6 cycloalkyl)(CH$_2$)$_n$— where n is 0-3 and said cycloalkyl is optionally substituted with CN, OH, $R^aR^bN$—, (1-3C)alkyl or (1-3C)alkoxy, (i) hetCyc$_1$(CH$_2$)$_m$— where m is 0-3, and (m) hetCyc$^1$C(=O)CH$_2$—.

In certain embodiments of Formula I, $R^2$ is $Ar^1$, where $Ar^1$ is phenyl substituted with one or more groups independently selected from halogen, cyano, C1-C3 alkyl, C1-C3 alkoxy, (C1-C3 alkyl)NHC(=O)—, (C1-C3 alkyl)C(=O)NH—, (cyclopropyl)C(=O)NH— and (cyclopropyl)NHC(=O)—, wherein each of said C1-C3 alkyl and C1-C3 alkoxy portions are optionally substituted with 1-3 fluoros.

In certain embodiments of Formula I, $R^2$ is $Ar^1$, where $Ar^2$ is phenyl substituted with one or more groups independently selected from halogen, cyano, C1-C3 alkyl, C1-C3 alkoxy and (C1-C3 alkyl)NHC(=O)—, wherein each of said C1-C3 alkyl and C1-C3 alkoxy portions is optionally substituted with 1-3 fluoros.

Non-limiting examples of $R^2$ when represented by $Ar^1$ include the structures:

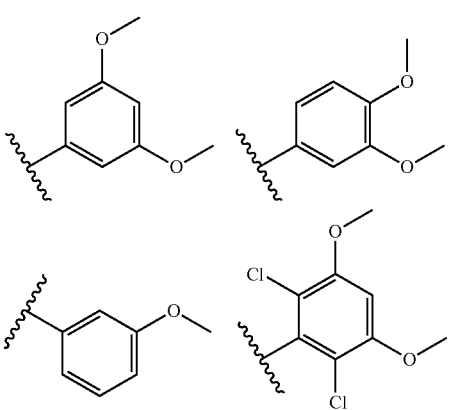

-continued

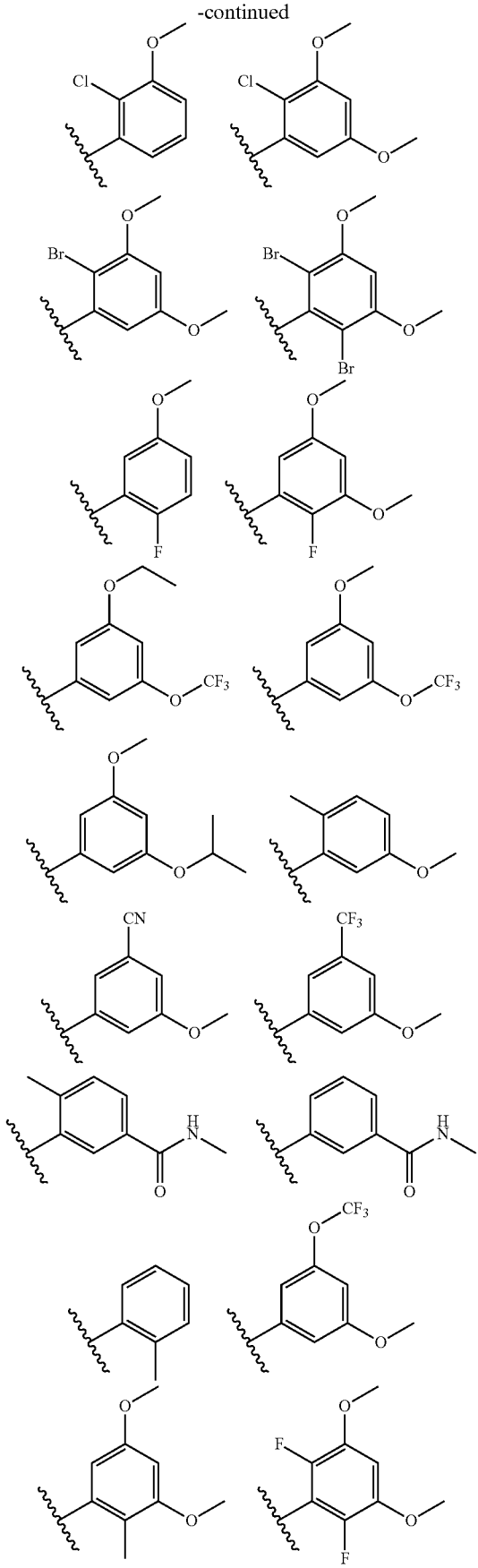

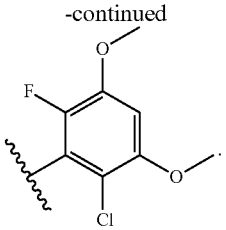

In certain embodiments of Formula I, $R^2$ is hetAr$^2$, where hetAr$^2$ is a 6-10 membered heteroaryl ring having 1-2 ring nitrogen atoms, wherein said ring is optionally substituted with one or more groups independently selected from halogen, C1-C3 alkyl, C1-C3 alkoxy, (C1-C3 alkyl)NHC(=O)—, (C1-C3 alkyl)C(=O)NH—, (C3-C4 cycloalkyl)C(=O)NH— and (C3-C4 cycloalkyl)NHC(=O)—, wherein each of said C1-C3 alkyl and C1-C3 alkoxy portions is optionally substituted with 1-3 fluoros.

In certain embodiments of Formula I, $R^2$ is hetAr$^2$, where hetAr$^2$ is a 6-10 membered heteroaryl ring having 1-2 ring nitrogen atoms, wherein said ring is optionally substituted with one or more groups independently selected from C1-C3 alkyl, C1-C3 alkoxy and (C1-C3 alkyl)NHC(=O)—, wherein each of said C1-C3 alkyl and C1-C3 alkoxy portions is optionally substituted with 1-3 fluoros.

Non-limiting examples of hetAr$^2$ include:

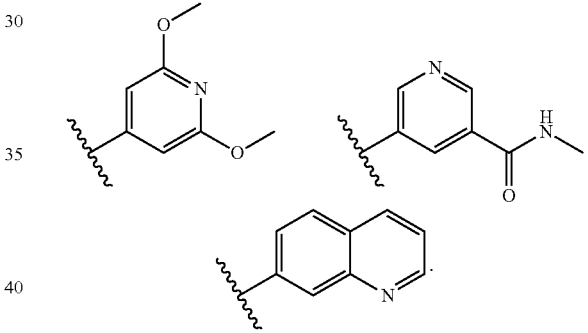

In certain embodiments of Formula I, $R^3$ is H.

In certain embodiments of Formula I, $R^3$ is C1-C4 alkyl. Non-limiting examples include methyl, ethyl, propyl, isopropyl and isobutyl.

In certain embodiments of Formula I, $R^3$ is (C3-C4) cycloalkyl. In certain embodiments of Formula I, $R^3$ is cyclopropyl. In certain embodiments of Formula I, $R^3$ is cyclobutyl.

Compounds of Formula I include compounds of Formula I-A, wherein:
X is N;
z is 1;
Ring A is

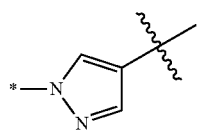 [SMILES: *c1cnn(*)c1]

wherein the wavy line indicates the point of attachment to the 6-membered ring comprising X and the asterisk indicates the point of attachment to $R^1$;

each $R^1$ is independently selected from the group consisting of (a) hydrogen, (b) C1-C6 alkyl (optionally substituted with 1-3 fluoros), (c) hydroxy(C1-C6 alkyl)- (optionally substituted with 1-3 fluoros), (d) dihydroxy(C1-C6 alkyl)-(optionally substituted with 1-3 fluoros), (e) cyano(C1-C6 alkyl)-, (f) $R^aR^bN$(C1-C6 alkyl)-, (g) (C1-C3 alkoxy)C1-C6 alkyl-(optionally substituted with 1-3 fluoros), (h) (C3-C6 cycloalkyl)$(CH_2)_n$— where n is 0-3 and said cycloalkyl is optionally substituted with CN, OH, $R^aR^bN$—, (1-3C)alkyl or (1-3C)alkoxy, (i) hetCyc$^1(CH_2)_m$— where m is 0-3, (j) hetCyc$^2(CH_2)_p$— where p is 0 or 1, (k) hetAr$^1(CH_2)_q$— where q is 1 or 2, (l) halogen and (m) hetCyc$^1$C(=O) $CH_2$—;

hetCyc$^1$ is a 4-7 membered saturated heterocyclic ring having 1-2 ring heteroatoms independently selected from N and O, wherein said heterocyclic ring is optionally substituted with one or more substituents independently selected from the group consisting of fluoro, HO, C1-C6 alkyl (optionally substituted with 1-3 fluoros), (C1-C6 alkoxy) C1-C6 alkyl- (optionally substituted with 1-3 fluoros), (C3-C6 cycloalkoxy)C1-C6 alkyl-, hydroxy(C1-C6 alkyl)-, $R^aR^dN$— and (C1-C6 alkyl)C(=O)—;

hetCyc$^2$ is a 7-10 membered heterospirocyclic ring having 1-2 ring heteroatoms independently selected from N and O, wherein said heterospirocyclic ring is optionally substituted with one or more substituents independently selected from the group consisting of C1-C6 alkyl (optionally substituted with 1-3 fluoros), (C1-C6 alkoxy)C1-C6 alkyl- (optionally substituted with 1-3 fluoros), (C3-C6 cycloalkoxy)C1-C6 alkyl-, hydroxy(C1-C6 alkyl)-, $R^cR^dN$— and (C1-C6 alkyl) C(=O)—;

hetAr$^1$ is a 6-membered heteroaryl ring having 1-2 ring nitrogen atoms, wherein said ring is optionally substituted with one or more substituents independently selected from C1-C6 alkyl and halogen;

$R^2$ is Ar$^1$ or hetAr$^2$;

Ar$^1$ is phenyl substituted with one or more groups independently selected from halogen, cyano, C1-C3 alkyl, C1-C3 alkoxy, (C1-C3 alkyl)NHC(=O)—, (C1-C3 alkyl)C (=O)NH—, (cyclopropyl)C(=O)NH— and (cyclopropyl) NHC(=O)—, wherein each of said C1-C3 alkyl and C1-C3 alkoxy portions is optionally substituted with 1-3 fluoros;

hetAr$^2$ is a 6-10 membered heteroaryl ring having 1-2 ring nitrogen atoms, wherein said heteroaryl ring is optionally substituted with one or more groups independently selected from halogen, C1-C3 alkyl, C1-C3 alkoxy, (C1-C3 alkyl) NHC(=O)—, (C1-C3 alkyl)C(=O)NH—, (C3-C4 cycloalkyl)C(=O)NH— and (C3-C4 cycloalkyl)NHC (=O)—, wherein each of said C1-C3 alkyl and C1-C3 alkoxy portions is optionally substituted with 1-3 fluoros;

$R^3$ is hydrogen, C1-C4 alkyl or (C3-C4)cycloalkyl; and $R^a$, $R^b$, $R^c$ and $R^d$ are independently hydrogen or C1-C6 alkyl optionally substituted with F, OH or C1-C6 alkoxy.

In one embodiment of Formula I-A, $R^2$ is Ar$^1$, wherein Ar$^1$ is as defined for Formula I-A.

In one embodiment of Formula I-A, $R^2$ is Ar$^1$, wherein Ar$^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl) NHC(=O)—.

In one embodiment of Formula I-A, $R^3$ is hydrogen.

In one embodiment of Formula I-A, $R^3$ is C1-C4 alkyl.

In one embodiment of Formula I-A, $R^3$ is (C3-C4)cycloalkyl.

In one embodiment of Formula I-A, $R^2$ is Ar$^1$, wherein Ar$^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl) NHC(=O)—, and $R^3$ is hydrogen.

In one embodiment of Formula I-A, $R^2$ is Ar$^1$, wherein Ar$^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl) NHC(=O)—, and $R^3$ is C1-C4 alkyl.

In one embodiment of Formula I-A, $R^2$ is Ar$^1$, wherein Ar$^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl) NHC(=O)—, and $R^3$ is (C3-C4)cycloalkyl.

In one embodiment of Formula I-A, $R^1$ is selected from (b) C1-C6 alkyl (optionally substituted with 1-3 fluoros), (c) hydroxy(C1-C6 alkyl)- (optionally substituted with 1-3 fluoros), (e) cyano(C1-C6 alkyl)-, (f) $R^aR^bN$(C1-C6 alkyl)-, (h) (C3-C6 cycloalkyl)$(CH_2)_n$— where n is 0-3 and said cycloalkyl is optionally substituted with CN, OH, $R^aR^bN$—, (1-3C)alkyl or (1-3C)alkoxy, (i) hetCyc$_1(CH_2)_m$— where m is 0-3, (j) hetCyc$^2(CH_2)_p$— where p is 0 or 1, and (m) hetCyc$^1$C(=O)CH$_2$—; and hetCyc$^1$, $R^a$, and $R^b$ are as defined for Formula I-A.

In one embodiment of Formula I-A, $R^1$ is C1-C6 alkyl (optionally substituted with 1-3 fluoros).

In one embodiment of Formula I-A, $R^1$ is hydroxy(C1-C6 alkyl)- (optionally substituted with 1-3 fluoros).

In one embodiment of Formula I-A, $R^1$ is cyano(C1-C6 alkyl)-.

In one embodiment of Formula I-A, $R^1$ is $R^aR^bN$(C1-C6 alkyl)-.

In one embodiment of Formula I-A, $R^1$ is (C3-C6 cycloalkyl)$(CH_2)_n$— where n is 0-3 and said cycloalkyl is optionally substituted with CN, OH, $R^aR^bN$—, (1-3C)alkyl or (1-3C)alkoxy, In one embodiment of Formula I-A, $R^1$ is hetCyc$_1$ $(CH_2)_m$— where m is 0-3. In one embodiment, m is 0, 1 or 2. In one embodiment, m is 0. In one embodiment, m is 1. In one embodiment, m is 2.

In one embodiment of Formula I-A, $R^1$ is hetCyc$^2$ $(CH_2)_p$— where p is 0 or 1.

In one embodiment of Formula I-A, $R^1$ is hetCyc$^1$C(=O) $CH_2$—.

In one embodiment of Formula I-A, $R^2$ is Ar$^1$, wherein Ar$^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl) NHC(=O)—; $R^3$ is hydrogen; $R^1$ is selected from (b) C1-C6 alkyl (optionally substituted with 1-3 fluoros), (c) hydroxy (C1-C6 alkyl)- (optionally substituted with 1-3 fluoros), (e) cyano(C1-C6 alkyl)-, (f) $R^aR^bN$(C1-C6 alkyl)-, (h) (C3-C6 cycloalkyl)$(CH_2)_n$— where n is 0-3 and said cycloalkyl is optionally substituted with CN, OH, $R^aR^bN$—, (1-3C)alkyl or (1-3C)alkoxy, (i) hetCyc$_1(CH_2)_m$— where m is 0-3, (j) hetCyc$^2(CH_2)_p$— where p is 0 or 1, and (m) hetCyc$^1$C(=O) CH$_2$—; and hetCyc$^1$, $R^a$, and $R^b$ are as defined for Formula I-A. In one embodiment, m is 0, 1 or 2. In one embodiment, m is 0. In one embodiment, m is 1. In one embodiment, m is 2.

In one embodiment of Formula I-A, $R^2$ is Ar$^1$, wherein Ar$^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl) NHC(=O)—; $R^3$ is C1-C4 alkyl; $R^1$ is selected from (b) C1-C6 alkyl (optionally substituted with 1-3 fluoros), (c) hydroxy(C1-C6 alkyl)- (optionally substituted with 1-3 fluoros), (e) cyano(C1-C6 alkyl)-, (f) $R^aR^bN$(C1-C6 alkyl)-, (h) (C3-C6 cycloalkyl)$(CH_2)_n$— where n is 0-3 and said cycloalkyl is optionally substituted with CN, OH, $R^aR^bN$—, (1-3C)alkyl or (1-3C)alkoxy, (i) hetCyc$_1$$(CH_2)_m$— where m is 0-3, (j) hetCyc$^2$$(CH_2)_p$— where p is 0 or 1, and (m) hetCyc$^1$C(=O)CH$_2$—; and hetCyc$^1$, $R^a$, and $R^b$ are as defined for Formula I-A. In one embodiment, m is 0, 1 or 2. In one embodiment, m is 0. In one embodiment, m is 1. In one embodiment, m is 2.

In one embodiment of Formula I-A, $R^2$ is $Ar^1$, wherein $Ar^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl) NHC(=O)—; $R^3$ is (C3-C4)cycloalkyl; $R^1$ is selected from (b) C1-C6 alkyl (optionally substituted with 1-3 fluoros), (c) hydroxy(C1-C6 alkyl)- (optionally substituted with 1-3 fluoros), (e) cyano(C1-C6 alkyl)-, (f) $R^aR^bN$(C1-C6 alkyl)-, (h) (C3-C6 cycloalkyl)$(CH_2)_n$— where n is 0-3 and said cycloalkyl is optionally substituted with CN, OH, $R^aR^bN$—, (1-3C)alkyl or (1-3C)alkoxy, (i) hetCyc$_1$$(CH_2)_m$— where m is 0-3, (j) hetCyc$^2$$(CH_2)_p$— where p is 0 or 1, and (m) hetCyc$^1$C(=O)CH$_2$—; and hetCyc$^1$, $R^a$, and $R^b$ are as defined for Formula I-A. In one embodiment, m is 0, 1 or 2. In one embodiment, m is 0. In one embodiment, m is 1. In one embodiment, m is 2.

In one embodiment of Formula I-A, $R^2$ is $Ar^1$, wherein $Ar^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl) NHC(=O)—; $R^3$ is hydrogen; and $R^1$ is C1-C6 alkyl (optionally substituted with 1-3 fluoros).

In one embodiment of Formula I-A, $R^2$ is $Ar^1$, wherein $Ar^1$ is phenyl optionally substituted with one or more groups independently selected from halogen, C1-C3 alkyl (optionally substituted with 1-3 fluoros), and C1-C3 alkoxy (optionally substituted with 1-3 fluoros); $R^3$ is hydrogen; and $R^1$ is hydroxy(C1-C6 alkyl)- (optionally substituted with 1-3 fluoros).

In one embodiment of Formula I-A, $R^2$ is $Ar^1$, wherein $Ar^1$ is phenyl optionally substituted with one or more groups independently selected from halogen, C1-C3 alkyl (optionally substituted with 1-3 fluoros), and C1-C3 alkoxy (optionally substituted with 1-3 fluoros); $R^3$ is hydrogen; and $R^1$ is cyano(C1-C6 alkyl)-.

In one embodiment of Formula I-A, $R^2$ is $Ar^1$, wherein $Ar^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl) NHC(=O)—; $R^3$ is hydrogen; and $R^1$ is $R^aR^bN$(C1-C6 alkyl)- where $R^a$, and $R^b$ are as defined for Formula I-A.

In one embodiment of Formula I-A, $R^2$ is $Ar^1$, wherein $Ar^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl) NHC(=O)—; $R^3$ is hydrogen; and $R^1$ is (C3-C6 cycloalkyl) $(CH_2)_n$— where n is 0-3 and said cycloalkyl is optionally substituted with CN, OH, $R^aR^bN$—, (1-3C)alkyl or (1-3C) alkoxy. In one embodiment said cycloalkyl is unsubstituted.

In one embodiment, said cycloalkyl is substituted with CN. In one embodiment, n is 0. In one embodiment n is 1.

In one embodiment of Formula I-A, $R^2$ is $Ar^1$, wherein $Ar^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl) NHC(=O)—; $R^3$ is hydrogen; $R^1$ is hetCyc$^1$$(CH_2)_m$— where m is 0-3; and hetCyc$^1$ is as defined for Formula I-A. In one embodiment, m is 0, 1 or 2. In one embodiment, m is 0. In one embodiment, m is 1. In one embodiment, m is 2.

In one embodiment of Formula I-A, $R^2$ is $Ar^1$, wherein $Ar^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl) NHC(=O)—; $R^3$ is hydrogen; and $R^1$ is hetCyc$^2$$(CH_2)_p$— where p is 0 or 1, and hetCyc$^2$ is as defined for Formula I-A. In one embodiment, p is 1. On one embodiment, hetCyc$^2$ $(CH_2)_p$— is

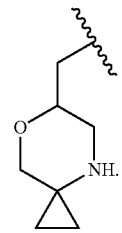

In one embodiment of Formula I-A, $R^2$ is $Ar^1$, wherein $Ar^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl) NHC(=O)—; $R^3$ is hydrogen; and $R^1$ is hetCyc$^1$C(=O) CH$_2$— where hetCyc$^1$ is as defined for Formula I-A. In one embodiment, hetCyc$^1$ is piperidinyl. In one embodiment, hetCyc$^1$C(=O)CH$_2$— is

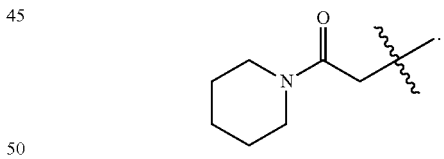

In one embodiment of Formula I-A, $R^2$ is Ar, wherein $Ar^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl) NHC(=O)—; $R^3$ is C1-C4 alkyl; and $R^1$ is C1-C6 alkyl (optionally substituted with 1-3 fluoros).

In one embodiment of Formula I-A, $R^2$ is $Ar^1$, wherein $Ar^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl) NHC(=O)—; $R^3$ is C1-C4 alkyl; and $R^1$ is $R^aR^bN$(C1-C6 alkyl)-, wherein $R^a$ and $R^b$ are as defined for Formula I-A. In one embodiment, $R^a$ and $R^b$ are independently selected from C1-C6 alkyl.

In one embodiment of Formula I-A, $R^2$ is $Ar^1$, where $Ar^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl)NHC(=O)—; $R^3$ is C1-C4 alkyl; and $R^1$ is hetCyc$_1$(CH$_2$)$_m$— where m is 0-3, and hetCyc$^1$ is as defined for Formula I-A.

In one embodiment of Formula I-A, $R^2$ is $Ar^1$, wherein $Ar^1$ is phenyl optionally substituted with one or more groups independently selected from halogen, cyano, C1-C3 alkyl (optionally substituted with 1-3 fluoros), C1-C3 alkoxy (optionally substituted with 1-3 fluoros) and (C1-C3 alkyl)NHC(=O)—; $R^3$ is C3-C4 cycloalkyl; and $R^1$ is C1-C6 alkyl (optionally substituted with 1-3 fluoros).

Compounds of Formula I include compounds of Formula I-B, wherein:
X is N;
z is 2 or 3;
Ring A is pyrazolyl;
each $R^1$ is independently selected from the group consisting of (a) hydrogen and (b) C1-C6 alkyl (optionally substituted with 1-3 fluoros);
$R^2$ is $Ar^1$;
$Ar^1$ is phenyl substituted with one or more groups independently selected from halogen, cyano, C1-C3 alkyl, C1-C3 alkoxy, (C1-C3 alkyl)NHC(=O)—, (C1-C3 alkyl)C(=O)NH—, (cyclopropyl)C(=O)NH— and (cyclopropyl)NHC(=O)—, wherein each of said C1-C3 alkyl and C1-C3 alkoxy portions is optionally substituted with 1-3 fluoros; and
$R^3$ is hydrogen, C1-C4 alkyl or (C3-C4)cycloalkyl.

In one embodiment of Formula I-B, $Ar^1$ is phenyl substituted with one or more groups independently selected from halogen and C1-C3 alkoxy.

In one embodiment of Formula I-B, $R^3$ is hydrogen.

In one embodiment of Formula I-B, $Ar^1$ is phenyl substituted with one or more groups independently selected from halogen and C1-C3 alkoxy, and $R^3$ is hydrogen.

Compounds of Formula I include compounds of Formula I-C, wherein:
X is CH;
z is 1;
Ring A is

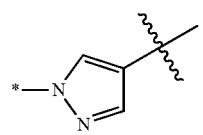 [SMILES: *c1cnn(*)c1]

wherein the wavy line indicates the point of attachment to the 6-membered ring comprising X and the asterisk indicates the point of attachment to $R^1$;
$R^1$ is selected from the group consisting of (a) hydrogen, (b) C1-C6 alkyl (optionally substituted with 1-3 fluoros), (c) hydroxy(C1-C6 alkyl)- (optionally substituted with 1-3 fluoros), (d) dihydroxy(C1-C6 alkyl)- (optionally substituted with 1-3 fluoros), (e) cyano(C1-C6 alkyl)-, (f) $R^aR^bN$(C1-C6 alkyl)-, (g) (C1-C3 alkoxy)C1-C6 alkyl- (optionally substituted with 1-3 fluoros), (h) (C3-C6 cycloalkyl)(CH$_2$)$_n$— where n is 0-3 and said cycloalkyl is optionally substituted with CN, OH, $R^aR^bN$—, (1-3C)alkyl or (1-3C) alkoxy, (i) hetCyc$_1$(CH$_2$)$_m$— where m is 0-3, (j) hetCyc$^2$(CH$_2$)$_p$— where p is 0 or 1, (k) hetAr$^1$(CH$_2$)$_q$— where q is 1 or 2, (l) halogen and (m) hetCyc$^1$C(=O)CH$_2$—;

hetCyc$^1$ is a 4-7 membered saturated heterocyclic ring having 1-2 ring heteroatoms independently selected from N and O, wherein said heterocyclic ring is optionally substituted with one or more substituents independently selected from the group consisting of fluoro, HO, C1-C6 alkyl (optionally substituted with 1-3 fluoros), (C1-C6 alkoxy) C1-C6 alkyl- (optionally substituted with 1-3 fluoros), (C3-C6 cycloalkoxy)C1-C6 alkyl-, hydroxy(C1-C6 alkyl)-, $R^cR^dN$— and (C1-C6 alkyl)C(=O)—;

hetCyc$^2$ is a 7-10 membered heterospirocyclic ring having 1-2 ring heteroatoms independently selected from N and O, wherein said heterospirocyclic ring is optionally substituted with one or more substituents independently selected from the group consisting of C1-C6 alkyl (optionally substituted with 1-3 fluoros), (C1-C6 alkoxy)C1-C6 alkyl- (optionally substituted with 1-3 fluoros), (C3-C6 cycloalkoxy)C1-C6 alkyl-, hydroxy(C1-C6 alkyl)-, $R^cR^dN$— and (C1-C6 alkyl)C(=O)—;

hetAr$^1$ is a 6-membered heteroaryl ring having 1-2 ring nitrogen atoms, wherein said ring is optionally substituted with one or more substituents independently selected from C1-C6 alkyl and halogen;

$R^2$ is $Ar^1$ or hetAr$^2$;
$Ar^1$ is phenyl substituted with one or more groups independently selected from halogen, cyano, C1-C3 alkyl, C1-C3 alkoxy, (C1-C3 alkyl)NHC(=O)—, (C1-C3 alkyl)C(=O)NH—, (cyclopropyl)C(=O)NH— and (cyclopropyl)NHC(=O)—, wherein each of said C1-C3 alkyl and C1-C3 alkoxy portions is optionally substituted with 1-3 fluoros;

hetAr$^2$ is a 6-membered heteroaryl ring having 1-2 ring nitrogen atoms, wherein said heteroaryl ring is optionally substituted with one or more groups independently selected from halogen, C1-C3 alkyl, C1-C3 alkoxy, (C1-C3 alkyl)NHC(=O)—, (C1-C3 alkyl)C(=O)NH—, (C3-C4 cycloalkyl)C(=O)NH— and (C3-C4 cycloalkyl)NHC(=O)—, wherein each of said C1-C3 alkyl and C1-C3 alkoxy portions is optionally substituted with 1-3 fluoros;

$R^3$ is hydrogen, C1-C4 alkyl or (C3-C4)cycloalkyl; and
$R^a$, $R^b$, $R^c$ and $R^d$ are independently hydrogen or C1-C6 alkyl optionally substituted with F, OH or C1-C6 alkoxy.

In one embodiment of Formula I-C, $R^2$ is $Ar^1$, wherein $Ar^1$ is as defined for Formula I-B.

In one embodiment of Formula I-C, $R^2$ is $Ar^1$, wherein $Ar^1$ is phenyl optionally substituted with one or more groups independently selected from halogen, C1-C3 alkyl (optionally substituted with 1-3 fluoros), and C1-C3 alkoxy (optionally substituted with 1-3 fluoros).

In one embodiment of Formula I-C, $R^3$ is hydrogen.
In one embodiment of Formula I-C, $R^3$ is C1-C4 alkyl.
In one embodiment of Formula I-C, $R^3$ is (C3-C4)cycloalkyl.

In one embodiment of Formula I-C, $R^2$ is $Ar^1$, wherein $Ar^1$ is phenyl optionally substituted with one or more groups independently selected from halogen, C1-C3 alkoxy (optionally substituted with 1-3 fluoros) and (C1-C3 alkyl)NHC(=O)—; and $R^3$ is hydrogen.

In one embodiment of Formula I-C, $R^2$ is $Ar^1$, wherein $Ar^1$ is phenyl optionally substituted with one or more groups independently selected from halogen, C1-C3 alkoxy (optionally substituted with 1-3 fluoros) and (C1-C3 alkyl)NHC(=O)—; and $R^3$ is C1-C4 alkyl.

In one embodiment of Formula I-C, $R^2$ is $Ar^1$, wherein $Ar^1$ is phenyl optionally substituted with one or more groups independently selected from halogen, C1-C3 alkoxy (optionally substituted with 1-3 fluoros) and (C1-C3 alkyl)NHC(=O)—; and $R^3$ is (C3-C4)cycloalkyl.

In one embodiment of Formula I-C, $R^1$ is independently selected from (b) C1-C6 alkyl (optionally substituted with 1-3 fluoros) and (i) hetCyc$_1$(CH$_2$)$_m$— where m is 0-3; and hetCyc$^1$ is defined for Formula I-C.

In one embodiment of Formula I-C, $R^2$ is Ar$^1$, wherein Ar$^1$ is phenyl optionally substituted with one or more groups independently selected from halogen, C1-C3 alkoxy (optionally substituted with 1-3 fluoros) and (C1-C3 alkyl)NHC(=O)—; $R^3$ is hydrogen; $R^1$ is independently selected from (b) C1-C6 alkyl (optionally substituted with 1-3 fluoros) and (i) hetCyc$_1$(CH$_2$)$_m$— where m is 0-3; and hetCyc$^1$ is defined for Formula I-C.

In one embodiment of Formula I-C, $R^2$ is Ar$^1$, wherein Ar$^1$ is phenyl optionally substituted with one or more groups independently selected from halogen, C1-C3 alkoxy (optionally substituted with 1-3 fluoros) and (C1-C3 alkyl)NHC(=O)—; $R^3$ is C1-C4 alkyl; $R^1$ is independently selected from (b) C1-C6 alkyl (optionally substituted with 1-3 fluoros) and (i) hetCyc$_1$(CH$_2$)$_m$— where m is 0-3; and hetCyc$^1$ is defined for Formula I-C.

In one embodiment of Formula I-C, $R^2$ is Ar$^1$, wherein Ar$^1$ is phenyl optionally substituted with one or more groups independently selected from halogen, C1-C3 alkoxy (optionally substituted with 1-3 fluoros) and (C1-C3 alkyl)NHC(=O)—; $R^3$ is (C3-C4)cycloalkyl; $R^1$ is independently selected from (b) C1-C6 alkyl (optionally substituted with 1-3 fluoros) and (i) hetCyc$_1$(CH$_2$)$_m$— where m is 0-3; and hetCyc$^1$ is defined for Formula I-C.

It will be appreciated that certain compounds provided herein may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention. For example, compounds of Formula I and salts thereof can exist in unsolvated as well as solvated forms with pharmaceutically acceptable solvents such as water, ethanol, and the like.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Non-limiting examples of salts include monochloride, dichloride, trifluoroacetic acid, and di-trifluoroacetic acid salts of compounds of Formula I.

In one embodiment, the compounds of Formula I include the compounds of Examples 1-62 and stereoisomers and pharmaceutically acceptable salts and solvates thereof. In one embodiment, the compounds of Examples 1-83 are in the free base form. In one embodiment, the compounds of Examples 1-83 are monochloride, dichloride, trifluoroacetic acid, or di-trifluoroacetic acid salts.

The term "pharmaceutically acceptable" indicates that the substance or composition is compatible chemically and/or toxicologically, with the other ingredients comprising a formulation, and/or the patient being treated therewith.

Compounds provided herein may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^1$H, $^2$H, $^3$H or mixtures thereof; when carbon is mentioned, it is understood to refer to $^{11}$C, $^{12}$C, $^{13}$C $^{14}$C or mixtures thereof; when nitrogen is mentioned, it is understood to refer to $^{13}$N, $^{14}$N, $^{15}$N or mixtures thereof; when oxygen is mentioned, it is understood to refer to $^{14}$O, $^{15}$O, $^{16}$O, $^{17}$O, $^{18}$O or mixtures thereof; and when fluoro is mentioned, it is understood to refer to $^{18}$F, $^{19}$F or mixtures thereof. The compounds provided herein therefore also comprise compounds with one or more isotopes of one or more atom, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present invention.

For illustrative purposes, Schemes 1 and 1A show general methods for preparing the compounds provided herein as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

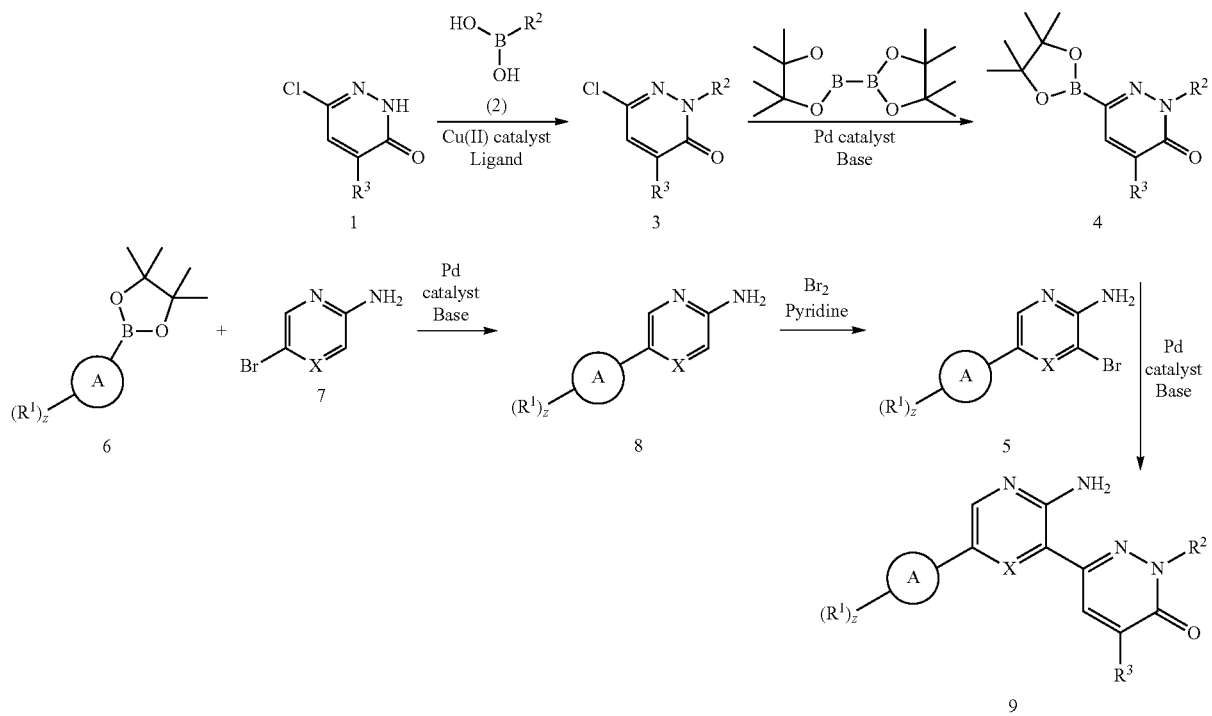

Scheme 1 shows a general scheme for the synthesis of compound 9 where X, $R^1$, $R^2$, $R^3$, Ring A and z are as defined for Formula I. Compound 3, where $R^3$ is as defined for Formula I, may be obtained by treating compound 1 (commercially available or prepared according to Scheme 2) with boronic acid 2, where $R^2$ is as defined for Formula I, in the presence of Cu(II) catalyst such as cupric acetate and a ligand such as pyridine. Compound 3 may be reacted with a dioxoborinane, such as bis(pinacolato)diboron, using appropriate Suzuki coupling reaction conditions (e.g., in the presence of a palladium (II) catalyst such as $Pd(OAc)_2$, $Pd_2(dba)_3$, $Pd(PPh_3)_4$ or $Pd(Dppf)_2$ and optionally in the presence of a suitable ligand such as XPhos and in the presence of an inorganic base such as potassium acetate or sodium carbonate), to provide compound 4 where $R^2$ and $R^3$ are as defined for Formula I. Compound 4 may be reacted with compound 5 (prepared as described below) where X, Ring A, $R^1$ and z are as defined for Formula I, using appropriate Suzuki coupling reaction conditions (e.g., in the presence of a palladium (II) catalyst such as $Pd(PPh_3)_4$, $Pd(Dppf)_2$, $Pd(OAc)_2$, or $Pd_2(dba)_3$, and an inorganic base such as potassium carbonate or sodium carbonate) to provide compound 9. Compound 5 may be prepared by reacting compound 6 (where $R^1$, Ring A and z are as defined for Formula I) with compound 7 (where X is as defined for Formula I) to provide compound 8, which may subsequently be brominated using standard conditions to provide compound 5. The syntheses of intermediates 3 and 6 which are not commercially available are described in the Examples.

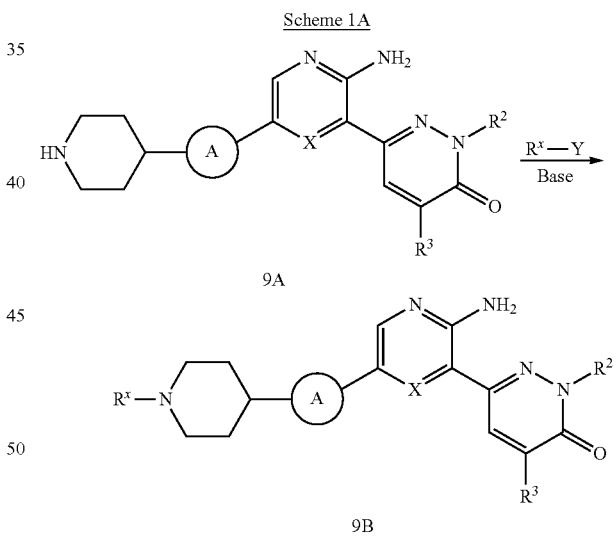

Scheme 1A shows a general scheme for the synthesis of compound 9B where X, $R^2$ and $R^3$ are as defined for Formula I, z is 1 and $R^1$ is a piperidine substituted with C1-C6 alkyl (optionally substituted with 1-3 fluoros), (C1-C3 alkoxy)C1-C6 alkyl (optionally substituted with 1-3 fluoros) or hydroxy(C1-C6 alkyl). Compound 9A, where X, $R^2$ and $R^3$ are as defined for Formula I, z is 1 and $R^1$ is a piperidine substituted with C1-C6 alkyl (optionally substituted with 1-3 fluoros), (C1-C3 alkoxy)C1-C6 alkyl (optionally substituted with 1-3 fluoros) or hydroxy(C1-C6 alkyl), prepared as described in Scheme 1, may be reacted with a compound having the formula $R^x$—Y, where $R^x$ is C1-C6 alkyl (optionally substituted with 1-3 fluoros), (C1-C3 alkoxy)C1-C6 alkyl (optionally substituted with 1-3 fluoros) or hydroxy(C1-C6 alkyl), and Y is a leaving group such as a halogen or a tosylate, under standard alkylation reaction conditions, for example in the presence of an inorganic base such as potassium carbonate, to provide compound 9B.

The compound of formulas 1, 3, 4, 5, 6, 8 and 9A as shown and described above for Schemes 1 and 1A are useful as intermediates for preparing compounds of Formula I and are provided as further aspects of the invention.

Further provided herein is a process for preparing of a compound of Formula I or a pharmaceutically acceptable salt thereof as defined herein which comprises:

(a) reacting a compound having the formula 5:

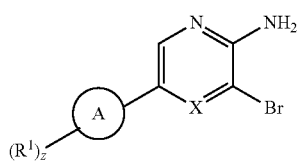

where X, Ring A, $R^1$ and z are as defined for Formula I, with a compound having the formula 4:

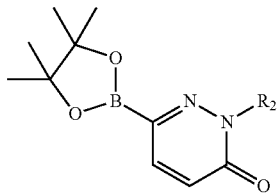

where $R^2$ is as defined for Formula I, in the presence of a palladium (II) catalyst and an inorganic base; or (b) for a compound of Formula I where X, $R^2$ and $R^3$ are as defined for Formula I, z is 1 and $R^1$ is a piperidine substituted with C1-C6 alkyl (optionally substituted with 1-3 fluoros), (C1-C3 alkoxy)C1-C6 alkyl (optionally substituted with 1-3 fluoros) or hydroxy(C1-C6 alkyl), reacting a compound having the formula 9A:

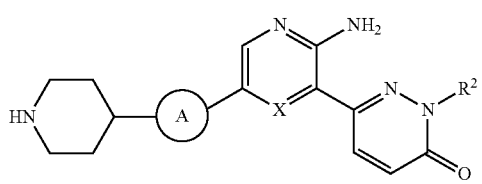

where X, $R^2$ and Ring A are as defined for Formula I, with a compound having the formula $R^x$—Y, where $R^x$ is C1-C6 alkyl (optionally substituted with 1-3 fluoros), (C1-C3 alkoxy)C1-C6 alkyl (optionally substituted with 1-3 fluoros) or hydroxy(C1-C6 alkyl), and Y is a leaving group such as a halogen or a tosylate, under standard alkylation reaction conditions; and removing any protecting groups if present and optionally forming a pharmaceutically acceptable salt.

The ability of test compounds to act as inhibitors of FGFR1, FGFR2 and/or FGFR3 may be demonstrated by the assay described in Example A. $IC_{50}s$ are shown in Table F.

Compounds of Formula I have been found to inhibit FGFR1, FGFR2 and/or FGFR3, and are therefore believed to be useful for treating diseases and disorders which can be treated with an inhibitor of FGFR1, FGFR2, FGFR3 and/or FGFR4, such as FGFR-associated diseases and disorders, e.g., proliferative disorders such as cancers, including hematological cancers and solid tumors.

In certain embodiments, compounds of Formula I are useful for preventing diseases and disorders as defined herein (for example cancer).

The term "preventing" as used herein means the prevention of the recurrence or spread, in whole or in part, of the disease or condition as described herein, or a symptom thereof.

As used herein, the word "a" before a noun represents one or more of the particular noun. For example, the phrase "a cell" represents "one or more cells."

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total). "Treatment" can also mean prolonging survival as compared to expected survival if not receiving treatment.

The term "FGFR-associated disease or disorder" as used herein refers to diseases or disorders associated with or having a dysregulation of a FGFR gene, a FGFR protein, or the expression or activity, or level of the same (e.g., one or more of the same) (e.g., any of the types of dysregulation of an FGFR gene, a FGFR protein, or expression or activity, or level of the same, described herein). A non-limiting example of an FGFR-associated disease or disorder is an FGFR-associated cancer.

As used herein, the term "FGFR-associated cancer" shall be defined to include cancers associated with or having dysregulation of a FGFR gene, a FGFR protein, or expression or activity, or level of the same (e.g., any of types of dysregulation of a FGFR gene, a FGFR protein, or expression or activity, or level of the same, described herein). Non-limiting examples of a FGFR-associated cancer are described herein.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer with dysregulation of a FGFR gene, a FGFR protein, or expression or activity, or level of the same (a FGFR-associated cancer) (e.g., as determined using a regulatory agency-approved, e.g., FDA-approved, assay or kit). In some embodiments, the subject has a tumor that is positive for dysregulation of a FGFR gene, a FGFR protein, or expression or activity, or level of the same (e.g., as determined using a regulatory agency-approved assay or kit). The subject can be a subject with a tumor(s) that is positive for dysregulation of a FGFR gene, a FGFR protein, or expression or activity, or level of the same (e.g., identified as positive using a regulatory agency-approved, e.g., FDA-approved, assay or kit). The subject can be a subject whose tumors have dysregulation of a FGFR gene, a FGFR protein, or expression or activity, or a level of the same (e.g., where the tumor is identified as such using a regulatory agency-approved, e.g., FDA-approved, kit or assay). In some embodiments, the subject is suspected of having a FGFR-associated cancer. In some embodiments, the subject has a clinical record indicating that the subject has a tumor that has dysregulation of a FGFR gene, a FGFR protein, or expression or activity, or level of the same (and optionally the clinical record indicates that the subject should be treated with any of the compositions provided herein).

The term "FGFR" or "FGFR protein" includes any of the FGFR proteins described herein (e.g., a FGFR1, a FGFR2, a FGFR3 or a FGFR4 protein, or isoforms thereof).

The term "FGFR gene" includes any of the FGFR genes described herein (e.g., a FGFR1, a FGFR2, a FGFR3 gene, or a FGFR4 gene).

The term "wildtype" or "wild-type" describes a nucleic acid (e.g., a FGFR gene or a FGFR mRNA) or protein (e.g., a FGFR protein) that is found in a subject that does not have a FGFR-associated disease, e.g., a FGFR-associated cancer (and optionally also does not have an increased risk of developing a FGFR-associated disease and/or is not suspected of having a FGFR-associated disease), or is found in a cell or tissue from a subject that does not have a FGFR-associated disease, e.g., a FGFR-associated cancer (and optionally also does not have an increased risk of developing a FGFR-associated disease and/or is not suspected of having a FGFR-associated disease).

The term "regulatory agency" is a country's agency for the approval of the medical use of pharmaceutical agents with the country. For example, a non-limiting example of a regulatory agency is the U.S. Food and Drug Administration (FDA).

The phrase "dysregulation of a FGFR gene, a FGFR protein, or expression or activity, or level of the same" is a genetic mutation (e.g., a FGFR gene translocation that results in the expression of a fusion protein, a deletion in a FGFR gene that results in the expression of a FGFR protein that includes a deletion of at least one amino acid as compared to the wild-type FGFR protein, or a mutation in a FGFR gene that results in the expression of a FGFR protein with one or more point mutations, an alternative spliced version of a FGFR mRNA that results in a FGFR protein that results in the deletion of at least one amino acid in the FGFR protein as compared to the wild-type FGFR protein), or a FGFR gene amplification that results in overexpression of a FGFR protein) or an autocrine activity resulting from the overexpression of a FGFR gene a cell, that results in a pathogenic increase in the activity of a kinase domain of a FGFR protein (e.g., a constitutively active kinase domain of a FGFR protein) in a cell. For example, a dysregulation of a FGFR gene, a FGFR protein, or expression or activity, or level of the same, can be a mutation in a FGFR1, FGFR2, FGFR3, or FGFR4 gene that encodes a FGFR protein that is constitutively active or has increased activity as compared to a protein encoded by a FGFR1, FGFR2, FGFR3, or FGFR4 gene that does not include the mutation. For example, a dysregulation of a FGFR gene, a FGFR protein, or expression or activity, or level of the same, can be the result of a gene or chromosome translocation which results in the expression of a fusion protein that contains a first portion of FGFR1, FGFR2, FGFR3, or FGFR4 that includes a functional kinase domain, and a second portion of a partner protein (i.e., that is not FGFR1, FGFR2, FGFR3, or FGFR4). In some examples, dysregulation of a FGFR gene, a FGFR protein, or expression or activity, can be a result of a gene translation of one FGFR1 gene with another FGFR1 gene. Non-limiting examples of fusion proteins that are a result of a FGFR gene translocation are described in Table 3.

A dysregulation of a FGFR gene, a FGFR protein, or expression or activity, or level of the same, can, e.g., include a mutation(s) in a FGFR1, FGFR2, FGFR3, or FGFR4 gene that results in a FGFR1, FGFR2, FGFR3, or FGFR4 protein containing at least one (e.g., two, three, four, or five) point mutations (e.g., one of more of the point mutations listed in Table 1).

A dysregulation of a FGFR gene, a FGFR protein, or expression or activity, or level of the same, can be a mutation in a FGFR1, FGFR2, FGFR3, or FGFR4 gene that results in a deletion of one or more contiguous amino acids (e.g., at least two, at least three, at least four, at least 5, at least 6, at least 7, at least 8, at least 9, at least 10, at least 15, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, at least 360, at least 370, at least 380, at least 390, or at least 400 amino acids) in the FGFR1, FGFR2, FGFR3, or FGFR4 protein (except for the deletion of amino acids in the kinase domain of FGFR1, FGFR2, FGFR3, or FGFR4 that would result in inactivation of the kinase domain).

In some examples, a dysregulation of a FGFR gene, a FGFR protein, or expression or activity, or level of the same, can include an alternate spliced form of a FGFR mRNA. In some examples, a dysregulation of a FGFR gene, a FGFR protein, or expression or activity, or level of the same, includes an amplification of a FGFR gene (e.g., one, two, three, or four additional copies of a FGFR1, FGFR2, FGFR3, and/or FGFR4 gene) that can result, e.g., in an autocrine expression of a FGFR gene in a cell.

The term "mammal" as used herein, refers to a warm-blooded animal that has or is at risk of developing a disease described herein and includes, but is not limited to, guinea pigs, dogs, cats, rats, mice, hamsters, and primates, including humans.

The phrase "time of survival" means the length of time between the identification or diagnosis of cancer (e.g., any of the cancers described herein) in a subject or patient by a medical professional and the time of death of the subject or patient (caused by the cancer). Methods of increasing the time of survival in a subject or patient having a cancer are described herein.

The term "metastasis" is an art known term and means the formation of an additional tumor (e.g., a solid tumor) at a site distant from a primary tumor in a subject or patient, where the additional tumor includes the same or similar cancer cells as the primary tumor.

The phrase "risk of developing a metastasis" means the risk that a subject or patient having a primary tumor will develop an additional tumor (e.g., a solid tumor) at a site distant from a primary tumor in a subject or patient over a set period of time, where the additional tumor includes the same or similar cancer cells as the primary tumor. Methods for reducing the risk of developing a metastasis in a subject or patient having a cancer are described herein.

The phrase "risk of developing additional metastases" means the risk that a subject or patient having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

The term "angiogenesis-related disorder" means a disease characterized in part by an increased number or size of blood vessels in a tissue in a subject or patient, as compared to a similar tissue from a subject not having the disease. Non-limiting examples of angiogenesis-related disorders include: cancer (e.g., any of the exemplary cancers described herein, such as prostate cancer, lung cancer, breast cancer, bladder cancer, renal cancer, colon cancer, gastric cancer, pancreatic cancer, ovarian cancer, melanoma, hepatoma, sarcoma, and lymphoma), exudative macular degeneration, proliferative diabetic diabetic retinopathy, ischemic retinopathy, retinopathy of prematurity, neovascular glaucoma, iritis rubeosis, corneal neovascularization, cyclitis, sickle cell retinopathy, and pterygium.

The term "resistant cancer cell to an anti-cancer drug" means a cancer cell that demonstrates an increased rate of growth and/or proliferation in the presence of an anti-cancer drug as compared to the rate of growth and/or proliferation of a similar cancer cell (or an average rate of growth and/or proliferation of a population of a similar cancer cells). For example, a cancer cell that demonstrates an increased rate of growth and/or proliferation in the presence of an anti-cancer drug (as compared to the rate of growth and/or proliferation of a similar cancer cell) can be present in a patient or a subject (e.g., a patient or a subject having a FGFR-associated cancer).

The term "increasing sensitivity to an anti-cancer drug" means a decrease in the rate of growth and/or proliferation of a resistant cancer cell (to an anti-cancer drug) when contacted with the anti-cancer drug and at least one of the compounds described herein, as compared to the rate of growth and/or proliferation of a resistant cancer cell when contacted with the anti-cancer drug alone.

The FGFR receptors (FGFR1, FGFR2, FGFR3, and FGFR4) share several structural features in common, including three extracellular immunoglobulin-like (Ig) domains, a hydrophobic transmembrane domain, and an intracellular split tyrosine kinase domain with a 14-amino acid insertion (Johnson et al., Adv. Cancer Res. 60:1-40, 1993; and Wilkie et al., Curr. Biol. 5:500-507, 1995). Several isoforms of each FGFR have been identified and are the result of alternative splicing of their mRNAs (Johnson et al., Mol. Cell. Biol. 11:4627-4634, 1995; and Chellaiah et al., J. Biol. Chem. 269:11620-11627, 1994). A few of the receptor variants that result from this alternative splicing have different ligand binding specificities and affinities (Zimmer et al., J. Biol. Chem. 268:7899-7903, 1993; Cheon et al., Proc. Natl. Acad. Sci. U.S.A. 91:989-993, 1994; and Miki et al., Proc. Natl. Acad. Sci. U.S.A. 89:246-250, 1992). Protein sequences for FGFR proteins and nucleic acids encoding FGFR proteins are known in the art. Exemplary amino acid sequences for exemplary wildtype isoforms of FGFR1 are SEQ ID NO: 1 and SEQ ID NO: 2. Exemplary amino acid sequences for exemplary wildtype isoforms of FGFR2 are SEQ ID NO: 2 and SEQ ID NO: 3. Exemplary amino acid sequences for exemplary wildtype isoforms of FGFR3 are SEQ ID NO: 5 and SEQ ID NO: 6. Exemplary amino acid sequences for exemplary wildpyte isoforms of FGFR4 are SEQ ID NO: 7 and SEQ ID NO: 8.

Signaling by FGFRs regulates key biological processes including cell proliferation, survival, migration, and differentiation. Dysregulation of a FGFR gene, a FGFR protein, or expression or activity, or level of the same, has been associated with many types of cancer. For example, dysregulation of FGFRs can occur by multiple mechanisms, such as FGFR gene overexpression, FGFR gene amplification, activating mutations (e.g., point mutations or truncations), and chromosomal rearrangements that lead to FGFR fusion proteins. Dysregulation of a FGFR gene, a FGFR protein, or expression or activity, or level of the same, can result in (or cause in part) the development of a variety of different FGFR-associated cancers. Non-limiting examples of the types of FGFR-associated cancers and the dysregulation of a FGFR gene, a FGFR protein, or expression or activity, or level of the same, that causes (or causes in part) the development of the FGFR-associated cancers are listed in Tables A-D.

For example, dysregulation of a FGFR1 gene, a FGFR1 protein, or expression or activity, or level of the same, can include FGFR1 gene amplification, a FGFR1 gene fusion from those listed in Table C, and/or one or more point mutations selected from those listed in Table A (e.g., one of more of T141R, R445W, N546K, K656E, and G818R). Dysregulation of a FGFR2 gene, a FGFR2 protein, or expression or activity, or level of the same, can, e.g., include FGFR2 gene amplification, a FGFR2 gene fusion from those listed in Table C, and/or one or more point mutations selected from those listed in Table A (e.g., one or more of S252W, P253R, A315T, D336N, Y375C, C382R, V395D, D471N, I547V, N549K, N549K, N549Y, and K659E). Dysregulation of a FGFR3 gene, a FGFR3 protein, or expression or activity, or level of the same can, e.g., include FGFR3 gene amplification, a FGFR3 gene fusion from those listed in Table C, and/or one or more point mutations selected from those listed in Table A (e.g., one or more of S131L, R248C, S249C, G370C, S371C, Y373C, G380R, R399C, E627K, K650E, K650M, V677I, and D785Y). Dysregulation of a FGFR4 gene, a FGFR4 protein, or expression or activity, or level of the same can, e.g., include FGFR4 gene amplification and/or one or more point mutations selected from those listed in Table A (e.g., one or more of R183S, R394Q, D425N, V510L, and R610H).

Additional examples of FGFR fusion proteins, FGFR point mutations, FGFR gene overexpression, or FGFR gene amplification that cause (or cause in part) the development of a FGFR-associated cancer are described in: Wu et al., Cancer Discovery 3:636, 2013; Wesche et al., Biochem. J. 437:199-213, 2011; Gallo et al., Cytokine Growth Factor Rev. 26:425-449, 2015; Parker et al., J. Pathol. 232:4-15, 2014; Katoh et al., Expert Rev. Anticancer Res. 10:1375-1379, 2010; Chang et al., PLoS One 9:e105524, 2014; Kelleher et al., Carcinogenesis 34:2198-2205, 2013; Katoh et al., Med. Res. Rev. 34:280-300, 2014; Knights et al., Pharmacol. Therapeutics 125:105-117, 2010; Turner et al., Sci. Transl. Med. 2:62ps56, 2010; Dutt et al., PLoS One 6(6):e20351, 2011; Weiss et al., Sci. Transl. Med. 2:62ra93, 2010; Becker et al., J. Neuropathol. Exp. Neurol. 74:743-754, 2015; Byron et al., PLoS One 7(2):e30801, 2012; van Rhihn et al., Eur. J. Human Genetics 10:819-824, 2002; Hart et al., Oncogene 19(29):3309-3320, 2000; Lin et al., Cancer Res. 68:664-673, 2008; and Helsten et al., Clin. Cancer Res., e-publication dated Sep. 15, 2015 (each of which is incorporated herein by reference). Additional non-limiting aspects and examples of FGFR fusion proteins, FGFR point mutations, FGFR gene overexpression, or FGFR gene amplification are described below.

Point Mutations

FGFR mutations that confer constitutive activation have been described in a number of congenital skeletal disorders (Turner N, Grose R., Nat Rev Cancer 2010; 10:116-129). FGFRs have been identified as among the most commonly mutated kinase genes in human cancers, with mutations in FGFR2 and FGFR3 being most prevalent (Turner N., Grose R., Nat Rev Cancer 2010; 10:116-129). For example, approximately 50% to 60% of non-muscle invasive and 17% of high-grade bladder cancers possess FGFR3 mutations that cause constitutive FGFR dimerization and activation (Cappellen D. et al., Nat Genet 1999; 23:18-20). Activating and oncogenic FGFR2 mutations located in the extracellular and kinase domains of the receptor have been described in 12% of endometrial carcinomas (Dutt A. et al., Proc Natl Acad Sci USA 2008; 105:8713-8717). Importantly, the FGFR2 mutations found in endometrial cancer confer sensitivity to FGFR inhibition (Dutt A. et al., Proc Natl Acad Sci USA 2008; 105:8713-8717). More recently, FGFR2 mutations have been described in 5% of squamous non-small cell lung cancers (NSCLC; Hammerman P. et al., Genomic characterization and targeted therapeutics in squamous cell lung cancer [abstract]. In: Proceedings of the 14th World Conference on Lung Cancer; 2011 3-7 July; Aurora (Colo.): International Association for the Study of Lung Cancer; 2011). FGFR3 mutations in bladder cancer and FGFR2 mutations in endometrial cancer are mutually exclusive with mutations in HRAS and KRAS, respectively. In addition, mutations in the FGFR4 kinase domain have been found in the childhood soft tissue sarcoma rhabdomyosarcoma, causing autophosphorylation and constitutive signaling (Taylor J G, et al., J Clin Invest 2009; 119:3395-407). FGFR1, FGFR2, FGFR3, and/or FGFR4 can include one, two, three, four, five, six, seven, eight, nine, ten, eleven, twelve, thirteen, fourteen, fifteen, sixteen, seventeen, eighteen, nineteen, or twenty different point mutations (as compared to an appropriate corresponding wildtype FGFR1, FGFR2, FGFR3, or FGFR4 amino acid sequence, respectively). Non-limiting examples of point mutations in FGFR1, FGFR2, FGFR3, or FGFR4 that are thought to cause (or cause in-part) a FGFR-associated cancer are listed in Table A.

TABLE A

FGFR Point Mutations

| FGFR | Point Mutation | Cancer |
|---|---|---|
| FGFR1 | N546K[1] R576W K656E | Brain cancer or glioneural tumors |
| FGFR1 | N546K K656E | Glioma |
| FGFR1 | N546K | Neuroblastoma |
| FGFR1 | N546K | Malignant peripheral nerve sheath tumor |
| FGFR1 | N546K | Paraganglioma |
| FGFR1 | N544K or N546K R574W or R576W K654E or K656E | Glioblastoma |
| FGFR1 | N544K or N546K K653I or K655I K654D or K656D K654E or K656E K654M or K656M K654N or K656N T656P or T658P | Pilocytic astrocytoma |
| FGFR1 | N544K or N546K K654E or K656E | Rosette forming glioneural tumor |
| FGFR1 | N546K | Pineal tumor |
| FGFR1 | S125L | Breast cancer |
| FGFR1 | P126S[2] | Neuroendocrine carcinoma of the breast |
| FGFR1 | P150S A268S S428F or S430F A429S or A431S G608D or G610D | Colorectal cancer |
| FGFR1 | S125L P252S | Skin cancer |
| FGFR1 | P252S | Melanoma |
| FGFR1 | R445W | Cutaneous squamous cell carcinoma |
| FGFR1 | R78H | Prostate cancer |
| FGFR1 | P25Q G70R T141R P252T W445W W471L V664L | Lung cancer |
| FGFR1 | T141R | Non-small cell lung carcinoma |
| FGFR1 | P252T | Lung adenocarcinoma |
| FGFR1 | V662L or V664L | Lung large cell carcinoma |
| FGFR1 | G70R T141R | Lung squamous cell carcinoma |
| FGFR1 | A268S | Stomach cancer |
| FGFR1 | K596N or K598N | Esophageal adenocarcinoma |
| FGFR1 | S125L | Gallbladder cancer |
| FGFR1 | E334Q | Head and neck squamous cell carcinoma |
| FGFR1 | P252R P252T N330I Y374C C381R R574W or R576W | Spermatocytic seminoma |
| FGFR1 | P253R V392A or V393A | Oral squamous cell carcinoma |
| FGFR1 | N546K | Sarcoma |
| FGFR1 | T141R | Endometrial adenocarcinoma |
| FGFR1 | T141R G818R | Urothelial carcinoma |
| FGFR1 | R661P N546K K656E | Dysembryoplastic neuroepithelial tumor[19] |
| FGFR1 | S125L | Dedifferentiated liposarcoma[24] |
| FGFR1 | V561M[25] | In vitro study |
| FGFR1 | N546K[26] V561M[26] | In vitro study |
| FGFR1 | V561M[30] | In vitro study |
| FGFR1 | N546K[31] V561M[31] | In vitro study |
| FGFR1 | V561M[32] Y563C[32] | In vitro study |
| FGFR2 | V395D K659E | Salivary gland carcinoma |
| FGFR2 | (A266_S267insSTVV66D) D336N | Carcinoma of unknown primary |
| FGFR2 | N549D or N550D N549K or N550K | Head and neck squamous cell carcinoma |
| FGFR2 | C382R or C383R | Esophageal cancer |
| FGFR2 | Y375C or Y376C N549K K641R or K642R | Adenoid cystic carcinoma |
| FGFR2 | R203H R210Q A315T D334N or D336N Q361R L551I or L552I P582L or P583L R664W or R665W E777K or E778K | Colorectal cancer (e.g., colorectal adenocarcinoma) |
| FGFR2 | M71T[3] M186T | Lymphoma |

TABLE A-continued

FGFR Point Mutations

| FGFR | Point Mutation | Cancer |
|---|---|---|
| FGFR2 | M71T[3] | Bladder cancer |
|  | M186T |  |
| FGFR2 | S24F | Skin cancer |
|  | V77M |  |
|  | E160A |  |
|  | H213Y |  |
|  | E219K |  |
|  | G227E |  |
|  | V248D |  |
|  | R251Q |  |
|  | G271E |  |
|  | G305R |  |
|  | W474X |  |
|  | E475K |  |
|  | D530N |  |
|  | E574K |  |
|  | E636K |  |
|  | M640I |  |
|  | I642V |  |
|  | A648T |  |
|  | S688F |  |
|  | G701S |  |
|  | P708S |  |
|  | R759X |  |
|  | R759Q |  |
|  | L770V |  |
| FGFR2 | S24F | Melanoma |
|  | V77M |  |
|  | W156* |  |
|  | E160A |  |
|  | H213Y |  |
|  | E219K |  |
|  | G227E |  |
|  | V248D |  |
|  | R251Q |  |
|  | G271E |  |
|  | G305R |  |
|  | T370R or T371R |  |
|  | W474X |  |
|  | E476K or E475K |  |
|  | D530N or D531N |  |
|  | E574K or E575K |  |
|  | E636K or E637K |  |
|  | M640I or M641I |  |
|  | I642V or I643V |  |
|  | A648T or A649T |  |
|  | S688F or S689F |  |
|  | G701S or G702S |  |
|  | P708S or P709S |  |
|  | R759X |  |
|  | R759Q or R760Q |  |
|  | L770V or L771V |  |
| FGFR2 | N549Y | Basal cell carcinoma |
| FGFR2 | S252W | Ovarian cancer or ovarian serous cancer |
|  | G272V |  |
|  | Y375C |  |
| FGFR2 | Q212K | Brain cancer |
|  | G462E |  |
|  | K659E or K660E |  |
| FGFR2 | K659E or K660E | Medulloblastoma |
| FGFR2 | K659E or K660E | Pilocytic astrocytoma |
| FGFR2 | I547V | Anaplastic astrocytoma |
| FGFR2 | R203C | Breast cancer |
|  | S252W |  |
|  | N549K or N550K |  |
|  | S587C or S588C |  |
|  | K659N or K660N |  |
| FGFR2 | S252W | Ovarian cancer, Fallopian tube carcinoma |
| FGFR2 | A97T | Cervical cancer or cervical squamous cell carcinoma |
|  | S252L |  |
|  | P256S |  |
|  | K405E or K406E |  |
|  | M584V or M585V |  |
|  | Y588D or Y589D |  |
|  | K659M or K660M |  |
| FGFR2 | E116K | Lung cancer |
|  | D138N |  |
|  | R190G |  |
|  | N211I |  |
|  | D247Y |  |
|  | P253L |  |
|  | P253R |  |
|  | D283N |  |
|  | W290C |  |
|  | G302W[4] |  |
|  | A315T |  |
|  | S320C |  |
|  | I380V or I381V |  |
|  | C382R or C383R |  |
|  | K420I or K421I |  |
|  | E470Q or E471Q |  |
|  | D479N or D480N |  |
|  | R496T[4] |  |
|  | M537I or M538I |  |
|  | H544Q or H545Q |  |
|  | G583W or G584W[4] |  |
|  | I590M or I591M |  |
|  | D602E or D603E |  |
|  | R612T |  |
|  | Q620K or Q621K |  |
|  | R625T or R626T |  |
|  | K659E or K660E |  |
|  | K659N or K660N |  |
|  | K660E |  |
|  | K660N |  |
|  | L772F or L773F |  |
|  | T786K or T787K |  |
|  | G847A[5] |  |
|  | G870C[5] |  |
|  | G1487C[5] |  |
| FGFR2 | E116K | Lung adenocarcinoma |
|  | P253L |  |
|  | I380V or I381V |  |
|  | K420I or K421I |  |
|  | D479N or D480N |  |
|  | H544Q or H545Q |  |
|  | G583V or G584V |  |
|  | I590M or I591M |  |
|  | Q620K or Q621K |  |
|  | R625T or R626T |  |
| FGFR2 | D138N | Squamous cell lung cancer |
|  | N211I |  |
|  | D247Y |  |
|  | S252W |  |
|  | P253R |  |
|  | D283N |  |
|  | W290C |  |
|  | G302W[4] |  |
|  | S320C[4] |  |
|  | C382R or C383R |  |
|  | E470Q or E471Q |  |
|  | M537I or M538I |  |
|  | G583W or G584W |  |
|  | D602E or D603E |  |
|  | K659E or K660E |  |
|  | K659N or K660N |  |
|  | L772F or L773F |  |
|  | T786K or T787K |  |
| FGFR2 | P253R | Non-small cell lung cancer |
|  | A315T |  |
| FGFR2 | A97T | Endometrioid endometrial cancer or endometrial cancer |
|  | D101Y |  |
|  | N211I |  |
|  | S252W |  |
|  | P253R |  |
|  | S272C |  |
|  | W290C |  |
|  | K310R |  |
|  | A314D |  |
|  | A315T |  |
|  | S372C |  |

TABLE A-continued

FGFR Point Mutations

| FGFR | Point Mutation | Cancer |
|---|---|---|
| | S373C | |
| | Y375C or Y376C | |
| | C382R or C383R | |
| | A389T or A390T | |
| | M391R or M392R | |
| | V395D or V396D | |
| | L397M or L398M | |
| | I547D or I548D | |
| | I547V or I548V | |
| | N549H or N550H | |
| | N549K or N550K | |
| | K659E or K660E | |
| | K659M or K660M | |
| | K659N or K660N | |
| FGFR2 | S267P | Stomach cancer |
| FGFR2 | (Truncation, intron 17) | Urothelial cancer |
| FGFR2 | N549K | Uterine carcinosarcoma |
| FGFR2 | Q212K | Gallbladder cancer |
| | D471N | |
| FGFR2 | Y375C | Pancreatic exocrine carcinoma |
| FGFR2 | C382R | Cholangiocarcinoma |
| FGFR2 | S252F | Spermatocytic seminoma |
| | S252W | |
| | P253R | |
| | P253S | |
| | S267P | |
| | F276V | |
| | C278F | |
| | Y281C | |
| | Q289P | |
| | W290C | |
| | A315S | |
| | G336R or G338R | |
| | Y338C or Y340C | |
| | Y338H or Y340H | |
| | T341P | |
| | C340F or C342F | |
| | C340R or C342R | |
| | C340S or C342S | |
| | C340W or C342W | |
| | C340Y or C342Y | |
| | A344G | |
| | A344P | |
| | S347C | |
| | S352C or S354C | |
| | Y375C or Y376C | |
| | K526E or K527E | |
| | N549K or N550K | |
| | K641R or K642R | |
| | G462E or G463E | |
| | K659E or K660E | |
| FGFR2 | S167P[13] | Gastric cancer |
| | Splice site mutation 940-2A-G[13] | |
| FGFR2 | M536I[14] | Endometrial cancer |
| | M538I[14] | |
| | I548V[14] | |
| | N550H[14] | |
| | N550K[14] | |
| | N550S[14] | |
| | V565I[14] | |
| | E566G[14] | |
| | L618M[14] | |
| | E719G[14] | |
| | Y770IfsX14[14] | |
| FGFR2 | K660M[17] | Uterine cancer |
| FGFR2 | K659E[21] | Head and neck adenoid cystic carcinoma |
| FGFR2 | K659E[23] | Breast cancer |
| FGFR2 | M536I[27] | Endometrial cancer |
| | M538I[27] | |
| | I548V[27] | |
| | N550H[27] | |
| | N550K[27] | |
| | N550S[27] | |
| | V565I[27] | |
| | E566G[27] | |
| | L618M[27] | |
| | K642N[1] | |
| | K660E[1] | |
| | E719G[27] | |
| | Y770IfsX14[27] | |
| FGFR2 | N550H[28] | Uterine cancer (K660M) |
| | V565I[28] | |
| | E566G[28] | |
| | K660M[28] | |
| FGFR2 | V562L[29] | In vitro study |
| FGFR2 | V564F[29] | |
| FGFR2 | M536I[33] | In vitro study |
| | M538I[33] | |
| | I548V[33] | |
| | N550H[33] | |
| | N550K[33] | |
| | N550S[33] | |
| | V565I[33] | |
| | E566G[33] | |
| | L618M[33] | |
| | E719G[33] | |
| | Y770IfsX14[33] | |
| FGFR2 | N550H[34] | In vitro study |
| | V565I[34] | |
| | E566G[34] | |
| | K660M[34] | |
| | K660N[34] | |
| FGFR2 | V562L[35] | In vitro study |
| | V564F[35] | |
| FGFR3 | R399C | Gastric cancer, gastroesophageal junction adenocarcinoma |
| FGFR3 | V677I | Endometrial adenocarcinoma |
| FGFR3 | R248C | Carcinoma of unknown primary |
| | S249C | |
| | R399C | |
| | D785Y | |
| FGFR3 | S249C | Anal squamous cell carcinoma |
| | G380R | |
| FGFR3 | R248C | Gallbladder cancer |
| | S249C | |
| | G370C or G372C | |
| | Y373C or Y375C | |
| | G380R or G382R | |
| | K650M or K652M | |
| | G697C or G699C | |
| FGFR3 | A341T | Esophageal cancer or esophageal adenocarcinoma |
| FGFR3 | R248C | Cervical cancer |
| | S249C | |
| | G372C | |
| | K652E | |
| FGFR3 | K650E | Testicular cancer |
| | K650Q | |
| | K650M | |
| | K650N | |
| | K650T | |
| FGFR3 | E466K | Brain cancer |
| FGFR3 | E466K or E468K | Glioblastoma |
| | R603Q or R605Q | |
| FGFR3 | K650E | Glioma |
| FGFR3 | Q209H | Head and neck cancer |
| | R248C | |
| | S249C | |
| | F386L or F388L | |
| | K413N or K415N | |
| | D617G | |
| | V630M | |
| | K650N or K652N | |
| | E686K | |
| | G697C | |
| FGFR3 | C228R | Colorectal cancer |
| | E322K | |
| | R399C or R401C | |
| | V677I or V679I | |

TABLE A-continued

FGFR Point Mutations

| FGFR | Point Mutation | Cancer |
|---|---|---|
| FGFR3 | D646Y or D648Y | Mesothelioma |
| FGFR3 | T79S | Lung cancer |
|  | R248C |  |
|  | S249C |  |
|  | R248H |  |
|  | S249C |  |
|  | G370C |  |
|  | S433C or S435C |  |
|  | K650E |  |
|  | K715M or K717M |  |
|  | T787K |  |
| FGFR3 | R248C | Non-small cell lung carcinoma |
|  | S249C |  |
|  | G370C |  |
|  | K650E |  |
| FGFR3 | T79S | Lung adenocarcinoma |
| FGFR3 | R248C | Squamous cell lung cancer |
|  | R248H |  |
|  | S249C |  |
|  | G370C |  |
|  | S433C or S435C |  |
|  | K650E |  |
|  | K715M or K717M |  |
|  | T787K[11] |  |
| FGFR3 | S131L | Urothelial carcinoma |
|  | R248C |  |
|  | S249C |  |
|  | G370C |  |
|  | G372C |  |
|  | Y373C |  |
|  | Y375C |  |
|  | A393E |  |
|  | R399C |  |
|  | K650E |  |
|  | K650M |  |
|  | K652E |  |
|  | K652M |  |
|  | K652T |  |
|  | C742T[6] |  |
|  | C746G[7] |  |
|  | G1114T[12] |  |
|  | A1124G[8] |  |
|  | G1144A |  |
|  | C1178A |  |
|  | A1954C |  |
|  | A1954G[12] |  |
| FGFR3 | S249C | Cervical cancer |
|  | K650E |  |
| FGFR3 | R248C | Lymphoepithelioma |
| FGFR3 | G197S | Multiple myeloma |
|  | Y241C |  |
|  | R248C |  |
|  | S249C |  |
|  | P250R |  |
|  | G370C |  |
|  | S371C |  |
|  | Y373C or Y375C |  |
|  | G380R |  |
|  | G382D or G384D |  |
|  | F384L or F386L |  |
|  | S433C or S435C |  |
|  | A441T |  |
|  | A452S |  |
|  | K650E or K652E |  |
|  | K650M or K652M |  |
|  | A717T |  |
|  | I726F |  |
|  | L794R or L796R |  |
|  | L795A or L797A |  |
|  | 807R[9] |  |
|  | 807C |  |
|  | Deletion of amino acids 795-808 |  |
| FGFR3 | E216K | Bladder cancer |
|  | D222N |  |
|  | G235D |  |
|  | R248C |  |
|  | S249C |  |
|  | P283S |  |
|  | V306I |  |
|  | H349Y |  |
|  | G370C or G372C |  |
|  | S371C or S373C |  |
|  | Y373C or Y375C |  |
|  | I376C or I378C |  |
|  | Y379C or Y381C |  |
|  | G380R or G382R |  |
|  | G382E |  |
|  | G382R |  |
|  | F384L or F386L |  |
|  | A391E or A393E |  |
|  | N540S or N542S |  |
|  | D646Y |  |
|  | K650E or K652E |  |
|  | K650Q or K652Q |  |
|  | K650M or K652M |  |
|  | K650T or K652T |  |
|  | K650N |  |
|  | K650T or K652T |  |
| FGFR3 | K650E (Activation Loop) | Lymphoma |
| FGFR3 | S249C | Prostate cancer |
|  | F384L[20] |  |
|  | A391E |  |
|  | F386L[20] |  |
| FGFR3 | R248C | Spermatocytic serminoma |
|  | S249C |  |
|  | P250R |  |
|  | E368K or E370K |  |
|  | G370C or G372C |  |
|  | S371C or S373C |  |
|  | Y373C or Y375C |  |
|  | G375C or G377C |  |
|  | G380R or G382R |  |
|  | A391E or A393E |  |
|  | N540K or N542K |  |
|  | N540S or N542S |  |
|  | N540T or N542T |  |
|  | N540V or N542V |  |
|  | K650E or K652E |  |
|  | K650M or K652M |  |
|  | K650N or K652N |  |
|  | K650Q or K652Q |  |
|  | K650T or K652T |  |
|  | G697C or G699C |  |
|  | 807C or 809C |  |
|  | 807G or 809G |  |
|  | 807R or 809R[10] |  |
|  | 807T or 809T |  |
| FGFR3 | Y373C | Thymic cancer |
| FGFR3 | G697C or G699C | Oral squamous cell cancer |
| FGFR3 | G370C | Cutaneous squamous cell carcinoma |
|  | S371C |  |
| FGFR3 | S249C | Renal cell carcinoma |
| FGFR3 | S249C | Pancreatic exocrine carcinoma |
| FGFR3 | R248C | Sarcoma |
|  | E627K |  |
| FGFR3 | R248C | Seborrheic keratosis |
|  | S249C |  |
|  | G370C or G372C |  |
|  | S371C or S373C |  |
|  | A391E or A393E |  |
|  | K650E or K652E |  |
|  | K650M or K652M |  |
| FGFR3 | S249C[16] | Breast cancer |
| FGFR3-IIIb | S248C[18] | Bladder cancer |
| FGFR3-IIIc | S248C[18] | Bladder cancer |
| FGFR3 | K650M[24] | Dedifferentiated liposarcoma |
| FGFR3 | V555M[37] | KMS-11 myeloma cell line derivative |
| FGFR4 | D425N | Carcinoid |
| FGFR4 | G388R | Bladder cancer |
| FGFR4 | G388R | Stomach cancer |

TABLE A-continued

FGFR Point Mutations

| FGFR | Point Mutation | Cancer |
|---|---|---|
| FGFR4 | G388R | Skin cancer |
| | P716R | |
| FGFR4 | Q144E | Brain cancer |
| | G388R | |
| | R394Q or R434Q | |
| FGFR4 | Q144E | Glioblastoma |
| | R394Q or R434Q | |
| FGFR4 | G388R | Prostate cancer |
| | R610H | |
| FGFR4 | G388R | Head and neck squamous cell carcinoma |
| | D631N or D671N | |
| FGFR4 | G388R | Liver cancer |
| | R394Q | |
| FGFR4 | G388R | Colorectal cancer (e.g., colorectal adenocarcinoma) |
| | P543Q or P583Q | |
| | A574S or A614S | |
| FGFR4 | E326K | Breast cancer |
| | Y367C | |
| | G388R | |
| | A444T or A484T | |
| | V510M or V550M | |
| | V510L | |
| | V550E | |
| | V550L | |
| FGFR4 | V550M | Neuroendocrine carcinoma of the breast |
| FGFR4 | G388R | Mammary carcinoma |
| FGFR4 | Q144E | Lung cancer |
| | R183S | |
| | S232I | |
| | G388R | |
| | R434Q | |
| | R616G | |
| | E681K | |
| | P712T | |
| | A729G | |
| | S732N or S772N | |
| | Q738K | |
| FGFR4 | R183S | Non-small cell lung carcinoma |
| FGFR4 | S732N or S772N | Lung neuroendocrine carcinoma |
| FGFR4 | Q144E | Lung squamous cell carcinoma |
| | R394Q or R434Q | |
| FGFR4 | R183S | Lung adenocarcinoma |
| | S232I | |
| | R576G or R616G | |
| | E641K or E681K | |
| | P672T or P712T | |
| | A689G or A729G | |
| FGFR4 | G388R | Sarcoma (e.g., soft tissue sarcoma) |
| | K535 | |
| | E550 | |
| FGFR4 | C56S | Rhabdomyosarcoma |
| | R72L | |
| | T112A | |
| | T122A | |
| | A175T | |
| | R234H | |
| | G388R | |
| | N495D or N535D | |
| | N495K or N535K | |
| | V510E or V550E | |
| | V510L or V550L | |
| | V510M or V550M | |
| | A514V or A554V | |
| | G536D or G576D | |
| FGFR4 | G183C of tyrosine kinase domain[15] | Stomach cancer |
| | G596C[15] | |
| | G636C[15] | |
| FGFR4 | P568Q[22] | Lung cancer |
| | R59W[22] | |
| FGFR4 | G388R[36] | Breast cancer |

[1]Each isoform of FGFR1, FGFR2, FGFR3, and FGFR4 has a different length, and thus, the corresponding amino acid position in one isoform of FGFR1, FGFR2, FGFR3, and FGFR4 may be different in another isoform of FGFR1, FGFR2, FGFR3, and FGFR4. The position of each point mutation listed above in each isoform of FGFR1, FGFR2, FGFR3, and FGFR4 can be identified by first identifying the isoform(s) of FGFR1, FGFR2, FGFR3, or FGFR4 which correspond to the specific point mutation listed above (by amino acid position and starting amino acid), and then aligning the amino acid sequence of identified isoform(s) of FGFR1, FGFR2, FGFR3, or FGFR4 with the amino acid sequences of the other isoforms of FGFR1, FGFR2, FGFR3, or FGFR4.
[2]Ang et al., Diagn. Mol. Pathol. Feb. 24, 2014 (Epub ahead of print).
[3]U.S. Patent Application Publication No. 2011/0008347.
[4]Gallo et al., Cytokine Growth Factor Rev. 26: 425-449, 2015.
[5]Davies et al., J. Cancer Res. 65: 7591, 2005.
[6]Kelleher et al., Carcinogenesis 34: 2198, 2013.
[7]Cazier et al., Nat. Commun. 5: 3756, 2014.
[8]Liu et al., Genet. Mol. Res. 13: 1109, 2014.
[9]Trudel et al., Blood 107: 4039, 2006.
[10]Gallo et al., Cytokine Growth Factor Rev. 26: 425, 2015.
[11]Liao et al., Cancer Res. 73: 5195-5205, 2013.
[12]Martincorena et al., Science 348: 880 (2015).
[13]U.S. Patent Application Publication No. US2016/0235744A1.
[14]U.S. Pat. No. 9,254,288B2.
[15]U.S. Pat. No. 9,267,176B2.
[16]U.S. Patent Application Publication No. S2016/0215350A1.
[17]European Patent Application Publication No. EP3023101A1.
[18]PCT Patent Application Publication No. WO2016105503A1.
[19]Rivera et al., Acta. Neuropathol., 131(6): 847-63, 2016.
[20]Lo Iacono et al., Oncotarget., 7(12): 14394-404, 2016.
[21]Deeken et al., Journal of Clinical Oncology, 34: Supp. Supplement 15, pp. iii93. Abstract Number: e17520, 2016 Annual Meeting of the American Society of Clinical Oncology, Chicago, IL.
[22]Sullivan et al., Journal of Clinical Oncology, 34: Supp. Supplement 15, pp. iii93. Abstract Number: 11596, 2016 Annual Meeting of the American Society of Clinical Oncology, Chicago, IL.
[23]Nguyen et al., Molecular Cancer Therapeutics, Vol. 14, No. 12, Supp. 2, Abstract Number: C199, AACR-NCI-EORTC International Conference: Molecular Targets and Cancer Therapeutics, 2015.
[24]Li et al., Hum. Pathol., 55: 143-50, 2016.
[25]European Patent No. EP2203449B1.
[26]Yoza et al., Genes Cells., (10): 1049-1058, 2016.
[27]U.S. Pat. No. 9,254,288B2.
[28]European Patent Application Publication No. 3023101A1.
[29]PCT Application Publication No. WO 2015/099127A1.
[30]European Patent No. EP2203449B1.
[31]Yoza et al., Genes Cells., (10): 1049-1058, 2016.
[32]Bunney et al., EbioMedicine, 2(3): 194-204, 2015.
[33]Byron et al., Neoplasia, 15(8): 975-88, 2013.
[34]European Patent Application Publication No. EP3023101A1.
[35]PCT Application Publication No. WO 2015/099127A1.
[36]Thussbas et al., J. Clin. Oncol., 24(23): 3747-55, 2006.
[37]Chell et al., Oncogene, 32(25): 3059-70, 2013.

FGFR Gene Amplification

FGFR amplification often leads to FGFR overexpression, which can provoke ligand-independent signaling. In breast cancer, amplification of the genoric locus of FGFR1 (8p11-12) occurs in approximately 10% of predominantly estrogen receptor (ER)-positive patients (Taylor J G, et al., J Clin Invest 2009; 119:3395-4307). In vitro studies support the potential oncogenic nature of FGFR1 amplification (Welm B E, et al., J Cell Biol 2002; 157:703-14); however, due to the gene-dense nature of the 8p11-12 amplicon in breast cancer, there is continuing debate about the identity of the driving oncogene. More recently, FGFR, has been found to be amplified in 22% of squamous NSCLC (Weiss J, et al., Sci Transl Med 2010; 2:62ra93), and these amplifications seem to confer dependence upon FGFR signaling. Unlike the broad amplicon containing FGFR1 found in breast cancers, the amplicon in lung is more focal; it remains to be seen if these differences influence the degree of oncogenic addiction to FGFR1. FGFR2 amplifications have been reported in up to 10% of gastric cancers, most of which are diffuse-type with relatively poor prognosis (Kunii K, et al., Cancer Res 2008; 68:2340-2348). Further, in an FGFR2-amplified gastric cancer cell line, Snu-16, FGFR2 downregulation led to significant inhibition of cell growth and survival that further translated into tumor growth regression in vivo (Xie L, et al., AZD4547, a potent and selective inhibitor of FGF-receptor tyrosine kinases 1, 2 and 3, inhibits the growth of FGF-receptor 2 driven gastric cancer models in vitro and in vivo. In: Proceedings of the American Association of Cancer Research Annual Meeting; 2011 Apr. 2-6; Orlando (Fla.). Philadelphia (Pa.): AACR; 2011. Abstract nr 1643). In some gastric cancer cell lines, FGFR2 amplification is accompanied by deletion of the coding exon located proximal to the C-terminus (Ueda T, et al., Cancer Res 1999; 59:6080-6086). This deletion impedes receptor internalization, thereby contributing to constitutive activation of the receptor. The presence of FGFR2 gene amplifications in gastric cancer is associated with sensitivity to inhibition of FGFR signaling by tyrosine kinase inhibitors and monoclonal antibodies in preclinical models (Zhao G, et al., Mol Cancer Ther 2011; 10:2200-2210; Zhao W M, et al., Clin Cancer Res 2010; 16:5750-5758). Non-limiting examples of FGFR-associated cancers that are caused (or caused in-part) by the amplification and/or overexpression of the FGFR1 gene, the FGFR2 gene, the FGFR3 gene, or the FGFR4 gene are listed in Table B.

TABLE B

Overexpression or Amplification of FGFR Genes and FGFR-Associated Cancer

| FGFR Gene | Type of Dysregulation | FGFR-Associated Cancer |
| --- | --- | --- |
| FGFR1 | Amplification or Overexpression | Breast cancer or carcinoma (e.g., hormone receptor-positive breast cancer, ductal carcinoma in situ (breast)), pancreatic ductal adenocarcinoma, pancreatic exocrine carcinoma, smoking-associated lung cancer, small cell lung cancer, lung adenocarcinoma, non-small cell lung cancer, squamous cell lung cancer or carcinoma, prostate cancer or carcinoma, ovarian cancer, fallopian tube carcinoma, bladder cancer, rhabdomyosarcoma, head and neck carcinoma (e.g., head and neck squamous cell carcinoma), esophageal cancer (e.g., esophageal squamous cell carcinoma), sarcoma (e.g., osteosarcoma), hepatocellular carcinoma, renal cell carcinoma, colorectal cancer (e.g., colorectal adenocarcinoma), prostate cancer, salivary gland tumors, glioblastoma multiforme, urinary bladder cancer, urothelial carcinoma, carcinoma of unknown primary, squamous non-lung tumors, gastric cancer, gastroesophageal junction carcinoma, adenoid cystic carcinoma, anal squamous cell carcinoma, oral squamous cell carcinoma, cholangiocarcinoma, hemangioendothelioma, leiomyosarcoma, melanoma, neuroendocrine carcinoma, squamous cell carcinoma, uterine carcinosarcoma |
| FGFR2 | Amplification | Gastric cancer, gastroesophageal junction adenocarcinoma, breast cancer (e.g., triple-negative breast cancer), colon cancer, colorectal cancer (e.g., colorectal adenocarcinoma), urothelial cancer, bladder adenocarcinoma, carcinoma of unknown primary, cholangiocarcinoma, endometrial adenocarcinoma, esophageal adenocarcinoma, gallbladder carcinoma, ovarian cancer, fallopian tube carcinoma, pancreatic exocrine carcinoma, sarcoma, squamous cell carcinoma |
| FGFR2 | Overexpression | Myxoid lipocarcinoma, rectal cancer, renal cell carcinoma, breast cancer |
| FGFR3 | Upregulation of Activity | Colorectal cancer, hepatocellular carcinoma, pancreatic exocrine carcinoma |
| FGFR3 | Overexpression | Multiple myeloma, thyroid carcinoma, |
| FGFR3 | Amplification | Bladder cancer and salivary adenoid cystic cancer, urothelial cancer, breast cancer, carcinoid, carcinoma of unknown primary, colorectal cancer (e.g., colorectal adenocarcinoma), gallbladder carcinoma, gastric cancer, gastroesophageal junction adenocarcinoma, glioma, mesothelioma, non-small cell lung carcinoma, small cell lung cancer, ovarian cancer, fallopian tube carcinoma, pancreatic exocrine carcinoma |
| FGFR4 | Amplification | Rhabdomyosarcoma, prostate cancer or carcinoma, breast cancer, urothelial cancer, carcinoid, carcinoma of unknown primary, esophageal adenocarcinoma, head and neck carcinoma, hepatocellular carcinoma, non-small cell lung carcinoma, ovarian cancer, fallopian tube carcinoma, peritoneal carcinoma, renal cell carcinoma |
| FGFR4 | Upregulation of Activity | Colorectal cancer, hepatocellular carcinoma, adrenal carcinoma, breast cancer |
| FGFR4 | Overexpression | Pancreatic intraepithelial neoplasia, and pancreatic ductal adenocarcinoma |

Fusion Proteins

Several FGFR translocations have been identified to play a role in defects in development and in a wide range of malignancies, whereby chromosomal rearrangement results in a nucleic acid sequence encoding a fusion protein that includes a kinase domain of an FGFR protein and an amino acid sequence from a partner protein. In some examples, fusion proteins are located in the cytosol, do not undergo lysosomal degradation, are not susceptible to feedback inhibition, and are permanently dimerized in the absence of ligand. Such translocations can lead to FGFR overexpression, permanent dimerization of the fusion protein-FGFR complex, and continuous signaling. The mechanism of proliferation is dependent on the type of fusion protein and seems to be disease specific (Jackson C C, et al., Hum Pathol 2010; 41:461-476). For example, a t(4; 14) intergenic translocation, bringing FGFR3 and the adjacent Multiple Myeloma SET domain (MMSET) gene under the control of the Ig heavy chain (IGH) promoter, has been identified in 10% to 20% of multiple myelomas and is associated with poor prognosis and dependence upon FGFR signaling (Chesi M, et al., Nat Genet 1997; 16:260-264; Qing J, et al., J Clin Invest 2009; 119:1216-1229). FGFR3 translocations are rarely found in prodromal conditions of multiple myeloma, implicating these translocations in the conversion to full multiple myeloma. Additional examples of FGFR fusion proteins and the specific FGFR-associated cancers that they cause (or cause in part) are listed in Table C. The expression of FGFR fusion proteins can, e.g., cause (or cause in part) cholangiocarcinoma, bladder cancer, lung cancer, and breast cancer. Additional examples of FGFR fusion proteins are known in the art.

TABLE C

FGFR Fusion Proteins

| FGFR | Fusion Partner | FGFR-Associated Cancer |
|---|---|---|
| FGFR1 | TACC1 | Glioblastoma multiforme |
| FGFR1 | FGFR1 | Urothelial carcinoma |
| FGFR1 | ZMYM2 | 8p11 myeloproliferative syndrome, ALL, CMD, T-lymphoblastic lymphoma, AML[2] |
| FGFR1 | CNTRL | Stem cell myeloproliferative disorders, EMS, AML, CML, T-cell lymphoma |
| FGFR1 | FGFR1OP2 | Myeloproliferative disorders, myeloproliferative disorder stem cell leukemia/lymphoma syndrome, acute myeloid leukemia, 8p11 myeloproliferative disorder, AML, MPN |
| FGFR1 | FGFR1OP(FOP) | Myeloproliferative disorders, e.g., acute myeloid leukemia, T-cell lymphoma, B-cell lymphoma, 8p11 myeloproliferative disorder |
| FGFR1 | ZNF198/RAMP/FIM/ZMYM2 | Myeloproliferative disorder stem cell leukemia/lymphoma syndrome |
| FGFR1 | FOP/FGFR1OP1 | Myeloproliferative disorder stem cell leukemia/lymphoma syndrome and lung cancer, myeloid and lymphoid neoplasms |
| FGFR1 | ZNF198/ZMYM2 | Myeloid and lymphoid neoplasms, 8p11 myeloproliferative disorder |
| FGFR1 | CEP110/CEP1/centriolin | Myeloid and lymphoid neoplasms; 8p11 myeloproliferative disorder |
| FGFR1 | CEP110/CEP1/centriolin | Myeloproliferative disorder stem cell leukemia/lymphoma syndrome; 8p11 myeloproliferative disorder |
| FGFR1 | BCR | Myeloproliferative disorder stem cell leukemia/lymphoma syndrome, 8p11 myeloproliferative disorder, AML, CML, ALL (e.g., B-ALL) |
| FGFR1 | LRRFIP1 | Myeloproliferative disorder stem cell leukemia/lymphoma syndrome, 8p11 myeloproliferative disorder, ALL, CMD, AML |
| FGFR1 | CPSF6 | Hematological Malignancies; 8p11 myeloproliferative disorder, CMD, MPN, AML |
| FGFR1 | BAG4 | Lung squamous cell carcinoma, non-small cell lung cancer |
| FGFR1 | ERLIN2 | Breast cancer |

TABLE C-continued

FGFR Fusion Proteins

| FGFR | Fusion Partner | FGFR-Associated Cancer |
|---|---|---|
| FGFR1 | TRIM24/TIF1 | Myeloproliferative disorder stem cell leukemia/lymphoma syndrome, 8p11 myeloproliferative disorder, AML, MPN |
| FGFR1 | MYO18A | Myeloproliferative disorder stem cell leukemia/lymphoma syndrome, 8p11 myeloproliferative disorder, MPN, AML |
| FGFR1 | CPSF6 | Myeloproliferative disorder stem cell leukemia/lymphoma syndrome |
| FGFR1 | HERV-K | Myeloproliferative disorder stem cell leukemia/lymphoma syndrome, 8p11 myeloproliferative disorder, CMD, MPD, AML |
| FGFR1 | PLAG1 | Head and neck cancer, pleomorphic salivary gland adenocarcinoma |
| FGFR1 | CUX1 | Leukemia, lymphoma, 8p11 myeloproliferative disorder, AML, MPN |
| FGFR1 | FOXO1 | Rhabdomyosarcoma, alveolar rhabdomyosarcoma |
| FGFR1 | SQSTM1 | Leukemia |
| FGFR1 | FN1 | Phosphaturic mesenchymal tumor |
| FGFR1 | NUP98 | 8p11 myeloproliferative disorder |
| FGFR1 | RANBP2/NUP358 | 8p11 myeloproliferative disorder, MPN, AML |
| FGFR1 | TPR | 8p11 myeloproliferative disorder, MPN, T-lymphoblastic lymphoma, MPN T-lymphoblastic lymphoma |
| FGFR1 | ZNF703 | Breast cancer |
| FGFR1 | NTM | Bladder cancer, bladder urothelial (transition cell) carcinoma |
| FGFR1[1] | ZNF343 | Osteosarcoma |
| FGFR1[3] | FOP2 | AML |
| FGFR1[7] | OP2 | AML |
| FGFR1[11] | TKD | Glioma |
| FGFR1[13] | TACC1 | Gastrointestinal stromal tumors |
| FGFR1[15] | ADAM32 | Embryonal Rhabdomyosarcoma |
| FGFR2 | CCAR2 | Lung squamous cell carcinoma |
| FGFR2 | CD44 | Gastric cancer |
| FGFR2 | BICC1 | Metastatic cholangiocarcinoma, cholangiocarcinoma, colorectal cancer, hepatocellular carcinoma, carcinoma of unknown primary |
| FGFR2 | SLC45A3 | Prostate cancer |
| FGFR2 | AFF3 | Breast cancer |
| FGFR2 | CASP7 | Breast cancer |
| FGFR2 | CCDC6 | Breast cancer, cholangiocarcinoma |
| FGFR2 | KIAA1598/SHOOTIN1 | Cholangiocarcinoma, intrahepatic cholangiocarcinoma |
| FGFR2 | KIAA1967 | Lung squamous cell cancer |
| FGFR2 | OFD1 | Thyroid cancer |
| FGFR2 | CIT | Lung adenocarcinoma |
| FGFR2 | AHCYL1 | Cholangiocarcinoma |
| FGFR2 | PPHLN1 | Cholangiocarcinoma |
| FGFR2 | TACC3 | Cholangiocarcinoma, intrahepatic cholangiocarcinoma |
| FGFR2 | MGEA5 | Cholangiocarcinoma, intrahepatic cholangiocarcinoma |
| FGFR2 | FAM76A | Ovarian cancer |
| FGFR2 | FRAG1 | Osteosarcoma |
| FGFR2 | NPM1 | Colorectal carcinoma (e.g., colorectal adenocarcinoma), large cell lung carcinoma |
| FGFR2 | TACC2 | Cancer of unknown primary, gastric cancer, gastroesophageal junction adenocarcinoma |
| FGFR2 | C10orf68 | Gastric cancer, gastroesophageal junction adenocarcinoma |

TABLE C-continued

FGFR Fusion Proteins

| FGFR | Fusion Partner | FGFR-Associated Cancer |
|---|---|---|
| FGFR2 | NCALD | Breast carcinoma |
| FGFR2 | NOL4 | Cholangiocarcinoma |
| FGFR2 | PPAPDC1A | Prostate carcinoma |
| FGFR2[5] | PARK2 | Cholangiocarcinoma |
| FGFR2[5] | ZDHHC6 | Cholangiocarcinoma |
| FGFR2[6] | TXLNA | Biliary tract cancer |
| FGFR2[6] | KCTD1 | Biliary tract cancer |
| FGFR2[6] | BICC1 type 2 | Biliary tract cancer |
| FGFR2[8] | CCDC147 | Cholangiocarcinoma |
| FGFR2[8] | VCL | Cholangiocarcinoma |
| FGFR2[9] | BUB1 | Cholangiocarcinoma |
| FGFR2[9] | CDCA8 | Cholangiocarcinoma |
| FGFR2[9] | DNAH5 | Cholangiocarcinoma |
| FGFR2[10] | FGFR2-OGDH | Anaplastic thyroid carcinoma |
| FGFR2[12] | CCDC3 | Breast carcinoma |
| FGFR2[14] | KIAA217 | Cholangiocarcinoma |
| FGFR2[16] | KIAA1598 | Intrahepatic cholangiocarcinoma |
| FGFR3 | ELAVL3 | Glioblastoma multiforme |
| FGFR3 | TACC3 | Bladder cancer, oral cancer, head and neck squamous cell carcinoma, lung squamous cell carcinoma, cervical carcinoma or cancer, cervical adenocarcinoma, gallbladder cancer or carcinoma, lung adenocarcinoma, non-small cell lung cancer, glioma, glioblastoma multiforme, carcinoma of unknown primary, endometrial adenocarcinoma, glioma, renal cell carcinoma, urothelial carcinoma, pancreatic exocrine carcinoma, urothelial carcinoma |
| FGFR3 | BAIAP2L1 | Bladder cancer, lung adenocarcinoma, lung squamous cell carcinoma |
| FGFR3 | IGH | Multiple myeloma |
| FGFR3 | MMSET | Multiple myeloma |
| FGFR3 | TEL/ETV6 | T-cell lymphoma |
| FGFR3 | JAKMIP1 | Bladder cancer, bladder urothelial (transition cell) carcinoma, urothelial carcinoma |
| FGFR3 | TNIP2 | Bladder urothelial (transition cell) carcinoma, urothelial carcinoma |
| FGFR3 | WHSC1 | Breast carcinoma |
| FGFR3 | ADD1 | Urothelial carcinoma |
| FGFR3[4] | RANBP17 | Breast carcinoma |

[1] Baroy et al., *PloS One*; 11(9): e0163859. doi: 10.1371/journal.pone.0163859, 2016.
[2] Ren et al., *Int. J. Cancer*, 139(4): 836-40, 2016.
[3] Marchwicka et al., *Cell Biosci.*, 6: 7. doi: 10.1186/s13578-016-0075-9, 2016.
[4] PCT Patent Application Publication No. WO 2014/071419A2.
[5] U.S. Patent Application Publication No. 2015/0366866A1.
[6] PCT Patent Application Publication No. WO 2016/084883A1.
[7] PCT Patent Application Publication No. WO 2016/030509A1.
[8] PCT Patent Application Publication No. WO 2015/150900A2.
[9] PCT Patent Application Publication No. WO 2015/120094A2.
[10] Kasaian et al., *BMC Cancer*, 15: 984, 2015.
[11] Vakil et al., *Neuro-Oncology*, 18: Supp. Supplement 3, pp. iii93. Abstract Number: LG-64, 17th International Symposium on Pediatric Neuro-Oncology, Liverpool, United Kingdom, 2016.
[12] Astsaturov et al., *Journal of Clinical Oncology*, 34: Supp. Supplement 15, Abstract Number: 11504, 2016 Annual Meeting of the American Society of Clinical Oncology, Chicago, IL.
[13] Heinrich et al., *Journal of Clinical Oncology*, 34: Supp. Supplement 15, Abstract Number: 11012, 2016 Annual Meeting of the American Society of Clinical Oncology, Chicago, IL.
[14] Hall et al., *Molecular Cancer Therapeutics*, Vol. 14, No. 12, Supp.2, Abstract Number: B151, AACR-NCI-EORTC International Conference: Molecular Targets and Cancer Therapeutics, 2015.
[15] Reuther et al., *Journal of Molecular Diagnostics*, Vol. 17, No. 6, pp. 813, Abstract Number: ST02, 2015 Annual Meeting of the Association for Molecular Pathology, Austin, TX.
[16] Moeini et al., *Clin. Cancer. Res.*, 22(2): 291-300, 2016.

Autocrine and Paracrine Signaling

Although many of the mechanisms discussed so far are the result of genetic dysregulation of the FGF/FGFR signaling axis, ligand-dependent signaling is also likely to play a key role in cancer development (e.g., described as "Upregulation of Activity" in Table 2). Autocrine FGF overproduction has been reported in many tumor types (Turner N, Grose R., Nat Rev Cancer 2010; 10:116-129). In vitro studies have shown that FGF5 overexpression has been associated with a number of tumor cell lines (lung, esophagus, melanoma, colon, and prostate; Hanada K, et al., Cancer Res 2001; 61:5511-5516), and in hepatocellular carcinomas (HCC), the upregulation of FGF2, 8, 17, and 18 initiates autocrine growth stimulation, cell survival, and neoangiogenesis (Uematsu S, et al., J Gastroenterol Hepatol 2005; 20:583-588; Hu M C, et al., Mol Cell Biol 1998; 18:6063-6074; Kin M, et al., J Hepatol 1997; 27:677-687; Gauglhofer C, et al., Hepatology 2011; 53:854-864). Further, HCC has been found to develop in transgenic mice overexpressing the hormonal FGF19 (Nicholes K, et al., Am J Pathol 2002; 160:2295-2307), and FGF19 is found on an amplicon on chromosome 11q that also invariably contains the adjacent FGF3, FGF4, and Cyclin D1 (CCND1) genes. This amplicon is found in various diseases, including head and neck squamous cell carcinoma, breast cancer, and squamous NSCLC. Although there is uncertainty about the key oncogenic gene on this amplicon or a presumption that it is CCND1, genetic knockdown of FGF19 inhibits the growth of HCC cell lines carrying the amplicon (Sawey E T, et al., Cancer Cell 2011; 19:347-358). Autocrine FGF2-FGFR1 feedback loops have also been reported in NSCLC cell lines and in human melanomas grown as subcutaneous tumors in nude mice (Marek L, et al., Mol Pharmacol 2009; 75:196-207; Wang Y, Becker D., Nat Med 1997; 3:887-893).

Paracrine production of FGFs has also been reported in multiple tumor types. High levels of serum FGF2 have been observed in small cell lung cancer and are associated with a poor prognosis (Ruotsalainen T, et al., Cancer Epidemiol Biomarkers Prev 2002; 11:1492-1495), possibly because of an FGF2-mediated cytoprotective effect, whereby the expression of antiapoptotic proteins are upregulated, promoting resistance to current anticancer treatments (Pardo O E, et al., EMBO J 2006; 25:3078-3088). Increased paracrine expression of one or more of FGF1, 2, 4, 5, 8, and 18 has been found to promote tumor neoangiogenesis in preclinical models via the main endothelial FGFRs, FGFR1 and 2 (Presta M, et al., Cytokine Growth Factor Rev 2005; 16:159-178). Poor prognosis has been associated with neoangiogenesis in ovarian cancer and melanomas (Birrer M J, et al., J Clin Oncol 2007; 25:2281-2287).

Altered FGFR mRNA Splicing

In addition to overexpression of FGFs, altered splicing of FGFR mRNAs is another mechanism by which ligand-dependent signaling is upregulated. Altered FGFR mRNA splicing can allow tumor cells to be stimulated by a broader range of FGFs than would be capable under normal physiologic conditions (Zhang X, et al., J Biol Chem 2006; 281:15694-15700). Altered splicing of the IgIII domains in FGFRs 1, 2, and 3 can switch receptor binding affinity in cancer cells towards FGFs found in the healthy stroma, creating an aberrant paracrine signaling loop (Wesche J, Haglund K, Haugsten E M. et al., Biochem J 2011; 437: 199-213). In bladder and prostate cancer cell lines, a switch from the FGFR2-IIIb isoform to the IIIc isoform has been associated with tumor progression, epithelial-mesenchymal transition, and increased invasiveness (Wesche J, et al., Biochem J 2011; 437:199-213).

Non-limiting examples of FGFR-associated cancers include urothelial carcinoma, breast carcinoma or cancer (e.g., hormone receptor-positive breast cancer, triple-negative breast cancer, neuroendocrine carcinoma of the breast, mammary carcinoma), endometriod endometrial cancer or endometrial cancer (e.g., endometrial adenocarcinoma), ovarian carcinoma or cancer (e.g., ovarian serous cancer), brain cancer (e.g., glioneural tumors, glioma, pilocytic astrocytoma, rosette-forming glioneural tumor), cholangiocarcinoma (e.g., intrahepatic cholangiocarcinoma, metastatic cholangiocarcinoma, medulloblastoma), gastric or stomach cancer (e.g., gastric adenocarcinoma), gastrointestinal stromal tumors, lung cancer (e.g., non-small cell lung carcinoma or lung large cell carcinoma, smoking-associated lung cancer, small cell lung cancer, lung adenocarcinoma, squamous cell lung cancer or carcinoma, lung neuroendocrine carcinoma), pancreatic cancer (e.g., pancreatic exocrine carcinoma, pancreatic ductal adenocarcinoma, pancreatic intraepithelial neoplasia), prostate cancer, colorectal carcinoma or cancer, rectal cancer, renal cell carcinoma, neuroendocrine carcinoma, head and neck (squamous) carcinoma or head and neck adenoid cystic carcinoma, skin cancer (e.g., melanoma), leiomyosarcoma, sarcoma (e.g., osteosarcoma or soft tissue sarcoma), osteosarcoma, bladder cancer, uterine cancer, urinary bladder cancer, rhabdomyosarcoma (e.g., alveolar rhabdomyosarcoma or embryonal rhabdomyosarcoma), esophageal cancer (e.g., esophageal adenocarcinoma), hepatocellular carcinoma or liver cancer, biliary tract cancer, salivary gland tumors (e.g., pleomorphic salivary gland adenocarcinoma), glioblatoma multiforme, myxoid lipocarcinoma, oral cancer (e.g., oral squamous cell carcinoma), thyroid cancer or carcinoma, anaplastic thyroid carcinoma, adenoid cystic carcinoma (e.g., salivary adenoid cystic cancer), glioblastoma multiforme, myeloproliferative disorders/hematological malignancies (e.g., 8p11 myeloproliferative syndrome, lymphoma (e.g., T-lymphoblastic lymphoma, T-cell lymphoma, B-cell lymphoma), leukemia (e.g., acute lymphoblatic leukemia (ALL), chronic myelogenous leukemia (CML), acute myeloid leukemia (AML)), myeloproliferative neoplasm, myeloid and lymphoid neoplasms, stem cell myeloproliferative disorders, myeloproliferative disorder stem cell leukemia/lymphoma syndrome, chronic myeloid disorder, myeloma (e.g., multiple myeloma)), phosphaturic mesenchymal tumor, cervical cancer (e.g., cervical squamous cell carcinoma), gallbladder cancer, spermatocytic seminoma, seborrheic keratosis, testicular cancer, mesothelioma, dysembryoplastic neuroepithelial tumor, and dedifferentiated liposarcoma. Additional examples of FGFR-associated cancers are listed in Tables 1-3.

Non-limiting examples of additional FGFR-associated diseases that are caused by dysregulation of FGFR are listed in Table D. A subject having any of the additional FGFR-associated diseases described herein or known in the art can be treated by administering to the subject a therapeutically effective amount of a compound of General Formula I (e.g., any of the exemplary compounds described herein).

TABLE D

Additional FGFR-associated diseases caused or caused in part by deregulation of a FGFR

| FGFR | | |
|---|---|---|
| FGFR1 | A344G | Jackson-Weiss Syndrome |
| FGFR1 | P252R | Pfeiffer Syndrome[1,8] |
| FGFR1 | Splice-site mutation (c.91 + 2T > A) | Hypogonadotropic Hypogonadism[2] |
| FGFR1 | G48S | Hypogonadotropic Hypogonadism 2 with or without anosmia |
| | G70R | |
| | N77K | |
| | R78C | |
| | G97D | |
| | Y99C | |
| | C101F | |

TABLE D-continued

Additional FGFR-associated diseases caused or caused in part by deregulation of a FGFR

| FGFR | | |
|---|---|---|
| | V102I | |
| | V116I | |
| | N117S | |
| | D129A | |
| | A167S | |
| | V174A | |
| | C178S | |
| | D224H | |
| | Y228D | |
| | G237D | |
| | G237S | |
| | I239T | |
| | L245P | |
| | R250Q | |
| | R250W | |
| | R254Q | |
| | G270D | |
| | V273M | |
| | E274G | |
| | V273M | |
| | E274G | |
| | C277Y | |
| | P283R | |
| | S332C | |
| | Y339C | |
| | L342S | |
| | A343V | |
| | S346C | |
| | G348R | |
| | P366L | |
| | R470L | |
| | P483T | |
| | A520T | |
| | I538V | |
| | V607M | |
| | K618N | |
| | H621R | |
| | R622G | |
| | R622Q | |
| | W666R | |
| | E670K | |
| | A671P | |
| | S685F | |
| | G687R | |
| | E692G | |
| | I693F | |
| | G703R | |
| | G703S | |
| | M719R | |
| | P722H | |
| | P722S | |
| | N724K | |
| | P745S | |
| | D768Y | |
| | P772S | |
| | V975I | |
| FGFR1 | N330I | Osteoglyophonic Dysplasia |
| | Y374C | |
| | C381R | |
| FGFR1 | L165S | Hartsfield Syndrome |
| | L191S | |
| | G490R | |
| | D623Y | |
| | R627T | |
| | N628K | |
| | C725Y | |
| FGFR1 | I300T | Trigonocephaly 1 |
| FGFR1 | c.730_731insG | Craniosynostosis[14] |
| FGFR1 | N546K | Encephalocraniocutaneous lipomatosis[31] |
| | K656E | |
| FGFR1 | P33Afs*17 | Kallman syndrome[37] |
| | Y654* | |
| | W4C | |
| | S96C | |
| | M719V | |

TABLE D-continued

Additional FGFR-associated diseases caused or caused in part by deregulation of a FGFR

| FGFR | | |
|---|---|---|
| | A353T in alternatively spliced xon 8A | |
| FGFR1 | FN1 | Tumor-induced osteomalacia (TIO)[38] |
| FGFR1 | C178S | Kallman syndrome[39] |
| FGFR1 | R473Q | Congenital heart disease associated with ambiguous genitalia[41] |
| FGFR2 | D321A | Pfeiffer Syndrome[9] |
| | T341P | |
| | C342R | |
| | C342Y | |
| FGFR2 | S267P | Crouzon Syndrome[10] |
| | C278F | |
| | Q289P | |
| | Y328C | |
| | Y340H | |
| | C342Y | |
| | C342R | |
| | C342S | |
| | C342F | |
| | S347C | |
| | S354C | |
| FGFR2 | S252W | Apert Syndrome[11] |
| | P253R | |
| FGFR2 | A344G | Jackson-Weiss Syndrome[12] |
| FGFR2 | W290C | Craniosynostosis[13] |
| | D321A | |
| | Y340C | |
| | C342R | |
| | C342S | |
| | C342W | |
| | N549H | |
| | K641R | |
| FGFR2 | N549T | Crouzon syndrome[20] |
| FGFR2 | S347C | Jackson-Weiss syndrome[20] |
| FGFR2 | S252L | Crouzon syndrome[20] |
| FGFR2 | W290R | Crouzon syndrome[22] |
| FGFR2 | Y281C | Crouzon syndrome[24] |
| | p.273insE | |
| FGFR2 | R255Q | Ectrodactyly Lethal Pulmonary Acinar Dysplasia[25] |
| FGFR2 | C382R | Papillomatous pedunculated sebaceous naevus (PPSN)[27] |
| FGFR2 | Y375C | Beare-Stevenson syndrome (BSS)[28] |
| | S372C | |
| FGFR2 | Atypical splice mutation (940-2A →G) | Apert syndrome[29] |
| FGFR3 | G375C | Achondroplasia |
| | G380R | |
| FGFR3 | P250R | Muenke Coronal Craniosynostosis |
| | P250L | |
| FGFR3 | K650E (Activation Loop) | Thanatophoric Dysplasia[3] |
| FGFR3 | G380R | Achondroplasia[4,5] |
| FGFR3 | Point mutation | Thanatophoric Dysplasia[6] |
| FGFR3 | N328I | Hypochondroplasia[7] |
| FGFR3 | K650M | Skeletal Dysplasia[16] |
| FGFR3 | R248C | Thanatophoric dysplasia type I[17] |
| | S248C | |
| | G370C | |
| | S371C | |
| | Y373C | |
| | X807R | |
| | X807C | |
| | X807G | |
| | X807S | |
| | X807W | |
| | K650M | |
| FGFR3 | K650E | Thanatophoric dysplasia type II[17] |
| FGFR3 | A391G | Crouzon syndrome[17] |
| FGFR3 | N540S | Hypochondroplasia[18] |
| | N540T | |
| FGFR3 | G374R | Achondroplasia[19] |
| FGFR3 | R248C | Seborrheic keratosis[19] |
| | A393E | |
| FGFR3 | L324H | Hypochondroplasia[21] |
| FGFR3 | c.746C > G | Thanatophoric Dysplasia type I[23] |
| FGFR3 | c.1138G > A | Achondroplasia[26] |
| FGFR3 | R248delinsLC | Thanatophoric dysplasia[30] |
| FGFR3 | K650T | Acanthosis nigricans[32] |
| FGFR3 | c.1959 + 19G > A | Achondroplasia[33] |
| FGFR3 | S348C | Achondroplasia[34] |
| FGFR3 | Y367C | Achondroplasia[35] |
| FGFR3 | S344C | Achondroplasia[36] |
| FGFR3 | R621H | CATSHL syndrome[40] |

[1] Yong-Xing et al., *Hum. Mol. Genet.* 9(13): 2001-2008, 2000.
[2] Eeva-Maria Laitinen et al., *PLoS One* 7(6): e39450, 2012.
[3] Hart et al., *Oncogene* 19(29): 3309-3320, 2000.
[4] Shiang et al., *Cell* 76: 335-342, 1994.
[5] Rosseau et al., *Nature* 371: 252-254, 1994.
[6] Tavormina et al., *Nature Genet.* 9: 321-328, 1995.
[7] Bellus et al., *Nature Genet.* 10: 357-359, 1995.
[8] Muenke et al., *Nature Genet.* 8: 269-274, 1994.
[9] Rutland et al., *Nature Genet.* 9: 173-176, 1995.
[10] Reardon et al., *Nature Genet.* 8: 98-103, 1994.
[11] Wilkie et al., *Nature Genet.* 9: 165-172, 1995.
[12] Jabs et al., *Nature Genet.* 8: 275-279, 1994.
[13] Japanese Patent No. JP05868992B2.
[14] Ye et al., *Plast. Reconstr. Surg.*, 137(3): 952-61, 2016.
[15] U.S. Patent No. 9447098B2.
[16] Bellus et al., *Am. J. Med. Genet.* 85(1): 53-65, 1999.
[17] PCT Patent Application Publication No. WO2016139227A1.
[18] Australian Patent Application Publication No. AU2014362227A1.
[19] Chinese Patent No. CN102741256B.
[20] Ohishi et al., *Am. J. Med. Genet. A.*, doi: 10.1002/ajmg.a.37992, 2016.
[21] Nagahara et al., *Clin. Pediatr. Endocrinol.*, 25(3): 103-106, 2016.
[22] Hibberd et al., *Am. J. Med. Genet. A.*, doi: 10.1002/ajmg.a.37862, 2016.
[23] Dias et al., *Exp. Mol. Pathol.*, 101(1): 116-23, 2016.
[24] Lin et al., *Mol. Med. Rep.*, 14(3): 1941-6, 2016.
[25] Barnett et al., *Hum. Mutat.*, 37(9): 955-63, 2016.
[26] Krstevska-Konstantinova et al., *Med. Arch.*, 70(2): 148-50, 2016.
[27] Kuentz et al., *Br. J. Dermatol.*, doi: 10.1111/bjd.14681, 2016.
[28] Ron et al., *Am. J. Case Rep.*, 15; 17: 254-8, 2016.
[29] Fernandes et al., *Am. J. Med. Genet. A.*, 170(6): 1532-7, 2016.
[30] Lindy et al., *Am. J. Med. Genet. A.*, 170(6): 1573-9, 2016.
[31] Bennett et al., *Am. J. Hum. Genet.*, 98(3): 579-87, 2016.
[32] Ichiyama et al., *J. Eur. Acad. Dermatol. Venereol.*, 30(3): 442-5, 2016.
[33] Zhao et al., *Int. J. Clin. Exp. Med.*, 8(10): 19241-9, 2015.
[34] Hasegawa et al., *Am. J. Med. Genet. A.*, 170A(5): 1370-2, 2016.
[35] Legeai-Mallet, *Endocr. Dev.*, 30: 98-105, 2016.
[36] Takagi, *Am. J. Med. Genet. A.*, 167A(11): 2851-4, 2015.
[37] Goncalves, *Fertil. Steril.*, 104(5): 1261-7.e1, 2015.
[38] Miller et al., *Journal of Clinical Oncology*, 34: Supp. Supplement 15, pp. iii93. Abstract Number: e22500, 2016 Annual Meeting of the American Society of Clinical Oncology, Chicago, IL.
[39] Sarabipour et al., *J. Mol. Biol.*, 428(20): 3903-3910, 2016.
[40] Escobar et al., *Am. J. Med. Genet. A.*, 170(7): 1908-11, 2016.
[41] Mazen et al., *Sex Dev.*, 10(1): 16-22, 2016.

Additional point mutations in FGFR1, FGFR2, FGFR3, and FGFR4 have been identified to result in resistance of a cancer cell to a FGFR inhibitor. Non-limiting examples of these mutations are depicted in Table E. In some embodiments, a FGFR-associated disorder (e.g., any of the cancers described herein) can have one or more of the point mutations listed in Table D. Also provided herein are methods of treating a subject that include identifying a subject having one or more of the point mutations listed in Table D, and administering to the identified subject a therapeutically effective amount of a compound of General Formula I (e.g., any of the exemplary compounds described herein), or a pharmaceutically acceptable salt of solvate thereof. Also provided are methods of treating a subject that include administering to a subject identified as having one or more of the point mutations listed in Table D a therapeutically effective amount of a compound of General Formula I (e.g., any of the exemplary compounds described herein).

TABLE E

Exemplary FGFR Inhibitor Resistance Point Mutations

| FGFR | Point Mutation | Cancer |
| --- | --- | --- |
| FGFR1 | V561M[3] | In vitro study |
| FGFR1 | N546K[5] V561M[5] | In vitro study |
| FGFR1 | V561M[7] Y563C[7] | In vitro study |
| FGFR2 | M536I[1] M538I[1] I548V[1] N550H[1] N550K[1] N550S[1] V565I[1] E566G[1] L618M[1] K642N[1] K660E[1] E719G[1] Y770IfsX14[1] | In vitro study |
| FGFR2 | N550H[2] V565I[2] E566G[2] K660M[2] K660N[2] | In vitro study |
| FGFR2 | V562L[4] V564F[4] | In vitro study |
| FGFR3 | V555M[6] | KMS-11 myeloma cell line derivative |
| FGFR4 | G388R[8] | Breast cancer |

In some embodiments, provided herein is a method for treating a subject diagnosed with a FGFR-associated disorder (e.g., a FGFR-associated cancer), that include administering to the subject a therapeutically effective amount of a compound of General Formula I (e.g., any of the exemplary compounds described herein), or a pharmaceutically acceptable salt or solvate thereof. For example, the FGFR-associated cancer can be any of exemplary FGFR-associated cancers described herein.

In some embodiments, the compounds of the present invention are useful for treating a FGFR-associated disease (e.g., a FGFR-associated cancer) in combination with one or more additional therapeutic agents or therapies that work by the same or a different mechanism of action.

In some embodiments, the additional therapeutic agent(s) is selected from the group of: receptor tyrosine kinase-targeted therapeutic agents, including cabozantinib, crizotinib, erlotinib, gefitinib, imatinib, lapatinib, nilotinib, pazopanib, pertuzumab, regorafenib, and sunitinib.

In some embodiments, the additional therapeutic agent(s) is selected from signal transduction pathway inhibitors, including, e.g., Ras-Raf-MEK-ERK pathway inhibitors (e.g., sorafenib, trametinib, or vemurafenib), PI3K-Akt-mTOR-S6K pathway inhibitors (e.g., everolimus, rapamycin, perifosine, or temsirolimus) and modulators of the apoptosis pathway (e.g., obataclax).

In some embodiments, the additional therapeutic agent(s) is selected from the group of: cytotoxic chemotherapeutics, including, e.g., arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

In some embodiments, the additional therapeutic agent(s) is selected from the group of angiogenesis-targeted therapies, including e.g., aflibercept and bevacizumab.

In some embodiments, the additional therapeutic agent(s) is selected from the group of immune-targeted agents, e.g., including aldesleukin, ipilimumab, lambrolizumab, nivolumab, and sipuleucel-T.

In some embodiments, the additional therapeutic agent(s) is selected from agents active against the downstream FGFR pathway, including, e.g., Ras, MEK, JNK, and p38 kinase inhibitor.

In some embodiments, the additional therapeutic agent or therapy is radiotherapy, including, e.g., radioiodide therapy, external-beam radiation, and radium 223 therapy. In some embodiments, the additional therapeutic agent(s) includes any one of the above listed therapies or therapeutic agents which are standards of care in cancers wherein the cancer has a dysregulation of a FGFR gene, a FGFR protein, or expression or activity, or level of the same.

Methods of detecting dysregulation of a FGFR gene, a FGFR protein, or expression or activity, or level of the same, include, e.g., detection of FGFR gene translocations, e.g., using Fluorescent In Situ Hybridization (FISH) (e.g., the commercially available kits from Empire Genomics and Cell Signaling Technology).

In some embodiments, provided herein is a method of treating cancer (e.g., a FGFR-associated cancer) in a patient, comprising administering to said subject a compound of General Formula I (e.g., any of the exemplary compounds described herein), or a pharmaceutically acceptable salt or solvate thereof, in combination with at least one additional therapy or therapeutic agent selected from radiotherapy (e.g., radioiodide therapy, external-beam radiation, or radium 223 therapy), cytotoxic chemotherapeutics (e.g., arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, or vincristine); tyrosine kinase targeted-therapeutics (e.g., afatinib, cabozantinib, cetuximab, crizotinib, dabrafenib, erlotinib, gefitinib, imatinib, lapatinib, nilotinib, pazopanib, panitumumab, pertuzumab, regorafenib, sunitinib, or trastuzumab); FGFR inhibitors (e.g., ARQ-087, AZD-4547, BGJ398, nintadanib (BIBF 1120), BLU9931, brivanib (BMS-582664), CH5183284, Dovitinib (TKI258, CHIR258), E-3810, EWMD-2076, JNJ-42756493, lenvatinib ((E7080), LY2874455, Orantinib (TSU-68, SU6668), PD089828, PD166866, PD173074, Ponatinib (AP-24534), Semaxanib (SU5416), SSR128129E, SU4984, SU5402, SUN11602), AB1010, BAY 1163877, Debio-1347, FGF401, FIIN-2, HMPL-453, MK-2461, pazopanib (Votrient, GW-786034), PD161570, PD173074, PF-477736, PHA-739358 (danusertib), PRN1371, regorafenib (Stivarga), SPP86, and Tyrphostin AG 1296 and TAS120; apoptosis modulators and signal transduction inhibitors (e.g. everolimus, perifosine, rapamycin, sorafenib, temsirolimus, trametinib, or vemurafenib); immune-targeted therapies (e.g., aldesleukin, interferon alfa-2b, ipilimumab, lambrolizumab, nivolumab, prednisone, or sipuleucel-T); and angiogenesis-targeted therapies (e.g., aflibercept or bevacizumab), wherein the amount of the compound of General Formula I (e.g., any of the exemplary compounds described herein), or a pharmaceutically acceptable salt or solvate thereof, in combination with the additional therapy or therapeutic agent, is effective in treating said cancer. These additional therapeutic agents may be administered with one or more doses of the compound of General Formula I, or the pharmaceutically acceptable salt or solvate thereof, as part of the same or separate dosage forms, via the same or different routes of administration, and on the same or different administration schedules according to standard pharmaceutical practice known to one skilled in the art. In some embodiments, provided herein is a method of treating cancer (e.g., a FGFR-associated cancer) in a patient, comprising administering to said subject a compound of General Formula I (e.g., any of the exemplary compounds described herein), or a pharmaceutically acceptable salt or solvate thereof, in combination with at least one additional therapy or therapeutic agent selected from radiotherapy (e.g., radioiodide therapy, external-beam radiation, or radium 223 therapy), cytotoxic chemotherapeutics (e.g., arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, or vincristine), tyrosine kinase targeted-therapeutics (e.g., afatinib, cabozantinib, cetuximab, crizotinib, dabrafenib, erlotinib, gefitinib, imatinib, lapatinib, nilotinib, pazopanib, panitumumab, pertuzumab, regorafenib, or sunitinib), apoptosis modulators and signal transduction inhibitors (e.g. everolimus, perifosine, rapamycin, sorafenib, temsirolimus, trametinib, or vemurafenib), immune-targeted therapies (e.g., aldesleukin, interferon alfa-2b, ipilimumab, lambrolizumab, nivolumab, prednisone, or sipuleucel-T) and angiogenesis-targeted therapies (e.g., aflibercept or bevacizumab), wherein the amount of the compound of General Formula I (e.g., any of the exemplary compounds described herein), or a pharmaceutically acceptable salt or solvate thereof, in combination with the additional therapy or therapeutic agent, is effective in treating said cancer. These additional therapeutic agents may be administered with one or more doses of the compound of General Formula I, or the pharmaceutically acceptable salt or solvate thereof, as part of the same or separate dosage forms, via the same or different routes of administration, and on the same or different administration schedules according to standard pharmaceutical practice known to one skilled in the art.

Also provided herein is (i) a pharmaceutical combination for treating cancer (e.g., a FGFR-associated cancer) in a subject in need thereof, which comprises (a) a compound of General Formula I (e.g., any of the exemplary compounds described herein), or a pharmaceutically acceptable salt or solvate thereof, (b) an additional therapeutic agent and (c) optionally at least one pharmaceutically acceptable carrier (e.g., for simultaneous, separate or sequential use for the treatment of a cancer), wherein the amounts of the compound of General Formula I, or the pharmaceutically acceptable salt or solvate thereof and of the additional therapeutic agent are together effective in treating said cancer; (ii) a pharmaceutical composition including such a combination; (iii) the use of such a combination for the preparation of a medicament for the treatment of cancer (e.g., a FGFR-associated cancer); and (iv) a commercial package or product including such a combination as a combined preparation for simultaneous, separate or sequential use; and to a method of treatment of cancer (e.g., FGFR-associated cancer) in a subject in need thereof.

Also provided are methods of treating a subject identified or diagnosed as having a FGFR-associated disease (e.g., a FGFR-associated cancer) (e.g., a subject that has been identified or diagnosed as having a FGFR-associated disease (e.g., a FGFR-associated cancer) through the use of a regulatory agency-approved, e.g., FDA-approved, kit for identifying dysregulation of a FGFR gene, a FGFR protein, or expression or activity, or level of the same, in a subject or a biopsy sample from the subject) (e.g., any of the FGFR-associated cancers described herein or known in the art) that include administering the subject a therapeutically effective amount of a compound of General Formula I (e.g., any of the exemplary compounds described herein), or a pharmaceutically acceptable salt or solvate thereof. Also provided is a compound of General Formula I (e.g., any of the exemplary compounds described herein), or a pharmaceutically acceptable salt or solvate thereof, for use in treating a FGFR-associated disease (e.g., a FGFR-associated cancer) in a subject identified or diagnosed as having a FGFR-associated disease (e.g., a FGFR-associated cancer) (e.g., a subject that has been identified or diagnosed as having a FGFR-associated cancer through the use of a regulatory agency-approved, e.g., FDA-approved, kit for identifying dysregulation of a FGFR gene, a FGFR protein, or expression or activity, or level of the same, in a subject or a biopsy sample from the subject) (e.g., any of the FGFR-associated cancers described herein or known in the art). Also provided is the use of a compound of General Formula I (e.g., any of the exemplary compounds described herein), or a pharmaceutically acceptable salt or solvate thereof, for the manufacture of a medicament for treating a FGFR-associated disease (e.g., FGFR-associated cancer) in a subject identified or diagnosed as having a FGFR-associated disease (e.g., FGFR-associated cancer) (e.g., a subject that has been identified or diagnosed as having a FGFR-associated cancer through the use of a regulatory agency-approved, e.g., FDA-approved, kit for identifying dysregulation of a FGFR gene, a FGFR protein, or expression or activity, or level of the same, in a subject or a biopsy sample from the subject) (e.g., any of the FGFR-associated cancers described herein or known in the art).

Also provided are methods of treating a subject (e.g., a subject suspected of having a FGFR-associated disease (e.g., a FGFR-associated cancer), a subject presenting with one or more symptoms of a FGFR-associated disease (e.g., a FGFR-associated cancer), or a subject having an elevated risk of developing a FGFR-associated disease (e.g., FGFR-associated cancer)) that include performing an assay (e.g., an assay that utilizes next generation sequencing, immunohistochemistry, or break apart FISH analysis) (e.g., using a regulatory agency-approved, e.g., FDA-approved, kit) on a sample obtained from the subject to determine whether the subject has dysregulation of a FGFR gene, a FGFR protein, or expression or activity, or level of the same, and administering (e.g., specifically or selectively administering) a therapeutically effective amount of a compound of General Formula I (e.g., any of the exemplary compounds described herein), or a pharmaceutically acceptable salt or solvate thereof, to a subject determined to have dysregulation of a FGFR gene, a FGFR protein, or expression or activity, or levels of the same. Additional assays, non-limiting assays that may be used in these methods are described herein. Additional assays are also known in the art. Also provided is use of a compound of General Formula I (e.g., any of the exemplary compounds described herein), or a pharmaceutically acceptable salt or solvate thereof, for use in treating a FGFR-associated disease (e.g., FGFR-associated cancer) in a subject identified or diagnosed as having a FGFR-associated disease (e.g., a FGFR-associated cancer) through a step of performing an assay (e.g., an in vitro assay) (e.g., an assay that utilizes next generation sequencing, immuno-histochemistry, or break apart FISH analysis) (e.g., using a regulatory agency-approved, e.g., FDA-approved, kit) on a sample obtained from the subject to determine whether the subject has dysregulation of a FGFR gene, a FGFR protein, or expression or activity, or level of the same, where the presence of dysregulation of a FGFR gene, a FGFR protein, or expression or activity, or level of the same, identifies that the subject has a FGFR-associated disorder (e.g., FGFR-associated cancer). Also provided is the use of a compound of General Formula I (e.g., any of the exemplary compounds described herein), or a pharmaceutically acceptable salt or solvate thereof, for the manufacture of a medicament for treating a FGFR-associated disease (e.g., FGFR-associated cancer) in a subject identified or diagnosed as having a FGFR-associated disease (e.g., FGFR-associated cancer) through a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the subject to determine whether the subject has dysregulation of a FGFR gene, a FGFR protein, or expression or activity, or level of the same, where the presence of dysregulation of a FGFR gene, a FGFR protein, or expression or activity, or level of the same, identifies that the subject has a FGFR-associated disease (e.g., FGFR-associated cancer). Some embodiments of any of the methods or uses described herein further include recording in the subject's clinical record (e.g., a computer readable medium) that the subject determined to have dysregulation of a FGFR gene, a FGFR protein, or expression or activity, or level of the same, through the performance of the assay, should be administered a compound of General Formula I (e.g., any of the exemplary compounds described herein), or a pharmaceutically acceptable salt or solvate thereof.

In some embodiments of any of the methods or uses described herein, the subject has been identified or diagnosed as having a cancer with dysregulation of a FGFR gene, a FGFR protein, or expression or activity, or level of the same (e.g., as determined using a regulatory agency-approved, e.g., FDA-approved, assay or kit). In some embodiments of any of the methods or uses described herein, the subject has a tumor that is positive for dysregulation of a FGFR gene, a FGFR protein, or expression or activity, or level of the same (e.g., as determined using a regulatory agency-approved assay or kit). In some embodiments of any of the methods or uses described herein, the subject can be a subject with a tumor(s) that is positive for dysregulation of a FGFR gene, a FGFR protein, or expression or activity, or level of the same (e.g., identified as positive using a regulatory agency-approved, e.g., FDA-approved, assay or kit). In some embodiments of any of the methods or uses described herein, the subject can be a subject whose tumors have dysregulation of a FGFR gene, a FGFR protein, or expression or activity, or a level of the same (e.g., where the tumor is identified as such using a regulatory agency-approved, e.g., FDA-approved, kit or assay). In some embodiments of any of the methods or uses described herein, the subject is suspected of having a FGFR-associated cancer. In some embodiments of any of the methods or uses described herein, the subject has a clinical record indicating that the subject has a tumor that has dysregulation of a FGFR gene, a FGFR protein, or expression or activity, or level of the same (and optionally the clinical record indicates that the subject should be treated with any of the compositions provided herein).

Also provided are methods of treating a subject that include administering a therapeutically effective amount of a compound of General Formula I (e.g., any of the exemplary compounds described herein), or a pharmaceutically acceptable salt or solvate thereof, to a subject having a clinical record that indicates that the subject has dysregulation of a FGFR gene, a FGFR protein, or expression or activity, or level of the same. Also provided is the use of a compound of General Formula I (e.g., any of the exemplary compounds described herein), or a pharmaceutically acceptable salt or solvate thereof, for the manufacture of a medicament for treating a FGFR-associated disease (e.g., FGFR-associated cancer) in a subject having a clinical record that indicates that the subject has dysregulation of a FGFR gene, a FGFR protein, or expression or activity, or level of the same. Also provided is the use of a compound of General Formula I (e.g., any of the exemplary compounds described herein), or a pharmaceutically acceptable salt or solvate thereof, for the manufacture of a medicament for treating a FGFR-associated disease (e.g., a FGFR-associated cancer) in a subject having a clinical record that indicates that the subject has dysregulation of a FGFR gene, a FGFR protein, or expression or activity, or level of the same. Some embodiments of these methods and uses can further include: a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the subject to determine whether the subject has dysregulation of a FGFR gene, a FGFR protein, or expression or activity, or level of the same, and recording information in a subject's clinical file (e.g., a computer-readable medium) that the subject has been identified to have dysregulation of a FGFR gene, a FGFR protein, or expression or activity, or level of the same.

Also provided are methods (e.g., in vitro methods) of selecting a treatment for a subject that include selecting a treatment including administration of a therapeutically effective amount of a compound of General Formula I (e.g., any of the exemplary compounds described herein), or a pharmaceutically acceptable salt or solvate thereof, for a subject identified or diagnosed as having a FGFR-associated disease (e.g., a FGFR-associated cancer) (e.g., a subject that has been identified or diagnosed as having a FGFR-associated cancer through the use of a regulatory agency-approved, e.g., FDA-approved, kit for identifying dysregulation of a FGFR gene, a FGFR protein, or expression or activity, or level of the same, in a subject or a biopsy sample from the subject) (e.g., any of the FGFR-associated cancers described herein or known in the art). Some embodiments can further include administering the selected treatment to the subject identified or diagnosed as having a FGFR-associated disease (e.g., a FGFR-associated cancer). Some embodiments can further include a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the subject to determine whether the subject has dysregulation of a FGFR gene, a FGFR protein, or expression or activity, or level of the same, and identifying or diagnosing a subject determined to have dysregulation of a FGFR gene, a FGFR protein, or expression or activity, or level of the same, as having a FGFR-associated disease (e.g., a FGFR-associated cancer).

Also provided are methods of selecting a treatment for a subject that include administration of a therapeutically effective amount of a compound of General Formula I (e.g., any of the exemplary compounds described herein), or a pharmaceutically acceptable salt or solvate thereof, wherein the methods include a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the subject to determine whether the subject has dysregulation of a FGFR gene, a FGFR protein, or expression or activity, or level of the same, and identifying or diagnosing a subject determined to have dysregulation of a FGFR gene, a FGFR protein, or expression or activity, or level of the same, as having a FGFR-associated cancer, and selecting a therapeutic treatment including administration of a therapeutically effective amount of a compound of General Formula I (e.g., any of the exemplary compounds described herein), or a pharmaceutically acceptable salt or solvate thereof, for the subject identified or diagnosed as having a FGFR-associated disease (e.g., a FGFR-associated cancer). Some embodiments further include administering the selected treatment to the subject identified or diagnosed as having a FGFR-associated disorder (e.g., a FGFR-associated cancer).

Also provided are methods of selecting a subject for treatment including administration of a therapeutically effective amount of a compound of General Formula I (e.g., any of the exemplary compounds described herein), or a pharmaceutically acceptable salt or solvate thereof, that include selecting, identifying, or diagnosing a subject having a FGFR-associated disorder (e.g., a FGFR-associated cancer), and selecting the subject for treatment including administration of a therapeutically effective amount of a compound of General Formula I (e.g., any of the exemplary compounds described herein), or a pharmaceutically acceptable salt or solvate thereof. In some embodiments, identifying or diagnosing a subject as having a FGFR-associated disease (e.g., an FGFR-associated cancer) can include a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the subject to determine whether the subject has dysregulation of a FGFR gene, a FGFR protein, or expression or activity, or level of the same, and identifying or diagnosing a subject determined to have dysregulation of a FGFR gene, a FGFR protein, or expression or activity, or level of the same, as having a FGFR-associated disorder (e.g., a FGFR-associated cancer). In some embodiments, the selecting a treatment can be used as part of a clinical study that includes administration of various treatments of an FGFR-associated disorder (e.g., a FGFR-associated cancer).

In some embodiments of any of the methods or uses described herein, an assay used determine whether the subject has dysregulation of a FGFR gene, a FGFR protein, or expression or activity, or level of the same, using a sample (e.g., a biological sample or a biopsy sample (e.g., a paraffin-embedded biopsy sample) from a subject (e.g., a subject suspected of having a FGFR-associated disease (e.g., a FGFR-associated cancer), a subject having one or more symptoms of a FGFR-associated disease (e.g., a FGFR-associated cancer), and/or a subject that has an increased risk of developing a FGFR-associated disease (e.g., a FGFR-associated cancer)) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a FGFR gene, a FGFR protein, or expression or activity, or levels of the same (see, e.g., the references cited herein).

Exemplary assays for detecting dysregulation of a FGFR gene, a FGFR protein, or expression or activity, or levels of the same are commercially available, e.g., FGFR Pathway Mutation PCR Array (Qiagen), HTG Edge FGFR Expression Assay (HTG Molecular Diagnostics), HTScan® FGF Receptor 1 Kinase Assay Kit (Cell Signaling Technology), Vysis LSI IGH/FGFR3 Dual Color, Dual Fusion Translocation Probe (Abbott Molecular), FGFR1 FISH Probe (Empire Genomics), FGFR1 FISH (Sonic Genomics), FISH IGH/FGFR3 (Quest Diagnostics), FGFR1 (8p11) [RUO] (Leica Biosystems), FGFR1 Break Apart FISH Probe (Empire Genomics), FGFR2/CEN10p FISH Probe (Abnova Corporation), FGFR2 (10q26) [ASR](Leica Biosystems), Anti-FGFR-4 (IN), Z-FISH (AnaSpec), ZytoLight® SPEC FGFR2 Break Apart Probe (Bio-Optica), FGFR3 (4p16.3) (ZytoVision), and ZytoLight® SPEC FGFR3/CEN4 Dual Color Probe (ZytoVision). Additional assays for detecting dysregulation of a FGFR gene, a FGFR protein, or expression or activity or levels of the same are known in the art.

Also provided are methods of increasing the time of remission of a FGFR-associated cancer in a patient that include (a) selecting, identifying, or diagnosing a patient as having a FGFR-associated cancer (e.g., any of the FGFR-associated cancers described herein), and (b) administering a therapeutically effective amount of a compound of General Formula I (e.g., any of the exemplary compounds described herein), or a pharmaceutically acceptable salt or solvate thereof. Also provided are methods of increasing the time of remission of a FGFR-associated cancer in a patient that include administering a therapeutically effective amount of a compound of General Formula I (e.g., any of the exemplary compounds described herein), or a pharmaceutically acceptable salt or solvate thereof to a patient having a FGFR-associated cancer (e.g., any of the exemplary FGFR-associated cancers described herein). In some examples of any of the methods of increasing the time of remission of a FGFR-associated cancer in a patient, the increase in the time of remission is compared to a control patient (e.g., a patient or a population of patients having the same or a similar type of FGFR-associated cancer). In some examples, the patient is not yet in remission. In other examples, the patient is already in remission. In some examples, the increase in remission is a statistically significant increase. In some examples, the increase in the time of remission is about 1 day to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, about 6 months, about 4 months, about 2 months, about 1 month, or about 2 weeks; about 2 weeks to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, about 6 months, about 4 months, about 2 months, or about 1 month; about 1 month to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, about 6 months, about 4 months, or about 2 months; about 2 month to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, about 6 months, or about 4 months; about 4 month to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 15 years, about 1 year, about 10 months, about 8 months, or about 6 months; about 6 month to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, or about 8 months; about 8 month to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, or about 10 months; about 10 month to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, or about 1 year; about 1 year to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, or about 1.5 years; about 1.5 years to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, to about 2 years; about 2 years to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, or about 2.5 years; about 2.5 years to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, or about 3 years; about 3 years to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, or about 3.5 years; about 3.5 years to about 10 years, about 9.5 years, about 9 years, about 8.5 years, about 8 years, about 7.5 years, about 7 years, about 6.5 years, about 6 years, about 5.5 years, about 5 years, about 4.5 years, or about 4 years; about 4 years to about 10 years, about 9.5 years, about 9 years, about 8.5 years, about 8 years, about 7.5 years, about 7 years, about 6.5 years, about 6 years, about 5.5 years, about 5 years, or about 4.5 years; about 4.5 years to about 10 years, about 9.5 years, about 9 years, about 8.5 years, about 8 years, about 7.5 years, about 7 years, about 6.5 years, about 6 years, about 5.5 years, or about 5 years; about 5 years to about 10 years, about 9.5 years, about 9 years, about 8.5 years, about 8 years, about 7.5 years, about 7 years, about 6.5 years, about 6 years, or about 5.5 years; about 5.5 years to about 10 years, about 9.5 years, about 9 years, about 8.5 years, about 8 years, about 7.5 years, about 7 years, about 6.5 years, or about 6 years; about 6 years to about 10 years, about 9.5 years, about 9 years, about 8.5 years, about 8 years, about 7.5 years, about 7 years, or about 6.5 years; about 6.5 years to about 10 years, about 9.5 years, about 9 years, about 8.5 years, about 8 years, about 7.5 years, or about 7 years; about 7 years to about 10 years, about 9.5 years, about 9 years, about 8.5 years, about 8 years, or about 7.5 years; about 7.5 years to about 10 years, about 9.5 years, about 9 years, about 8.5 years, or about 8 years; about 8 years to about 10 years, about 9.5 years, about 9 years, or about 8.5 years; about 8.5 years to about 10 years, about 9.5 years, or about 9 years; about 9 years to about 10 years or about 9.5 years; or about 9.5 years to about 10 years (e.g., compared to a control patient, e.g., a patient or a population of patients having the same or a similar type of FGFR-associated cancer).

Also provided is a compound of General Formula I or pharmaceutically acceptable salt or solvate thereof for use in increasing the time of remission of a FGFR-associated cancer in a patient. Also provided is the use of a compound of General Formula I or a pharmaceutically acceptable salt or solvate thereof in the manufacture of a medicament for increasing the time of remission of a FGFR-associated cancer in a patient.

Methods for determining whether or not a patient is in remission are known by those skilled in the art. For example, a PET scan, MRI, CT scan, ultrasound, and X-ray of the patient's body may be obtained, and such data can be used to determine whether or not a patient is in remission. In some examples, diagnostic tests can be performed on samples from a patient (e.g., a blood sample or a biopsy) to determine whether or not the patient is still in remission.

Also provided are methods of increasing the time of survival of a patient having a FGFR-associated cancer that include: selecting, diagnosing, or identifying a patient as having a FGFR-associated cancer; and administering to a subject selected, diagnosed, or identified as having a FGFR-associated cancer a therapeutically effective amount of a compound of General Formula I or a pharmaceutically acceptable salt or solvate thereof. Also provided are methods of increasing the time of survival of a patient having a FGFR-associated cancer that include administering to a subject having a FGFR-associated cancer a therapeutically effective amount of a compound of General Formula I or a pharmaceutically acceptable salt or solvate thereof. In some embodiments of any of the methods of increasing the time of survival of a subject having a FGFR-associated cancer, the increase in the time of survival is compared to a control patient (e.g., a patient or a population of patients having the same or a similar type of FGFR-associated cancer). In some examples, the patient can have an early stage of a FGFR-associated cancer (e.g., Stage 1 or 2). In some embodiments, the patient can have a late stage of a FGFR-associated cancer (e.g., Stage 3 or 4). In some examples, the increase in the time of survival is a statistically significant increase. In some examples, the increase in the time of survival is about 1 day to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, about 6 months, about 4 months, about 2 months, about 1 month, or about 2 weeks; about 2 weeks to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, about 6 months, about 4 months, about 2 months, or about 1 month; about 1 month to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, about 6 months, about 4 months, or about 2 months; about 2 months to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, about 6 months, or about 4 months; about 4 months to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, or about 6 months; about 6 months to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, or about 8 months; about 8 months to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, or about 10 months; about 10 months to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, or about 1 year; about 1 year to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, or about 1.5 years; about 1.5 year to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, or about 2 years; about 2 year to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, or about 2.5 years; about 2.5 year to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, or about 3 years; about 3 year to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, or about 3.5 years; about 3.5 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, or about 4 years; about 4 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, or about 4.5 years; about 4.5 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, or about 5 years; about 5 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, or about 5.5 years; about 5.5 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, or about 6 years; about 6 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, or about 6.5 years; about 6.5 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, or about 7 years; about 7 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, or about 7.5 years; about 7.5 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, or about 8 years; about 8 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, or about 8.5 years; about 8.5 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, or about 9 years; about 9 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, or about 9.5 years; about 9.5 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, or about 10 years; about 10 years to about 40 years, about 38 years, about 36 years, about 34 years, about 32 years, about 30 years, about 28 years, about 26 years, about 24 years, about 22 years, about 20 years, about 18 years, about 16 years, about 14 years, or about 12 years; about 12 years to about 40 years, about 38 years, about 36 years, about 34 years, about 32 years, about 30 years, about 28 years, about 26 years, about 24 years, about 22 years, about 20 years, about 18 years, about 16 years, or about 14 years; about 14 years to about 40 years, about 38 years, about 36 years, about 34 years, about 32 years, about 30 years, about 28 years, about 26 years, about 24 years, about 22 years, about 20 years, about 18 years, or about 16 years; about 16 years to about 40 years, about 38 years, about 36 years, about 34 years, about 32 years, about 30 years, about 28 years, about 26 years, about 24 years, about 22 years, about 20 years, or about 18 years; about 18 years to about 40 years, about 38 years, about 36 years, about 34 years, about 32 years, about 30 years, about 28 years, about 26 years, about 24 years, about 22 years, or about 20 years; about 20 years to about 40 years, about 38 years, about 36 years, about 34 years, about 32 years, about 30 years, about 28 years, about 26 years, about 24 years, or about 22 years; about 22 years to about 40 years, about 38 years, about 36 years, about 34 years, about 32 years, about 30 years, about 28 years, about 26 years, or about 24 years; about 24 years to about 40 years, about 38 years, about 36 years, about 34 years, about 32 years, about 30 years, about 28 years, or about 26 years; about 26 years to about 40 years, about 38 years, about 36 years, about 34 years, about 32 years, about 30 years, or about 28 years; about 28 years to about 40 years, about 38 years, about 36 years, about 34 years, about 32 years, or about 30 years; about 30 years to about 40 years, about 38 years, about 36 years, about 34 years, or about 32 years; about 32 years to about 40 years, about 38 years, about 36 years, or about 34 years; about 34 years to about 40 years, about 38 years, or about 36 years; about 36 years to about 40 years or about 38 years; or about 38 years to about 40 years (e.g., compared to a control patient, e.g., a patient or a population of patients having the same or a similar type of FGFR-associated cancer).

Also provided is the use of a compound of General Formula I or a pharmaceutically acceptable salt or solvate thereof for increasing the time of survival of a patient having a FGFR-associated cancer. Also provided is the use of a compound of General Formula I or a pharmaceutically acceptable salt or solvate thereof for the manufacture of a medicament for increasing the time of survival of a patient having a FGFR-associated cancer.

Also provided are methods of decreasing the risk of developing a metastasis or an additional metastasis in a patient having a FGFR-associated cancer that include: selecting, identifying, or diagnosing a patient as having a FGFR-associated cancer, and administering a therapeutically effective amount of a compound of General Formula I or a pharmaceutically acceptable salt or solvate thereof to the patient selected, identified, or diagnosed as having a FGFR-associated cancer. Also provided are methods of decreasing the risk of developing a metastasis or an additional metastasis in a patient having a FGFR-associated cancer that includes administering a therapeutically effective amount of a compound of General Formula I or a pharmaceutically acceptable salt or solvent thereof to a patient having a FGFR-associated cancer. The decrease in the risk of developing a metastasis or an additional metastasis in a patient having a FGFR-associated cancer can be compared to the risk of developing a metastasis or an additional metastasis in the patient prior to treatment, or as compared to a patient or a population of patients having a similar or the same FGFR-associated cancer that has received no treatment or a different treatment. The decrease in the risk of developing a metastasis or an additional metastasis can be about 1% to about 99%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, or about 5%; about 5% to about 99%, about 95%, about 90%, about 85%, about 80%, about 75%, about 70%, about 65%, about 60%, about 55%, about 50%, about 45%, about 40%, about 35%, about 30%, about 25%, about 20%, about 15%, or about 10%; about 10% to about 99%, about 95%, about 90%, about 85%, about 80%, about 75%, about 70%, about 65%, about 60%, about 55%, about 50%, about 45%, about 40%, about 35%, about 30%, about 25%, about 20%, or about 15%; about 15% to about 99%, about 95%, about 90%, about 85%, about 80%, about 75%, about 70%, about 65%, about 60%, about 55%, about 50%, about 45%, about 40%, about 35%, about 30%, about 25%, or about 20%; about 20% to about 99%, about 95%, about 90%, about 85%, about 80%, about 75%, about 70%, about 65%, about 60%, about 55%, about 50%, about 45%, about 40%, about 35%, about 30%, or about 25%; about 25% to about 99%, about 95%, about 90%, about 85%, about 80%, about 75%, about 70%, about 65%, about 60%, about 55%, about 50%, about 45%, about 40%, about 35%, or about 30%; about 30% to about 99%, about 95%, about 90%, about 85%, about 80%, about 75%, about 70%, about 65%, about 60%, about 55%, about 50%, about 45%, about 40%, or about 35%; about 35% to about 99%, about 95%, about 90%, about 85%, about 80%, about 75%, about 70%, about 65%, about 60%, about 55%, about 50%, about 45%, or about 40%; about 40% to about 99%, about 95%, about 90%, about 85%, about 80%, about 75%, about 70%, about 65%, about 60%, about 55%, about 50%, or about 45%; about 45% to about 99%, about 95%, about 90%, about 85%, about 80%, about 75%, about 70%, about 65%, about 60%, about 55%, or about 50%; about 50% to about 99%, about 95%, about 90%, about 85%, about 80%, about 75%, about 70%, about 650%, about 60%, or about 55%; about 55% to about 99%, about 95%, about 90%, about 85%, about 80%, about 75%, about 70%, about 65%, or about 60%; about 60% to about 99%, about 95%, about 90%, about 85%, about 80%, about 75%, about 70%, or about 65%; about 65% to about 99%, about 95%, about 90%, about 85%, about 80%, about 75%, or about 70%; about 70% to about 99%, about 95%, about 90%, about 85%, about 80%, or about 75%; about 75% to about 99%, about 95%, about 90%, about 85%, or about 80%; about 80% to about 99%, about 95%, about 90%, or about 85%; about 85% to about 99%, about 95%, or about 90%; about 90% to about 99% or about 90%; or about 95% to about 99% as compared to the risk of developing a metastasis or an additional metastasis in the patient prior to treatment, or as compared to a patient or a population of patients having a similar or the same FGFR-associated cancer that has received no treatment or a different treatment.

In some examples, the risk of developing a metastasis or an additional metastasis is over about 2 weeks, 1 month, 1.5 months, 2 months, 2.5 months, 3 months, 3.5 months, 4 months, 4.5 months, 5 months, 5.5 months, 6 months, 6.5 months, 7 months, 7.5 months, 8 months, 8.5 months, 9 months, 9.5 months, 10 months, 10.5 months, 11 months, 11.5 months, 12 months, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, or 10 years.

Also provided is the use of a compound of General Formula I or a pharmaceutically acceptable salt or solvate thereof for decreasing the risk of developing a metastasis or an additional metastasis in a patient having a FGFR-associated cancer. Also provided is the use of a compound of General Formula I or a pharmaceutically acceptable salt or solvate thereof for the manufacture of a medicament for decreasing the risk of developing a metastasis or an additional metastasis in a patient having a FGFR-associated cancer.

Also provided are methods of increasing sensitivity of a resistant cancer cell to an anti-cancer drug that include: selecting, identifying, or diagnosing a patient as having a resistant cancer cell (e.g., a resistant FGFR-associated cancer cell, e.g., a cancer cell identified as having one or more of the point mutations listed in Table E), and administering to the selected, identified, or diagnosed subject a therapeutically effective amount of a compound of General Formula I or a pharmaceutically acceptable salt or solvate thereof. Also provided are methods of increasing sensitivity of a resistant cancer cell to an anti-cancer drug that include administering to a patient having a resistant cancer cell to an anti-cancer drug a therapeutically effective amount of a compound of General Formula I or a pharmaceutically acceptable salt or solvate thereof. Some embodiments of any of these methods further include administering the anti-cancer drug to the patient. In such examples, the anti-cancer drug can be co-administered with the compound of General Formula I or a pharmaceutically acceptable salt or solvate thereof. In some examples, the anti-cancer drug can be administered at substantially the same time as the compound of General Formula I or a pharmaceutically acceptable salt or solvate thereof. In some examples, a first dose of the compound of General Formula I is administered prior to the first dose of the anti-cancer compound. In some examples, a first dose of the anti-cancer compound is administered prior to the first dose of the compound of General Formula I or a pharmaceutically acceptable salt or solvate thereof. In some examples, the increase in the sensitivity of the resistant cancer cell to the anti-cancer drug can result in a decrease in the rate of growth and/or proliferation of the resistant cancer cell when contacted with the anti-cancer drug and at least one of the compounds described herein, of between about 1% to about 100%, 95%, 90%, 85%, 80%, 75%, 70%, 65%, 60%, 55%, 50%, 45%, 40%, 35%, 30%, 25%, 20%, 15%, 10%, or 5%; about 2% to about 100%, 95%, 90%, 85%, 80%, 75%, 70%, 65%, 60%, 55%, 50%, 45%, 40%, 35%, 30%, 25%, 20%, 15%, 10%, or 5%; about 3% to about 100%, 95%, 90%, 85%, 80%, 75%, 70%, 65%, 60%, 55%, 50%, 45%, 40%, 35%, 30%, 25%, 20%, 15%, 10%, or 5%; about 5% to about 100%, 95%, 90%, 85%, 80%, 75%, 70%, 65%, 60%, 55%, 50%, 45%, 40%, 35%, 30%, 25%, 20%, 15%, or 10%; about 5% to about 100%, 95%, 90%, 85%, 80%, 75%, 70%, 65%, 60%, 55%, 50%, 45%, 40%, 35%, 30%, 25%, 20%, 15%, 10%, or 5%; about 5% to about 100%, 95%, 90%, 85%, 80%, 75%, 70%, 65%, 60%, 55%, 50%, 45%, 40%, 35%, 30%, 25%, 20%, 15%, or 10%; about 10% to about 100%, 95%, 90%, 85%, 80%, 75%, 70%, 65%, 60%, 55%, 50%, 45%, 40%, 35%, 30%, 25%, 20%, 15%, 10%, or 5%; about 5% to about 100%, 95%, 90%, 85%, 80%, 75%, 70%, 65%, 60%, 55%, 50%, 45%, 40%, 35%, 30%, 25%, 20%, or 15%; about 15% to about 100%, 95%, 90%, 85%, 80%, 75%, 70%, 65%, 60%, 55%, 50%, 45%, 40%, 35%, 30%, 25%, 20%, 15%, 10%, or 5%; about 5% to about 100%, 95%, 90%, 85%, 80%, 75%, 70%, 65%, 60%, 55%, 50%, 45%, 40%, 35%, 30%, 25%, or 20%; about 20% to about 100%, 95%, 90%, 85%, 80%, 75%, 70%, 65%, 60%, 55%, 50%, 45%, 40%, 35%, 30%, 25%, 20%, 15%, 10%, or 5%; about 5% to about 100%, 95%, 90%, 85%, 80%, 75%, 70%, 65%, 60%, 55%, 50%, 45%, 40%, 35%, 30%, or 25%; about 25% to about 100%, 95%, 90%, 85%, 80%, 75%, 70%, 65%, 60%, 55%, 50%, 45%, 40%, 35%, 30%, 25%, or 20%; about 20% to about 100%, 95%, 90%, 85%, 80%, 75%, 70%, 65%, 60%, 55%, 50%, 45%, 40%, 35%, 30%, 25%, 20%, 15%, 10%, or 5%; about 5% to about 100%, 95%, 90%, 85%, 80%, 75%, 70%, 65%, 60%, 55%, 50%, 45%, 40%, 35%, or 30%; about 30% to about 100%, 95%, 90%, 85%, 80%, 75%, 70%, 65%, 60%, 55%, 50%, 45%, 40%, or 35%; about 35% to 100%, 95%, 90%, 85%, 80%, 75%, 70%, 65%, 60%, 55%, 50%, 45%, or 40%; about 40% to about 100%, 95%, 90%, 85%, 80%, 75%, 70%, 65%, 60%, 55%, 50%, or 45%; about 45% to about 100%, 95%, 90%, 85%, 80%, 75%, 70%, 65%, 60%, 55%, or 50%; about 50% to about 100%, 95%, 90%, 85%, 80%, 75%, 70%, 65%, 60%, or 55%; about 55% to about 100%, 95%, 90%, 85%, 80%, 75%, 70%, 65%, or 60%; about 60% to about 100%, 95%, 90%, 85%, 80%, 75%, 70%, or 65%; about 65% to about 100%, 95%, 90%, 85%, 80%, 75%, or 70%; about 70% to about 100%, 95%, 90%, 85%, 80%, or 75%; about 75% to about 100%, 95%, 90%, 85%, or 80%; about 80% to about 100%, 95%, 90%, or 85%; about 85% to about 100%, 95%, or 90%; about 90% to about 100% or 95%; or about 95% to about 100%, as compared to the rate of growth and/or proliferation of a resistant cancer cell when contacted with the anti-cancer drug alone.

A method of treating an angiogenesis-related disorder (e.g., any of the angiogenesis-related disorders described herein or known in the art) in a patient that include: identifying, selecting, or diagnosing a angiogenesis-related disorder in a patient, and administering to the identified, selected, or diagnosed patient with a therapeutically effective amount of a compound of General Formula I or a pharmaceutically acceptable salt or solvate thereof. A method of treating an angiogenesis-related disorder in a patient that includes administering a therapeutically effective amount of a compound of General Formula I or a pharmaceutically acceptable salt or solvent thereof to a patient having an angiogenesis-related disorder. In some examples, the treating can result in a decrease in the diameter of a blood vessel and/or a decrease in the number of blood vessels in a tissue in need of a reduction in the number of blood vessels (e.g., as compared to the diameter of the blood vessel and/or the number of blood vessels in the tissue in the patient prior to treatment). In some examples the methods can result in, e.g., a decrease in the diameter of a blood vessel of about 1% to about 80%, 75%, 70%, 65%, 60%, 55%, 50%, 45%, 40%, 35%, 30%, 25%, 20%, 15%, 10%, or 5%; about 2% to about 80%, 75%, 70%, 65%, 60%, 55%, 50%, 45%, 40%, 35%, 30%, 25%, 20%, 15%, 10%, or 5%; about 3% to about 80%, 75%, 70%, 65%, 60%, 55%, 50%, 45%, 40%, 35%, 30%, 25%, 20%, 15%, 10%, or 5%; about 5% to about 80%, 75%, 70%, 65%, 60%, 55%, 50%, 45%, 40%, 35%, 30%, 25%, 20%, 15%, or 10%; about 10% to about 80%, 75%, 70%, 65%, 60%, 55%, 50%, 45%, 40%, 35%, 30%, 25%, 20%, or 15%; about 15% to about 80%, 75%, 70%, 65%, 60%, 55%, 50%, 45%, 40%, 35%, 30%, 25%, or 20%; about 20% to about 80%, 75%, 70%, 65%, 60%, 55%, 50%, 45%, 40%, 35%, 30%, or 25%; about 25% to about 80%, 75%, 70%, 65%, 60%, 55%, 50%, 45%, 40%, 35%, or 30%; about 30% to about 80%, 75%, 70%, 65%, 60%, 55%, 50%, 45%, 40%, or 35%; about 35% to about 80%, 75%, 70%, 65%, 60%, 55%, 50%, 45%, or 40%; about 40% to about 80%, 75%, 70%, 65%, 60%, 55%, 50%, or 45%; about 45% to about 80%, 75%, 70%, 65%, 60%, 55%, or 50%; about 50% to about 80%, 75%, 70%, 65%, 60%, or 55%; about 55% to about 80%, 75%, 70%, 65%, or 60%; about 60% to about 80%, 75%, 70%, or 65%; about 65% to about 80%, 75%, or 70%; about 70% to about 80% or 75%; or about 75% to about 80% (e.g., as compared to the diameter of the blood vessel in the patient prior to treatment). In some examples the methods can result in, e.g., a decrease in the number of blood vessels in a tissue in need of a reduction in the number of blood vessels of about 5% to about 80%, 75%, 70%, 65%, 60%, 55%, 50%, 45%, 40%, 35%, 30%, 25%, 20%, 15%, or 10%; about 10% to about 80%, 75%, 70%, 65%, 60%, 55%, 50%, 45%, 40%, 35%, 30%, 25%, 20%, or 15%; about 15% to about 80%, 75%, 70%, 65%, 60%, 55%, 50%, 45%, 40%, 35%, 30%, 25%, or 20%; about 20% or about 80%, 75%, 70%, 65%, 60%, 55%, 50%, 45%, 40%, 35%, 30%, or 25%; about 25% to about 80%, 75%, 70%, 65%, 60%, 55%, 50%, 45%, 40%, 35%, or 30%; about 30% to about about 80%, 75%, 70%, 65%, 60%, 55%, 50%, 45%, 40%, or 35%; about 35% to about 80%, 75%, 70%, 65%, 60%, 55%, 50%, 45%, or 40%; about 40% to about 80%, 75%, 70%, 65%, 60%, 55%, 50%, or 45%; about 45% to about 80%, 75%, 70%, 65%, 60%, 55%, or 50%; about 50% to about 80%, 75%, 70%, 65%, 60%, or 55%; about 55% to about 80%, 75%, 70%, 65%, or 60%; about 60% to about 80%, 75%, 70%, or 65%; about 65% to about 80%, 75%, or 70%; about 70% to about 80% or 75%; or about 75% to about 80% (e.g., as compared to the diameter of the blood vessel and/or the number of blood vessels in the tissue in the patient prior to treatment). These methods can also result in a decrease in the rate of formation of new blood vessels in a tissue in need thereof in a patient having an angiogenesis-related disorder (e.g., as compared to the rate of formation of new blood vessels in the tissue in the patient prior to treatment, or the rate of formation of new blood vessels in a patient or a population of patients having the same or similar angiogenesis-related disorder). The decrease in the rate of formation of a new blood vessels in a tissue in need thereof in a patient having an angiogenesis-related disorder can be about 1% to about 100%, 95%, 90%, 85%, 80%, 75%, 70%, 65%, 60%, 55%, 50%, 45%, 40%, 35%, 30%, 25%, 20%, 15%, 10%, or 5%; about 5% to about 100%, 95%, 90%, 85%, 80%, 75%, 70%, 65%, 60%, 55%, 50%, 45%, 40%, 35%, 30%, 25%, 20%, 15%, or 10%; about 10% to about 100%, 95%, 90%, 85%, 80%, 75%, 70%, 65%, 60%, 55%, 50%, 45%, 40%, 35%, 30%, 25%, 20%, or 15%; about 15% to 100%, 95%, 90%, 85%, 80%, 75%, 70%, 65%, 60%, 55%, 50%, 45%, 40%, 35%, 30%, 25%, or 20%; about 20% to 100%, 95%, 90%, 85%, 80%, 75%, 70%, 65%, 60%, 55%, 50%, 45%, 40%, 35%, 30%, or 25%; about 25% to 100%, 95%, 90%, 85%, 80%, 75%, 70%, 65%, 60%, 55%, 50%, 45%, 40%, 35%, or 30%; about 30% to 100%, 95%, 90%, 85%, 80%, 75%, 70%, 65%, 60%, 55%, 50%, 45%, 40%, or 35%; about 35% to 100%, 95%, 90%, 85%, 80%, 75%, 70%, 65%, 60%, 55%, 50%, 45%, or 40%; about 40% to 100%, 95%, 90%, 85%, 80%, 75%, 70%, 65%, 60%, 55%, 50%, or 45%; about 45% to 100%, 95%, 90%, 85%, 80%, 75%, 70%, 65%, 60%, 55%, or 50%; about 50% to 100%, 95%, 90%, 85%, 80%, 75%, 70%, 65%, 60%, or 55%; about 55% to 100%, 95%, 90%, 85%, 80%, 75%, 70%, 65%, or 60%; about 60% to 100%, 95%, 90%, 85%, 80%, 75%, 70%, or 65%; about 65% to 100%, 95%, 90%, 85%, 80%, 75%, or 70%; about 70% to 100%, 95%, 90%, 85%, 80%, or 75%; about 75% to 100%, 95%, 90%, 85%, or 80%; about 80% to 100%, 95%, 90%, or 85%; about 85% to 100%, 95%, or 90%; about 90% to about 100% or 95%; or about 95% to about 100% (e.g., as compared to the rate of formation of new blood vessels in the tissue in the patient prior to treatment, or the rate of formation of new blood vessels in a patient or a population of patients having the same or similar angiogenesis-related disorder).

Also provided is the use of a compound of General Formula I or a pharmaceutically acceptable salt or solvent thereof for treating an angiogenesis-related disorder in a patient. Also provided is the use of a compound of General Formula I or a pharmaceutically acceptable salt or solvate thereof in the manufacture of a medicament for treating an angiogenesis-related disorder in a patient.

Also provided are methods for treating cancer in a patient in need thereof, the method comprising: (a) determining if the cancer in the patient is an FGFR-associated cancer (e.g., using a regulatory-agency approved, e.g., FDA-approved, kit for identifying dysregulation of dysregulation of a FGFR gene, a FGFR protein, or expression or activity or level of any of the same, in a patient or a biopsy sample from the patient, or by performing any of the non-limiting examples of assays described herein); and (b) if the cancer in the patient is determined to be an FGFR-associated cancer, administering to the patient a therapeutically effective amount of a compound of Formula I or a pharmaceutically acceptable salt or solvate thereof.

Also provided is use of a compound of Formula I or a pharmaceutically acceptable salt or solvate thereof for use in treating an FGFR-associated cancer (e.g., any of the FGFR-associated cancers described herein) in a patient identified or diagnosed as having an FGFR-associated cancer through a step of performing an assay (e.g., an in vitro assay) (e.g., an assay that utilizes next generation sequencing, immunohistochemistry, or break apart FISH analysis) (e.g., using a regulatory agency-approved, e.g., FDA-approved kit) on a sample obtained from the patient to determine whether the patient has dysregulation of a FGFR gene, a FGFR protein, or expression or activity or level of any of the same, where the presence of dysregulation of a FGFR gene, a FGFR protein, or expression or activity or level of any of the same, identifies that the patient has an FGFR-associated cancer. Also provided is the use of a compound of Formula I or a pharmaceutically acceptable salt or solvate thereof for the manufacture of a medicament for treating an FGFR-associated cancer in a patient identified or diagnosed as having an FGFR-associated cancer through a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the patient to determine whether the patient has a dysregulation of a FGFR gene, a FGFR protein, or expression or activity or level of any of the same where the presence of dysregulation of a FGFR gene, a FGFR protein, or expression or activity or level of any of the same, identifies that the patient has an FGFR-associated cancer. Some embodiments of any of the methods or uses described herein further include recording in the patient's clinical record (e.g., a computer readable medium) that the patient determined to have dysregulation of a FGFR gene, a FGFR protein, or expression or activity or level of any of the same, through the performance of the assay, should be administered a compound of Formula I or a pharmaceutically acceptable salt or solvate thereof.

Also provided is a compound of Formula I or a pharmaceutically acceptable salt or solvate thereof, for use in the treatment of a cancer (e.g., an FGFR-associated cancer) in a patient in need thereof or a patient identified or diagnosed as having an FGFR-associated cancer (e.g., a patient that has been identified or diagnosed as having an FGFR-associated cancer through the use of a regulatory agency-approved, e.g., FDA-approved, kit for identifying dysregulation of a FGFR gene, a FGFR protein, or expression or activity or level of any of the same, in a patient or a biopsy sample from the sample) (e.g., any of the FGFR-associated cancers described herein or known in the art). Also provided is the use of a compound of Formula I or a pharmaceutically acceptable salt or solvate thereof for the manufacture of a medicament for treating a cancer (e.g., an FGFR-associated cancer) in a patient identified or diagnosed as having an FGFR-associated cancer (e.g., a patient that has been identified or diagnosed as having an FGFR-associated cancer through the use of a regulatory agency-approved, e.g., FDA-approved, kit for identifying dysregulation of a FGFR gene, a FGFR protein, or expression or activity or level of any of the same, in a patient or a biopsy sample from the patient) (e.g., any of the FGFR-associated cancers described herein or known in the art).

In some embodiments of any of the methods or uses described herein, the patient has been identified or diagnosed as having a cancer with dysregulation of a FGFR gene, a FGFR protein, or expression or activity or level of any of the same (e.g., as determined using a regulatory agency-approved, e.g., FDA-approved, assay or kit). In some embodiments of any of the methods or uses described herein, the patient has a tumor that is positive for dysregulation of a FGFR gene, a FGFR protein, or expression or activity or level of any of the same (e.g., as determined using a regulatory-agency-approved assay or kit). In some embodiments of any of the methods or uses described herein, the patient can be a patient with a tumor(s) that is positive for dysregulation of a FGFR gene, a FGFR protein, or expression or activity or level of any of the same (e.g., identified as positive using a regulatory agency-approved, e.g., FDA-approved, assay or kit). In some embodiments of any of the methods or uses described herein, the patient can be a patient whose tumors have dysregulation of a FGFR gene, a FGFR protein, or expression or activity or level of any of the same (e.g., where the tumor is identified as such using a regulatory agency-approved, e.g., FDA-approved, kit or assay). In some embodiments of any of the methods or uses described herein, the patient is suspected of having an FGFR-associated cancer. In some embodiments of any of the methods or uses described herein, the patient has a clinical record indicating that the patient has a tumor that has dysregulation of a FGFR gene, a FGFR protein, or expression or activity or level of any of the same (and optionally the clinical record indicates that the patient should be treated with any of the compounds of Formula I or a pharmaceutically acceptable salts or solvates thereof or compositions provided herein).

Also provided herein are methods of selecting a treatment for a patient that include administration of a therapeutically effective amount of a compound of Formula I or a pharmaceutically acceptable salt or solvate thereof that include a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the patient to determine whether the patient has dysregulation of a FGFR gene, a FGFR protein, or expression or activity or level of any of the same, identifying or diagnosing a patient determined to have dysregulation of a FGFR gene, a FGFR protein, or expression or activity or level of any of the same, as having an FGFR-associated cancer, and selecting a therapeutic treatment including administration of a therapeutically effective amount of a compound of Formula I or a pharmaceutically acceptable salt or solvate thereof to the patient identified or diagnosed as having an FGFR-associated cancer. Some embodiments further include administering the selected treatment to the patient identified or diagnosed as having an FGFR-associated cancer.

In some embodiments of any of the methods or uses described herein, the cancer (e.g., FGFR-associated cancer) is a hematological cancer. In some embodiments of any of the methods or uses described herein, the cancer (e.g., an FGFR-associated cancer) is a solid tumor. In some embodiments of any of the methods or uses described herein, the cancer (e.g., FGFR-associated cancer) is any of the exemplary cancers (e.g., any of the exemplary FGFR-associated cancers) described herein.

Also provided herein is a method of treating a disease or disorder mediated by FGFR (e.g., dysregulation of a FGFR gene, a FGFR protein, or expression or activity or level of any of the same) in a patient in need of such treatment, the method comprising administering to the patient a therapeutically effective amount of a compound of Formula I or a pharmaceutically acceptable salt or solvate thereof or a pharmaceutical composition thereof. For example, the FGFR-associated disease can be any of the FGFR-associated cancers described herein or known in the art.

Although the genetic basis of tumorigenesis may vary between different cancer types, the cellular and molecular mechanisms required for metastasis appear to be similar for all solid tumor types. During a metastatic cascade, the cancer cells lose growth inhibitory response, undergo alterations in adhesiveness and produce enzymes that can degrade extracellular matrix components. This leads to detachment of tumor cells from the original tumor, infiltration into the circulation through newly formed vasculature (e.g., lymph vessels or blood vessels), migration and extravasation of the tumor cells at favorable distant sites, where they may form colonies. A number of genes have been identified as being promoters or suppressors of metastasis. FGFR proteins have been implicated for a role in metastasis (Qian et al., Oncogene 33:3411-3421, 2014).

Accordingly, also provided herein are methods for inhibiting, preventing, aiding in the prevention, or decreasing the symptoms of metastasis of a cancer (e.g., a FGFR-associated cancer) in a patient in need thereof, the method comprising administering to the patient a therapeutically effective amount of a compound of Formula I or a pharmaceutically acceptable salt or solvate thereof. Such methods can be used in the treatment of one or more of the cancers described herein. In some embodiments, the cancer is an FGFR-associated cancer. In some embodiments, the compound of Formula I or a pharmaceutically acceptable salt or solvate thereof is used in combination with an additional therapy or another therapeutic agent, including a chemotherapeutic agent, such as a kinase inhibitor.

Also provided is a method for inhibiting activity of FGFR1, FGFR2, FGFR3 and/or FGFR4 in a mammalian cell, comprising contacting the cell with a compound of Formula I or a pharmaceutically acceptable salt or solvate thereof. In one embodiment, the contacting is performed in vitro. In another embodiment, the contacting is performed in vivo (e.g., in a human). In one embodiment, when the contacting is performed in vivo, the method can include administering an effective amount of a compound of Formula I or a pharmaceutically acceptable salt or solvate thereof to a subject. In some embodiments, the mammalian cell is a mammalian cancer cell. In one embodiment, the mammalian cancer cell is any cancer as described herein. In some embodiments, the mammalian cancer cell is an FGFR-associated cancer cell.

As used herein, the term "contacting" refers to the bringing together of indicated moieties in an in vitro system or an in vivo system. For example, "contacting" an FGFR with a compound provided herein includes the administration of a compound provided herein to an individual or patient, such as a human, having FGFR1, FGFR2, FGFR3 and/or FGFR4, as well as, for example, introducing a compound provided herein into a sample containing a cellular or purified preparation containing the FGFR1, FGFR2, FGFR3 and/or FGFR4.

In the field of medical oncology it is normal practice to use a combination of different forms of treatment to treat each patient with cancer. In medical oncology the other component(s) of such conjoint treatment or therapy in addition to compositions provided herein may be, for example, surgery, radiotherapy, and chemotherapeutic agents, such as kinase inhibitors, signal transduction inhibitors and/or monoclonal antibodies. Compounds of Formula I therefore may also be useful as adjuvants to cancer treatment, that is, they can be used in combination with one or more additional therapies or therapeutic agents, for example a chemotherapeutic agent that works by the same or by a different mechanism of action.

In some embodiments of any the methods described herein, the compound of Formula I (or a pharmaceutically acceptable salt or solvate thereof) is administered in combination with a therapeutically effective amount of at least one additional therapeutic agent selected from one or more additional therapies or therapeutic (e.g., chemotherapeutic) agents. Non-limiting examples of additional therapeutic agents include: receptor tyrosine kinase-targeted therapeutic agents, such as afatinib, cabozantinib, cetuximab, crizotinib, dabrafenib, erlotinib, gefitinib, imatinib, lapatinib, lestaurtinib, nilotinib, pazopanib, panitumumab, pertuzumab, sunitinib, AG 879, AZ-23, AZ623, Gö 6976, GNF-5837, GTx-186, GW 441756, LOXO-101, MGCD516, RPI-1, RXDX101, and TSR-011; FGFR-targeted therapeutic agents, such as signal transduction pathway inhibitors, such as Ras-Raf-MEK-ERK pathway inhibitors (e.g., binimetinib, selumetinib, encorafinib, sorafenib, trametinib, and vemurafenib), PI3K-Akt-mTOR-S6K pathway inhibitors (e.g. everolimus, rapamycin, perifosine, temsirolimus), other kinase inhibitors, such as baricitinib, brigatinib, capmatinib, danusertib, ibrutinib, milciclib, quercetin, regorafenib, ruxolitinib, semaxanib, AP32788, BLU285, BLU554, INCB39110, INCB40093, INCB50465, INCB52793, INCB54828, MGCD265, NMS-088, NMS-1286937, PF 477736, PLX3397, PLX7486, PLX8394, PLX9486, PRN1008, PRN1371, RXDX103, RXDX106, RXDX108, and TG101209; FGFR inhibitors (e.g., ARQ-087, AZD-4547, BGJ398, nintadanib (BIBF 1120), BLU9931, brivanib (BMS-582664), CH5183284, Dovitinib (TKI258, CHIR258), E-3810, EWMD-2076, JNJ-42756493, lenvatinib ((E7080), LY2874455, Orantinib (TSU-68, SU6668), PD089828, PD166866, PD173074, Ponatinib (AP-24534), Semaxanib (SU5416), SSR128129E, SU4984, SU5402, SUN11602), AB1010, BAY 1163877, Debio-1347, FGF401, FIIN-2, HMPL-453, MK-2461, pazopanib (Votrient, GW-786034), PD161570, PD173074, PF-477736, PHA-739358 (danusertib), PRN1371, regorafenib (Stivarga), SPP86, and Tyrphostin AG 1296, and TAS120; checkpoint inhibitors, such as ipilimumab, tremelimumab, nivolumab, pidilizumab, MPDL3208A, MEDI4736, MSB0010718C, BMS-936559, BMS-956559, BMS-935559 (MDX-1105), AMP-224, and pembrolizumab; modulators of the apoptosis pathway (e.g. obataclax); cytotoxic chemotherapeutics, such as arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine; angiogenesis-targeted therapies, such as aflibercept and bevacizumab; immune-targeted agents, such as aldesleukin, interferon alfa-2b, ipilimumab, lambrolizumab, nivolumab, prednisone, sipuleucel-T; radiotherapy, such as radioiodide therapy, external-beam radiation, and radium 223 therapy.

Yet other therapeutic agents that can be administered with a compound of Formula I or a pharmaceutically acceptable salt or solvate thereof, include FGFR inhibitors such as those described, for example, LY2874455 (Lilly), dovitinib (TKI258) (Novartis), BGJ398 (Novartis), AZD4547 (AstraZeneca), ponatinib (Ariad), E-3810 (EOS), JNJ-42756493 (Astex/Janssen), and ARQ 087 (ArQule).

In some embodiments, the amount of a compound of Formula I or a pharmaceutically acceptable salt or solvate thereof is, in combination with the at least one additional therapeutic agent, effective in treating the cancer (e.g., an FGFR-associated cancer). The at least one additional therapeutic agent may be administered with a compound of Formula I or a pharmaceutically acceptable salt or solvate thereof as part of the same or separate dosage forms, via the same or different routes of administration, and on the same or different administration schedules according to standard pharmaceutical practice known to one skilled in the art.

Also provided herein is (i) a pharmaceutical combination for treating cancer in a patient in need thereof, which comprises (a) a compound of Formula I or a pharmaceutically acceptable salt or solvate thereof, (b) at least one additional therapeutic agent (e.g., any of the exemplary additional therapeutic agents described herein or known in the art), and (c) optionally at least one pharmaceutically acceptable carrier for simultaneous, separate or sequential use for the treatment of cancer, wherein the amounts of the compound of Formula I or pharmaceutically acceptable salt or solvate thereof and of the additional therapeutic agent are together effective in treating the cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer a patient in need thereof. In one embodiment the patient is a human.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of Formula I or a pharmaceutically acceptable salt or solvate thereof and at least one additional therapeutic agent (e.g., a chemotherapeutic agent), are both administered to a patient simultaneously in the form of a single composition or dosage. The term "non-fixed combination" means that a compound of Formula I or a pharmaceutically acceptable salt or solvate thereof and at least one additional therapeutic agent (e.g., chemotherapeutic agent) are administered to a patient as separate compositions or dosages, either simultaneously, concurrently or sequentially with variable intervening time limits, wherein such administration provides effective levels of the two or more compounds in the body of the patient. These also apply to cocktail therapies, e.g. the administration of three or more active ingredients Accordingly, also provided herein is a method of treating cancer, comprising administering to a patient in need thereof a pharmaceutical combination for treating cancer which comprises (a) a compound of Formula I or pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of Formula I or pharmaceutically acceptable salt or solvate thereof and the additional therapeutic agent are together effective in treating the cancer. In one embodiment, the compound of Formula I or pharmaceutically acceptable salt or solvate thereof, and the additional therapeutic agent are administered simultaneously as separate dosages. In one embodiment, the compound of Formula I or pharmaceutically acceptable salt or solvate thereof, and the additional therapeutic agent are administered as separate dosages sequentially in any order, in jointly therapeutically effective amounts, e.g. in daily or intermittently dosages. In one embodiment, compound of Formula I or pharmaceutically acceptable salt or solvate thereof, and the additional therapeutic agent are administered simultaneously as a combined dosage.

Also provided herein is a compound of Formula I or a pharmaceutically acceptable salt or solvate thereof, for use in the treatment of an FGFR-associated disease or disorder as defined hereinabove.

Also provided herein are methods of treating a FGFR-associated disease (e.g., a FGFR-associated cancer, e.g., any of the FGFR-associated cancers described herein or known in the art) in a patient that include: (a) administering to a patient identified or diagnosed as having an FGFR-associated disease (e.g., an FGFR-associated cancer) one or more doses of a first FGFR inhibitor over a treatment period; (b) determining a level of phosphate in a biological sample including blood, serum, or plasma obtained from the patient after the treatment period; (c) selecting a patient having an elevated level of phosphate in the biological sample as compared to a reference level of phosphate; and (d) ceasing administration of the first FGFR inhibitor (or instructing the selected patient to cease administration) and initiating administration of a therapeutically effective amount of a compound of Formula I or pharmaceutically acceptable salt or solvate thereof, or a pharmaceutical agent or composition comprising a compound of Formula I or pharmaceutically acceptable salt or solvate thereof (e.g., any of the pharmaceutical agents or compositions described herein), to the selected patient. Some embodiments of these methods can further include identifying or diagnosing a patient as having a FGFR-associated disease (e.g., a FGFR-associated cancer) using any of the methods described herein.

In certain embodiments of these methods, the treatment period can be from about 1 day to about 30 days (e.g., from about 1 day to about 15 days; e.g. about 7 days; e.g., from about 16 days to about 30 days, e.g., about 21 days). In other embodiments of these methods, the treatment period can be from 30 days to about 12 months (e.g., from about 30 days to about 9 months, from about 30 days to about 6 months, from about 30 days to about 120 days, from about 30 days to about 90 days, from about 30 days to about 60 days). In still other embodiments, the treatment period is 7 days or more or 21 days or more (e.g., more than 7 days or more than 21 days to about 12 months, more than 7 days or more than 21 days to about 9 months, more than 7 days or more than 21 days to about 6 months, more than 7 days or more than 21 days to about 120 days, more than 7 days or more than 21 days to about 90 days, more than 7 days or more than 21 days to about 60 days, more than 7 days or more than 21 days to about 30 days).

In some embodiments of these methods, the treatment period is at least or about 1 day, at least or about 2 days, at least or about 3 days, at least or about 4 days, at least or about 5 days, at least or about 6 days, at least or about 7 days, at least or about 8 days, at least or about 9 days, at least or about 10 days, at least or about 11 days, at least or about 12 days, at least or about 13 days, at least or about 14 days, at least or about 15 days, at least or about 16 days, at least or about 17 days, at least or about 18 days, at least or about 19 days, at least or about 20 days, at least or about 21 days, at least or about 22 days, at least or about 23 days, at least or about 24 days, at least or about 25 days, at least or about 26 days, at least or about 27 days, at least or about 28 days, at least or about 29 days, at least or about 30 days, at least or about 31 days, at least or about 45 days, at least or about 60 days, at least or about 90 days, at least or about 120 days, at least or about 6 months, at least or about 9 months, at least or about 12 months.

As used herein, the term "first FGFR inhibitor" means an FGFR inhibitor that is not a compound of Formula I or a salt or solvate thereof, or a pharmaceutical composition that includes a compound of Formula I or a salt or solvate thereof. Non-limiting examples of first FGFR inhibitor include JNJ-42756493 or BGJ398.

In some embodiments, the treatment period is at least 7 days (e.g., at least or about 8 days, at least or about 9 days, at least or about 10 days, at least or about 11 days, at least or about 12 days, at least or about 13 days, at least or about 14 days, at least or about 15 days, at least or about 16 days, at least or about 17 days, at least or about 18 days, at least or about 19 days, at least or about 20 days, at least or about 21 days, at least or about 22 days, at least or about 23 days, at least or about 24 days, at least or about 25 days, at least or about 26 days, at least or about 27 days, at least or about 28 days, at least or about 29 days, or at least or about 30 days), the FGFR inhibitor is JNJ-42756493, and a daily dose of about 6 mg to about 12 mg (e.g., about 6 mg to about 11 mg, about 10 mg, about 9 mg, about 8 mg, or about 7 mg; about 7 mg to about 12 mg, about 11 mg, about 10 mg, about 9 mg, or about 8 mg; about 8 mg to about 12 mg, about 11 mg, about 10 mg, or about 9 mg; about 9 mg to about 12 mg, about 11 mg, or about 10 mg; about 10 mg to about 12 mg or about 11 mg; or about 11 mg to about 12 mg) of the first FGFR inhibitor is administered to the patient over the treatment period.

In some embodiments, the treatment period is at least 21 days (e.g., at least or about 22 days, at least or about 23 days, at least or about 24 days, at least or about 25 days, at least or about 26 days, at least or about 27 days, at least or about 28 days, at least or about 29 days, at least or about 30 days, at least or about 31 days, at least or about 32 days, at least or about 33 days, at least or about 34 days, at least or about 35 days, at least or about 36 days, at least or about 37 days, at least or about 38 days, at least or about 39 days, or at least or about 40 days) the first FGFR is BGJ398, and a daily dose of about 50 mg to about 125 mg (e.g., about 50 mg to about 120 mg, about 115 mg, about 110 mg, about 105 mg, about 100 mg, about 95 mg, about 90 mg, about 85 mg, about 80 mg, about 75 mg, about 70 mg, about 65 mg, about 60 mg, or about 55 mg; about 55 mg to about 120 mg, about 115 mg, about 110 mg, about 105 mg, about 100 mg, about 95 mg, about 90 mg, about 85 mg, about 80 mg, about 75 mg, about 70 mg, about 65 mg, or about 60 mg; about 60 mg to about 120 mg, about 115 mg, about 110 mg, about 105 mg, about 100 mg, about 95 mg, about 90 mg, about 85 mg, about 80 mg, about 75 mg, about 70 mg, or about 65 mg; about 65 mg to about 120 mg, about 115 mg, about 110 mg, about 105 mg, about 100 mg, about 95 mg, about 90 mg, about 85 mg, about 80 mg, about 75 mg, or about 70 mg; about 70 mg to about 120 mg, about 115 mg, about 110 mg, about 105 mg, about 100 mg, about 95 mg, about 90 mg, about 85 mg, about 80 mg, or about 75 mg; about 75 mg to about 120 mg, about 115 mg, about 110 mg, about 105 mg, about 100 mg, about 95 mg, about 90 mg, about 85 mg, or about 80 mg; about 80 mg to about 120 mg, about 115 mg, about 110 mg, about 105 mg, about 100 mg, about 95 mg, about 90 mg, or about 85 mg; about 85 mg to about 120 mg, about 115 mg, about 110 mg, about 105 mg, about 100 mg, about 95 mg, or about 90 mg; about 90 mg to about 120 mg, about 115 mg, about 110 mg, about 105 mg, about 100 mg, or about 95 mg; about 95 mg to about 120 mg, about 115 mg, about 110 mg, about 105 mg, or about 100 mg; about 100 mg to about 120 mg, about 115 mg, about 110 mg, or about 105 mg; about 105 mg to about 120 mg, about 115 mg, or about 110 mg; about 110 mg to about 120 mg or about 115 mg; or about 115 mg to about 120 mg) of the first FGFR inhibitor is administered to the patient over the treatment period.

Hyperphosphatemia refers to an abnormally elevated level of phosphate in the blood. In some embodiments, the presence of hyperphosphatemia in a subject (e.g., a patient) can be determined by measuring a level(s) of phosphate in a biological sample including blood, serum, or plasma (e.g., peripheral blood) obtained from the patient after a particular treatment period (e.g., any of the treatment periods described herein). Determining the phosphate level in peripheral blood can be achieved using conventional methods known in the art (see, e.g., serum phosphate test offered, e.g., by the Mayo Clinic Laboratories, which utilizes the Roche Phosphorus reagent (Roche Diagnostics, Inc.; the test is based on the reaction of phosphate with ammonium molybdate to form ammonium phosphomolybdate (without reduction)).

In certain embodiments, the serum phosphate level exhibited by a subject (e.g., a subject treated with a first FGFR inhibitor; e.g., a subject selected in step (c) above) is at least or about 5 mg/dL, at least or about 5.5 mg/dL, at least or about 6.0 mg/dL, at least or about 6.5 mg/dL, at least or about 7.0 mg/dL, at least or about 7.5 mg/dL, at least or about 8.0 mg/dL, at least or about 8.5 mg/dL, at least or about 9.0 mg/dL, at least or about 9.5 mg/dL, at least or about 10 mg/dL, at least or about 10.5 mg/dL, at least or about 11 mg/dL, at least or about 11.5 mg/dL, at least or about 12 mg/dL, at least or about 12.5 mg/dL, at least or about 13 mg/dL, at least or about 13.5 mg/dL, at least or about 14 mg/dL, or at least or about 15 mg/dL. In some embodiments, the reference level of phosphate can be the level in a healthy subject or the average level in a population of healthy subjects (e.g., subjects not having hyperphosphatemia or a subjects not at risk for developing hyperphosphatemia, such as those having a serum phosphate level of from about 2.0 mg/dL to about 5.0 mg/dL; e.g., from about 2.5 mg/dL to about 4.5 mg/dL).

In some examples, the step (c) further includes selecting a patient having an elevated level of phosphate in the biological sample as compared to a reference level of phosphate (e.g., any of the reference level of phosphate described herein) and one or both of: (i) a calcium-phosphate product (serum calcium in mg/dL×serum phosphate in mg/dL) of at least or about 50 mg$^2$/dL$^2$ (e.g., at least or about 52 mg$^2$/dL$^2$, at least or about 54 mg$^2$/dL$^2$, at least or about 56 mg$^2$/dL$^2$, at least or about 58 mg$^2$/dL$^2$, at least or about 60 mg$^2$/dL$^2$, at least or about 62 mg$^2$/dL$^2$, at least or about 64 mg$^2$/dL$^2$, at least or about 66 mg$^2$/dL$^2$, at least or about 68 mg$^2$/dL$^2$, at least or about 70 mg$^2$/dL$^2$, at least or about 72 mg$^2$/dL$^2$, at least or about 74 mg$^2$/dL$^2$, at least or about 76 mg$^2$/dL$^2$, at least or about 78 mg$^2$/dL$^2$, at least or about 80 mg$^2$/dL$^2$, at least or about 82 mg$^2$/dL$^2$, at least or about 84 mg$^2$/dL$^2$, at least or about 86 mg$^2$/dL$^2$, at least or about 88 mg$^2$/dL$^2$, at least about 90 mg$^2$/dL$^2$, at least or about 92 mg$^2$/dL$^2$, at least or about 94 mg$^2$/dL$^2$, at least or about 96 mg$^2$/dL$^2$, at least about 98 mg$^2$/dL$^2$, or at least about 100 mg$^2$/dL$^2$) in the biological sample and (ii) a serum creatinine level of grade 1 or greater (e.g., grade 2, grade 3) in the biological sample. Exemplary assays for determining the calcium level of a biological sample including blood, serum, or plasma are commercially available from BioVision Inc. (Milpitas, Calif.) and Sigma-Aldrich (St. Louis, Mo.). Exemplary assays for determining the creatinine level in a biological sample including blood, serum, or plasma are commercially available from BioVision Inc. (Milpitas, Calif.) and Diazyme (Poway, Calif.). In other embodiments, the subject exhibits a serum phosphate level of greater than about 7.0 mg/dL (e.g., a serum phosphate level of greater than 7 mg/dL lasting for more than 7 days despite phosphate-lowering therapies). In still other embodiments, the subject exhibits a serum phosphate level of greater than about 9.0 mg/dL (e.g., a serum phosphate level of greater than about 9.0 mg/dL for any duration despite phosphate-lowering therapies). In still other embodiments, the subject exhibits a serum phosphate level of greater than about 10.0 mg/dL (e.g., a serum phosphate level of greater than about 10.0 mg/dL for any duration).

In some embodiments, the patient is administered a therapeutically effective amount of a phosphate binder over the treatment period. Non-limiting examples of phosphate binders include aluminum salts (e.g., Alucaps and Basaljel), calcium carbonate (e.g., Calcichew and Titralac), calcium acetate (e.g., Lenal Ace and PhosLo), sevelamer hydrochloride (e.g., Renegel or Renvela), and lanthanum carbonate (e.g., Fosrenol). In some embodiments, the patient is administered a therapeutically effective amount of a phosphate binder each day over the treatment period. The phosphate binder can be administered at a total daily dose of about 2.0 g to about 5.0 g (e.g., about 2.0 g to about 4.8 g, about 4.6 g, about 4.4 g, about 4.2 g, about 4.0 g, about 3.8 g, about 3.6 g, about 3.4 g, about 3.2 g, about 3.0 g, about 2.8 g, about 2.6 g, about 2.4 g, or about 2.2 g; about 2.2 g to about 5.0 g, about 4.8 g, about 4.6 g, about 4.4 g, about 4.2 g, about 4.0 g, about 3.8 g, about 3.6 g, about 3.4 g, about 3.2 g, about 3.0 g, about 2.8 g, about 2.6 g, or about 2.4 g; about 2.4 to about 5.0 g, about 4.8 g, about 4.6 g, about 4.4 g, about 4.2 g, about 4.0 g, about 3.8 g, about 3.6 g, about 3.4 g, about 3.2, about 3.0 g, about 2.8 g, or about 2.6 g; about 2.6 g to about 5.0 g, about 4.8 g, about 4.6 g, about 4.4 g, about 4.2 g, about 4.0 g, about 3.8 g, about 3.6 g, about 3.4 g, about 3.2, about 3.0 g, or about 2.8 g; about 2.8 g to about 5.0 g, about 4.8 g, about 4.6 g, about 4.4 g, about 4.2 g, about 4.0 g, about 3.8 g, about 3.6 g, about 3.4 g, about 3.2 g, or about 3.0 g; about 3.0 g to about 5.0 g, about 4.8 g, about 4.6 g, about 4.4 g, about 4.2 g, about 4.0 g, about 3.8 g, about 3.6 g, about 3.4 g, or about 3.2 g; about 3.2 g to about 5.0 g, about 4.8 g, about 4.6 g, about 4.4 g, about 4.2 g, about 4.0 g, about 3.8 g, about 3.6 g, or about 3.4 g; about 3.4 g to about 5.0 g, about 4.8 g, about 4.6 g, about 4.4 g, about 4.2 g, about 4.0 g, about 3.8 g, or about 3.6 g; about 3.6 g to about 5.0 g, about 4.8 g, about 4.6 g, about 4.4 g, about 4.2 g, about 4.0 g, or about 3.8 g; about 3.8 g to about 5.0 g, about 4.8 g, about 4.6 g, about 4.4 g, about 4.2 g, or about 4.0 g; about 4.0 g to about 5.0 g, about 4.8 g, about 4.6 g, about 4.4 g, or about 4.2 g; about 4.2 g to about 5.0 g, about 4.8 g, about 4.6 g, or about 4.4 g; about 4.4 g to about 5.0 g, about 4.8 g, or about 4.6 g; about 4.6 g to about 5.0 g or about 4.8 g; or about 4.8 g to about 5.0 g) over the treatment period. In some embodiments of these methods, step (d) further includes ceasing administration of the phosphate binder to the selected patient or instructing the selected patient to cease administration of the phosphate binder. In some embodiments of these methods, step (d) further includes administering a decreased dose of the phosphate binder to the selected patient relative to the dose of the phosphate binder administered to the patient over the treatment period.

Also provided herein are methods of treating a FGFR-associated cancer (e.g., any of the FGFR-associated cancers described herein or known in the art) in a patient that includes administering a therapeutically effective dose of a compound of Formula I or a pharmaceutically acceptable salt or solvate thereof, or a pharmaceutical composition including a compound of Formula I or a pharmaceutically acceptable salt or solvate thereof, to a patient identified or diagnosed as having an FGFR-associated cancer over a treatment period of at least 8 days, where the patient is determined to have about the same or a decreased level of phosphate in one or more biological sample(s) including blood, serum, or plasma obtained from the patient over the treatment period as compared to a reference level of phosphate (e.g., any of the reference levels of phosphate described herein). In some embodiments of any of these methods, the patient is identified or diagnosed as having a FGFR-associated cancer using any of the methods described herein or known in the art. Some embodiments of any of these methods can further include identifying or diagnosing a subject as having a FGFR-associated cancer using any of the methods described herein or known in the art. In some embodiments, the treatment period of at least 8 days can be any of the exemplary treatment periods (or ranges of treatment periods) described herein. In some embodiments, the patient is administered a daily dose of a compound of Formula I or a pharmaceutically acceptable salt or solvate thereof, or or a pharmaceutical composition including a compound of Formula I or a pharmaceutically acceptable salt or solvate thereof (e.g., any of the pharmaceutical compositions described herein) over the treatment period.

In some embodiments of these methods, the patient is administered a low dose of a phosphate binder (e.g., any of the exemplary phosphate binders described herein or known in the art) over the treatment period. In some embodiments of these methods, the phosphate binder is sevelamer hydrochloride. In some embodiments of these methods, the lose dose of the phosphate binder (e.g., sevelamer hydrochloride) can be a total daily administration of about 0.1 g to about 2.0 g (e.g., about 0.1 g to about 1.9 g, about 1.8 g., about 1.7 g, about 1.6 g, about 1.5 g, about 1.4 g, about 1.3 g, about 1.2 g, about 1.1 g, about 1.0 g, about 0.9 g, about 0.8 g, about 0.7 g, about 0.6 g, about 0.5 g, about 0.4 g, about 0.3 g, or about 0.2 g; about 0.2 g to about 1.9 g, about 1.8 g., about 1.7 g, about 1.6 g, about 1.5 g, about 1.4 g, about 1.3 g, about 1.2 g, about 1.1 g, about 1.0 g, about 0.9 g, about 0.8 g, about 0.7 g, about 0.6 g, about 0.5 g, about 0.4 g, or about 0.3 g; about 0.3 g to about 1.9 g, about 1.8 g., about 1.7 g, about 1.6 g, about 1.5 g, about 1.4 g, about 1.3 g, about 1.2 g, about 1.1 g, about 1.0 g, about 0.9 g, about 0.8 g, about 0.7 g, about 0.6 g, about 0.5 g, or about 0.4 g; about 0.4 g to about 1.9 g, about 1.8 g., about 1.7 g, about 1.6 g, about 1.5 g, about 1.4 g, about 1.3 g, about 1.2 g, about 1.1 g, about 1.0 g, about 0.9 g, about 0.8 g, about 0.7 g, about 0.6 g, or about 0.5 g; about 0.5 g to about 1.9 g, about 1.8 g., about 1.7 g, about 1.6 g, about 1.5 g, about 1.4 g, about 1.3 g, about 1.2 g, about 1.1 g, about 1.0 g, about 0.9 g, about 0.8 g, about 0.7 g, or about 0.6 g; about 0.6 g to about 1.9 g, about 1.8 g., about 1.7 g, about 1.6 g, about 1.5 g, about 1.4 g, about 1.3 g, about 1.2 g, about 1.1 g, about 1.0 g, about 0.9 g, about 0.8 g, or about 0.7 g; about 0.7 g to about 1.9 g, about 1.8 g., about 1.7 g, about 1.6 g, about 1.5 g, about 1.4 g, about 1.3 g, about 1.2 g, about 1.1 g, about 1.0 g, about 0.9 g, or about 0.8 g; about 0.8 g to about 1.9 g, about 1.8 g., about 1.7 g, about 1.6 g, about 1.5 g, about 1.4 g, about 1.3 g, about 1.2 g, about 1.1 g, about 1.0 g, or about 0.9 g; about 0.9 g to about 1.9 g, about 1.8 g., about 1.7 g, about 1.6 g, about 1.5 g, about 1.4 g, about 1.3 g, about 1.2 g, about 1.1 g, or about 1.0 g; about 1.0 g to about 1.9 g, about 1.8 g., about 1.7 g, about 1.6 g, about 1.5 g, about 1.4 g, about 1.3 g, about 1.2 g, or about 1.1 g; about 1.1 g to about 1.9 g, about 1.8 g., about 1.7 g, about 1.6 g, about 1.5 g, about 1.4 g, about 1.3 g, or about 1.2 g; about 1.2 g to about 1.9 g, about 1.8 g., about 1.7 g, about 1.6 g, about 1.5 g, about 1.4 g, or about 1.3 g; about 1.3 g to about 1.9 g, about 1.8 g., about 1.7 g, about 1.6 g, about 1.5 g, or about 1.4 g; about 1.4 g to about 1.9 g, about 1.8 g., about 1.7 g, about 1.6 g, or about 1.5 g; about 1.5 g to about 1.9 g, about 1.8 g., about 1.7 g, or about 1.6 g; about 1.6 g to about 1.9 g, about 1.8 g., or about 1.7 g; about 1.7 g to about 2.0 g, about 1.9 g, or about 1.8 g; about 1.8 g to about 2.0 g or about 1.9 g; or about 1.9 g to about 2.0 g) of the phosphate binder.

In some embodiments, the patient is determined to have about the same or a decreased level of phosphate in one or more (e.g., two, three, four, five, or six) biological sample(s) including blood, serum, or plasma obtained from the patient at 1 day, 2 days, 3 days, 4 days, 5 days, 6 days, 7 days (1 week), 8 days, 9 days, 10 days, 11 days, 12 days, 13 days, 14 days (2 weeks), 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, or 100 days following the start of the treatment period as compared to a reference level of phosphate (e.g., any of the reference levels of phosphate described herein).

Also provided are methods of treating a FGFR-associated cancer (e.g., any of the FGFR-associated cancers described herein or known in the art) that include administering a therapeutically effective dose of a compound of Formula I or a pharmaceutically acceptable salt or solvate thereof, or a pharmaceutical composition including a compound of Formula I or a pharmaceutically acceptable salt or solvate thereof (e.g., any of the pharmaceutical compositions described herein) to a patient identified or diagnosed as having an FGFR-associated cancer over a treatment period (e.g., any of the treatment periods described herein), wherein the patient is not administered a phosphate binder (e.g., any of the phosphate binders described herein or known in the art) over or during the treatment period. In some embodiments of any of these methods, the patient is identified or diagnosed as having a FGFR-associated cancer using any of the methods described herein or known in the art. Some embodiments of any of these methods can further include identifying or diagnosing a subject as having a FGFR-associated cancer using any of the methods described herein or known in the art. In some embodiments, the treatment period can be any of the exemplary treatment periods described herein or any of the exemplary ranges of treatment periods described herein. In some embodiments, the patient is administered a daily dose of a compound of Formula I or a pharmaceutically acceptable salt or solvate thereof, or a pharmaceutical composition including a compound of Formula I or a pharmaceutically acceptable salt or solvate thereof (e.g., any of the pharmaceutical compositions described herein) over the treatment period.

Also provided herein are methods of treating a FGFR-associated cancer (e.g., any FGFR-associated cancer described herein or known in the art) in a patient that include administering a therapeutically effective dose of a compound of Formula I or pharmaceutically acceptable salt or solvate thereof, or a pharmaceutical composition including a compound of Formula I or a pharmaceutically acceptable salt or solvate thereof (e.g., any of the pharmaceutical compositions described herein) to a patient identified or diagnosed as having an FGFR-associated cancer over a treatment period (e.g., any of the treatment periods described herein), wherein the patient is further administered a low dose of a phosphate binder (e.g., any of the phosphate binders described herein, e.g., sevelamer hydrochloride) (e.g., any of the low doses of a phosphate binder described herein) over or over at least a part of the treatment period. Some embodiments of any of these methods can further include identifying or diagnosing a subject as having a FGFR-associated cancer using any of the methods described herein or known in the art. In some embodiments, the treatment period can be any of the exemplary treatment periods described herein or any of the exemplary ranges of treatment periods described herein. In some embodiments, the patient is administered a daily dose of a compound of Formula I or a pharmaceutically acceptable salt or solvate thereof, or a pharmaceutical composition including a compound of Formula I or a pharmaceutically acceptable salt or solvate thereof (e.g., any of the pharmaceutical compositions described herein) over the treatment period.

Also provided are methods of treating a patient having a FGFR-associated cancer (e.g., any of the FGFR-associated cancers described herein or known in the art) that include administering a therapeutically effective dose of a compound of Formula I or a pharmaceutically acceptable salt or solvate thereof, or a pharmaceutical composition including a compound of Formula I of a pharmaceutically acceptable salt or solvate thereof (e.g., any of the pharmaceutical compositions described herein) to a patient identified or diagnosed as having an FGFR-associated cancer over a treatment period (e.g., any of the treatment periods described herein), where the patient does not experience or is less likely to experience one or more (e.g., two, three, four, five, six, seven, eight, or nine) of soft tissue calcification, stomatitis, dry mouth, nail changes, fatigue, asthenia, anorexia, malaise, and muscle aches over the treatment period or after the treatment period (e.g., as compared to a patient or a population of patients having the same FGFR-associated cancer and administered a therapeutically effective dose of a FGFR inhibitor that is not a compound of Formula I or a pharmaceutically acceptable salt or solvate thereof, or a pharmaceutical composition including a compound of Formula I or a pharmaceutically acceptable salt or solvate thereof, over the same treatment period). Some embodiments of any of these methods can further include identifying or diagnosing a subject as having a FGFR-associated cancer using any of the methods described herein or known in the art. In some embodiments, the treatment period can be any of the exemplary treatment periods described herein or any of the exemplary ranges of treatment periods described herein. In some embodiments, the patient is administered a daily dose of a compound of Formula I or a pharmaceutically acceptable salt or solvate thereof, or a pharmaceutical composition including a compound of Formula I or a pharmaceutically acceptable salt or solvate thereof (e.g., any of the pharmaceutical compositions described herein) over the treatment period.

In some embodiments of these methods, the patient is not administered a phosphate binder (e.g., any of the phosphate binders described herein or known in the art) during the treatment period. In such methods, the patient can be, e.g., less likely to experience one or more (e.g., two, three, four, five, six, seven, eight, or nine) of soft tissue calcification, stomatitis, dry mouth, nail changes, fatigue, asthenia, anorexia, malaise, and muscle aches over the treatment period or after the treatment period (e.g., as compared to a patient or a population of patients having the same FGFR-associated cancer and administered a therapeutically effective dose of a FGFR inhibitor that is not a compound of Formula I or a pharmaceutically acceptable salt or solvate thereof, or a pharmaceutical composition including a compound of Formula I or a pharmaceutically acceptable salt or solvate thereof, and is not administered a phosphate binder, over the same treatment period).

In some embodiments of these methods, the patient is administered a low dose of a phosphate binder (e.g., any of the phosphate binders described herein, e.g., sevelamer hydrochloride) (e.g., any of the exemplary low doses of a phosphate binder described herein). In such methods, the patient can be, e.g., less likely to experience one or more (e.g., two, three, four, five, six, seven, eight, or nine) of soft tissue calcification, stomatitis, dry mouth, nail changes, fatigue, asthenia, anorexia, malaise, and muscle aches over the treatment period or after the treatment period (e.g., as compared to a patient or a population of patients having the same FGFR-associated cancer and administered a therapeutically effective dose of a FGFR inhibitor that is not a compound of Formula I or a pharmaceutically acceptable salt or solvate thereof, or a pharmaceutical composition including a compound of Formula I or a pharmaceutically acceptable salt or solvate thereof, and is administered the same low dose of phosphate binder, over the same treatment period).

The level of soft tissue calcification can be detected/determined in a patient by a medical professional using, e.g., ultrasound, radiography, computed tomography, and magnetic resonance imaging. The level of stomatitis, dry mouth, nail changes, fatigue, asthenia, anorexia, malaise, and muscle aches in a patient can be determined by a medical professional through the physical examination of the patient and/or interviewing the patient (e.g., using a survey).

In some embodiments, the patient is less likely to experience one or more (e.g., two, three, four, five, six, seven, eight, or nine) of soft tissue calcification, stomatitis, dry mouth, nail changes, fatigue, asthenia, anorexia, malaise, and muscle aches over the treatment period or after the treatment period (e.g., as compared to a patient or a population of patients having the same FGFR-associated cancer and administered a therapeutically effective dose of a FGFR inhibitor that is not a compound of Formula I or a pharmaceutically acceptable salt or solvate thereof, or a pharmaceutical composition including a compound of Formula I or a pharmaceutically acceptable salt or solvate thereof, and is administered the same low dose of phosphate binder, over the same treatment period).

The phrase "effective amount" means an amount of compound that, when administered to a patient in need of such treatment, is sufficient to (i) treat a particular disease, condition, or disorder mediated by FGFR1, FGFR2 FGFR3 and/or FGFR4, (ii) attenuate, ameliorate, or eliminate one or more symptoms of the particular disease, condition, or disorder, or (iii) delay the onset of one or more symptoms of the particular disease, condition, or disorder described herein. The amount of a compound of Formula I that will correspond to such an amount will vary depending upon factors such as the particular compound, disease condition and its severity, the identity (e.g., weight) of the patient in need of treatment, but can nevertheless be routinely determined by one skilled in the art.

When employed as pharmaceuticals, the compounds provided herein can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable Also provided herein pharmaceutical compositions which contain, as the active ingredient, a compound as provided herein or a pharmaceutically acceptable salt or solvate thereof, in combination with one or more pharmaceutically acceptable carriers (excipients). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In one embodiment, the composition is formulated for oral administration. In one embodiment, the composition is formulated as a tablet or capsule.

The compositions comprising a compound provided herein or a pharmaceutically acceptable salt or solvate thereof can be formulated in a unit dosage form, each dosage containing from about 5 to about 1,000 mg (1 g), more usually about 100 mg to about 500 mg, of the active ingredient. The term "unit dosage form" refers to physically discrete units suitable as unitary dosages for human subjects and other patients, each unit containing a predetermined quantity of active material (i.e., a compound for Formula I as provided herein) calculated to produce the desired therapeutic effect, in association with a suitable pharmaceutical excipient.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like. In some embodiments, the active compound is administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

Provided herein are pharmaceutical kits useful, for example, in the treatment of FGFR-associated diseases or disorders, such as cancer, which include one or more containers containing a pharmaceutical composition comprising a therapeutically effective amount of a compound provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

EXAMPLES

The following examples illustrate the invention.

Synthetic Examples

Synthesis of Synthetic Intermediates

| | Abbreviations |
|---|---|
| ACN | Acetonitrile |
| bis(pinacolato)diboron | 4,4,4',4',5,5,5',5'-octamethyl-2,2'-bi(1,3,2-dioxaborolane) |
| Boc | t-butoxycarbonyl |
| $Cu(OAc)_2$ | Copper (II) Acetate |
| DCM | Dichloromethane |
| DIPEA | N,N-Diisopropylethylamine |
| DMF | N,N-Dimethylformamide |
| dppf | 1,1'-bis(diphenylphosphanyl) ferrocene |
| eq | equivalent/equivalents |
| $Et_2O$ | Diethyl ether |
| EtOAc | Ethyl Acetate |
| EtOH | Ethanol |
| GFF paper or GF/F paper | Whatman glass microfiber filter paper |
| h | hour/hours |
| HATU | 2-(7-Aza-1H-benzotriazole-1-yl)-1,1,3,3-tetramethyluronium hexafluorophosphate |
| iPrOH | Isopropanol |
| KOAc | Potassium Acetate |
| MeOH | Methanol |
| min | minute/minutes |
| MsCl | methansulfonyl chloride |
| NBS | N-Bromosuccinimide |
| $Pd(OAc)_2$ | Palladium (II) Acetate |
| $Pd(PPh_3)_4$ | Tetrakis(triphenylphosphine)palladium (0) |
| $PdCl_2(dppf) \cdot CH_2Cl_2$ | 1,1'-Bis(diphenylphosphino)ferrocene-palladium(II)dichloride dichloromethane complex |
| TEA | Triethylamine |
| TFA | Trifluoroacetic acid |
| THF | tetrahydrofuran |
| TLC | thin layer chromatography |
| X-Phos | dicyclohexyl(2',4',6'-triisopropyl-[1,1'-biphenyl]-2-yl)phosphine |

Synthesis of Synthetic Intermediates

Intermediate S1

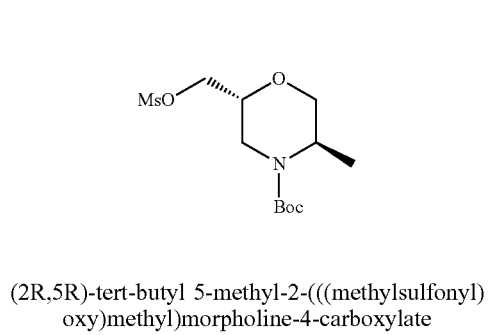

(2R,5R)-tert-butyl 5-methyl-2-(((methylsulfonyl)oxy)methyl)morpholine-4-carboxylate A cold (0° C.) solution of (2R,5R)-tert-butyl 2-(hydroxymethyl)-5-methylmorpholine-4-carboxylate (275 mg, 1.19 mmol) and DIPEA (312 μL, 1.78 mmol) in DCM (6 mL) was treated with MsCl (110 μL, 1.43 mmol). The resulting mixture was stirred overnight at ambient temperature. The mixture was partitioned between saturated NaHCO$_{3(aq)}$ (30 mL) and DCM (20 mL), and the aqueous extracts were washed with additional DCM (2×10 mL). The combined organic extracts were washed with brine (10 mL), dried over anhydrous Na$_2$SO$_{4(s)}$, filtered and concentrated under vacuum affording the title compound (367 mg, 99% yield). This material was of sufficient purity to be used directly without further purification.

The following intermediates shown in Table S1 were prepared according the method used for the synthesis of Intermediate S1 using the appropriate chiral hydroxymethyl-(morpholine)carboxylate starting materials. The reaction progression in each was followed by TLC (50% Hexanes/EtOAc, KMnO$_4$ stain) and reaction times were adjusted as necessary.

Intermediate S6

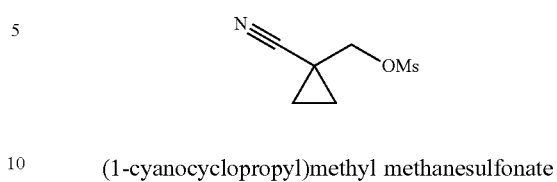

(1-cyanocyclopropyl)methyl methanesulfonate

A solution of 1-(hydroxymethyl)cyclopropanecarbonitrile (1.14 g, 11.7 mmol) in DCM (24 mL) was treated with TEA (3.50 mL, 25.8 mmol). The resulting reaction mixture was cooled to 0° C., treated dropwise with MsCl (1.37 mL, 17.6 mmol) and stirred for 1 h at 0° C. The reaction mixture was stirred at ambient temperature for an additional 2 h before being diluted with additional DCM (100 mL) and washed with brine (25 mL). The organic extracts were dried over anhydrous Na$_2$SO$_{4(s)}$, filtered and concentrated under vacuum to afford the title compound (2.057 g, 100% yield). This material was of sufficient purity to be used directly without further purification. 1H NMR (400 MHz, DMSO-d6) δ 4.27 (s, 2H), 3.23 (s, 3H), 1.42-1.38 (m, 2H), 1.21-1.18 (m, 2H).

Intermediate P1

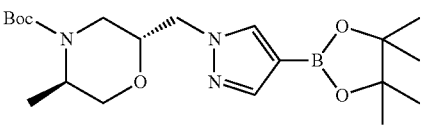

TABLE S1

| Intermediate | Structure | Name |
|---|---|---|
| S2 | MsO⭢⟨morpholine, 5-Me, Boc⟩ | tert-butyl (2S,5R)-5-methyl-2-(((methylsulfonyl)oxy)methyl)morpholine-4-carboxylate |
| S3 | MsO⭢⟨morpholine, 5,5-diMe, Boc⟩ | tert-butyl (S)-5,5-dimethyl-2-(((methylsulfonyl)oxy)methyl)morpholine-4-carboxylate |
| S4 | MsO⭢⟨morpholine, 5,5-diMe, Boc⟩ | tert-butyl (R)-5,5-dimethyl-2-(((methylsulfonyl)oxy)methyl)morpholine-4-carboxylate |
| S5 | MsO⭢⟨oxa-azaspiro octane, Boc⟩ | tert-butyl (R)-6-(((methylsulfonyl)oxy)methyl)-7-oxa-4-azaspiro[2.5]octane-4-carboxylate | tert-butyl (2R,5R)-5-methyl-2-((4-(4,4,5,5-tetram-ethyl-1,3,2-dioxaborolan-2-yl)-1H-pyrazol-1-yl)methyl)morpholine-4-carboxylate A mixture of 4-(4,4,5,5-tetramethyl-1,3,2-dioxaborolan-2-yl)-1H-pyrazole (276 mg, 1.42 mmol), (2R,5R)-tert-butyl 5-methyl-2-(((methylsulfonyl)oxy)methyl)morpholine-4-carboxylate (Intermediate S1; 367 mg, 1.19 mmol), and $Cs_2CO_{3(s)}$ (966 mg, 2.97 mmol) was suspended in DMF (5.93 mL) and stirred for 1 day at ambient temperature. The mixture was partitioned between EtOAc (100 mL) and $H_2O$ (50 mL). The organic extracts were separated and then dried over anhydrous $Na_2SO_{4(s)}$, filtered and concentrated under vacuum. The crude residue was purified by silica chromatography (0-100% EtOAc/Hexanes) to afford the title compound (483 mg, 100% yield). MS (apci) m/z=408.2 (M+H).

The following intermediates shown in Table P1 were prepared according the method used for the synthesis of Intermediate P1, tert-butyl (2R,5R)-5-methyl-2-((4-(4,4,5,5-tetramethyl-1,3,2-dioxaborolan-2-yl)-1H-pyrazol-1-yl)methyl)morpholine-4-carboxylate, using the appropriate chiral methanesulfonoxy-methyl-morpholine-4-carboxylate starting materials (Intermediates S2-S5 from Table S1). All compounds were purified using a method similar to that used for purifying Intermediate P1 utilizing the appropriate gradient for the silica chromatography.

Intermediate P6

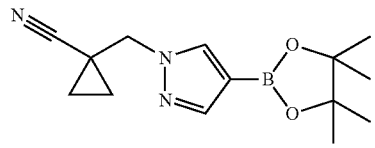

1-((4-(4,4,5,5-tetramethyl-1,3,2-dioxaborolan-2-yl)-1H-pyrazol-1-yl)methyl)cyclopropane-1-carbonitrile A solution of 4-(4,4,5,5-tetramethyl-1,3,2-dioxaborolan-2-yl)-1H-pyrazole (1.52 g, 7.83 mmol) in DMA (31 mL) was treated with 1-cyanocyclopropyl)methyl methanesulfonate (Intermediate S6; 1.99 g, 11.4 mmol), $Cs_2CO_{3(s)}$ (3.83 g, 11.8 mmol) and 4A molecular sieves (250 mg). The resulting suspension was stirred for 16 h at 100° C. After cooling to ambient temperature, the reaction mixture was filtered, and the solids collected were rinsed with EtOAc (50 mL). The filtrate was diluted with toluene (150 mL) and concentrated under vacuum. The resulting crude residue was azeotroped with toluene (150 mL) several times to remove most of the DMA and subsequently purified by silica chromatography (5-75% Hexanes/EtOAc as the gradient eluent) to afford the

TABLE P1

| Intermediate | Structure | Name | MS (apci) m/z |
|---|---|---|---|
| P2 | 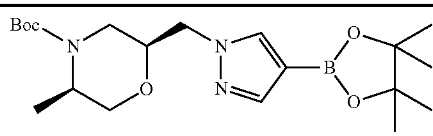 | tert-butyl (2S,5R)-5-methyl-2-((4-(4,4,5,5-tetramethyl-1,3,2-dioxaborolan-2-yl)-1H-pyrazol-1-yl)methyl)morpholine-4-carboxylate | 408.3 (M + H) |
| P3 | 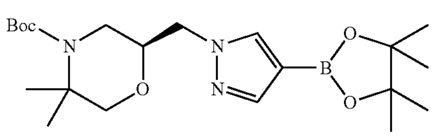 | tert-butyl (S)-5,5-dimethyl-2-((4-(4,4,5,5-tetramethyl-1,3,2-dioxaborolan-2-yl)-1H-pyrazol-1-yl)methyl)morpholine-4-carboxylate | 422.2 (M + H) |
| P4 | 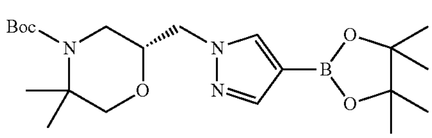 | tert-butyl (R)-5,5-dimethyl-2-((4-(4,4,5,5-tetramethyl-1,3,2-dioxaborolan-2-yl)-1H-pyrazol-1-yl)methyl)morpholine-4-carboxylate | 422.2 (M + H) |
| P5 | | tert-butyl (R)-6-((4-(4,4,5,5-tetramethyl-1,3,2-dioxaborolan-2-yl)-1H-pyrazol-1-yl)methyl)-7-oxa-4-azaspiro[2.5]octane-4-carboxylate | 420.2 (M + H) | title compound (1.38 g, 65% yield). ¹H NMR (400 MHz, DMSO-d₆) δ 8.03 (s, 1H), 7.65 (s, 1H), 4.28 (s, 2H), 1.33-1.23 (m, 16H).

Intermediate P7

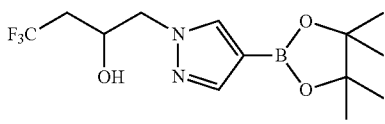

4,4,4-trifluoro-1-(4-(4,4,5,5-tetramethyl-1,3,2-dioxaborolan-2-yl)-1H-pyrazol-1-yl)butan-2-ol A mixture of 4-(4,4,5,5-tetramethyl-1,3,2-dioxaborolan-2-yl)-1H-pyrazole (500 mg, 2.58 mmol), 2-(2,2,2-trifluoroethyl)oxirane (390 mg, 3.09 mmol), and Cs₂CO₃₍ₛ₎ (1.68 g, 5.15 mmol) was suspended in DMF (2.58 mL) and stirred overnight at 80° C. The mixture was partitioned between EtOAc (50 mL) and H₂O (25 mL). The organic extracts were separated then dried over anhydrous Na₂SO₄₍ₛ₎ filtered and concentrated under vacuum to afford the title compound (825 mg, 100% yield). MS (apci) m/z=321.1 (M+H). This material was of sufficient purity to be used directly without further purification.

Intermediate P8

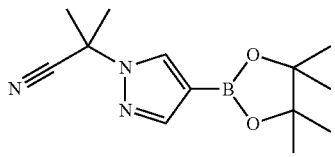 [SMILES: CC(C)(C#N)n1cc(B2OC(C)(C)C(C)(C)O2)cn1]

2-methyl-2-(4-(4,4,5,5-tetramethyl-1,3,2-dioxaborolan-2-yl)-1H-pyrazol-1-yl)propanenitrile Step 1: Preparation of 2-(4-(4,4,5,5-tetramethyl-1,3,2-dioxaborolan-2-yl)-1H-pyrazol-1-yl)acetonitrile A solution of 4-(4,4,5,5-tetramethyl-1,3,2-dioxaborolan-2-yl)-1H-pyrazole (5.11 g, 26.3 mmol) in DMF (50 mL) was treated with bromoacetonitrile (2.20 mL, 31.6 mmol) and K₂CO₃₍ₛ₎ (5.46 g, 39.5 mmol). The resulting suspension was stirred for 24 h at 100° C. The reaction mixture was cooled to ambient temperature, diluted with water (100 mL) then extracted with EtOAc (3×250 mL). The combined organic extracts were washed with water (3×50 mL) and brine (50 mL) then dried over anhydrous Na₂SO₄₍ₛ₎. Following filtration, the organic extracts were concentrated under vacuum then purified by silica chromatography (10-60% Hexanes/EtOAc as the gradient eluent) to afford the title compound (2.42 g, 39% yield). ¹H NMR (400 MHz, DMSO-d₆) δ 8.04 (s, 1H), 7.71 (s, 1H), 5.49 (s, 2H), 1.25 (s, 12H).

Step 2: Preparation of 2-methyl-2-(4-(4,4,5,5-tetramethyl-1,3,2-dioxaborolan-2-yl)-1H-pyrazol-1-yl)propanenitrile A cold (0° C.) solution of 2-(4-(4,4,5,5-tetramethyl-1,3,2-dioxaborolan-2-yl)-1H-pyrazol-1-yl)acetonitrile (2.42 g, 10.4 mmol) in THF (26 mL) was treated with iodomethane (1.94 mL, 31.1 mmol) then drop-wise with sodium bis(trimethylsilyl)amide (22.8 mL, 22.8 mmol). The resulting mixture was stirred 1 h at 0° C. before quenching with the addition of saturated NH₄Cl₍ₐq₎ (25 mL). At ambient temperature the reaction mixture was then partitioned between EtOAc (250 mL) and water (100 mL). The organic extracts were washed again with water (50 mL) and brine (50 mL), then dried over anhydrous Na₂SO₄₍ₛ₎, filtered and concentrated under vacuum. The crude residue was purified by silica chromatography (5-50%, Hexanes/EtOAc as the gradient eluent) to afford the title compound (1.35 g, 50% yield). ¹H NMR (400 MHz, DMSO-d₆) δ 8.20 (s, 1H), 7.75 (s, 1H), 1.97 (s, 6H), 1.26 (s, 12H).

Intermediate P9

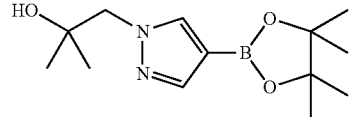 [SMILES: CC(C)(O)Cn1cc(B2OC(C)(C)C(C)(C)O2)cn1]

2-methyl-1-(4-(4,4,5,5-tetramethyl-1,3,2-dioxaborolan-2-yl)-1H-pyrazol-1-yl)propan-2-ol A mixture of 4-(4,4,5,5-tetramethyl-1,3,2-dioxaborolan-2-yl)-1H-pyrazole (2.16 g, 11.1 mmol) and Cs₂CO₃₍ₛ₎ (3.81 g, 11.7 mmol) in 2,2-dimethyloxirane (3 mL, 33.6 mmol) was stirred overnight at 100° C. The reaction mixture was filtered through GFF paper and the filtrate was concentrated under vacuum to afford the title compound (2.48 g, 84% yield). This material was of sufficient purity to be used directly without further purification. ¹H NMR (CDCl3) δ 7.81 (s, 1H), 7.69 (s, 1H Intermediate Y1

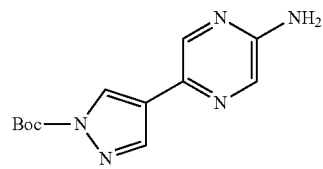 [SMILES: CC(C)(C)OC(=O)n1cc(-c2cnc(N)cn2)cn1]

tert-butyl 4-(5-aminopyrazin-2-yl)-1H-pyrazole-1-carboxylate

A mixture of 2-amino-5-bromopyrazine (100 mg, 0.575 mmol), tert-butyl 4-(4,4,5,5-tetramethyl-1,3,2-dioxaborolan-2-yl)-1H-pyrazole-1-carboxylate (338 mg, 1.15 mmol), PdCl₂(dppf)·CH₂Cl₂ (47.3 mg, 0.0575 mmol), K₂CO₃₍ₛ₎ (238 mg, 1.72 mmol) was suspended in a mixture of dioxane (5.75 mL) and water (1.15 mL). The mixture was sparged with Ar₍g₎, then sealed and stirred for 4 h at 90° C. After cooling to ambient temperature, the reaction mixture was diluted with EtOAc, filtered then concentrated under vacuum. The crude residue was purified by silica chromatography (70-100% EtOAc in Hexanes as the eluent) to afford the title compound (84 mg, 56% yield). MS (apci) m/z=162.1 (desBoc M+H).

The following 4-(5-aminopyrazin-2-yl)-1H-pyrazole intermediates, shown in Table Y1, were prepared in a manner similar to the method used for the synthesis of Intermediate Y1, using the appropriate arylboronate starting materials (commercially available or synthesized according to Examples provided herein), excess $K_2CO_{3(s)}$ (0.1-0.2 equivalents), 0.1-0.2 M in 5:1 dioxane:water and temperatures between 85-90° C. Reaction progression in each was followed by LCMS and reactions times were adjusted as necessary. All compounds were purified by silica chromatography as in Intermediate Y1 utilizing the appropriate eluent.

TABLE Y1

| Intermediate | Structure | Name | MS (apci) m/z |
|---|---|---|---|
| Y9 | 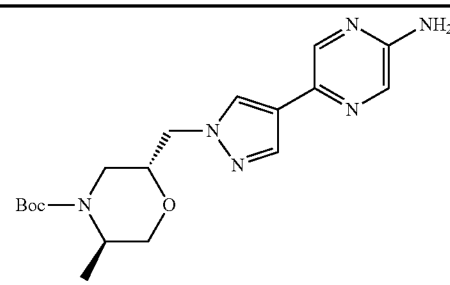 | (2R,5R)-tert-butyl 2-((4-(5-aminopyrazin-2-yl)-1H-pyrazol-1-yl)methyl)-5-methylmorpholine-4-carboxylate | 275.1 [(M − Boc) + H] |
| Y10 | 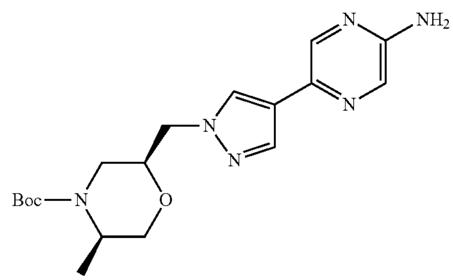 [SMILES: C[C@@H]1CO[C@H](Cn2cc(-c3cnc(N)cn3)cn2)CN1C(=O)OC(C)(C)C] | (2S,5R)-tert-butyl 2-((4-(5-aminopyrazin-2-yl)-1H-pyrazol-1-yl)methyl)-5-methylmorpholine-4-carboxylate | 275.1 [(M − Boc) + H] |
| Y11 | 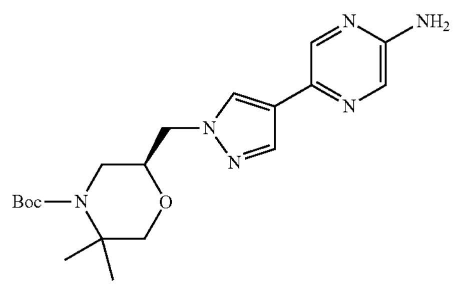 [SMILES: CC(C)(C)OC(=O)N1C[C@@H](Cn2cc(-c3cnc(N)cn3)cn2)OCC1(C)C] | tert-butyl (S)-2-((4-(5-aminopyrazin-2-yl)-1H-pyrazol-1-yl)methyl)-5,5-dimethylmorpholine-4-carboxylate | 389.2 (M + H) |
| Y12 | 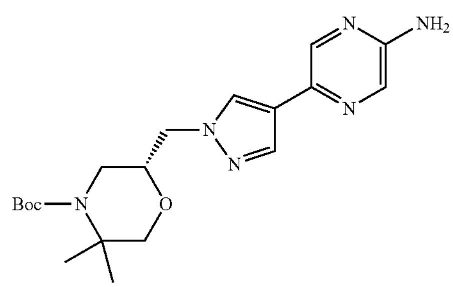 [SMILES: CC(C)(C)OC(=O)N1C[C@H](Cn2cc(-c3cnc(N)cn3)cn2)OCC1(C)C] | tert-butyl (R)-2-((4-(5-aminopyrazin-2-yl)-1H-pyrazol-1-yl)methyl)-5,5-dimethylmorpholine-4-carboxylate | 389.2 (M + H) |
| Y13 | 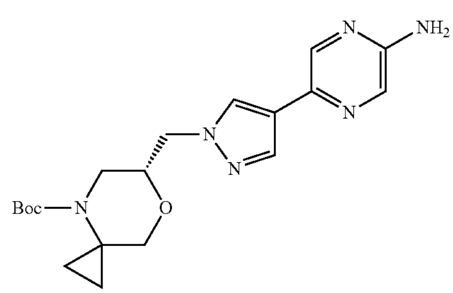 [SMILES: CC(C)(C)OC(=O)N1C[C@H](Cn2cc(-c3cnc(N)cn3)cn2)OCC12CC2] | tert-butyl (R)-6-((4-(5-aminopyrazin-2-yl)-1H-pyrazol-1-yl)methyl)-7-oxa-4-azaspiro[2.5]octane-4-carboxylate | 387.2 (M + H) |

Intermediate Y2

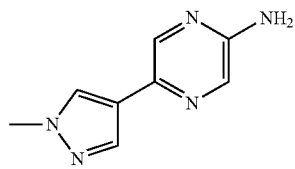

5-(1-methyl-1H-pyrazol-4-yl)pyrazin-2-amine

A solution of 2-amino-5-bromopyrazine (5.7 g, 33 mmol) in 4:1 dioxane:water (300 mL) was treated with 1-methyl-4-(4,4,5,5-tetramethyl-1,3,2-dioxaborolan-2-yl)-1H-pyrazole (7.2 g, 34 mmol), PdCl$_2$(dppf)·CH$_2$Cl$_2$ (1.3 g, 1.6 mmol), K$_2$CO$_{3(s)}$ (14 g, 98 mmol). The mixture was sparged with Ar$_{(g)}$, then sealed and stirred for 16 h at 100° C. After cooling to ambient temperature, the reaction mixture was diluted with 4:1 DCM/iPrOH (500 mL), and the resulting solution was extracted with water (2×100 mL). The organic extracts were dried over anhydrous Na$_2$SO$_{4(s)}$, filtered and concentrated under vacuum. The resulting crude residue was purified by silica chromatography (1-30% DCM/MeOH as the gradient eluent) to afford the title compound (63.4 mg, 63% yield). MS (apci) m/z=176.1 (M+H).

Intermediate Y3

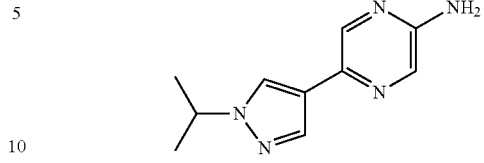

5-(1-isopropyl-1H-pyrazol-4-yl)pyrazin-2-amine

A mixture of 2-amino-5-bromopyrazine (0.505 g, 2.90 mmol), 1-isopropyl-4-(4,4,5,5-tetramethyl-1,3,2-dioxaborolan-2-yl)-1H-pyrazole (0.822 g, 3.48 mmol), Pd(PPh$_3$)$_4$ (0.168 g, 0.145 mmol), 2M Na$_2$CO$_{3(aq)}$ (3.05 mL, 6.09 mmol) in dioxane (9 mL) was stirred overnight at 90° C. After cooling to ambient temperature, the reaction mixture was diluted with DCM then extracted with water and brine. The organic extracts were dried over anhydrous Na$_2$SO$_{4(s)}$, filtered then concentrated under vacuum. The resulting crude residue was purified by silica chromatography to afford the title compound (0.415 g, 70% yield). MS (apci) m/z=204.1 (M+H).

The following 4-(5-aminopyrazin-2-yl)-1H-pyrazole intermediates, shown in Table Y3, were prepared according the method used for the synthesis of Intermediate Y3 using the appropriate arylboronate starting materials (commercially available or prepared as described herein). Reaction progression in each was followed by LCMS and reaction time was adjusted as necessary. All compounds were purified by silica chromatography according to the method for the isolation of Intermediate Y3 utilizing the appropriate eluent.

TABLE Y3

| Intermediate # | Structure | Name | MS (apci) m/z |
|---|---|---|---|
| Y4 | 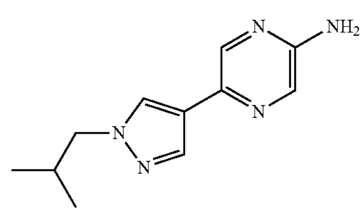 [SMILES: CC(C)Cn1cc(-c2cnc(N)cn2)cn1] | 5-(1-isobutyl-1H-pyrazol-4-yl)pyrazin-2-amine | 218.1 (M + H) |
| Y6 | 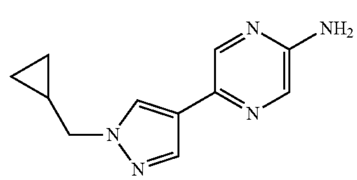 [SMILES: Nc1cnc(-c2cnn(CC3CC3)c2)cn1] | 5-(1-(cyclopropylmethyl)-1H-pyrazol-4-yl)pyrazin-2-amine | 216.1 (M + H) |
| Y7 | 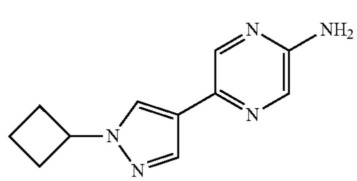 [SMILES: Nc1cnc(-c2cnn(C3CCC3)c2)cn1] | 5-(1-cyclobutyl-1H-pyrazol-4-yl)pyrazin-2-amine | 216.1 (M + H) |

TABLE Y3-continued

| Intermediate # | Structure | Name | MS (apci) m/z |
|---|---|---|---|
| Y8 | 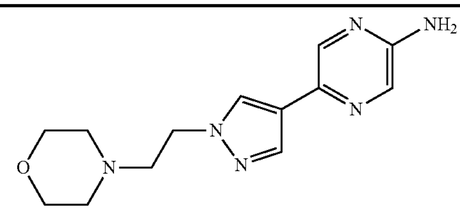 | 5-(1-(2-morpholinoethyl)-1H-pyrazol-4-yl)pyrazin-2-amine | 275.1 (M + H) |
| Y17 | 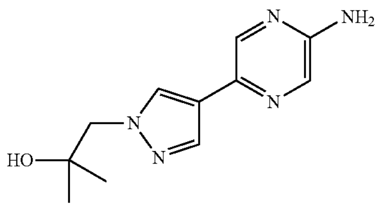 [SMILES: CC(C)(O)Cn1cc(-c2cnc(N)cn2)cn1] | 1-(4-(5-aminopyrazin-2-yl)-1H-pyrazol-1-yl)-2-methylpropan-2-ol | 234.2 (M + H) |

Intermediate Y5

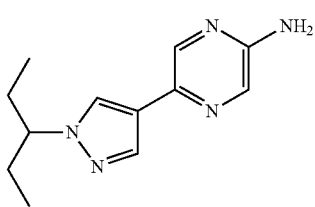 [SMILES: CCC(CC)n1cc(-c2cnc(N)cn2)cn1]

5-(1-(pentan-3-yl)-1H-pyrazol-4-yl)pyrazin-2-amine

A mixture of 2-amino-5-bromopyrazine (90.6 mg, 0.521 mmol), 1-(pentan-3-yl)-4-(4,4,5,5-tetramethyl-1,3,2-dioxaborolan-2-yl)-1H-pyrazole (194 mg, 0.573 mmol), PdCl$_2$(dppf)·CH$_2$Cl$_2$ (42.84 mg, 0.0521 mmol), K$_2$CO$_{3(s)}$ (216 mg, 1.56 mmol) was suspended in a mixture of dioxane (5.21 mL), and water (1.04 mL). The mixture was sparged with Ar$_{(g)}$, then sealed and stirred overnight at 90° C. After cooling to ambient temperature, the reaction mixture was diluted with DCM and water. The organic extracts were washed with water and brine then dried over anhydrous Na$_2$SO$_{4(s)}$, filtered and concentrated under vacuum. The resulting crude residue was purified by silica chromatography (70-100% EtOAc in Hexanes as the eluent) to afford the title compound (40 mg, 33% yield). MS (apci) m/z=232.1 (M+H).

Intermediate Y14

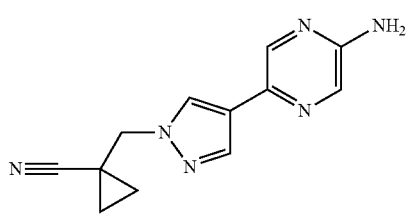 [SMILES: N#CC1(Cn2cc(-c3cnc(N)cn3)cn2)CC1]

1-((4-(5-aminopyrazin-2-yl)-1H-pyrazol-1-yl)methyl)cyclopropane-1-carbonitrile

A solution of 1-((4-(4,4,5,5-tetramethyl-1,3,2-dioxaborolan-2-yl)-1H-pyrazol-1-yl)methyl)cyclopropanecarbonitrile (Intermediate P6; 560.0 mg, 2.050 mmol) in 4:1 dioxane: water (10 mL) was treated with 2-amino-5-bromopyrazine (356.7 mg, 2.050 mmol), Pd(PPh$_3$)$_4$(236.9 mg, 0.2050 mmol), K$_2$CO$_{3(s)}$ (850.1 mg, 6.151 mmol). The mixture was sparged with Ar$_{(g)}$, then sealed and stirred for 16 h at 100° C. After cooling to ambient temperature, the reaction mixture was diluted with 4:1 DCM:iPrOH (200 mL) and the resulting solution was extracted with water (2×50 mL). The organic extracts were dried over anhydrous Na$_2$SO$_{4(s)}$, filtered and concentrated under vacuum. The resulting crude residue was purified by silica chromatography (1-30% DCM/MeOH as the gradient eluent) to afford the title compound (246.6 mg, 51% yield). MS (apci) m/z=241.1 (M+H).

Intermediate Y15

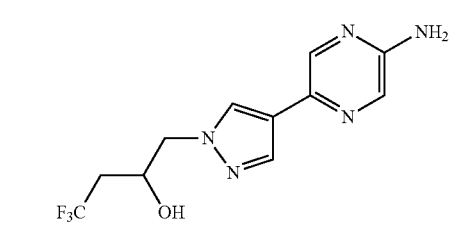

1-(4-(5-aminopyrazin-2-yl)-1H-pyrazol-1-yl)-4,4,4-trifluorobutan-2-ol

The title compound was prepared (83.2 mg, 23% yield) according to the method described for Intermediate Y14, using 4,4,4-trifluoro-1-(4-(4,4,5,5-tetramethyl-1,3,2-dioxaborolan-2-yl)-1H-pyrazol-1-yl)butan-2-ol (Intermediate P7) in place of 1-((4-(4,4,5,5-tetramethyl-1,3,2-dioxaborolan-2-yl)-1H-pyrazol-1-yl)methyl)cyclopropanecarbonitrile (Intermediate P6). MS (apci) m/z=288.0 (M+H).

Intermediate Y16

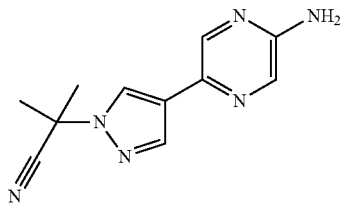 [SMILES: CC(C)(C#N)n1cc(-c2cnc(N)cn2)cn1]

2-(4-(5-aminopyrazin-2-yl)-1H-pyrazol-1-yl)-2-methylpropanenitrile

A solution of 2-amino-5-bromopyrazine (258.9 mg, 1.488 mmol) in 4:1 dioxane:water (10 mL) was treated with 1-((4-(4,4,5,5-tetramethyl-1,3,2-dioxaborolan-2-yl)-1H-pyrazol-1-yl)methyl)cyclopropanecarbonitrile (Intermediate P8; 560.0 mg, 2.050 mmol), PdCl$_2$(dppf)•CH$_2$Cl$_2$ (122.4 mg, 0.1488 mmol), K$_2$CO$_{3(s)}$ (616.9 mg, 4.464 mmol). The mixture was sparged with Ar$_{(g)}$, then sealed and stirred for 16 h at 100° C. After cooling to ambient temperature, the reaction mixture was diluted with 4:1 DCM:iPrOH (250 mL) and the resulting solution was extracted with water (2×50 mL). The organic extracts were dried over anhydrous Na$_2$SO$_{4(s)}$, filtered and concentrated under vacuum. The resulting crude residue was purified by C18 reverse phase chromatography (5-95% water/ACN with 0.1% TFA as the gradient eluent) to afford the title compound as a TFA salt. The TFA salt was dissolved in 4:1 DCM:iPrOH (100 mL) and extracted with saturated NaHCO$_{3(aq)}$ (1×25 mL). The organic extracts were dried over anhydrous Na$_2$SO$_{4(s)}$, filtered and concentrated under vacuum to cleanly afford the title compound (77 mg, 23% yield). MS (apci) m/z=229.1 (M+H).

Intermediate Y18

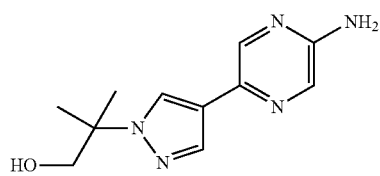 [SMILES: CC(C)(CO)n1cc(-c2cnc(N)cn2)cn1]

2-(4-(5-aminopyrazin-2-yl)-1H-pyrazol-1-yl)-2-methylpropan-1-ol

The title compound was prepared (97.2 mg, 23% yield) according to the method described for Intermediate Y16, using 2-methyl-2-(4-(4,4,5,5-tetramethyl-1,3,2-dioxaborolan-2-yl)-1H-pyrazol-1-yl)propan-1-ol in place of 1-((4-(4,4,5,5-tetramethyl-1,3,2-dioxaborolan-2-yl)-1H-pyrazol-1-yl)methyl)cyclopropanecarbonitrile (Intermediate P9). MS (apci) m/z=234.1 (M+H).

Intermediate Y19

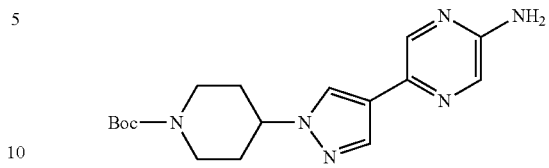

tert-butyl 4-(4-(5-aminopyrazin-2-yl)-1H-pyrazol-1-yl)piperidine-1-carboxylate

A mixture of 2-amino-5-bromopyrazine (5.0 g, 28.7 mmol), tert-butyl 4-(4-(4,4,5,5-tetramethyl-1,3,2-dioxaborolan-2-yl)-1H-pyrazol-1-yl)piperidine-1-carboxylate (11.9 g, 31.6 mmol), Pd(PPh$_3$)$_4$(3.32 g, 2.87 mmol), 2M Na$_2$CO$_{3(aq)}$ (35.9 mL, 71.8 mmol) in dioxane (57.5 mL) was purged with N$_{2(g)}$ for 6 min then sealed and stirred for 16 h at 90° C. After cooling to ambient temperature, the reaction mixture was diluted with EtOAc (300 mL) and washed with water (2×80 mL). The combined organic extracts were dried over anhydrous MgSO$_{4(s)}$, filtered and concentrated under vacuum. The resulting crude residue was precipitated from hot ACN (X mL) to provide pure title compound (6.35 g). Mother liquor was concentrated under vacuum and the residue obtained was purified by flash chromatography on silica gel (Redi Sep 220 g) eluting with 5-60% acetone/DCM (15CV) to provide additional title compound (3.17 g; 96% total yield). MS (apci) m/z=245.1 [(M-Boc)+H]. MS data are for the purified forms of batch 1 and batch 2.

Intermediate Y20

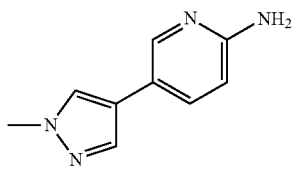

5-(1-methyl-1H-pyrazol-4-yl)pyridin-2-amine

A solution of 2-amino-5-bromopyrazine 1.03 g, 5.95 mmol) in 4:1 dioxane:water (20 mL) was treated with 1-methyl-4-(4,4,5,5-tetramethyl-1,3,2-dioxaborolan-2-yl)-1H-pyrazole (1.30 g, 6.25 mmol), PdCl$_2$(dppf)•CH$_2$Cl$_2$ (0.490 g, 0.595 mmol), K$_2$CO$_{3(s)}$ (2.47 g, 17.9 mmol). The mixture was sparged with Ar$_{(g)}$, then sealed and stirred for 16 h at 100° C. After cooling to ambient temperature, the reaction mixture was diluted with 4:1 DCM:iPrOH (250 mL) and the resulting solution was extracted with water (2×50 mL). The organic extracts were dried over anhydrous Na$_2$SO$_{4(s)}$, filtered and concentrated under vacuum. The resulting crude residue was purified by silica chromatography (1-30% DCM/MeOH as the gradient eluent) to afford the title compound (845.5 mg, 82% yield). MS (apci) m/z=175.1 (M+H).

Intermediate Y21

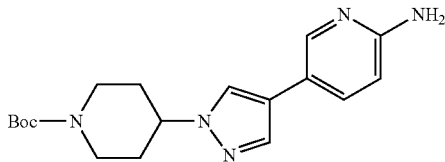 [SMILES: CC(C)(C)OC(=O)N1CCC(n2cc(-c3ccc(N)nc3)cn2)CC1]

tert-butyl 4-(4-(6-aminopyridin-3-yl)-1H-pyrazol-1-yl)piperidine-1-carboxylate

The title compound was prepared (1.12 g, 85% yield) according to the method described for Intermediate Y21, using tert-butyl 4-(4-(4,4,5,5-tetramethyl-1,3,2-dioxaborolan-2-yl)-1H-pyrazol-1-yl)piperidine-1-carboxylate in place of 1-methyl-4-(4,4,5,5-tetramethyl-1,3,2-dioxaborolan-2-yl)-1H-pyrazole and a step wise gradient eluent system of 5-60% DCM/EtOAc then 1-25% DCM/MeOH in the silica chromatography. MS (apci) m/z=344.1 (M+H).

Intermediate L1

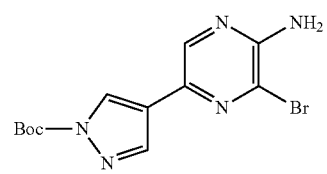 [SMILES: CC(C)(C)OC(=O)n1cc(-c2cnc(N)c(Br)n2)cn1]

tert-butyl 4-(5-amino-6-bromopyrazin-2-yl)-1H-pyrazole-1-carboxylate

A solution of tert-butyl 4-(5-aminopyrazin-2-yl)-1H-pyrazole-1-carboxylate (Intermediate Y1; 84 mg, 0.32 mmol) in CHCl$_3$ (3.2 mL) was treated with pyridine (29 µL, 0.35 mmol) and the resulting solution was cooled to 0° C. Br$_2$ (17 µL, 0.34 mmol) was added dropwise to the solution and the resulting reaction mixture was stirred at 0° C. for 30 min. The reaction mixture was then stirred at ambient temperature for 2 h prior to quenching with 10% Na$_2$S$_2$O$_{3(aq)}$. The resulting biphasic mixture was extracted with DCM. The organic extracts were dried over anhydrous Na$_2$SO$_{4(s)}$, filtered and concentrated under vacuum. The resulting crude residue was purified by silica chromatography (30-100% EtOAc in Hexanes as the gradient eluent) to afford the title compound (69 mg, 63% yield). MS (apci) m/z=242.0 [(M-Boc)+H+2], 240 [(M-Boc)+H], with Br pattern.

The following intermediates shown in Table L1 were prepared according the method used for the synthesis of Intermediate L1. Reaction progression in each was followed by LCMS and reaction time was adjusted as necessary. All compounds were purified by silica chromatography according the method used for purifying Intermediate L1 using the appropriate gradient eluent.

TABLE L1

| Intermediate # | Structure | Name | MS (apci) m/z |
|---|---|---|---|
| L5 | ![structure] | 3-bromo-5-(1-(pentan-3-yl)-1H-pyrazol-4-yl)pyrazin-2-amine | 312.0 ([(M + H) + 2] 310 (M + H) (with bromine pattern) |
| L19 | ![structure] | tert-butyl 4-(4-(5-amino-6-bromopyrazin-2-yl)-1H-pyrazol-1-yl)piperidine-1-carboxylate | 369.0 ([(des(tBu)M + H) + 2] 367 (des(tBu)M + H) (with bromine pattern) |

Intermediate L2

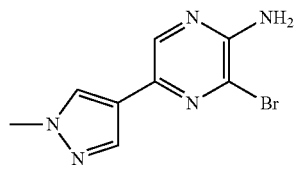

3-bromo-5-(1-methyl-1H-pyrazol-4-yl)pyrazin-2-amine

A cold (0° C.) solution of 5-(1-methyl-1H-pyrazol-4-yl)pyrazin-2-amine (Intermediate Y2; 0.210 g, 1.20 mmol) and pyridine (0.107 mL, 1.32 mmol) in CHCl$_3$ (10 mL) was treated a solution of Br$_2$ (0.422 g, 2.64 mmol) in CHCl$_3$ (4 mL). The resulting reaction mixture was maintained at 0° C. for 5 min and then allowed to stir at ambient temperature for 2 h. The reaction mixture was then diluted with DCM (50 mL) prior to quenching with saturated Na$_2$S$_2$O$_{3(aq)}$ (20 mL). The resulting biphasic mixture was separated, the organic extracts were reserved and the aqueous extracts were washed with DCM (50 mL). The combined organic extracts were dried over anhydrous Na$_2$SO$_{4(s)}$, filtered and concentrated under vacuum. The resulting crude residue was purified by silica chromatography (1:1 EtOAc/Hexanes as the eluent) to afford the title compound (0.266 g, 87% yield). MS (apci) m/z=256.0 [(M+H)+2], 254.0 (M+H), with Br pattern.

Intermediate L3

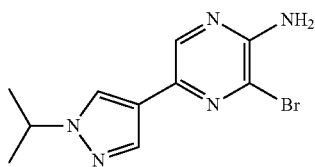 [SMILES: CC(C)n1cc(-c2cnc(N)c(Br)n2)cn1]

3-bromo-5-(1-isopropyl-1H-pyrazol-4-yl)pyrazin-2-amine

A cold (0° C.) solution of 5-(1-isopropyl-1H-pyrazol-4-yl)pyrazin-2-amine (Intermediate Y3; 0.365 g, 1.80 mmol) and pyridine (0.160 mL, 1.98 mmol) in CHCl₃ (12 mL) was treated with Br₂ (0.0971 mL, 1.89 mmol). The reaction mixture was stirred overnight at ambient temperature then diluted with DCM and extracted with saturated $Na_2S_2O_{3(aq)}$. The organic extracts were washed with brine, then dried over anhydrous $Na_2SO_{4(s)}$, filtered and concentrated under vacuum. The resulting crude residue was purified by silica chromatography to afford the title compound (0.247 g, 49% yield). MS (apci) m/z=282.0 (M+H), 284.0 [[(M+H)+2]] (bromine pattern).

The following intermediates shown in Table L3 were prepared according the method used for the synthesis of Intermediate L3 in CHCl₃ (0.1-0.15 M). Reaction progression in each was followed by LCMS and reaction time was adjusted as necessary. All compounds were purified by silica chromatography according the method used for isolating Intermediate L3 using the appropriate gradient eluent.

TABLE L3

| Intermediate # | Structure | Name | MS (apci) m/z |
|---|---|---|---|
| L4 | 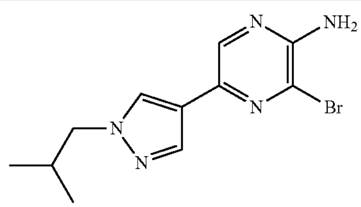 [SMILES: CC(C)Cn1cc(-c2cnc(N)c(Br)n2)cn1] | 3-bromo-5-(1-isobutyl-1H-pyrazol-4-yl)pyrazin-2-amine | 296.0 (M + H), 298.0 [(M + H) + 2] (with bromine pattern) |
| L6 | 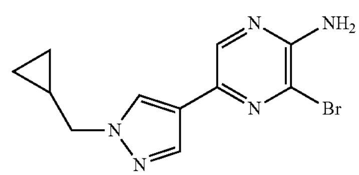 [SMILES: Nc1ncc(-c2cnn(CC3CC3)c2)nc1Br] | 3-bromo-5-(1-(cyclopropylmethyl)-1H-pyrazol-4-yl)pyrazin-2-amine | 294.0 (M + H), 296.0 [[(M + H) + 2]] (with bromine pattern) |
| L7 | 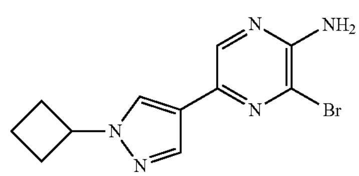 [SMILES: Nc1ncc(-c2cnn(C3CCC3)c2)nc1Br] | 3-bromo-5-(1-cyclobutyl-1H-pyrazol-4-yl)pyrazin-2-amine | 296.0 [[(M + H) + 2]], 294.0 (M + H) (with bromine pattern) |
| L8 | 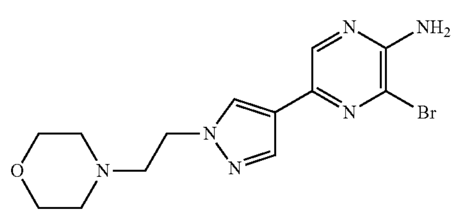 [SMILES: Nc1ncc(-c2cnn(CCN3CCOCC3)c2)nc1Br] | 3-bromo-5-(1-(2-morpholinoethyl)-1H-pyrazol-4-yl)pyrazin-2-amine | 354.9 [(M + H) + 2], 353.0 (M + H) (with bromine pattern) |
| L17 | 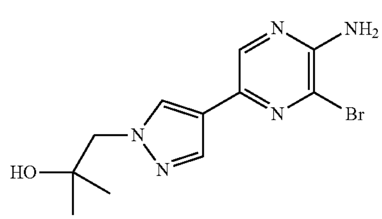 [SMILES: CC(C)(O)Cn1cc(-c2cnc(N)c(Br)n2)cn1] | 1-(4-(5-amino-6-bromopyrazin-2-yl)-1H-pyrazol-1-yl)-2-methylpropan-2-ol | 314.0 [[(M + H) + 2]], 312.0 (M + H) (with bromine pattern) |

Intermediate L10

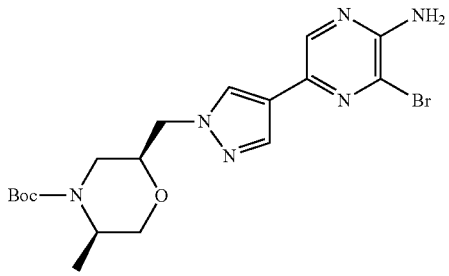 [SMILES: C[C@@H]1CO[C@H](Cn2cc(-c3cnc(N)c(Br)n3)cn2)CN1C(=O)OC(C)(C)C]

tert-butyl (2S,5R)-2-((4-(5-amino-6-bromopyrazin-2-yl)-1H-pyrazol-1-yl)methyl)-5-methylmorpholine-4-carboxylate A solution of (2S,5R)-tert-butyl 2-((4-(5-aminopyrazin-2-yl)-1H-pyrazol-1-yl)methyl)-5-methylmorpholine-4-carboxylate (Intermediate Y10; 150 mg, 0.401 mmol) and pyridine (35.61 µL, 0.441 mmol) in $CHCl_3$ (4.01 mL) was cooled to 0° C., stirred for 30 min, then treated dropwise with $Br_2$ (21.552 µL, 0.421 mmol). The reaction mixture, then was stirred overnight at ambient temperature prior to quenching with 10% $Na_2S_2O_{3(aq)}$. The resulting biphasic mixture was extracted with DCM (3×). The organic extracts were washed with water (2×) and brine then dried over anhydrous $MgSO_{4(s)}$, filtered and concentrated under vacuum. The resulting crude residue was purified by silica chromatography (60-100% EtOAc/Hexanes as the gradient eluent) to afford the title compound (50 mg, 28% yield). MS (apci) m/z=455.0 [(M+H)+2], 453 (M+H), with Br pattern.

The following intermediates shown in Table L10 were prepared according the method used for the synthesis of Intermediate L10 in $CHCl_3$ (0.1-0.2 M), from the appropriate starting materials prepared as described herein. Reaction progression was followed by LCMS and reaction time was adjusted as necessary. All compounds were purified by silica chromatography as in Intermediate L10 using the appropriate gradient eluent.

TABLE L10

| Intermediate # | Structure | Name | MS (apci) m/z |
|---|---|---|---|
| L9 [a] | 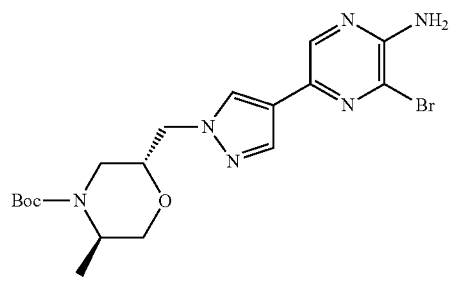 [SMILES: C[C@@H]1CO[C@@H](Cn2cc(-c3cnc(N)c(Br)n3)cn2)CN1C(=O)OC(C)(C)C] | tert-butyl (2R,5R)-2-((4-(5-amino-6-bromopyrazin-2-yl)-1H-pyrazol-1-yl)methyl)-5-methylmorpholine-4-carboxylate | 455.0 [(M + H) + 2] 453 (M + H) |
| L11 | 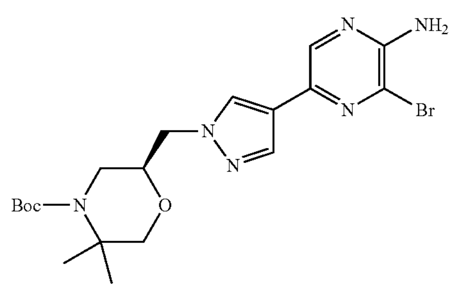 [SMILES: CC(C)(C)OC(=O)N1C[C@@H](Cn2cc(-c3cnc(N)c(Br)n3)cn2)OCC1(C)C] | tert-butyl (S)-2-((4-(5-amino-6-bromopyrazin-2-yl)-1H-pyrazol-1-yl)methyl)-5,5-dimethylmorpholine-4-carboxylate | 467.0 (M+), 469.1 (M + 2) |
| L12 | 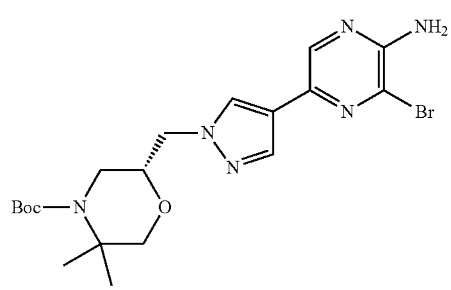 [SMILES: CC(C)(C)OC(=O)N1C[C@H](Cn2cc(-c3cnc(N)c(Br)n3)cn2)OCC1(C)C] | tert-butyl (R)-2-((4-(5-amino-6-bromopyrazin-2-yl)-1H-pyrazol-1-yl)methyl)-5,5-dimethylmorpholine-4-carboxylate | 467.1 (M+), 469.1 (M + 2) |

TABLE L10-continued

| Intermediate # | Structure | Name | MS (apci) m/z |
|---|---|---|---|
| L13 | (structure shown) | tert-butyl (R)-6-((4-(5-amino-6-bromopyrazin-2-yl)-1H-pyrazol-1-yl)methyl)-7-oxa-4-azaspiro[2.5]octane-4-carboxylate | 465.1 (M+), 467.1 (M + 2) |

*a* Additional Br₂ (0.5 equivalents) was necessary

Intermediate L16

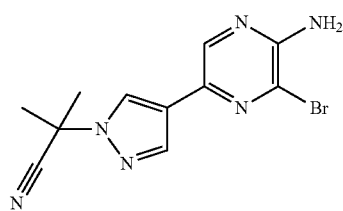 [SMILES: CC(C)(C#N)n1cc(-c2cnc(N)c(Br)n2)cn1]

2-(4-(5-amino-6-bromopyrazin-2-yl)-1H-pyrazol-1-yl)-2-methylpropanenitrile

A solution of 2-(4-(5-aminopyrazin-2-yl)-1H-pyrazol-1-yl)-2-methylpropanenitrile (Intermediate Y16; 77.0 mg, 0.337 mmol) in CHCl₃ (3.4 mL) was treated with pyridine (30.1 μL, 0.371 mmol). The resulting solution was cooled to 0° C. and then treated with Br₂ (18.2 μL, 0.354 mmol). The reaction mixture was stirred 16 h at ambient temperature prior to quenching with 10% Na₂S₂O₃$_{(aq)}$ (10 mL). The resulting biphasic mixture was diluted with 4:1 DCM:iPrOH (50 mL) and washed with water (2×25 mL). The combined organic extracts were dried over anhydrous Na₂SO₄$_{(s)}$, filtered and concentrated under vacuum. The resulting crude residue was purified by silica chromatography (1-25% DCM/MeOH as the gradient eluent) to afford the title compound (79.3 mg, 77% yield). MS (apci) m/z=307.0 [(M+H)+2], 308.9 (M+H), with Br pattern.

The following intermediates shown in Table L16 were prepared according the method used for the synthesis of Intermediate L16 from the appropriate starting materials prepared as described herein. Reaction progression in each was followed by LCMS and reaction time was adjusted as necessary. All compounds were purified by silica chromatography according to the method for isolating Intermediate L16 using the appropriate gradient eluent.

TABLE L16

| Intermediate # | Structure | Name | MS (apci) m/z |
|---|---|---|---|
| L14 | (structure shown) | 1-((4-(5-amino-6-bromopyrazin-2-yl)-1H-pyrazol-1-yl)methyl)cyclopropane-1-carbonitrile | 320.9 [(M + H) + 2] 319.0 (M + H) (with bromine pattern) |
| L15 | (structure shown) | 1-(4-(5-amino-6-bromopyrazin-2-yl)-1H-pyrazol-1-yl)-4,4,4-trifluorobutan-2-ol | 367.9 [(M + H) + 2] 366 (M + H) (with bromine pattern) |
| L18 | (structure shown) | 2-(4-(5-amino-6-bromopyrazin-2-yl)-1H-pyrazol-1-yl)-2-methylpropan-1-ol | 314.0 [(M + H) + 2] 312 (M + H) (with bromine pattern) |

Intermediate L20

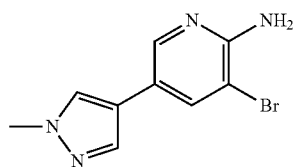

3-bromo-5-(1-methyl-1H-pyrazol-4-yl)pyridin-2-amine

A solution of 5-(1-methyl-1H-pyrazol-4-yl)pyridin-2-amine (Intermediate Y20; 845.5 mg, 4.854 mmol) in CHCl$_3$ (25 mL) was treated with pyridine (431.8 μL, 5.339 mmol). The resulting solution was cooled to 0° C. then treated with Br$_2$ (261.1 μL, 5.096 mmol). The reaction mixture was stirred 16 h at ambient temperature prior to quenching with 10% Na$_2$S$_2$O$_{3(aq)}$ (10 mL). The resulting biphasic mixture was extracted with CHCl$_3$ (2×100 mL). The combined organic extracts washed with 10% Na$_2$S$_2$O$_{3(aq)}$ (25 mL), then dried over anhydrous Na$_2$SO$_{4(s)}$, filtered and concentrated under vacuum. The resulting crude residue was purified by silica chromatography (1-25% DCM/MeOH as the gradient eluent) to afford the title compound (500.5 mg, 41% yield). MS (apci) m/z=254.9 [(M+H)+2], 252.9 (M+H), with Br pattern.

Intermediate L21

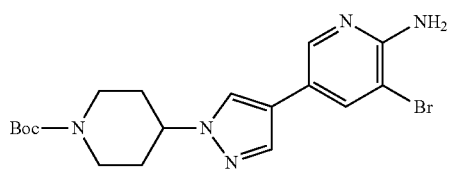 [SMILES: CC(C)(C)OC(=O)N1CCC(n2cc(-c3cnc(N)c(Br)c3)cn2)CC1]

tert-butyl 4-(4-(6-amino-5-bromopyridin-3-yl)-1H-pyrazol-1-yl)piperidine-1-carboxylate The title compound was prepared (622.4 mg, 45% yield) according to the method described for Intermediate L20, using tert-butyl 4-(4-(6-aminopyridin-3-yl)-1H-pyrazol-1-yl)piperidine-1-carboxylate (Intermediate Y21) in place of 5-(1-methyl-1H-pyrazol-4-yl)pyridin-2-amine with excess bromine/pyridine (1.6 eq each) and a gradient eluent system of 10-90% DCM/EtOAc in the silica chromatography. MS (apci) m/z=424 [(M+H)+2], 422.0 (M+H) with Br pattern.

Intermediate L22

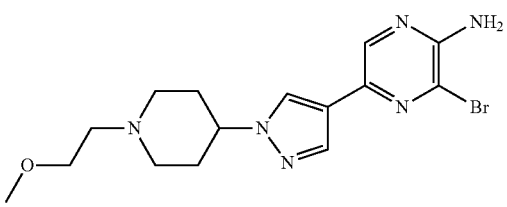 [SMILES: COCCN1CCC(n2cc(-c3cnc(N)c(Br)n3)cn2)CC1]

3-bromo-5-(1-(1-(2-methoxyethyl)piperidin-4-yl)-1H-pyrazol-4-yl)pyrazin-2-amine

Step 1: Tert-butyl 4-(4-(5-amino-6-bromopyrazin-2-yl)-1H-pyrazol-1-yl)piperidine-1-carboxylate (Intermediate L19; 2.0 g, 4.7 mmol) was treated with TFA (5 mL) and stirred at ambient temperature. After 30 minutes, the TFA was removed in vacuo and the residue was treated with 4N HCl in dioxane (50 mL) to form the HCl salt. The resulting mixture was concentrated in vacuo and the residue was dried under high vacuum to a constant weight to provide 3-bromo-5-(1-(piperidin-4-yl)-1H-pyrazol-4-yl)pyrazin-2-amine dihydrochloride (2.1 g, 5.3 mmol, 112% yield) as a white solid. MS (apci) m/z=325 [(M+H)+2], 323.0 (M+H) with Br pattern.

Step 2: 3-Bromo-5-(1-(piperidin-4-yl)-1H-pyrazol-4-yl)pyrazin-2-amine dihydrochloride (1.9 g, 4.797 mmol) was dissolved in DMF (100 mL) and treated with K$_2$CO$_3$ (2.652 g, 19.19 mmol). The mixture was cooled to 0° C. and treated dropwise with 1-bromo-2-methoxyethane (0.4508 ml, 4.797 mmol) while maintaining the internal temperature at 0° C., and then allowed to warm to ambient temperature while stirring for 72 hours. The reaction mixture was poured into ice water (1.0 L) and extracted with 5% IPA in DCM. The organics were washed with brine, then, dried over MgSO$_4$, filtered and concentrated in vacuo. The crude product was purified by flash chromatography (2-15% MeOH in DCM with 2% NH$_4$OH) to provide the title compound (1.2 g, 3.147 mmol, 65.62% yield) as an off white solid. MS (apci) m/z=383.1 [(M+H)+2], 381 (M+H) with Br pattern.

Intermediate X2

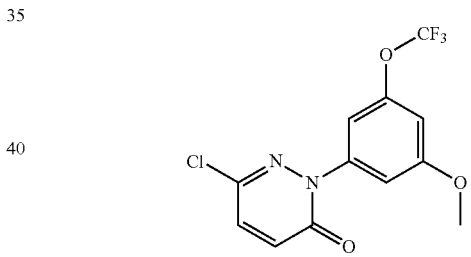

6-chloro-2-(3-methoxy-5-(trifluoromethoxy)phenyl)pyridazin-3 (2H)-one

A mixture of 6-chloropyridazin-3(2H)-one (0.125 g, 0.958 mmol), (3-methoxy-5-(trifluoromethoxy)phenyl)boronic acid (0.339 g, 1.44 mmol), Cu(OAc)$_2$ (0.0348 g, 0.192 mmol) and pyridine (0.155 mL, 1.92 mmol) in DCM (9.58 mL) was stirred overnight at ambient temperature. The mixture was diluted with DCM and washed with water and brine then dried over anhydrous Na$_2$SO$_{4(s)}$, filtered and concentrated under vacuum. The resulting crude residue was purified by silica chromatography to afford the title compound (307 mg, 82% yield). MS (apci) m/z=323.0 [(M+H)+2], 321.0 (M+H) with Cl pattern.

The following intermediates, shown in Table X2 were prepared according the method used for the synthesis of Intermediate X2 using the appropriate arylboronic acid starting materials. Reaction progression in each was followed by LCMS and reaction time was adjusted as necessary. All compounds were purified by silica chromatography according to the method used to isolate Intermediate X2.

TABLE X2

| Intermediate | Structure | Name | Spectral Data |
|---|---|---|---|
| X1 [a] | 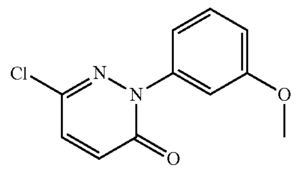 [SMILES: COc1cccc(-n2nc(Cl)ccc2=O)c1] | 6-chloro-2-(3-methoxyphenyl)pyridazin-3(2H)-one | $^1$H NMR (DMSO-$d_6$) δ 7.60 (d, 1H), 7.38 (t, 1H), 7.12 (d, 1H), 7.07 (m, 2H), 7.00 (m, 1H), 3.75 (s, 3H) |
| X5 | 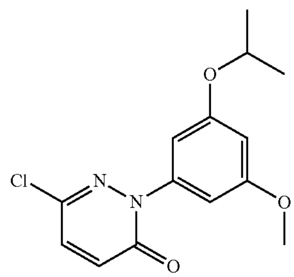 [SMILES: COc1cc(OC(C)C)cc(-n2nc(Cl)ccc2=O)c1] | 6-chloro-2-(3-isopropoxy-5-methoxyphenyl)pyridazin-3(2H)-one | MS (apci) m/z = 297.1 [(M + H) + 2], 295.0 (M + H) with Cl pattern |
| X7* | 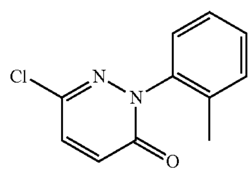 | 6-chloro-2-(o-tolyl)pyridazin-3(2H)-one | $^1$H NMR (CDCl$_3$) δ 7.30 (m, 4H), 7.04 (d, 1H), 2.19 (s, 3H) |

[a] used 10 times the amount of Cu(OAc)$_2$ used for preparing Intermediate X2 but otherwise the procedure was as described for Intermediate X2

Intermediate X3

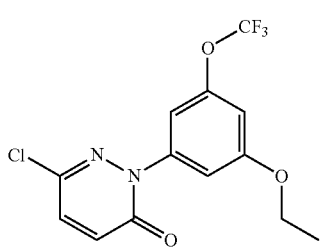 [SMILES: CCOc1cc(OC(F)(F)F)cc(-n2nc(Cl)ccc2=O)c1]

6-chloro-2-(3-ethoxy-5-(trifluoromethoxy)phenyl)pyridazin-3 (2H)-one 6-chloro-2-(3-ethoxy-5-(trifluoromethoxy)phenyl)pyridazin-3(2H)-one was made according to the procedure of Intermediate X2 substituting (3-methoxy-5-(trifluoromethoxy)phenyl)boronic acid for (3-ethoxy-5-(trifluoromethoxy)phenyl)boronic acid.

Intermediate X4

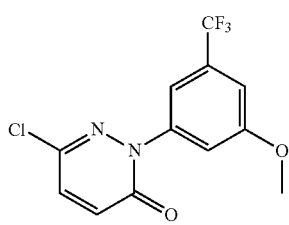 [SMILES: COc1cc(-n2nc(Cl)ccc2=O)cc(C(F)(F)F)c1]

6-chloro-2-(3-methoxy-5-(trifluoromethyl)phenyl)pyridazin-3 (2H)-one 6-chloro-2-(3-methoxy-5-(trifluoromethyl)phenyl)pyridazin-3(2H)-one was made according to the procedure for Intermediate X2, substituting (3-methoxy-5-(trifluoromethoxy)phenyl)boronic acid for (3-methoxy-5-(trifluoromethyl)phenyl)boronic acid.

Intermediate X6

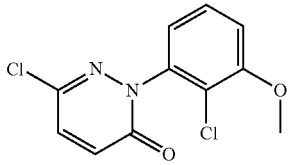 [SMILES: COc1cccc(-n2nc(Cl)ccc2=O)c1Cl]

6-chloro-2-(2-chloro-3-methoxyphenyl)pyridazin-3 (2H)-one 6-chloro-2-(2-chloro-3-methoxyphenyl)pyridazin-3(2H)-one was made according to the procedure for Intermediate X2, substituting (3-methoxy-5-(trifluoromethoxy)phenyl)boronic acid for (2-chloro-3-methoxyphenyl)boronic acid.

Intermediate X8

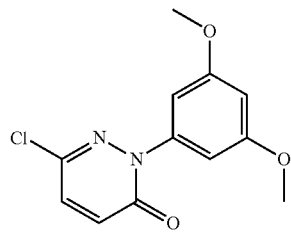 [SMILES: COc1cc(OC)cc(-n2nc(Cl)ccc2=O)c1]

6-chloro-2-(3,5-dimethoxyphenyl)pyridazin-3(2H)-one

A solution of 6-chloropyridazin-3(2H)-one (506.5 mg, 3.880 mmol) in DCM (38 mL) was treated with 3,5-dimethoxyphenylboronic acid (776.8 mg, 4.268 mmol), Cu(OAc)$_2$ (1410 mg, 7.760 mmol), and pyridine (627.7 µL, 7.760 mmol). The resulting mixture was stirred open to the atmosphere for 60 h at ambient temperature. The reaction mixture was filtered, and the filtrate was concentrated under vacuum. The resulting crude residue was purified by silica chromatography (5-60% DCM/EtOAc as the gradient eluent) to afford the title compound (560 mg, 54% yield). MS (apci) m/z=269.0 [(M+H)+2], 267.0 (M+H), with Cl pattern.

The following intermediates shown in Table X8 were prepared according the method used for the synthesis of Intermediate X8 using the appropriate arylboronic acid starting materials. Reaction progression in each was followed by LCMS and reaction time was adjusted as necessary. All compounds were purified by silica chromatography according to the method used to isolate Intermediate X8.

Intermediate X10

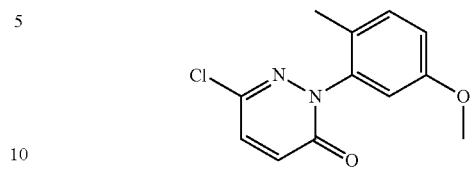

6-chloro-2-(5-methoxy-2-methylphenyl)pyridazin-3(2H)-one

A solution of 6-chloropyridazin-3(2H)-one (811.1 mg, 6.214 mmol) in DCM (31 mL) was treated with (5-methoxy-2-methylphenyl)boronic acid (1031 mg, 6.214 mmol), Cu(OAc)$_2$ (2257 mg, 12.43 mmol), and pyridine (1005 µL, 12.43 mmol). The resulting mixture was stirred open to the atmosphere for 16 h at ambient temperature. The reaction mixture was filtered, and the filtrate was concentrated under vacuum. The resulting crude residue was purified by C18 reverse phase chromatography (5-95% water/ACN with 0.1% TFA as the gradient eluent) to afford the title compound as a TFA salt. The TFA salt was dissolved in 4:1 DCM:iPrOH (100 mL) and extracted with saturated NaHCO$_{3(aq)}$ (1×25 mL). The organic extracts were dried over anhydrous Na$_2$SO$_{4(s)}$, filtered and concentrated under vacuum cleanly affording the title compound (251 mg, 16% yield). MS (apci) m/z=253.0 [(M+H)+2], 251.0 (M+H) with Cl pattern.

TABLE X8

| Intermediate | Structure | Name | Spectral Data |
|---|---|---|---|
| X9 | ![structure] | 6-chloro-2-(3,4-dimethoxyphenyl)pyridazin-3(2H)-one | MS (apci) m/z = 269.0 [(M + H) + 2], 267.0 (M + H), with Cl pattern |
| X16 | ![structure] | methyl 3-(3-chloro-6-oxopyridazin-1(6H)-yl)benzoate | $^1$H NMR (400 MHz, DMSO-d$_6$) δ 8.15-8.14 (m, 1H), 8.03-8.00 (m, 1H), 7.89-7.86 (m, 1H), 7.69-7.65 (m, 2H), 7.21-7.18 (d, 1H), 3.89 (s, 3H) |

Intermediate X11

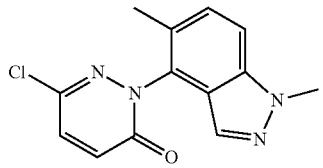 [SMILES: Cc1ccc2c(cnn2C)c1-n1nc(Cl)ccc1=O]

6-chloro-2-(1,5-dimethyl-1H-indazol-4-yl)pyridazin-3 (2H)-one

The title compound was prepared (52 mg, 12% yield) according to the method described for Intermediate X10, using 1,5-dimethyl-1H-indazole-4-boronic acid in place of (5-methoxy-2-methylphenyl)boronic acid. MS (apci) m/z=277.0 [(M+H)+2], 275.0 (M+H) with Cl pattern.

Intermediate X12

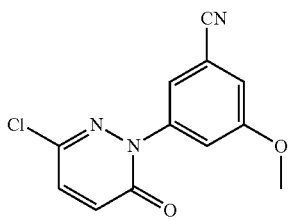

3-(3-chloro-6-oxopyridazin-1 (6H)-yl)-5-methoxybenzonitrile

Step 1: Preparation of (3-cyano-5-methoxyphenyl)boronic acid

A mixture of 3-methoxy-5-(4,4,5,5-tetramethyl-1,3,2-dioxaborolan-2-yl)benzonitrile (0.450 g, 1.74 mmol), sodium periodate (1.11 g, 5.21 mmol) and 1 M $CH_3COONH_{4(aq)}$ (3.47 mL, 3.47 mmol) in acetone (7 mL) was stirred 3 h at ambient temperature. The reaction was quenched with 4 M $HCl_{(aq)}$ (1 mL) then stirred for 20 min. The mixture was then diluted with EtOAc and extracted with water and brine, then dried over anhydrous $Na_2SO_{4(s)}$, filtered and concentrated under vacuum to afford the title compound (0.300 g, 98% yield).

Step 2: Preparation of 3-(3-chloro-6-oxopyridazin-1 (6H)-yl)-5-methoxybenzonitrile A mixture of 6-chloropyridazin-3(2H)-one (0.200 g, 1.53 mmol), (3-cyano-5-methoxyphenyl)boronic acid (0.298 g, 1.69 mmol), $Cu(OAc)_2$ (0.0557 g, 0.306 mmol) and pyridine (0.273 mL, 3.37 mmol) in DCM (9.58 mL) was stirred overnight at ambient temperature. The mixture was then diluted with DCM and extracted with water and brine, then dried over anhydrous $Na_2SO_{4(s)}$, filtered and concentrated under vacuum. The resulting crude residue was purified by silica chromatography to afford the title compound (197 mg, 49% yield). $^1$H NMR ($CDCl_3$) δ 7.60 (t, 1H), 7.49 (t, 1H), 7.28 (d, 1H), 7.18 (m, 1H), 7.40 (d, 1H), 3.88 (s, 3H).

Intermediate X13

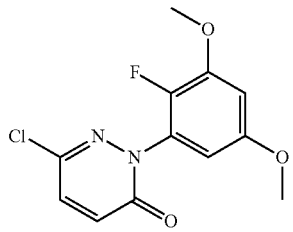 [SMILES: COc1cc(OC)c(F)c(-n2nc(Cl)ccc2=O)c1]

6-chloro-2-(2-fluoro-3,5-dimethoxyphenyl)pyridazin-3 (2H)-one

Step 1: Preparation of (2-fluoro-3,5-dimethoxyphenyl)hydrazine

A cold (0° C.) solution of 2-fluoro-3,5-dimethoxyaniline (1.00 g, 5.84 mmol) in 12.5 M $HCl_{(aq)}$ (7.01 mL, 87.6 mmol) was slowly treated with $NaNO_{2(s)}$ (0.605 g, 8.76 mmol) then stirred for 1 h at ambient temperature. The resulting reaction mixture then was treated with $SnCl_2 \cdot H_2O$ (2.64 g, 11.7 mmol), and stirred overnight at ambient temperature. The reaction mixture then was filtered, washing the solids with water. The filtrate was cooled to 0° C. and slowly basified with the addition of NaOH pellets. The resulting mixture was extracted with ethyl acetate (5×250 mL), and the combined organic extracts were washed with brine, then dried over anhydrous $Na_2SO_{4(s)}$, filtered and concentrated under vacuum to afford the title compound (724 mg, 67% yield). MS (apci) m/z=187.1 (M+H). This material was used without purification in the subsequent step.

Step 2: Preparation of 1-(2-fluoro-3,5-dimethoxyphenyl)-1,2-dihydropyridazine-3,6-dione A solution of furan-2,5-dione (0.381 g, 3.89 mmol) and (2-fluoro-3,5-dimethoxyphenyl)hydrazine (from step 1; 0.724 g, 3.89 mmol) in EtOH (absolute; 19.4 mL) was heated for 1 day at 95° C. then treated with 6 N HCl in iPrOH (2.5 mL). After 3 h the reaction mixture was concentrated under vacuum. The resulting residue was suspended in DCM and the insoluble material was removed by filtration. The filtrate then was concentrated under vacuum, and the residue was purified by silica chromatography (0-100% EtOAc/hexanes as the gradient eluent) to cleanly afford the title compound (140.5 mg, 14% yield). MS (apci) m/z=267.0 (M+H).

Step 3: Preparation of 6-chloro-2-(2-fluoro-3,5-dimethoxyphenyl)pyridazin-3 (2H)-one A solution of 1-(2-fluoro-3,5-dimethoxyphenyl)-1,2-dihydropyridazine-3,6-dione (140 mg, 0.526 mmol) in $POCl_3$ (490 μL, 5.26 mmol) was heated at 85° C. for 1 h. The reaction mixture was then concentrated under vacuum, and the resulting residue was partitioned between EtOAc and saturated $NaHCO_{3(aq)}$. The phases were separated and treated independently. The aqueous extracts were washed with EtOAc (2×) and the organic extracts from the wash were combined with the original organic extract. The combined organic extracts were washed with brine then dried over anhydrous $Na_2SO_{4(s)}$, filtered and the concentrated under vacuum. The resulting residue was purified by silica chromatography (0-100% EtOAc/hexanes as the gradient eluent) to afford the title compound (94 mg, 63% yield). MS (apci) m/z=285.0 (M+H).

Intermediate X14

6-chloro-2-(2-fluoro-5-methoxyphenyl)pyridazin-3(2H)-one

Step 1: Preparation of 1-(2-fluoro-5-methoxyphenyl)-1,2-dihydropyridazine-3,6-dione A solution of furan-2,5-dione (255 mg, 2.60 mmol) and (2-fluoro-3,5-dimethoxyphenyl)hydrazine hydrochloride (500 mg, 2.60 mmol) in EtOH (absolute; 152 mL, 2.60 mmol) was heated for 1 day at 95° C. The reaction mixture was concentrated under vacuum, and the resulting residue was purified by silica chromatography (0-100% EtOAc/hexanes as the gradient eluent) to cleanly afford the title compound (300 mg, 49% yield). MS (apci) m/z=237.0 (M+H).

Step 2: Preparation of 6-chloro-2-(2-fluoro-5-methoxyphenyl)pyridazin-3(2H)-one

A solution of 1-(2-fluoro-5-methoxyphenyl)-1,2-dihydropyridazine-3,6-dione (90 mg, 0.38 mmol) in POCl$_3$ (355 µL, 3.8 mmol) was heated at 85° C. for 1 h. The reaction mixture was then concentrated under vacuum, and the resulting residue was partitioned between EtOAc and saturated NaHCO$_{3(aq)}$. The phases were separated and treated independently. The aqueous extracts were washed with EtOAc (2×), and the organic extracts from the wash were combined with the original organic extract. The combined organic extracts were washed with brine then dried over anhydrous Na$_2$SO$_{4(s)}$, filtered and the concentrated under vacuum. The resulting residue was purified by silica chromatography (0-100% EtOAc/hexanes as the gradient eluent) to afford the title compound (38 mg, 39% yield). MS (apci) m/z=255.0 (M+H).

Intermediate X15

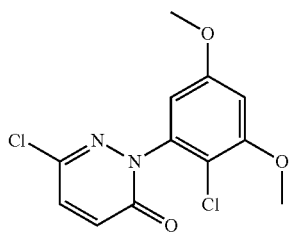 [SMILES: COc1cc(OC)c(Cl)c(-n2nc(Cl)ccc2=O)c1]

6-chloro-2-(2-chloro-3,5-dimethoxyphenyl)pyridazin-3 (2H)-one

A cold (0° C.) solution of 6-chloro-2-(3,5-dimethoxyphenyl)pyridazin-3(2H)-one (Intermediate X8; 0.357 g, 1.34 mmol) in ACN (13.4 mL) was treated with SO$_2$Cl$_2$ (0.109 mL, 1.34 mmol) and stirred for 20 min. The resulting mixture was quenched with the addition of saturated NaHCO$_{3(aq)}$. The resulting biphasic mixture was extracted with EtOAc. The organic extracts were washed successively with water and brine then dried over anhydrous Na$_2$SO$_{4(s)}$, filtered and the concentrated under vacuum. The resulting crude residue was purified by silica chromatography to afford the title compound (310 mg, 77% yield). $^1$H NMR (CDCl$_3$) δ 7.29 (d, 1H), 7.04 (d, 1H), 6.58 (m, 2H), 3.90 (s, 3H), 3.81 (s, 3H).

Intermediate O2

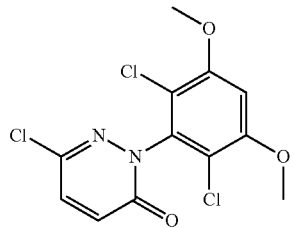 [SMILES: COc1cc(OC)c(Cl)c(-n2nc(Cl)ccc2=O)c1Cl]

6-chloro-2-(2-chloro-3,5-dimethoxyphenyl)pyridazin-3 (2H)-one

A cold (0° C.) solution of 6-chloro-2-(3,5-dimethoxyphenyl)pyridazin-3(2H)-one (2.496 g, 9.360 mmol) in ACN (93.60 mL, 9.360 mmol) was treated with sulfuryl dichloride (1.484 mL, 18.25 mmol) and stirred for 1 hr. The resulting mixture was quenched with the addition of saturated NaHCO$_{3(aq)}$. The resulting biphasic mixture was extracted with DCM. The organic extracts were washed successively with water and brine then dried over anhydrous Na$_2$SO$_{4(s)}$, filtered and then concentrated in vacuo to afford the title compound (3.1 g, 99% yield). This material was of sufficient purity to be used directly without further purification. $^1$H NMR (CDCl$_3$) δ 7.29 (d, 1H), 7.04 (d, 1H), 6.65 (s, 1H), 3.94 (s, 6H).

Intermediate X17

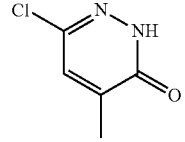

6-chloro-4-methylpyridazin-3 (2H)-one

Step 1: Preparation of 6-chloro-3-methoxy-4-methylpyridazine

A solution of 2,2,6,6-tetramethylpiperidine (12.9 ml, 76.1 mmol) in THF (100 mL) was sparged with N$_{2(g)}$ then cooled to −78° C. The −78° C. solution was treated slowly with 2.5 M n-butyllithium in hexane (30.4 mL, 76.1 mmol) then warmed to 0° C. and stirred for 1 h. The resulting reaction mixture was cooled to −78° C. then treated with a 0.46 M solution of 3-Chloro-6-methoxypyridazine in THF (75 mL, 34.6 mmol). After stirring at −78° C. for 1 h, the reaction mixture was treated with iodomethane (4.74 mL, 76.1 mmol), and stirred for an additional 30 min at −78° C. The reaction mixture was quenched with saturated NH$_4$Cl$_{(aq)}$ (50 mL), warmed to ambient temperature, diluted with water (50 mL) and extracted with EtOAc (2×250 mL). The combined organic extracts were washed with brine (1×50 mL), dried over anhydrous Na$_2$SO$_{4(s)}$, filtered and concentrated under vacuum to afford the title compound (3.31 g, 60% yield). MS (apci) m/z=159.0 (M+H).

Step 2: Preparation of
6-chloro-4-methylpyridazin-3(2H)-one

A solution of 6-chloro-3-methoxy-4-methylpyridazine (3.31 g, 20.9 mmol) in 4:1 dioxane:water (100 mL) was treated with 12.0 M HCl$_{(aq)}$ (1.91 mL, 23.0 mmol) and stirred for 60 h at 60° C. The reaction mixture was concentrated under vacuum, and the resulting crude residue was purified by silica chromatography (1-30% DCM/MeOH with 2% NH$_4$OH as the gradient eluent) to afford the title compound (2.99 g, 99% yield). $^1$H NMR (400 MHz, DMSO-d$_6$) δ 13.03 (s, 1H), 7.44 (s, 1H), 2.05 (s, 3H).

Intermediate X18

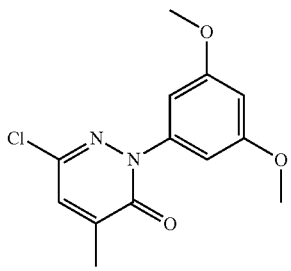 [SMILES: COc1cc(OC)cc(-n2nc(Cl)cc(C)c2=O)c1]

6-chloro-2-(3,5-dimethoxyphenyl)-4-methyl-
pyridazin-3 (2H)-one

A solution of 6-chloro-4-methylpyridazin-3-ol (Intermediate X17; 500 mg, 3.46 mmol) in DCM (20.3 mL) and pyridine (1 mL, 3.46 mmol) was treated with (3,5-dimethoxyphenyl)boronic acid (1.26 g, 6.92 mmol), Cu(OAc)$_2$ (1.26 g, 6.92 mmol), and pyridine 1-oxide (1.32 g, 13.8 mmol). The resulting mixture was stirred open to the atmosphere overnight at ambient temperature. The reaction mixture was diluted with DCM (100 mL) and filtered. The filtrate was washed with water (2×30 mL), and the organics were dried over anhydrous Na$_2$SO$_{4(s)}$, filtered and concentrated under vacuum. The crude residue was precipitated from MeOH to cleanly afford the title compound (780 mg, 80%). MS (apci) m/z=281.1 (M+H), 283.0 [(M+H)+2] (with Cl pattern).

Intermediate X19

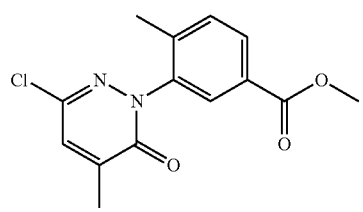 [SMILES: COC(=O)c1ccc(C)c(-n2nc(Cl)cc(C)c2=O)c1]

methyl 3-(3-chloro-5-methyl-6-oxopyridazin-1
(6H)-yl)-4-methylbenzoate

A solution of 6-chloro-4-methylpyridazin-3-ol (Intermediate X17; 0.50 g, 3.4 mmol) in DCM (20 mL) was treated with (5-(methoxycarbonyl)-2-methylphenyl)boronic acid (1.0 g, 5.2 mmol), Cu(OAc)$_2$ (1.2 g, 6.9 mmol), pyridine 1-oxide (327 mg, 3.44 mmol) and pyridine (1.1 g, 14 mmol). The resulting mixture was stirred at ambient temperature open to the atmosphere for one overnight. The reaction mixture was diluted with DCM (100 mL) and washed with water (2×30 mL). The organic extracts were dried over anhydrous Na$_2$SO$_{4(s)}$, filtered and concentrated under vacuum. The crude residue was purified by silica gel flash chromatography (2-55% EtOAc/hexane as the gradient eluent) to afford the title compound (2.99 g, 99% yield). MS (apci) m/z=293.0 (M+H), 295.0 [(M+H)+2] (with Cl pattern).

Intermediate X20

4-bromo-6-chloropyridazin-3 (2H)-one

A solution of 6-chloropyridazin-3-ol (5.01 g, 38.38 mmol), KBr (13.70 g, 115.1 mmol), and KOAc (5.650 g, 57.57 mmol) in water (80 mL) was stirred for 15 min then treated with Br$_2$ (5.90 mL, 115 mmol). The resulting mixture was stirred under an atmosphere of N$_{2(g)}$ for 2 h at 90° C.

After cooling to ambient temperature the reaction mixture was quenched with 10% Na$_2$S$_2$O$_{3(aq)}$ (100 mL). The resulting biphasic suspension was filtered, and the filter cake was successively rinsed with water (100 mL) then 10% Na$_2$S$_2$O$_{3(aq)}$ (100 mL). The solid filter cake was dried under high vacuum for 16 h to cleanly afford the title compound (6.14 g, 76% yield). $^1$H NMR (400 MHz, DMSO-d$_6$) δ 13.52 (s, 1H), 8.20 (s, 1H).

Intermediate X21

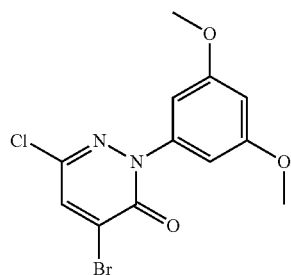 [SMILES: COc1cc(OC)cc(-n2nc(Cl)cc(Br)c2=O)c1]

4-bromo-6-chloro-2-(3,5-dimethoxyphenyl) pyridazin-3 (2H)-one

A mixture of 4-bromo-6-chloropyridazin-3(2H)-one (Intermediate X20; 0.504 g, 2.41 mmol), (3,5-dimethoxyphenyl)boronic acid (0.482 g, 2.65 mmol), Cu(OAc)$_2$ (0.0874 g, 0.481 mmol) and pyridine (0.389 mL, 4.81 mmol) in DCM (24.1 mL) was stirred overnight at ambient temperature The mixture was then diluted with DCM and extracted with water. The organic extracts were washed with brine, then dried aver anhydrous Na$_2$SO$_{4(s)}$, filtered and concentrated under vacuum. The resulting crude residue was purified by silica chromatography to afford the title compound (0.574 g, 69% yield). $^1$H NMR (CDCl$_3$) δ 7.69 (s, 1H), 6.73 (d, 2H), 6.51 (t, 1H), 3.81 (s, 6H).

Intermediate X22

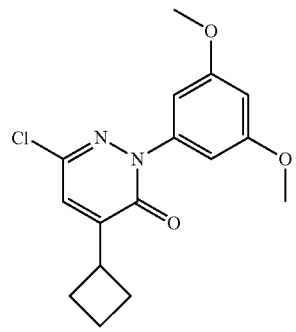 [SMILES: COc1cc(OC)cc(-n2nc(Cl)cc(C3CCC3)c2=O)c1]

6-chloro-4-cyclobutyl-2-(3,5-dimethoxyphenyl) pyridazin-3 (2H)-one

A cold (0° C.) solution of 4-bromo-6-chloro-2-(3,5-dimethoxyphenyl)pyridazin-3(2H)-one (Intermediate X21; 413.7 mg, 1.197 mmol) in THF (12 mL) was treated with 0.5 M cyclobutylmagnesium chloride hexane (3591 μL, 1.796 mmol) and stirred for 1 h at 0° C. The reaction was quenched with the addition of water (25 mL) and the volatiles were removed under vacuum. The remaining aqueous mixture was diluted with EtOAc (100 mL) and washed successively with water (2×25 mL) and brine (25 mL). The organic extracts were dried over anhydrous Na$_2$SO$_{4(s)}$, filtered and concentrated under vacuum. The resulting residue was purified by silica chromatography (5-60% Hexanes/EtOAc as the gradient eluent) to afford the title compound (283 mg, 72% yield). MS (apci) m/z=311.0 [(M+H)+2], 309.0 (M+H) with Cl pattern.

The following intermediates shown in Table X22 were prepared according to the method used for the synthesis of Intermediate X22 using the appropriate alkylmagnesium halide starting materials and 4-bromo-6-chloro-2-(3,5-dimethoxyphenyl)pyridazin-3(2H)-one. Reaction progression in each was followed by LCMS and reaction time was adjusted as necessary. All compounds were purified using a method similar to that used to isolate Intermediate X22 utilizing the appropriate gradient eluent.

TABLE X22

| Intermediate | Structure | Name | MS (apci) m/z |
|---|---|---|---|
| X23 | 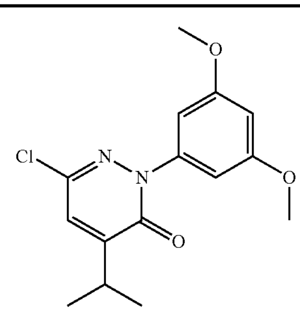 | 6-chloro-2-(3,5-dimethoxyphenyl)-4-isopropylpyridazin-3(2H)-one | 311.0 [(M + H) + 2], 309.0 (M + H) with Cl pattern |

TABLE X22-continued

| Intermediate | Structure | Name | MS (apci) m/z |
|---|---|---|---|
| X24 | 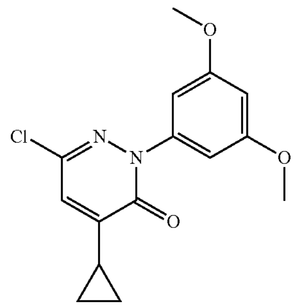 [SMILES: COc1cc(OC)cc(-n2nc(Cl)cc(C3CC3)c2=O)c1] | 6-chloro-4-cyclopropyl-2-(3,5-dimethoxyphenyl)pyridazin-3(2H)-one | 309.0 [(M + H) + 2], 307.0 (M + H) with Cl pattern |

Intermediate X25

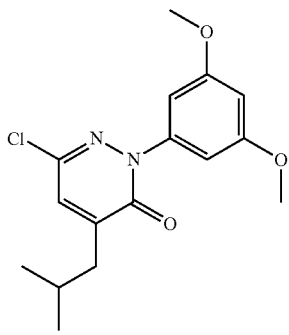 [SMILES: COc1cc(OC)cc(-n2nc(Cl)cc(CC(C)C)c2=O)c1]

6-chloro-2-(3,5-dimethoxyphenyl)-4-isobutylpyridazin-3 (2H)-one

A cold (0° C.) solution of 4-bromo-6-chloro-2-(3,5-dimethoxyphenyl)pyridazin-3(2H)-one (Intermediate X21; 0.150 g, 0.434 mmol) in THF (2.89 mL) was treated with 2 M isobutylmagnesium bromide in $Et_2O$ (0.434 mL, 0.868 mmol). The reaction was stirred overnight at ambient temperature and then worked up with EtOAc and water. The organics were washed with brine, then dried over anhydrous $Na_2SO_{4(s)}$, filtered and concentrated under vacuum. The resulting residue was purified by silica chromatography to afford the title compound (0.035 g, 25% yield).

The following intermediates, shown in Table X25 were prepared according the method used for the synthesis of Intermediate X25 using the appropriate alkylmagnesium halide starting materials and 4-bromo-6-chloro-2-(3,5-dimethoxyphenyl)pyridazin-3(2H)-one. All compounds were purified by silica chromatography utilizing the appropriate gradient.

TABLE X25

| Intermediate | Structure | Name |
|---|---|---|
| X26 | 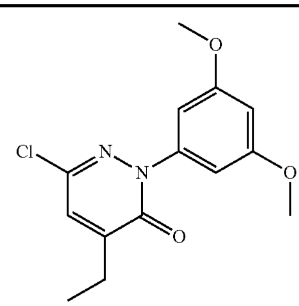 | 6-chloro-2-(3,5-dimethoxyphenyl)-4-ethylpyridazin-3(2H)-one |
| X27 | 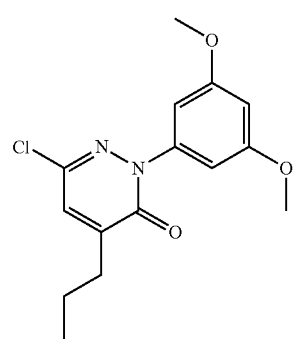 [SMILES: CCCc1cc(Cl)nn(-c2cc(OC)cc(OC)c2)c1=O] | 6-chloro-2-(3,5-dimethoxyphenyl)-4-propylpyridazin-3(2H)-one |

Intermediate X28

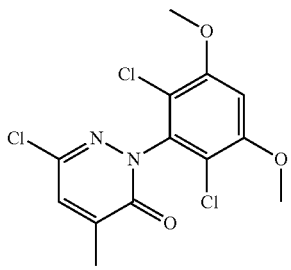 [SMILES: COc1cc(OC)c(Cl)c(-n2nc(Cl)cc(C)c2=O)c1Cl]

6-chloro-2-(2,6-dichloro-3,5-dimethoxyphenyl)-4-methylpyridazin-3(2H)-one

Sulfuryl chloride (0.152 mL, 1.88 mmol) was added to 6-chloro-2-(3,5-dimethoxyphenyl)-4-methylpyridazin-3(2H)-one (Intermediate X18; 0.264 g, 0.940 mmol) in ACN (6.27 mL) at 0° C. This was then stirred at room temp for 20 min. The mixture was then quenched with saturated aqueous $Na_2CO_3$. The mixture was partitioned between EtOAc and water. The combined organic layers were washed with water and brine, dried over $Na_2SO_4$, and concentrated. The residue was purified on a silica column using Hexanes:EtOAc (10-90%) to give 6-chloro-2-(2,6-dichloro-3,5-dimethoxyphenyl)-4-methylpyridazin-3(2H)-one (0.198 g, 0.566 mmol, 60.2% yield) MS (apci) m/z=349.0 (M+H).

Intermediate X29

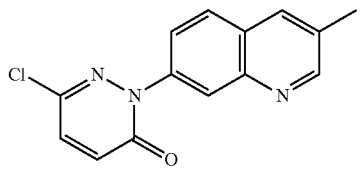 [SMILES: Cc1cnc2cc(-n3nc(Cl)ccc3=O)ccc2c1]

6-chloro-2-(3-methylquinolin-7-yl)pyridazin-3 (2H)-one

Step 1: Preparation of (3-methylquinolin-7-yl)boronic acid

A solution of 7-bromo-3-methylquinoline (258 mg, 1.16 mmol), 5,5,5',5'-tetramethyl-2,2'-bi(1,3,2-dioxaborinane) (656 mg, 2.90 mmol), PdCl2(dppf)*dcm (47.4 mg, 0.0581 mmol), and KOAc (342 mg, 3.49 mmol) in dioxane (5809 µL, 1.16 mmol) was sparged with $N_{2(g)}$ for 5 min at ambient temperature and then heated at 90° C. overnight. After cooling to ambient temperature, the reaction mixture was partitioned between EtOAc and water. The combined organic extracts were washed with brine, dried over anhydrous $Na_2SO_{4(s)}$, filtered and concentrated under vacuum to afford the title compound with higher than expected mass, but assumed with quantitative yield (217 mg, 100% yield). MS (apci) m/z=188.1 (M+H).

Step 2: Preparation of: 6-chloro-2-(3-methylquinolin-7-yl)pyridazin-3(2H)-one: A mixture of 6-chloropyridazin-3 (2H)-one (0.140 g, 1.07 mmol), (3-methylquinolin-7-yl) boronic acid, (0.221 g, 1.18 mmol), Cu(OAc)2 (0.0390 g, 0.215 mmol) and pyridine (0.191 ml, 2.36 mmol) in DCM (10.7 mL, 1.07 mmol) was stirred at room temperature overnight. The reaction mixture was partitioned between EtOAc and water. The organic extracts were washed with brine, then dried over anhydrous $Na_2SO_{4(s)}$, filtered and concentrated under vacuum. The resulting residue was purified by silica chromatography to afford the title compound (25 mg, 8.6% yield). MS (apci) m/z=274.0 [(M+H)+2], 272.0 (M+H) with Cl pattern.

Intermediate X30

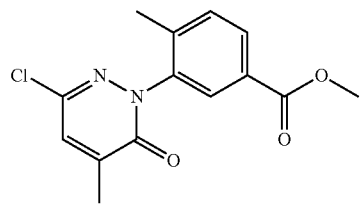

Methyl 3-(3-chloro-5-methyl-6-oxopyridazin-1 (6H)-yl)-4-methylbenzoate

A solution of 6-chloro-4-methylpyridazin-3-ol (0.5 g, 3.5 mmol) in dichloromethane (20 mL, 3.4 mmol) was treated with (5-(methoxycarbonyl)-2-methylphenyl)boronic acid (1 g, 5.15 mmol), copper(II) acetate (1.25 g, 6.87 mmol), pyridine 1-oxide (33 mg, 3.44 mmol), and pyridine (1.1 g, 13.75 mmol). The resulting mixture was stirred overnight at RT. The mixture was diluted with DCM (100 mL) and washed with water (2×30 mL). The organic layer was separated, dried ($Na_2SO_4$), filtered and concentrated in vacuo. The residue was purified by flash chromatography on silica gel (Redi Sep 80 g) eluting with 2-55% EtOAc/hexane to provide methyl 3-(3-chloro-5-methyl-6-oxopyridazin-1 (6H)-yl)-4-methylbenzoate (430 mg, 43% yield) as a solid. LCMS (APCI+) m/z 293.0 (M+1); retention time=4.086 min.

Intermediate R1

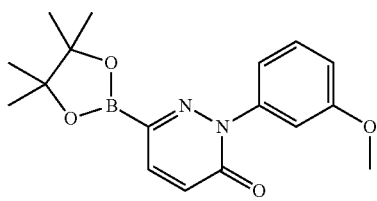

2-(3-methoxyphenyl)-6-(4,4,5,5-tetramethyl-1,3,2-dioxaborolan-2-yl)pyridazin-3 (2H)-one A solution of 6-chloro-2-(3-methoxyphenyl)pyridazin-3 (2H)-one (Intermediate X1; 104 mg, 0.439 mmol) in dioxane (6 mL) was treated with bis(pinacolato)diboron (123 mg, 0.483 mmol), Pd(OAc)$_2$ (10.8 mg, 0.0483 mmol), X-Phos (34.6 mg, 0.0725 mmol), and KOAc (129 mg, 1.32 mmol). The mixture was sparged with $Ar_{(g)}$, then sealed and stirred for 16 h at 100° C. After cooling to ambient temperature, the reaction mixture was filtered, and the filter cake was washed with EtOAc (50 mL). The filtrate was concentrated under vacuum to afford the title compound (157 mg, 109% crude yield). This material was used directly without further purification.

Intermediate R2

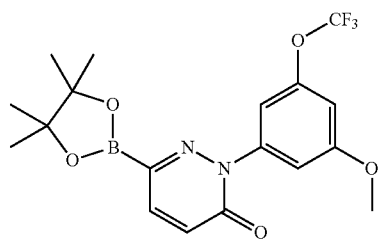

2-(3-methoxy-5-(trifluoromethoxy)phenyl)-6-(4,4,5,5-tetramethyl-1,3,2-dioxaborolan-2-yl)pyridazin-3(2H)-one A mixture of 6-chloro-2-(3-methoxy-5-(trifluoromethoxy)phenyl)pyridazin-3(2H)-one (Intermediate X2; 0.253 g, 0.789 mmol), bis(pinacolato)diboron (0.220 g, 0.868 mmol), $Pd(OAc)_2$ (0.0177 g, 0.0789 mmol), X-Phos (0.0564 g, 0.118 mmol), and KOAc (0.232 g, 2.37 mmol) in dioxane (2.63 mL) was sparged with $Ar_{(g)}$ for 5 min at ambient temperature then stirred for 1 h at 100° C. After cooling to ambient temperature, the reaction mixture was partitioned between EtOAc and water. The organic extracts were washed with brine, then dried over anhydrous $Na_2SO_{4(s)}$, filtered and concentrated under vacuum to afford the title compound (320 mg, 98% yield). MS (apci) m/z=287.0 (M–B(OR)$_2$+H). This material was of sufficient purity to be used directly without further purification.

The following intermediates shown in Table R2 were prepared according the method used for the synthesis of Intermediate R2 using the appropriate 6-chloro-2-(Aryl)pyridazin-3(2H)-one starting materials (Intermediates X3-X7, X11-X12, X15). Reaction progression for each was followed by LCMS and reaction time was adjusted as necessary.

TABLE R2

| Intermediate | Structure | Name | MS (apci) m/z |
|---|---|---|---|
| R3 | 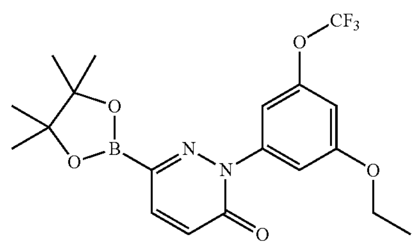 | 2-(3-ethoxy-5-(trifluoromethoxy)phenyl)-6-(4,4,5,5-tetramethyl-1,3,2-dioxaborolan-2-yl)pyridazin-3(2H)-one | 301.1 (M – B(OR)$_2$ + H) |
| R4 | 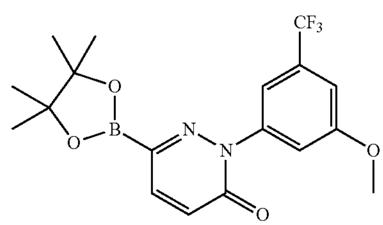 | 2-(3-methoxy-5-(trifluoromethyl)phenyl)-6-(4,4,5,5-tetramethyl-1,3,2-dioxaborolan-2-yl)pyridazin-3(2H)-one | 271.1 (M – B(OR)$_2$ + H) |
| R5 | 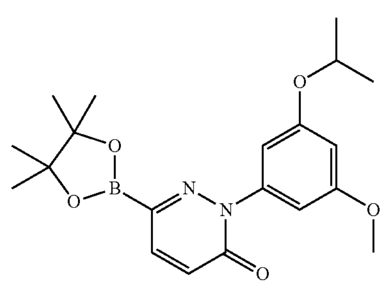 | 2-(3-isopropoxy-5-methoxyphenyl)-6-(4,4,5,5-tetramethyl-1,3,2-dioxaborolan-2-yl)pyridazin-3(2H)-one | 261.1 (M – B(OR)$_2$ + H) |

TABLE R2-continued

| Intermediate | Structure | Name | MS (apci) m/z |
|---|---|---|---|
| R6 | 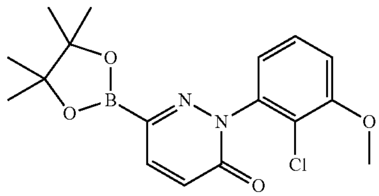 | 2-(2-chloro-3-methoxyphenyl)-6-(4,4,5,5-tetramethyl-1,3,2-dioxaborolan-2-yl)pyridazin-3(2H)-one | 237 (M − B(OR)$_2$ + H) |
| R12 | 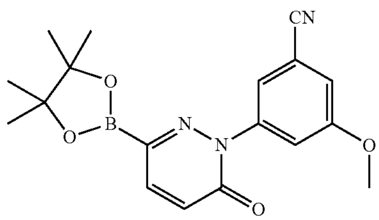 | 3-methoxy-5-(6-oxo-3-(4,4,5,5-tetramethyl-1,3,2-dioxaborolan-2-yl)pyridazin-1(6H)-yl)benzonitrile | 226.1 (M − B(OR)$_2$ + H) |
| R15 | 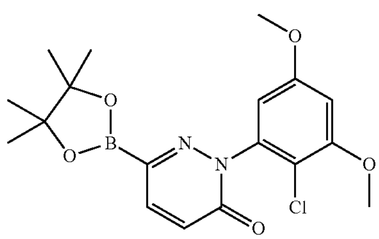 | 2-(2-chloro-3,5-dimethoxyphenyl)-6-(4,4,5,5-tetramethyl-1,3,2-dioxaborolan-2-yl)pyridazin-3(2H)-one | 267 (M − B(OR)$_2$ + H) |
| R16 | 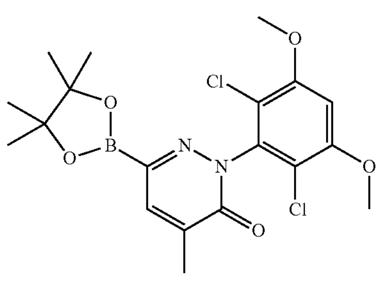 | 2-(2,6-dichloro-3,5-dimethoxyphenyl)-4-methyl-6-(4,4,5,5-tetramethyl-1,3,2-dioxaborolan-2-yl)pyridazin-3(2H)-one | 315 (M − B(OR)$_2$ + H) |
| R17 | 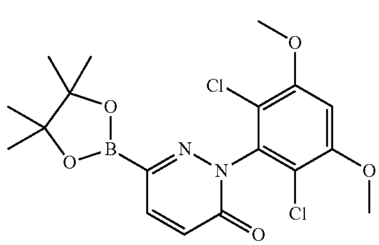 | 2-(2,6-dichloro-3,5-dimethoxyphenyl)-6-(4,4,5,5-tetramethyl-1,3,2-dioxaborolan-2-yl)pyridazin-3(2H)-one | 301 (M − B(OR)$_2$ + H) |

Intermediate R7

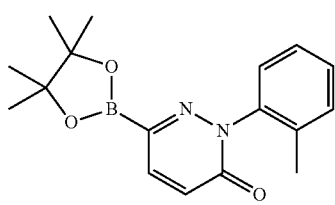 [SMILES: Cc1ccccc1-n1nc(B2OC(C)(C)C(C)(C)O2)ccc1=O]

6-(4,4,5,5-tetramethyl-1,3,2-dioxaborolan-2-yl)-2-(o-tolyl)pyridazin-3(2H)-one 6-(4,4,5,5-tetramethyl-1,3,2-dioxaborolan-2-yl)-2-(o-tolyl)pyridazin-3 (2H)-one was made according the procedure of Intermediate R2, substituting Intermediate X2 with Intermediate X7.

Intermediate R8

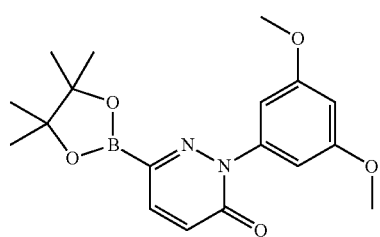

2-(3,5-dimethoxyphenyl)-6-(4,4,5,5-tetramethyl-1,3,2-dioxaborolan-2-yl)pyridazin-3 (2H)-one A solution of 6-chloro-2-(3,5-dimethoxyphenyl)pyridazin-3(2H)-one (Intermediate X8; 47.9 mg, 0.180 mmol) in dioxane (1.8 mL) was treated with bis(pinacolato)diboron (50.2 mg, 0.198 mmol), Pd(OAc)$_2$ (4.03 mg, 0.0180 mmol), X-Phos (12.8 mg, 0.0269 mmol), and KOAc (52.9 mg, 0.539 mmol). The mixture was sparged with Ar$_{(g)}$, then sealed and stirred for 16 h at 100° C. After cooling to ambient temperature, the reaction mixture was diluted with 4:1 DCM:iPrOH (25 mL) then extracted with water (2×10 mL). The organic extracts were dried over anhydrous Na$_2$SO$_{4(s)}$, filtered and concentrated under vacuum to afford the title compound (64 mg, 99% yield). MS (apci) m/z=233.1 (desB(OR)$_2$ M+H). This material was of sufficient purity to be used directly without further purification.

The following intermediates shown in Table R8, were prepared according the method used for the synthesis of Intermediate R8 using the appropriate 6-chloro-2-(Aryl)pyridazin-3(2H)-one starting materials (Intermediates X9, X10). Reaction progression in each was followed by LCMS and reaction time was adjusted as necessary.

TABLE R8

| Intermediate | Structure | Name | MS (apci) m/z = |
|---|---|---|---|
| R9 | 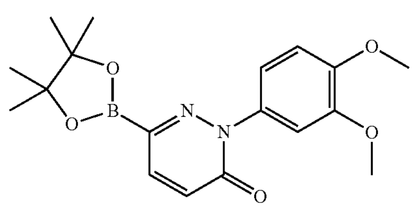 | 2-(3,4-dimethoxyphenyl)-6-(4,4,5,5-tetramethyl-1,3,2-dioxaborolan-2-yl)pyridazin-3(2H)-one | 277.0 (B(OH)$_2$M+), 233.0 (M − B(OR)$_2$ + H) |
| R10 | 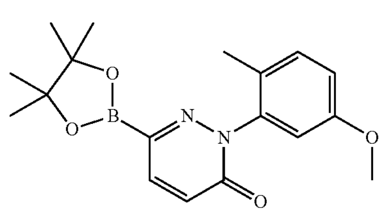 | 2-(5-methoxy-2-methylphenyl)-6-(4,4,5,5-tetramethyl-1,3,2-dioxaborolan-2-yl)pyridazin-3(2H)-one | 261.0 (B(OH)$_2$M+), 217.1 (M − B(OR)$_2$ + H) |

Intermediate R13

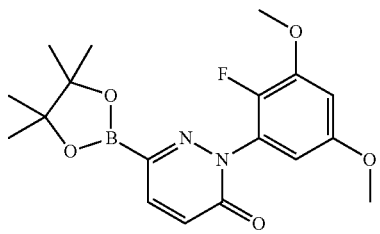

2-(2-fluoro-3,5-dimethoxyphenyl)-6-(4,4,5,5-tetramethyl-1,3,2-dioxaborolan-2-yl)pyridazin-3 (2H)-one A solution of 6-chloro-2-(2-fluoro-3,5-dimethoxyphenyl)pyridazin-3(2H)-one (Intermediate X13; 94 mg, 0.33 mmol) in dioxane (1.2 mL) was treated with bis(pinacolato)diboron (0.17 g, 0.66 mmol), Pd(OAc)$_2$ (7.4 mg, 0.033 mmol), X-Phos (23.6 mg, 0.050 mmol), and KOAc (97 mg, 0.99 mmol). The mixture was sparged with Ar$_{(g)}$, then sealed and stirred for 3 h at 90° C. After cooling to ambient temperature, the reaction mixture was partitioned between EtOAc and water. The organic extracts were reserved and the aqueous extracts were independently washed with EtOAc (3×). The combined organic extracts were dried over anhydrous Na$_2$SO$_{4(s)}$, filtered and concentrated under vacuum to afford the title compound (124.2 mg, 75% yield). MS (apci) m/z=251.1 (desB(OR)$_2$ M+H). This material was of sufficient purity to be used directly without further purification.

Intermediate R14

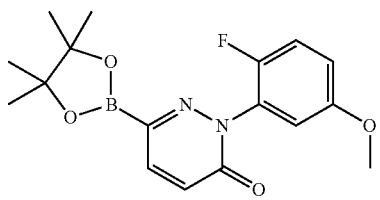

2-(2-fluoro-5-methoxyphenyl)-6-(4,4,5,5-tetramethyl-1,3,2-dioxaborolan-2-yl)pyridazin-3 (2H)-one The title compound was prepared (116.9 mg, 50% yield) according to the method described for Intermediate R14, using 6-chloro-2-(2-fluoro-5-methoxyphenyl)pyridazin-3 (2H)-one (Intermediate X14) in place of 6-chloro-2-(2-fluoro-3,5-dimethoxyphenyl)pyridazin-3(2H)-one (Intermediate X13). MS (apci) m/z=221.1 (desB(OR)$_2$ M+H). This material was of sufficient purity to be used directly without further purification.

Intermediate R18

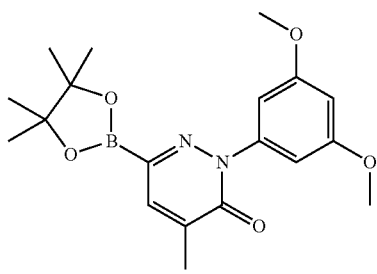

2-(3,5-dimethoxyphenyl)-4-methyl-6-(4,4,5,5-tetramethyl-1,3,2-dioxaborolan-2-yl)pyridazin-3 (2H)-one A solution of 6-chloro-2-(3,5-dimethoxyphenyl)-4-methylpyridazin-3(2H)-one (Intermediate X18; 199.4 mg, 0.7103 mmol) in dioxane (7.1 mL) was treated with bis(pinacolato)diboron (198.4 mg, 0.7814 mmol), Pd(OAc)$_2$ (15.95 mg, 0.07103 mmol), X-Phos (50.80 mg, 0.1066 mmol), and KOAc (209.1 mg, 2.131 mmol). The mixture was sparged with Ar$_{(g)}$, then sealed and stirred for 1 h at 100° C. After cooling to ambient temperature, the reaction mixture was diluted with 4:1 DCM:iPrOH (50 mL) then extracted with water (2×25 mL). The organic extracts were dried over anhydrous Na$_2$SO$_{4(s)}$, filtered and concentrated under vacuum to afford the title compound (264 mg, 100% yield). MS (apci) m/z=291.1 (B(OH)$_2$ M+H), 247.1 (desB(OR)$_2$ M+H). This material was of sufficient purity to be used directly without further purification.

Intermediate R19

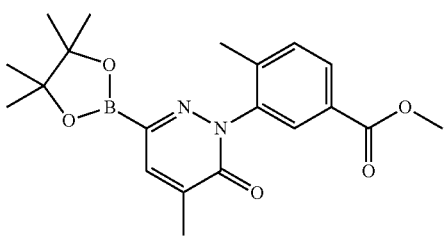

methyl 4-methyl-3-(5-methyl-6-oxo-3-(4,4,5,5-tetramethyl-1,3,2-dioxaborolan-2-yl)pyridazin-1 (6H)-yl)benzoate A mixture of methyl 3-(3-chloro-5-methyl-6-oxopyridazin-1 (6H)-yl)-4-methylbenzoate (Intermediate X19; 425 mg, 1.45 mmol), bis(pinacolato)diboron (553 mg, 2.18 mmol), Pd(OAc)$_2$ (32.6 mg, 0.145 mmol), X-Phos (104 mg, 0.218 mmol), and KOAc (427 mg, 4.36 mmol) in dioxane (14.5 mL) was sparged with N$_{2(g)}$, then sealed and stirred for 6 h at 100° C. After cooling to ambient temperature, the reaction mixture was diluted with 4:1 DCM:iPrOH (100 mL) then extracted with water (2×30 mL). The organic extracts were dried over anhydrous MgSO$_{4(s)}$, filtered and concentrated under vacuum to afford the crude title compound. MS (apci) m/z=384.1 (M+), 259.0 [(M−B(OR)₂)+H]. This material was of sufficient purity to be used directly without further purification.

Intermediate R22

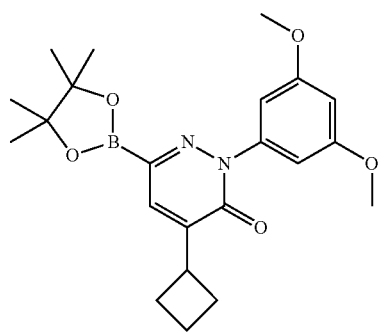

4-cyclobutyl-2-(3,5-dimethoxyphenyl)-6-(4,4,5,5-tetramethyl-1,3,2-dioxaborolan-2-yl)pyridazin-3(2H)-one A solution of 6-chloro-4-cyclobutyl-2-(3,5-dimethoxyphenyl)pyridazin-3(2H)-one (Intermediate X22; 149.6 mg, 0.4664 mmol) in dioxane (5.0 mL) was treated with bis(pinacolato)diboron (130.3 mg, 0.5130 mmol), Pd(OAc)₂ (10.47 mg, 0.04664 mmol), X-Phos (33.35 mg, 0.06996 mmol), and KOAc (137.3 mg, 1.399 mmol). The mixture was sparged with Ar$_{(g)}$, then sealed and stirred for 1 h at 100° C. After cooling to ambient temperature, the reaction mixture was diluted with 4:1 DCM:iPrOH (50 mL) and then extracted with water (2×25 mL). The organic extracts were dried over anhydrous Na₂SO₄$_{(s)}$, filtered and concentrated under vacuum to afford the title compound (192.2 mg, 100% yield). MS (apci) m/z=261.0 (B(OH)₂ M+H), 217.1 (M−B(OR)₂+H). This material was of sufficient purity to be used directly without further purification.

The following intermediates shown in Table R22 were prepared according the method used for the synthesis of Intermediate R22 using the appropriate starting materials (Intermediates X23-X27). Reaction progression in each was followed by LCMS and reaction time was adjusted as necessary.

TABLE R22

| Intermediate | Structure | Name |
|---|---|---|
| R23 | 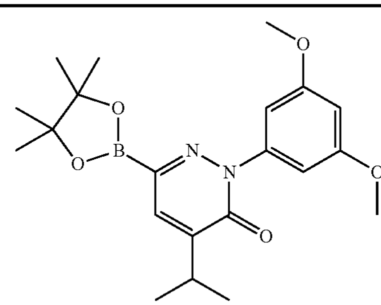 | 2-(3,5-dimethoxyphenyl)-4-isopropyl-6-(4,4,5,5-tetramethyl-1,3,2-dioxaborolan-2-yl)pyridazin-3(2H)-one |
| R24 | 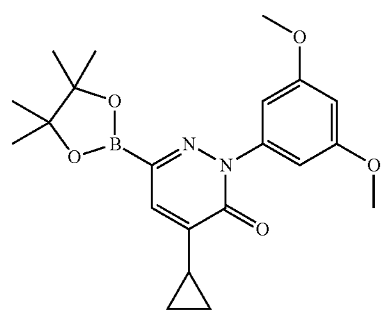 | 4-cyclopropyl-2-(3,5-dimethoxyphenyl)-6-(4,4,5,5-tetramethyl-1,3,2-dioxaborolan-2-yl)pyridazin-3(2H)-one |
| R25 | 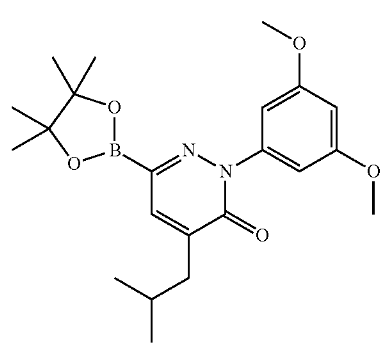 | 2-(3,5-dimethoxyphenyl)-4-isobutyl-6-(4,4,5,5-tetramethyl-1,3,2-dioxaborolan-2-yl)pyridazin-3(2H)-one |

TABLE R22-continued

| Intermediate | Structure | Name |
|---|---|---|
| R26 | 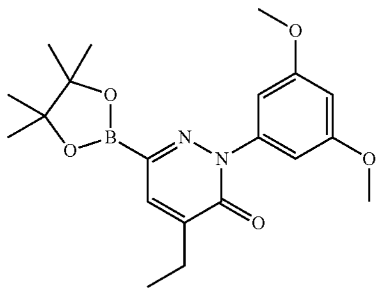 | 2-(3,5-dimethoxyphenyl)-4-ethyl-6-(4,4,5,5-tetramethyl-1,3,2-dioxaborolan-2-yl)pyridazin-3(2H)-one |
| R27 | 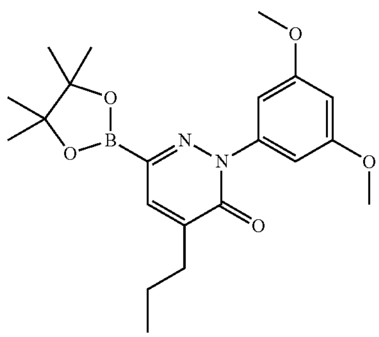 | 2-(3,5-dimethoxyphenyl)-4-propyl-6-(4,4,5,5-tetramethyl-1,3,2-dioxaborolan-2-yl)pyridazin-3(2H)-one |

Intermediate R28

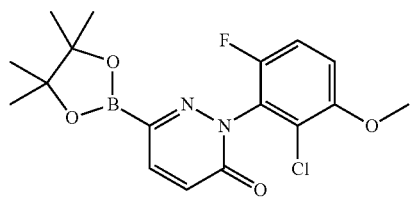

2-(2-chloro-6-fluoro-3-methoxyphenyl)-6-(4,4,5,5-tetramethyl-1,3,2-dioxaborolan-2-yl)pyridazin-3(2H)-one A solution of 6-chloro-2-(2-chloro-6-fluoro-3-methoxyphenyl)pyridazin-3(2H)-one (ArkPharm, 180 mg, 0.622 mmol), bis(pinacolato)diboron (316 mg, 1.24 mmol), palladium(II) acetate (14.0 mg, 0.062 mmol), X-PHOS (45 mg, 0.093 mmol), and potassium acetate (183 mg, 1.87 mmol). was degassed with nitrogen, sealed, and heated to 100° C. overnight (16 hrs). The mixture was cooled to ambient temperature then diluted with 4:1 DCM:IPA and washed with water. The organic layer was dried over $Na_2SO_4$ and concentrated. The residue was carried forward to next step without further purification. LCMS (APCI+) m/z=255.0; retention time 1.60 min.

Intermediate R29

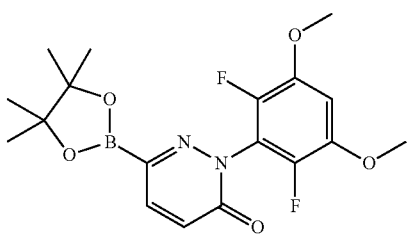

2-(2,6-difluoro-3,5-dimethoxyphenyl)-6-(4,4,5,5-tetramethyl-1,3,2-dioxaborolan-2-yl)pyridazin-3(2H)-one A solution of 6-chloro-2-(2,6-difluoro-3,5-dimethoxyphenyl)pyridazin-3(2H)-one (ArkPharm 163 mg, 0.539 mmol), bis(pinacolato)diboron (274 mg, 1.08 mmol), palladium(II) acetate (12.1 mg, 0.0539 mmol), X-PHOS (38.5 mg, 0.081 mmol), and potassium acetate (159 mg, 1.62 mmol) was sparged with nitrogen, sealed, and heated to 100° C. for 16 h. The reaction mixture was cooled to ambient temperature, then diluted with 4:1 DCM:IPA, washed with water, dried over $Na_2SO_4$, filtered through fluted filter paper and concentrated. The residue was used without further purification in excess in a subsequent reaction. LCMS (APCI+) m/z 269.1 (fragment: M-pinacolboronate); Retention time=1.70 min.

Intermediate R30

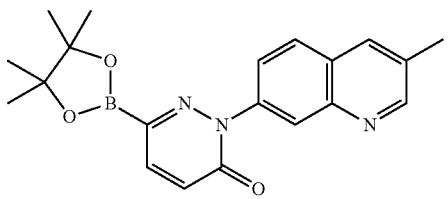

2-(3-methylquinolin-7-yl)-6-(4,4,5,5-tetramethyl-1,3,2-dioxaborolan-2-yl)pyridazin-3 (2H)-one A mixture of 6-chloro-2-(3-methylquinolin-7-yl)pyridazin-3 (2H)-one (Intermediate X29; 25 mg, 0.09 mmol), Bis(Pinacolato)diboron (70.1 mg, 0.28 mmol), Pd(OAc)$_2$ (2.1 mg, 0.01 mmol), and XPHOS (6.6 mg, 0.01 mmol) in dioxane (0.6 mL) was sparged with Ar$_{(g)}$ for 5 min at ambient temperature, then stirred for 3 h at 90° C. After cooling to ambient temperature, the reaction mixture was partitioned between EtOAc and water. The organic extracts were washed with brine, then dried over anhydrous Na$_2$SO$_{4(s)}$, filtered and concentrated under vacuum to afford the title compound (21.8 mg, 99% yield). MS (apci) m/z=238.1 (M-B(OR)$_2$+H). This material was of sufficient purity to be used directly without further purification.

Intermediate R31

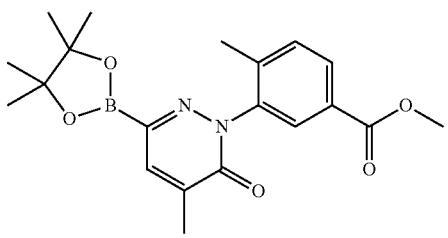

Methyl 4-methyl-3-(5-methyl-6-oxo-3-(4,4,5,5-tetramethyl-1,3,2-dioxaborolan-2-yl)pyridazin-1 (6H)-yl)benzoate A glass pressure tube was charged with Intermediate X30 [methyl 3-(3-chloro-5-methyl-6-oxopyridazin-1 (6H)-yl)-4-methylbenzoate] (425 mg, 1.45 mmol), bis(pinacolato)diboron (553 mg, 2.2 mmol), palladium (II) acetate (33 mg, 0.145 mmol), XPHOS (104 mg, 0.22 mmol), potassium acetate (427.5 mg, 4.4 mmol) and 1,4-dioxane (14519 µL, 1.45 mmol). The mixture was sparged with N$_2$. The tube was sealed with a Teflon screw cap and heated at 100° C. with stirring for 6 hrs. The mixture was then cooled to 0° C., diluted with 4:1 DCM:IPA (100 mL) and washed with water. The organic layer was separated, dried over MgSO$_4$ and concentrated under reduced pressure. The crude product was used immediately in a subsequent reaction.

Intermediate M1

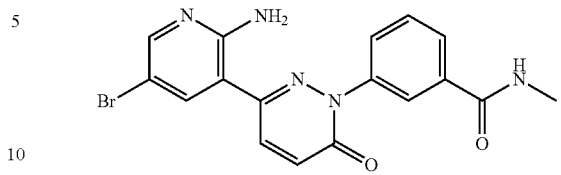

3-(3-(2-amino-5-bromopyridin-3-yl)-6-oxopyridazin-1(6H)-yl)-N-methylbenzamide

Step 1: Preparation of methyl 3-(3-(2-aminopyridin-3-yl)-6-oxopyridazin-1(6H)-yl)benzoate A solution of methyl 3-(3-chloro-6-oxopyridazin-1(6H)-yl)benzoate (Intermediate X16; 531.9 mg, 2.010 mmol) in 4:1 dioxane:water (15 mL) was treated with t-butyl 3-(4,4,5,5-tetramethyl-1,3,2-dioxaborolan-2-yl)pyridin-2-ylcarbamate (643.5 mg, 2.010 mmol), Pd(PPh$_3$)$_4$ (232.2 mg, 0.2010 mmol), K$_2$CO$_{3(s)}$ (833.3 mg, 6.029 mmol). The mixture was sparged with Ar$_{(g)}$, then sealed and stirred for 16 h at 100° C. After cooling to ambient temperature, the reaction mixture was diluted with EtOAc (200 mL), and the resulting solution was extracted with water (2×50 mL) then brine (25 mL). The organic extracts were dried over anhydrous Na$_2$SO$_{4(s)}$, filtered and concentrated under vacuum. The resulting crude residue was purified by C18 reverse phase chromatography (2-75% water/ACN with 0.1% TFA as the gradient eluent) to afford the title compound as a TFA salt. The TFA salt was dissolved in 4:1 DCM:iPrOH (50 mL) and extracted with saturated NaHCO$_{3(aq)}$ (1×25 mL). The organic extracts were dried over anhydrous Na$_2$SO$_{4(s)}$, filtered and concentrated under vacuum cleanly affording the title compound (160.5 mg, 25% yield). MS (apci) m/z=323.1 (M+H).

Step 2: Preparation of methyl 3-(3-(2-amino-5-bromopyridin-3-yl)-6-oxopyridazin-1(6H)-yl)benzoate A solution of methyl 3-(3-(2-aminopyridin-3-yl)-6-oxopyridazin-1(6H)-yl)benzoate (from step 1; 160.5 mg, 0.4980 mmol) in ACN (5.0 mL) was treated with NBS (97.49 mg, 0.5478 mmol) then stirred for 16 hr at ambient temperature then concentrated under vacuum. The resulting residue was triturated with EtOAc (10 mL) filtered to afford the title compound (169.0 mg, 85% yield). MS (apci) m/z=403.0 [(M+H)+2], 401.0 (M+H), with Br pattern.

Step 3: Preparation of 3-(3-(2-amino-5-bromopyridin-3-yl)-6-oxopyridazin-1(6H)-yl)benzoic acid A solution of methyl 3-(3-(2-amino-5-bromopyridin-3-yl)-6-oxopyridazin-1(6H)-yl)benzoate (from step 2; 142.8 mg, 0.3559 mmol) in 1:1 THF:MeOH (3.6 mL) was treated with 2 M KOH$_{(aq)}$ (889.8 µL, 1.780 mmol) then stirred for 1 h at 70° C. After cooling to ambient temperature, the reaction mixture was diluted with water (10 mL). The resulting suspension was filtered, and the filter cake was washed with water (2×10 mL). The solids were dried under high vacuum for 16 h at 55° C. to afford the title compound

Step 4: Preparation of 3-(3-(2-amino-5-bromopyridin-3-yl)-6-oxopyridazin-1(6H)-yl)-N-methylbenzamide A solution of methyl 3-(3-(2-amino-5-bromopyridin-3-yl)-6-oxopyridazin-1(6H)-yl)benzoic acid (from step 3; 93.8 mg, 0.242 mmol) in DMF (2.5 mL) was treated with methylamine hydrochloride (49.1 mg, 0.727 mmol), HATU (110 mg, 0.291 mmol), and DIPEA (211 μL, 1.21 mmol). The resulting mixture was stirred for 2 h at ambient temperature before directly chromatographing the reaction mixture using C18 reverse phase chromatography (5-95% water/ACN w/0.1% TFA as the gradient eluent) to afford the title compound as the TFA salt. The TFA salt was dissolved in 4:1 DCM:iPrOH (25 mL) and extracted with saturated NaHCO$_{3(aq)}$ (1×10 mL). The organic extracts were dried over anhydrous Na$_2$SO$_{4(s)}$, filtered and concentrated under vacuum cleanly affording the title compound (47.6 mg, 49% yield). MS (apci) m/z=402.0 [(M+H)+2], 400.0 (M+H), with Br pattern.

Intermediate M2

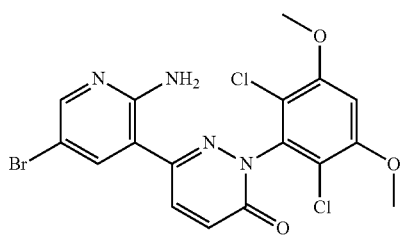 [SMILES: COc1cc(OC)c(Cl)c(-n2nc(-c3cc(Br)cnc3N)ccc2=O)c1Cl]

6-(2-amino-5-bromopyridin-3-yl)-2-(2,6-dichloro-3,5-dimethoxyphenyl)pyridazin-3 (2H)-one

Step 1: Preparation of 6-(2-aminopyridin-3-yl)-2-(3,5-dimethoxyphenyl)pyridazin-3(2H)-one A solution of t-Butyl 3-(4,4,5,5-tetramethyl-1,3,2-dioxaborolan-2-yl)pyridin-2-ylcarbamate (923.4 mg, 2.884 mmol) in 4:1 dioxane:water (15 mL) was treated with 6-chloro-2-(3,5-dimethoxyphenyl)pyridazin-3 (2H)-one (Intermediate X8; 807.5 mg, 3.028 mmol), Pd(PPh$_3$)$_4$(333.2 mg, 0.2884 mmol), K$_2$CO$_{3(s)}$ (1195 mg, 8.652 mmol). The mixture was sparged with Ar$_{(g)}$, then sealed and stirred for 16 h at 100° C. After cooling to ambient temperature, the reaction mixture was diluted with 4:1 DCM:iPrOH (100 mL), and the resulting solution was extracted with water (2×50 mL). The organic extracts were dried over anhydrous Na$_2$SO$_{4(s)}$, filtered and concentrated under vacuum. The resulting crude residue was purified by silica chromatography (1-25% DCM/MeOH as the gradient eluent) to afford the title compound (505.5 mg, 54% yield). MS (apci) m/z=325.1 (M+H).

Step 2: Preparation of 6-(2-aminopyridin-3-yl)-2-(2,6-dichloro-3,5-dimethoxyphenyl)pyridazin-3(2H)-one A cold (0° C.) solution of 6-(2-aminopyridin-3-yl)-2-(3,5-dimethoxyphenyl)pyridazin-3(2H)-one (from step 1; 12.7 mg, 0.0392 mmol) in ACN (0.8 mL) was treated with SO$_2$Cl$_2$ (6.33 μL, 0.0783 mmol) then stirred for 30 min at ambient temperature. The resulting mixture was quenched with the addition of saturated NaHCO$_{3(aq)}$ (10 mL). The resulting biphasic mixture was extracted with 4:1 DCM:iPrOH (2×25 mL). The combined organic extracts were dried over anhydrous Na$_2$SO$_{4(s)}$, filtered and concentrated under vacuum to afford the title compound (13.1 mg, 85% yield). MS (apci) m/z=396.9 [(M+H)+4], 394.9 [(M+H)+2], 392.9 (M+H), with di Cl pattern.

Step 3: Preparation of 6-(2-amino-5-bromopyridin-3-yl)-2-(2,6-dichloro-3,5-dimethoxyphenyl)pyridazin-3(2H)-one A solution of 6-(2-aminopyridin-3-yl)-2-(2,6-dichloro-3,5-dimethoxyphenyl)pyridazin-3(2H)-one (from step 2; 12.0 mg, 0.0305 mmol) in ACN (0.6 mL) was treated with NBS (5.97 mg, 0.0336 mmol) then stirred for 16 h at ambient temperature. The resulting mixture was diluted with 4:1 DCM:iPrOH (25 mL) and extracted with water (2×10 mL). The organic extracts were dried over anhydrous Na$_2$SO$_{4(s)}$, filtered and concentrated under vacuum to afford the title compound (14.4 mg, 100% yield). MS (apci) m/z=474.9 [(M+H)+4], 472.9 [(M+H)+2], 470.9 (M+H) with di Cl pattern.

Intermediate M3

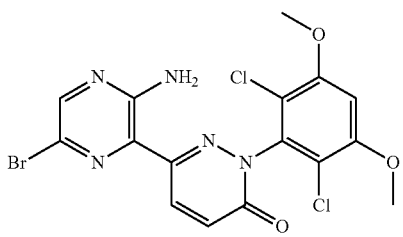 [SMILES: COc1cc(OC)c(Cl)c(-n2nc(-c3nc(Br)cnc3N)ccc2=O)c1Cl]

6-(3-amino-6-bromopyrazin-2-yl)-2-(2,6-dichloro-3,5-dimethoxyphenyl)pyridazin-3 (2H)-one 3,5-Dibromopyrazin-2-amine (0.417 g, 1.65 mmol) and sodium carbonate (2.62 ml, 5.24 mmol) were added to a solution of 2-(2,6-dichloro-3,5-dimethoxyphenyl)-6-(4,4,5,5-tetramethyl-1,3,2-dioxaborolan-2-yl)pyridazin-3(2H)-one (Intermediate R17; 0.640 g, 1.50 mmol) in 1,4-dioxane (15.0 ml, 1.50 mmol). The reaction mixture was stirred at 55° C. for 20 hrs. The reaction was quenched with water (50 mL) and extracted with DCM. The combined organic extracts were washed with water and brine, dried over Na$_2$SO$_4$ and concentrated in vacuo. The residue was triturated with DCM (50 mL) and filtered to obtain title compound (0.207 g, 0.438 mmol, 29.2% yield). MS (apci) m/z=477.9 [(M+H)+4], 475.9 [(M+H)+2], 473.9 (M+H), 471.9 (M−H) with di Cl+Br pattern.

Intermediate M4

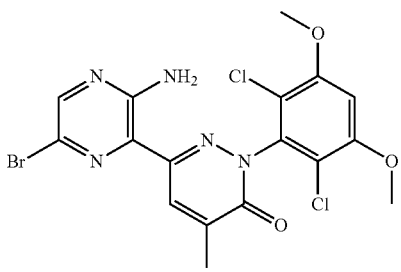 [SMILES: COc1cc(OC)c(Cl)c(-n2nc(-c3nc(Br)cnc3N)cc(C)c2=O)c1Cl]

6-(3-amino-6-bromopyrazin-2-yl)-2-(2,6-dichloro-3,5-dimethoxyphenyl)-4-methylpyridazin-3 (2H)-one A mixture of 3,5-dibromopyrazin-2-amine (0.585 g, 2.31 mmol), 2-(2,6-dichloro-3,5-dimethoxyphenyl)-4-methyl-6-(4,4,5,5-tetramethyl-1,3,2-dioxaborolan-2-yl)pyridazin-3 (2H)-one (Intermediate R16; 0.927 g, 2.10 mmol), Pd (PPh$_3$)$_4$ (0.182 g, 0.158 mmol) and Na$_2$CO$_3$ (2.21 mL, 4.41 mmol) in dioxane (10.5 ml, 2.10 mmol) was stirred at 55° C. for 8 hours. The reaction was quenched with water and extracted with DCM. The combined organic extracts were washed with water and brine, dried over Na$_2$SO$_4$ and concentrated in vacuo. The crude residue was purified by flash chromatography (1-9% MeOH in DCM) to give the title compound (0.187 g, 0.384 mmol, 18.3% yield). MS (apci) m/z=491.9 [(M+H)+4], 489.9 [(M+H)+2], 487.9 (M+H), 485.9 (M−H) with di Cl+Br pattern

Preparation of Synthetic Examples

Example 1

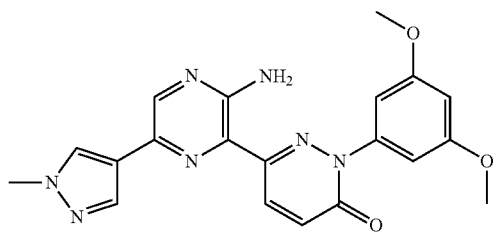

6-(3-amino-6-(1-methyl-1H-pyrazol-4-yl)pyrazin-2-yl)-2-(3,5-dimethoxyphenyl)pyridazin-3 (2H)-one A solution of 2-(3,5-dimethoxyphenyl)-6-(4,4,5,5-tetramethyl-1,3,2-dioxaborolan-2-yl)pyridazin-3(2H)-one (Intermediate R8; 275.0 mg, 0.7677 mmol) in 4:1 dioxane:water (7.7 mL) was treated with 3-bromo-5-(1-methyl-1H-pyrazol-4-yl)pyrazin-2-amine (Intermediate L2; 204.8 mg, 0.8061 mmol), PdCl$_2$(dppf)·CH$_2$Cl$_2$ (63.16 mg, 0.07677 mmol), K$_2$CO$_{3(s)}$ (318.3 mg, 2.303 mmol). The resulting mixture was sparged with Ar$_{(g)}$, then sealed and stirred for 16 h at 100° C. After cooling to ambient temperature, the reaction mixture was diluted with 4:1 DCM:iPrOH (150 mL), and extracted with water (2×50 mL). The organic extracts were dried over anhydrous Na$_2$SO$_{4(s)}$, filtered and concentrated under vacuum. The resulting crude residue was purified by silica chromatography (5-80% DCM/Acetone as the gradient eluent) to afford the title compound (189.6 mg, 61% yield). MS (apci) m/z=406.1 (M+H). $^1$H NMR (400 MHz, DMSO-d$_6$) δ 8.67-8.65 (d, 1H), 8.48 (s, 1H), 8.30 (s, 1H), 8.02 (s, 1H), 7.31 (s, 2H), 7.22-7.20 (d, 1H), 6.86-6.85 (d, 2H), 6.63-6.62 (m, 1H), 3.89 (s, 3H), 3.79 (s, 6H).

The following compounds shown in Table 1 were prepared according the method used in Example 1 using the appropriate 3-bromo-5-(pyrazoyl)pyrazin-2-amines (Intermediates L2, L14, L15, L16, L19) and 2-(Aryl)-6-(4,4,5,5-tetramethyl-1,3,2-dioxaborolan-2-yl)pyridazin-3(2H)-one (Intermediate R1, R8, R9; 1.00-1.2 equivalents). Reaction progression in each was followed by LCMS and reaction time was adjusted as necessary. All compounds were purified using a method similar to that followed in Example 1 utilizing the appropriate gradient eluent.

TABLE 1

| Ex # | Structure | Name | MS (apci) m/z |
|---|---|---|---|
| 2* | 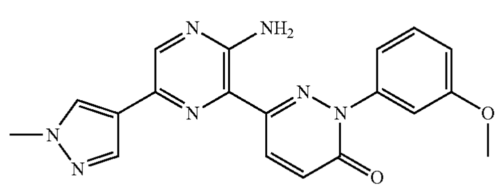 | 6-(3-amino-6-(1-methyl-1H-pyrazol-4-yl)pyrazin-2-yl)-2-(3-methoxyphenyl)pyridazin-3(2H)-one | 376.0 (M + H) |
| 3 | 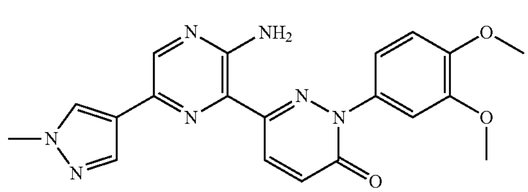 | 6-(3-amino-6-(1-methyl-1H-pyrazol-4-yl)pyrazin-2-yl)-2-(3,4-dimethoxyphenyl)pyridazin-3(2H)-one | 406.1 (M + H) |

TABLE 1-continued

| Ex # | Structure | Name | MS (apci) m/z |
|---|---|---|---|
| 4 | 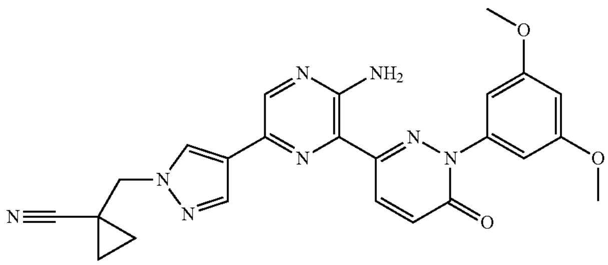 [SMILES: COc1cc(OC)cc(-n2nc(-c3nc(-c4cnn(CC5(C#N)CC5)c4)cnc3N)ccc2=O)c1] | 1-((4-(5-amino-6-(1-(3,5-dimethoxyphenyl)-6-oxo-1,6-dihydropyridazin-3-yl)pyrazin-2-yl)-1H-pyrazol-1-yl)methyl)cyclopropane-1-carbonitrile | 471.1 (M + H) |
| 5 | 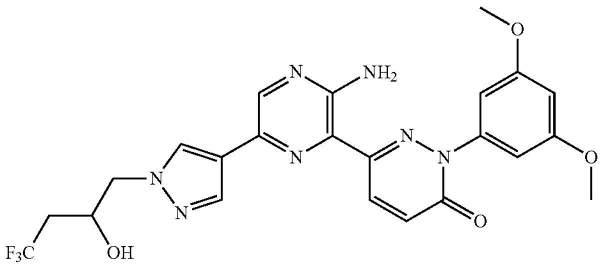 [SMILES: COc1cc(OC)cc(-n2nc(-c3nc(-c4cnn(CC(O)CC(F)(F)F)c4)cnc3N)ccc2=O)c1] | 6-(3-amino-6-(1-(4,4,4-trifluoro-2-hydroxybutyl)-1H-pyrazol-4yl)pyrazin-2-yl)-2-(3,5-dimethoxyphenyl)pyridazin-3(2H)-one | 518.0 (M + H) |
| 6 | 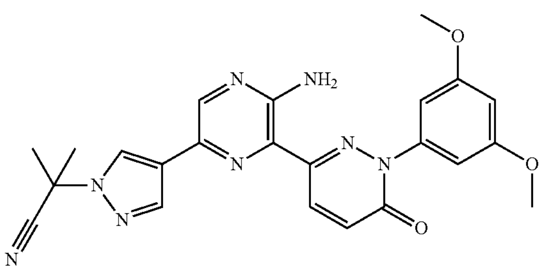 [SMILES: COc1cc(OC)cc(-n2nc(-c3nc(-c4cnn(C(C)(C)C#N)c4)cnc3N)ccc2=O)c1] | 2-(4-(5-amino-6-(1-(3,5-dimethoxyphenyl)-6-oxo-1,6-dihydropyridazin-3-yl)pyrazin-2-yl)-1H-pyrazol-1-yl)-2-methylpropanenitrile | 459.1 (M + H) |
| 7 | 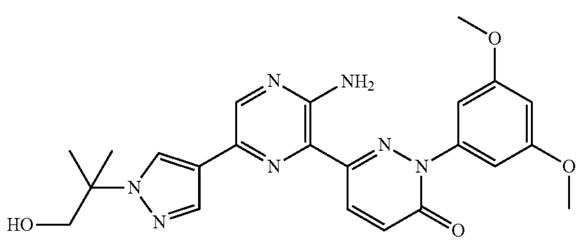 [SMILES: COc1cc(OC)cc(-n2nc(-c3nc(-c4cnn(C(C)(C)CO)c4)cnc3N)ccc2=O)c1] | 6-(3-amino-6-(1-(1-hydroxy-2-methylpropan-2-yl)-1H-pyrazol-4-yl)pyrazin-2-yl)-2-(3,5-dimethoxyphenyl)pyridazin-3(2H)-one | 464.1 (M + H) |

*EtOAc was used as the work up solvent in place of 4:1 DCM iPrOH

Example 8

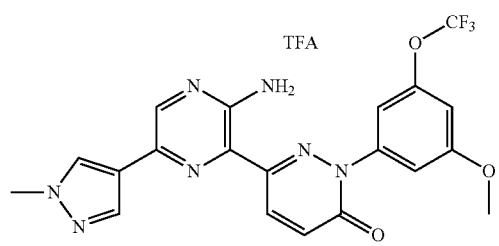

6-(3-amino-6-(1-methyl-1H-pyrazol-4-yl)pyrazin-2-yl)-2-(3-methoxy-5-(trifluoromethoxy)phenyl)pyridazin-3(2H)-one 2,2,2-trifluoroacetate salt A suspension of 3-bromo-5-(1-methyl-1H-pyrazol-4-yl)pyrazin-2-amine (Intermediate L2; 0.100 g, 0.394 mmol), 2-(3-methoxy-5-(trifluoromethoxy)phenyl)-6-(4,4,5,5-tetramethyl-1,3,2-dioxaborolan-2-yl)pyridazin-3(2H)-one (Intermediate R2; 0.243 g, 0.590 mmol), Pd(PPh$_3$)$_4$(0.0341 g, 0.0295 mmol) and 2M Na$_2$CO$_{3(aq)}$ (0.413 mL, 0.826 mmol) in dioxane (1.0 mL) was sparged with Ar$_{(g)}$, then sealed and stirred for 8 h at 90° C. After cooling to ambient temperature, the reaction mixture was filtered to remove solids. The filtrate was concentrated under vacuum, and the resulting crude residue was purified by C18 reverse phase chromatography (5-95% ACN:water with 0.1% TFA) to afford the title compound (0.1014 g, 46% yield). MS (apci) m/z=460.1 (M+H).

The following compounds shown in Table 2, were prepared according the method used in Example 8 using the appropriate 3-bromo-5-(pyrazoyl)pyrazin-2-amines (Intermediates L2, L3, L5, L17) and 2-(Aryl)-6-(4,4,5,5-tetramethyl-1,3,2-dioxaborolan-2-yl)pyridazin-3(2H)-one (Intermediate R3, R4, R6, R7, R8, R12). Reaction progression in each was followed by LCMS and reaction time was adjusted as necessary. All compounds were purified using a method similar to that used in Example 8 utilizing the appropriate gradient eluent and in each case the mono-TFA salt was isolated.

TABLE 2

| Ex # | Structure | Name | MS (apci) m/z |
|---|---|---|---|
| 9 | 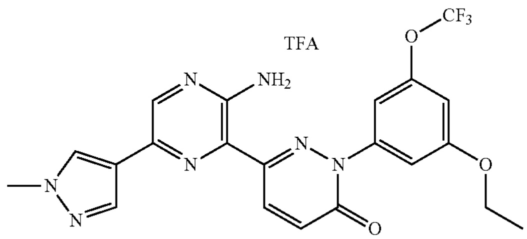 [SMILES: CCOc1cc(OC(F)(F)F)cc(-n2nc(-c3nc(-c4cnn(C)c4)cnc3N)ccc2=O)c1] | 6-(3-amino-6-(1-methyl-1H-pyrazol-4-yl)pyrazin-2-yl)-2-(3-ethoxy-5-(trifluoromethoxy)phenyl)pyridazin-3(2H)-one 2,2,2-trifluoroacetate salt | 474.1 (M + H) |
| 10 | 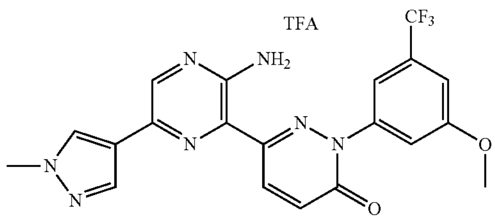 | 6-(3-amino-6-(1-methyl-1H-pyrazol-4-yl)pyrazin-2-yl)-2-(3-methoxy-5-(trifluoromethyl)phenyl)pyridazin-3(2H)-one 2,2,2-trifluoroacetate salt | 444.1 (M + H) |
| 11 | 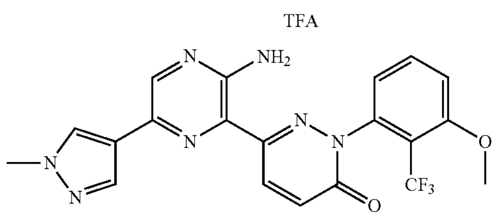 | 6-(3-amino-6-(1-methyl-1H-pyrazol-4-yl)pyrazin-2-yl)-2-(2-chloro-3-methoxyphenyl)pyridazin-3(2H)-one 2,2,2-trifluoroacetate salt | 410.1 (M + H) |
| 12 | 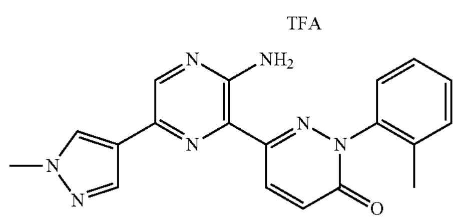 [SMILES: Cc1ccccc1-n1nc(-c2nc(-c3cnn(C)c3)cnc2N)ccc1=O] | 6-(3-amino-6-(1-methyl-1H-pyrazol-4-yl)pyrazin-2-yl)-2-(o-tolyl)pyridazin-3(2H)-one 2,2,2-trifluoroacetate salt | 360.1 (M + H) |
| 13 | 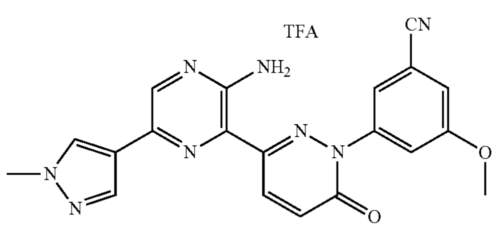 | 3-(3-(3-amino-6-(1-methyl-1H-pyrazol-4-yl)pyrazin-2-yl)-6-oxopyridazin-1(6H)-yl)-5-methoxybenzonitrile 2,2,2-trifluoroacetate salt | 401.1 (M + H) |
| 14 | 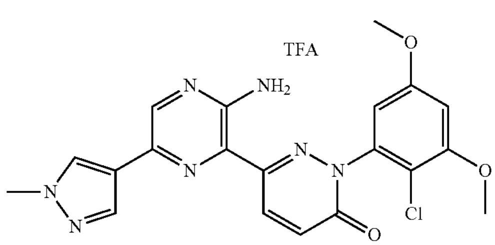 | 6-(3-amino-6-(1-methyl-1H-pyrazol-4-yl)pyrazin-2-yl)-2-(2-chloro-3,5-dimethoxyphenyl)pyridazin-3(2H)-one (2,2,2-trifluoroacetate) salt | 440.1 (M + H) |

TABLE 2-continued

| Ex # | Structure | Name | MS (apci) m/z |
|---|---|---|---|
| 15 | TFA | 6-(3-amino-6-(1-isopropyl-1H-pyrazol-4-yl)pyrazin-2-yl)-2-(3,5-dimethoxyphenyl)pyridazin-3(2H)-one 2,2,2-trifluoroacetate | 434.1 (M + H) |
| 16 | TFA | 6-(3-amino-6-(1-(pentan-3-yl)-1H-pyrazol-4-yl)pyrazin-2-yl)-2-(3,5-dimethoxyphenyl)pyridazin-3(2H)-one 2,2,2-trifluoroacetate salt | 462.2 (M + H) |
| 17 | TFA | 6-(3-amino-6-(1-(cyclopropylmethyl)-1H-pyrazol-4-yl)pyrazin-2-yl)-2-(3,5-dimethoxyphenyl)pyridazin-3(2H)-one 2,2,2-trifluoroacetate salt | 446.2 (M + H) |
| 18 | TFA | 6-(3-amino-6-(1-(2-hydroxy-2-methylpropyl)-1H-pyrazol-4-yl)pyrazin-2-yl)-2-(3,5-dimethoxyphenyl)pyridazin-3(2H)-one 2,2,2-trifluoroacetate salt | 464.2 (M + H) |

Example 19

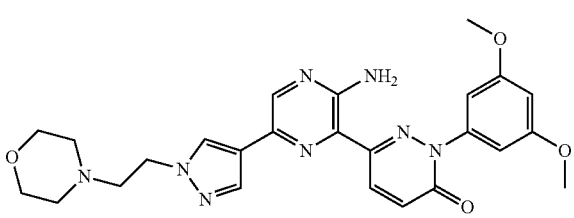 [SMILES: COc1cc(OC)cc(-n2nc(-c3nc(-c4cnn(CCN5CCOCC5)c4)cnc3N)ccc2=O)c1]

6-(3-amino-6-(1-(2-morpholinoethyl)-1H-pyrazol-4-yl)pyrazin-2-yl)-2-(3,5-dimethoxyphenyl)pyridazin-3 (2H)-one A suspension of 3-bromo-5-(1-(2-morpholinoethyl)-1H-pyrazol-4-yl)pyrazin-2-amine (Intermediate L8; 0.044 g, 0.125 mmol), 2-(3,5-dimethoxyphenyl)-6-(4,4,5,5-tetramethyl-1,3,2-dioxaborolan-2-yl)pyridazin-3(2H)-one (Intermediate R8; 0.0892 g, 0.249 mmol), Pd(PPh$_3$)$_4$ (0.0108 g, 0.00934 mmol) and 2M Na$_2$CO$_{3(aq)}$ (0.131 mL, 0.262 mmol) in dioxane (1 mL) was sparged with Ar$_{(g)}$, then sealed and stirred for 8 h at 90° C. After cooling to ambient temperature, the reaction mixture was filtered to remove solids. The filtrate was concentrated under vacuum, and the resulting crude residue was purified by silica chromatography (5-95% DCM:(DCM:MeOH:NHOH$_4$ (90:10:1)) to afford the title compound (0.0538 g, 86% yield). MS (apci) m/z=505.2 (M+H).

The following compounds shown in Table 3 were prepared according the method used in Example 19 using the appropriate 3-bromo-5-(pyrazoyl)pyrazin-2-amines (Intermediates L2, L4, L7) and 2-(Aryl)-6-(4,4,5,5-tetramethyl-1,3,2-dioxaborolan-2-yl)pyridazin-3(2H)-one (Intermediate R5, R8). Reaction progression in each was followed by LCMS and reaction time was adjusted as necessary. All compounds were purified using a method similar to that followed in Example 19 utilizing the appropriate gradient eluent.

TABLE 3

| Ex # | Structure | Name | MS (apci) m/z |
|---|---|---|---|
| 20 | 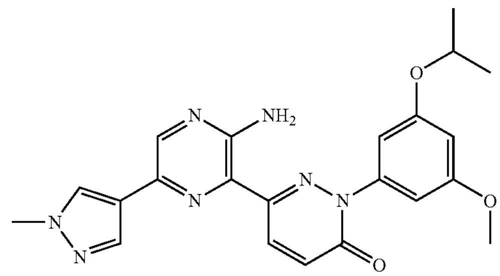 [SMILES: COc1cc(OC(C)C)cc(-n2nc(-c3nc(-c4cnn(C)c4)cnc3N)ccc2=O)c1] | 6-(3-amino-6-(1-methyl-1H-pyrazol-4-yl)pyrazin-2-yl)-2-(3-isopropoxy-5-methoxyphenyl)pyridazin-3(2H)-one | 434.2 (M + H) |
| 21 | 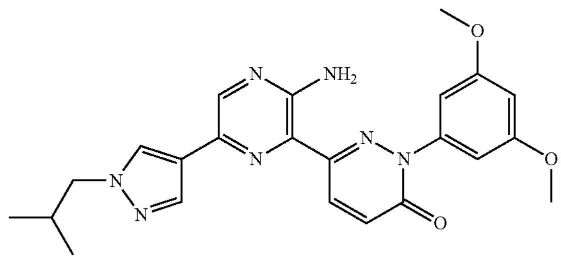 [SMILES: COc1cc(OC)cc(-n2nc(-c3nc(-c4cnn(CC(C)C)c4)cnc3N)ccc2=O)c1] | 6-(3-amino-6-(1-isobutyl-1H-pyrazol-4-yl)pyrazin-2-yl)-2-(3,5-dimethoxyphenyl)pyridazin-3(2H)-one | 448.2 (M + H) |
| 22 | 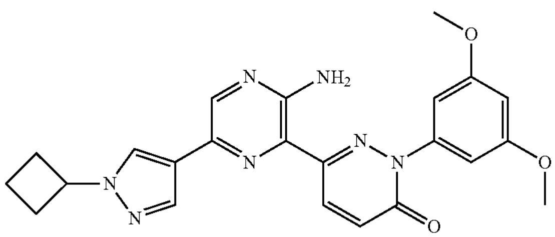 [SMILES: COc1cc(OC)cc(-n2nc(-c3nc(-c4cnn(C5CCC5)c4)cnc3N)ccc2=O)c1] | 6-(3-amino-6-(1-cyclobutyl-1H-pyrazol-4-yl)pyrazin-2-yl)-2-(3,5-dimethoxyphenyl)pyridazin-3(2H)-one | 446.2 (M + H) |

Example 23

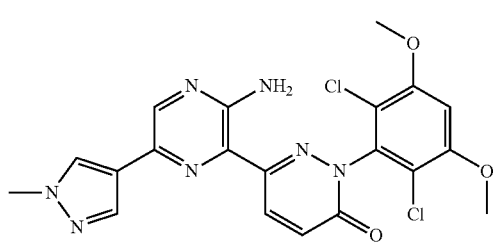

6-(3-amino-6-(1-methyl-1H-pyrazol-4-yl)pyrazin-2-yl)-2-(2,6-dichloro-3,5-dimethoxyphenyl)pyridazin-3 (2H)-one A cold (0° C.) solution of 6-(3-amino-6-(1-methyl-1H-pyrazol-4-yl)pyrazin-2-yl)-2-(3,5-dimethoxyphenyl)pyridazin-3(2H)-one (Example 1; 13.6 mg, 0.0335 mmol) in ACN (0.7 mL) was treated with $SO_2Cl_2$ (5.42 μL, 0.0671 mmol) then stirred for 30 min at ambient temperature. The resulting mixture was quenched with the addition of saturated $NaHCO_{3(aq)}$ (10 mL). The resulting biphasic mixture was extracted with 4:1 DCM:iPrOH (2×25 mL). The combined organic extracts were dried over anhydrous $Na_2SO_{4(s)}$, filtered and concentrated under vacuum. The resulting crude residue was purified by silica chromatography (5-50% DCM/Acetone as the gradient eluent) to afford the title compound (189.6 mg, 61% yield). MS (apci) m/z=476.0 [(M+H)+2], 474.1 (M+H), with di Cl pattern. $^1$H NMR (400 MHz, DMSO-$d_6$) δ 8.73-8.70 (d, 1H), 8.47 (s, 1H), 8.27 (s, 1H), 8.00 (s, 1H), 7.30-7.27 (d, 1H), 7.09 (s, 1H), 7.03 (s, 2H), 3.94 (s, 6H), 3.85 (s, 3H).

Example 24

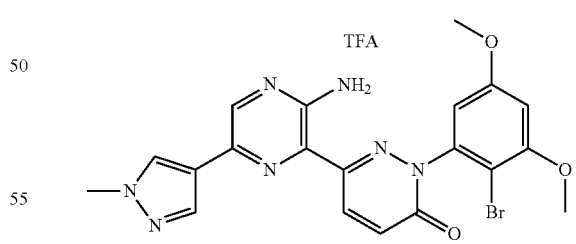

6-(3-amino-6-(1-methyl-1H-pyrazol-4-yl)pyrazin-2-yl)-2-(2-bromo-3,5-dimethoxyphenyl)pyridazin-3 (2H)-one 2,2,2-trifluoroacetate salt A cold (0° C.) solution of 6-(3-amino-6-(1-methyl-1H-pyrazol-4-yl)pyrazin-2-yl)-2-(3,5-dimethoxyphenyl)pyridazin-3(2H)-one (Example 1; 100 mg, 0.247 mmol) in DCM (1.23 mL) was treated with NBS (43.9 mg, 0.247 mmol) then stirred for 3 h at ambient temperature. The resulting mixture was diluted with Ethyl Acetate, washed with Brine (2×), then dried over anhydrous Na$_2$SO$_{4(s)}$, filtered and concentrated under vacuum. The resulting crude residue was purified by silica gel chromatography (30-100% EtOAc/Hexanes as the gradient eluent) to afford the title compound in about 75% purity (17.4 mg, 15% yield). Additional purification by C18 reverse phase chromatography (5-95% Acetonitrile in Water with 0.1% TFA as gradient eluent) provided clean title compound. MS (apci) m/z=484.0 (M+H), with di Br pattern. $^1$H NMR (400 MHz, CDCl$_3$) δ 8.67-8.64 (d, 1H), 8.26 (s, 1H), 7.92 (s, 1H), 7.83 (s, 1H), 7.20-7.17 (d, 1H), 6.65-6.60 (m, 2H), 6.27 (broad s, 2H), 3.96 (s, 3H), 3.92 (s, 3H), 3.82 (s, 3H).

Example 25

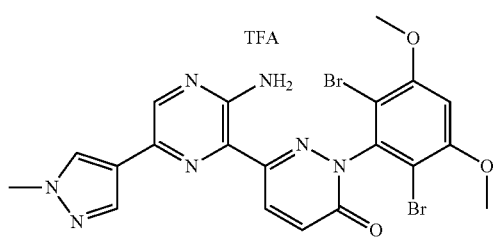

6-(3-amino-6-(1-methyl-1H-pyrazol-4-yl)pyrazin-2-yl)-2-(2,6-dibromo-3,5-dimethoxyphenyl)pyridazin-3(2H)-one 2,2,2-trifluoroacetate salt A cold (0° C.) solution of 6-(3-amino-6-(1-methyl-1H-pyrazol-4-yl)pyrazin-2-yl)-2-(3,5-dimethoxyphenyl)pyridazin-3(2H)-one (Example 1; 20 mg, 0.0493 mmol) in DCM (0.247 mL mL) was treated with NBS (15 mg, 0.0843 mmol) then stirred overnight at ambient temperature. The resulting mixture was diluted with Ethyl Acetate, washed with Brine (2×), then dried over anhydrous Na$_2$SO$_{4(s)}$, filtered and concentrated under vacuum. The resulting crude residue was purified by C18 reverse phase chromatography (5-95% Acetonitrile in Water with 0.1% TFA as the gradient) to afford the title compound (7 mg, 25% yield). MS (apci) m/z=564.0 (M+H), with di Br pattern. $^1$H NMR (400 MHz, CDCl$_3$) δ 8.84-8.81 (d, 1H), 8.36 (s, 1H), 8.16 (s, 1H), 8.03 (s, 1H), 7.27-7.24 (d, 1H), 6.95 (s, 1H), 4.00 (s, 6H), 3.94 (s, 3H).

Example 26

(R)-6-(3-amino-6-(1-((5,5-dimethylmorpholin-2-yl)methyl)-1H-pyrazol-4-yl)pyrazin-2-yl)-2-(3,5-dimethoxyphenyl)pyridazin-3 (2H)-one Step 1: Preparation of tert-butyl (R)-2-((4-(5-amino-6-(1-(3,5-dimethoxyphenyl)-6-oxo-1,6-dihydropyridazin-3-yl)pyrazin-2-yl)-1H-pyrazol-1-yl)methyl)-5,5-dimethylmorpholine-4-carboxylate A suspension of tert-butyl (R)-2-((4-(5-amino-6-bromopyrazin-2-yl)-1H-pyrazol-1-yl)methyl)-5,5-dimethylmorpholine-4-carboxylate (Intermediate L12; 100 mg, 0.214 mmol), 2-(3,5-dimethoxyphenyl)-6-(4,4,5,5-tetramethyl-1,3,2-dioxaborolan-2-yl)pyridazin-3(2H)-one (Intermediate R8; 192 mg, 0.535 mmol), Pd(PPh$_3$)$_4$(24.7 mg, 0.0214 mmol), and 2M Na$_2$CO$_{3(aq)}$ (321 μL, 0.642 mmol) in dioxane (2.14 mL) was sparged with Ar$_{(g)}$, then sealed and stirred 2 h at 90° C. After cooling to ambient temperature, the reaction mixture was diluted with EtOAc and filtered to remove solids. The filtrate was concentrated under vacuum, and the resulting crude residue was purified by silica chromatography (60-100% EtOAc in Hexanes) to afford the title compound (35 mg, 26% yield). MS (apci) m/z=619.2 (M+H).

Step 2: Preparation of (R)-6-(3-amino-6-(1-((5,5-dimethylmorpholin-2-yl)methyl)-1H-pyrazol-4-yl)pyrazin-2-yl)-2-(3,5-dimethoxyphenyl)pyridazin-3 (2H)-one The tert-butyl (R)-2-((4-(5-amino-6-(1-(3,5-dimethoxyphenyl)-6-oxo-1,6-dihydropyridazin-3-yl)pyrazin-2-yl)-1H-pyrazol-1-yl)methyl)-5,5-dimethylmorpholine-4-carboxylate (35 mg, 0.057 mmol) was dissolved in 1:1 TFA:DCM (8.0 mL) then stirred 1 h at ambient temperature. The reaction mixture was concentrated under vacuum then purified by C18 reverse phase chromatography (5-95% ACN in H$_2$O with 0.1% TFA as the gradient as the gradient eluent). The chromatographic fractions containing the title compound were combined then neutralized with saturated NaHCO$_{3(aq)}$ and extracted with DCM. The organic extracts were then dried over anhydrous Na$_2$SO$_{4(s)}$, filtered and concentrated under vacuum to afford the title compound (24.5 mg, 84% yield). MS (apci) m/z=519.2 (M+H).

Example 27

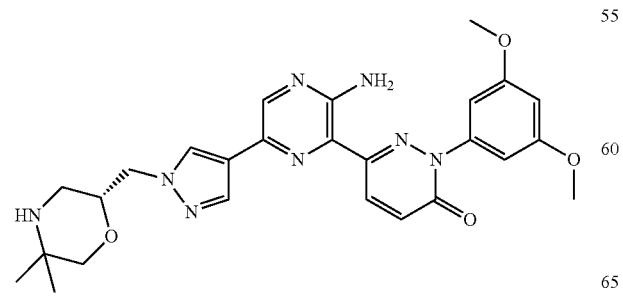

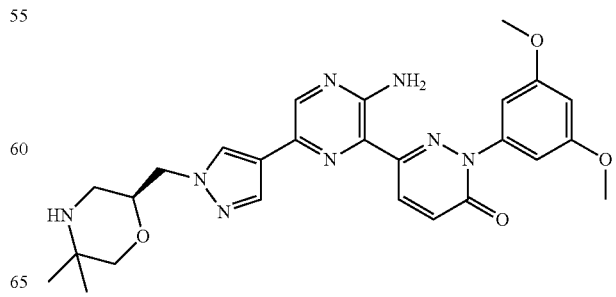

(S)-6-(3-amino-6-(1-((5,5-dimethylmorpholin-2-yl)methyl)-1H-pyrazol-4-yl)pyrazin-2-yl)-2-(3,5-dimethoxyphenyl)pyridazin-3 (2H)-one Step 1: Preparation of tert-butyl (S)-2-((4-(5-amino-6-(1-(3,5-dimethoxyphenyl)-6-oxo-1,6-dihydropyridazin-3-yl)pyrazin-2-yl)-1H-pyrazol-1-yl)methyl)-5,5-dimethylmorpholine-4-carboxylate The title compound was prepared and isolated according to the method described in step 1 of Example 26, using tert-butyl (S)-2-((4-(5-amino-6-bromopyrazin-2-yl)-1H-pyrazol-1-yl)methyl)-5,5-dimethylmorpholine-4-carboxylate (Intermediate L11) in place of tert-butyl (R)-2-((4-(5-amino-6-bromopyrazin-2-yl)-1H-pyrazol-1-yl)methyl)-5,5-dimethylmorpholine-4-carboxylate (Intermediate L12). The title compound was carried on to step 2, without silica chromatography. MS (apci) m/z=446.2 (M+H).

Step 2: Preparation of (S)-6-(3-amino-6-(1-((5,5-dimethylmorpholin-2-yl)methyl)-1H-pyrazol-4-yl)pyrazin-2-yl)-2-(3,5-dimethoxyphenyl)pyridazin-3 (2H)-one The title compound was prepared and isolated according to the method described in step 2 of Example 26, using the crude residue from step 1 and neutralizing with 1 M NaOH$_{(aq)}$ instead of NaHCO$_{3(aq)}$ resulting in a 46% yield (39 mg,). MS (apci) m/z=519.2 (M+H).

Example 28

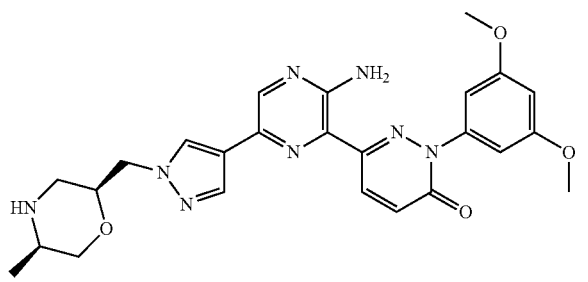

6-(3-amino-6-(1-(((2S,5R)-5-methylmorpholin-2-yl)methyl)-1H-pyrazol-4-yl)pyrazin-2-yl)-2-(3,5-dimethoxyphenyl)pyridazin-3 (2H)-one Step 1: Preparation of tert-butyl (2S,5R)-2-((4-(5-amino-6-(1-(3,5-dimethoxyphenyl)-6-oxo-1,6-dihydropyridazin-3-yl)pyrazin-2-yl)-1H-pyrazol-1-yl)methyl)-5-methylmorpholine-4-carboxylate The title compound was prepared and isolated according to the method described in step 1 of Example 26, with the exception that the reaction required overnight stirring at 90° C. and utilized tert-butyl (2S,5R)-2-((4-(5-amino-6-bromopyrazin-2-yl)-1H-pyrazol-1-yl)methyl)-5-methylmorpholine-4-carboxylate (Intermediate L10) in place of tert-butyl (R)-2-((4-(5-amino-6-bromopyrazin-2-yl)-1H-pyrazol-1-yl)methyl)-5,5-dimethylmorpholine-4-carboxylate (Intermediate L12). The title compound was carried on to step 2, without silica chromatography (23 mg, 34% yield). MS (apci) m/z=605.2 (M+H).

Step 2: Preparation of 6-(3-amino-6-(1-(((2S,5R)-5-methylmorpholin-2-yl)methyl)-1H-pyrazol-4-yl)pyrazin-2-yl)-2-(3,5-dimethoxyphenyl)pyridazin-3 (2H)-one Using the crude residue from step 1, the title compound was prepared, isolated, purified and neutralized according to the method described in step 2 of Example 26, with the exception that the reaction was allowed to stir 2 d at ambient temperature prior to isolation/purification (7.0 mg, 84% yield). MS (apci) m/z=505.2 (M+H).

Example 29

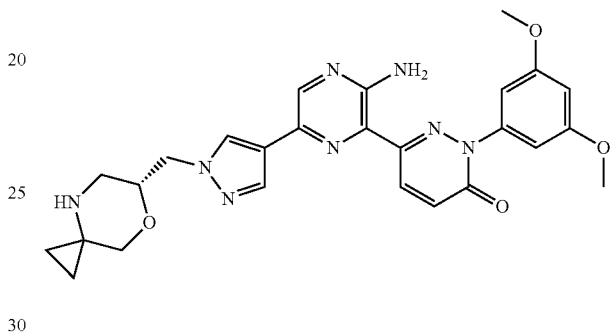

(R)-6-(6-(1-(((7-oxa-4-azaspiro[2.5]octan-6-yl)methyl)-1H-pyrazol-4-yl)-3-aminopyrazin-2-yl)-2-(3,5-dimethoxyphenyl)pyridazin-3 (2H)-one Step 1: Preparation of tert-butyl (R)-6-((4-(5-amino-6-(1-(3,5-dimethoxyphenyl)-6-oxo-1,6-dihydropyridazin-3-yl)pyrazin-2-yl)-1H-pyrazol-1-yl)methyl)-7-oxa-4-azaspiro[2.5]octane-4-carboxylate The title compound was prepared and isolated according to the method described in step 1 of Example 26, using of tert-butyl (R)-6-((4-(5-amino-6-bromopyrazin-2-yl)-1H-pyrazol-1-yl)methyl)-7-oxa-4-azaspiro[2.5] octane-4-carboxylate (Intermediate L13) in place of tert-butyl (R)-2-((4-(5-amino-6-bromopyrazin-2-yl)-1H-pyrazol-1-yl)methyl)-5,5-dimethylmorpholine-4-carboxylate (Intermediate L12). The title compound was purified by silica chromatography (30-75% EtOAc in Hexanes) which provide the title compound in 38% yield (15 mg). MS (apci) m/z=617.2 (M+H).

Step 2: Preparation of (R)-6-(6-(1-(((7-oxa-4-azaspiro[2.5]octan-6-yl)methyl)-1H-pyrazol-4-yl)-3-aminopyrazin-2-yl)-2-(3,5-dimethoxyphenyl)pyridazin-3 (2H)-one Using the purified material from step 1, the title compound was prepared, isolated, purified and neutralized according to the method described in step 2 of Example 27 (12.1 mg, 96% yield). MS (apci) m/z=517.2 (M+H).

Example 30

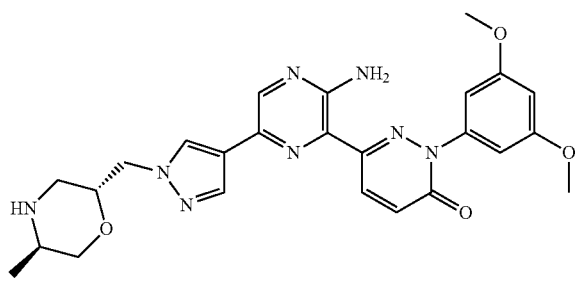

6-(3-amino-6-(1-(((2R,5R)-5-methylmorpholin-2-yl)methyl)-1H-pyrazol-4-yl)pyrazin-2-yl)-2-(3,5-dimethoxyphenyl)pyridazin-3 (2H)-one

Step 1: Preparation of tert-butyl (2R,5R)-2-((4-(5-amino-6-(1-(3,5-dimethoxyphenyl)-6-oxo-1,6-dihydropyridazin-3-yl)pyrazin-2-yl)-1H-pyrazol-1-yl)methyl)-5-methylmorpholine-4-carboxylate The title compound was prepared and isolated according to the method described in step 1 of Example 26, using of tert-butyl (2R,5R)-2-((4-(5-amino-6-bromopyrazin-2-yl)-1H-pyrazol-1-yl)methyl)-5-methylmorpholine-4-carboxylate (Intermediate L9) in place of tert-butyl (R)-2-((4-(5-amino-6-bromopyrazin-2-yl)-1H-pyrazol-1-yl)methyl)-5,5-dimethylmorpholine-4-carboxylate (Intermediate L12). The title compound was purified by silica chromatography (30-75% EtOAc in Hexanes) which provided the title compound in 31% yield (23 mg). MS (apci) m/z=605.2 (M+H).

Step 2: Preparation of 6-(3-amino-6-(1-(((2R,5R)-5-methylmorpholin-2-yl)methyl)-1H-pyrazol-4-yl)pyrazin-2-yl)-2-(3,5-dimethoxyphenyl)pyridazin-3 (2H)-one Using the purified material from step 1, the title compound was prepared, isolated, purified according to the method described in step 2 of Example 26 which provided the title compound in 91% yield (17.4 mg). MS (apci) m/z=505.2 (M+H).

Example 31

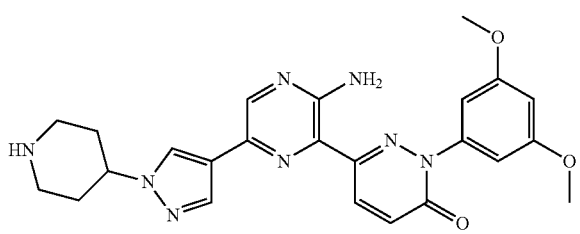 [SMILES: COc1cc(OC)cc(-n2nc(-c3nc(-c4cnn(C5CCNCC5)c4)cnc3N)ccc2=O)c1]

6-(3-amino-6-(1-(piperidin-4-yl)-1H-pyrazol-4-yl)pyrazin-2-yl)-2-(3,5-dimethoxyphenyl)pyridazin-3 (2H)-one

Step 1: Preparation of tert-butyl 4-(4-(5-amino-6-(1-(3,5-dimethoxyphenyl)-6-oxo-1,6-dihydropyridazin-3-yl)pyrazin-2-yl)-1H-pyrazol-1-yl)piperidine-1-carboxylate A suspension of tert-butyl 4-(4-(5-amino-6-bromopyrazin-2-yl)-1H-pyrazol-1-yl)piperidine-1-carboxylate (Intermediate L19; 398.9 mg, 0.9423 mmol), 2-(3,5-dimethoxyphenyl)-6-(4,4,5,5-tetramethyl-1,3,2-dioxaborolan-2-yl)pyridazin-3(2H)-one (Intermediate R8; 371.3 mg, 1.037 mmol), PdCl$_2$(dppf)·CH$_2$Cl$_2$ (77.52 mg, 0.09423 mmol) and K$_2$CO$_{3(s)}$ (390.7 mg, 2.827 mmol) in 4:1 dioxane:water (10 mL) was sparged with Ar$_{(g)}$, then sealed and stirred 16 h at 100° C. After cooling to ambient temperature, the reaction mixture was diluted with 4:1 DCM:iPrOH (200 mL) and washed with water (2×50 mL). The organic extracts were dried over anhydrous Na$_2$SO$_{4(s)}$, filtered and concentrated under vacuum. The crude residue was purified by silica chromatography (5-95% DCM-Acetone as the gradient eluent) to afford the title compound which was immediately carried on to step 2. MS (apci) m/z=575.3 (M+H).

Step 2: Preparation of 6-(3-amino-6-(1-(piperidin-4-yl)-1H-pyrazol-4-yl)pyrazin-2-yl)-2-(3,5-dimethoxyphenyl)pyridazin-3(2H)-one The tert-butyl 4-(4-(5-amino-6-(1-(3,5-dimethoxyphenyl)-6-oxo-1,6-dihydropyridazin-3-yl)pyrazin-2-yl)-1H-pyrazol-1-yl)piperidine-1-carboxylate was dissolved in 1:1 TFA:DCM (5.0 mL) then stirred 30 min at ambient temperature. The reaction mixture was concentrated under vacuum then purified by C18 reverse phase chromatography (5-95% ACN in H$_2$O with 0.1% TFA as the gradient eluent) to afford the title compound as a TFA salt. The TFA salt was dissolved in 4:1 DCM:iPrOH (50 mL) and extracted with saturated NaHCO$_{3(aq)}$ (1×25 mL). The organic extracts were dried over anhydrous Na$_2$SO$_{4(s)}$, filtered and concentrated under vacuum to cleanly afford the title compound (213.2 mg, 48% yield). MS (apci) m/z=475.2 (M+H).

Example 32

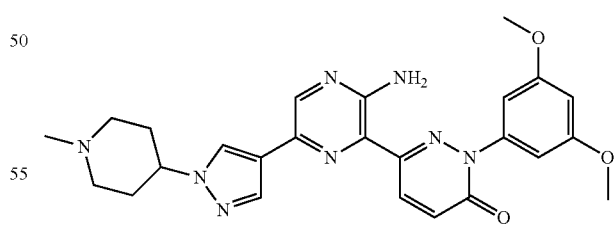

6-(3-amino-6-(1-(1-methylpiperidin-4-yl)-1H-pyrazol-4-yl)pyrazin-2-yl)-2-(3,5-dimethoxyphenyl)pyridazin-3 (2H)-one A solution of 6-(3-amino-6-(1-(piperidin-4-yl)-1H-pyrazol-4-yl)pyrazin-2-yl)-2-(3,5-dimethoxyphenyl)pyridazin-3 (2H)-one (Example 31; 187.2 mg, 0.3945 mmol) in 1:1 DCM:MeOH (4 mL) was treated with formaldehyde (592.9

µL, 7.890 mmol) and stirred 15 min at ambient temperature. The resulting reaction mixture was treated with sodium triacetoxyborohydride (334.4 mg, 1.578 mmol) and stirred 16 h at ambient temperature. The reaction mixture was concentrated under vacuum then purified by C18 reverse phase chromatography (5-95% water-ACN w/0.1% TFA as the gradient eluent) to afford the title compound as a TFA salt. The TFA salt was dissolved in 4:1 DCM:iPrOH (50 mL) and extracted with saturated NaHCO$_{3(aq)}$ (1×25 mL). The organic extracts were dried over anhydrous Na$_2$SO$_{4(s)}$, filtered and concentrated under vacuum to afford the title compound along with imine contaminants. The residue then was dissolved in 1:1:1 TFA:ACN:water (6 mL) and stirred for 15 min at ambient temperature then concentrated under vacuum. The resultant residue was dissolved in 4:1 DCM:iPrOH (50 mL) and extracted with saturated NaHCO$_{3(aq)}$ (1×25 mL). The organic extracts were dried over anhydrous Na$_2$SO$_{4(s)}$, filtered and concentrated under vacuum. The residue was purified further by silica chromatography (1-30% DCM-MeOH w/2% NH$_4$OH as the gradient eluent) to cleanly afford the title compound (28.5 mg, 15% yield). MS (apci) m/z=489.1 (M+H). $^1$H NMR (400 MHz, DMSO-d$_6$) δ 8.71-8.69 (d, 1H), 8.49 (s, 1H), 8.42 (s, 1H), 8.04 (s, 1H), 7.31 (s, 2H), 7.21-7.19 (d, 1H), 6.86-6.85 (d, 2H), 6.63-6.62 (t, 1H), 4.19-4.13 (m, 1H), 3.79 (s, 6H), 2.93-2.88 (m, 2H), 2.25 (s, 3H), 2.15-1.97 (m, 6H).

Example 33

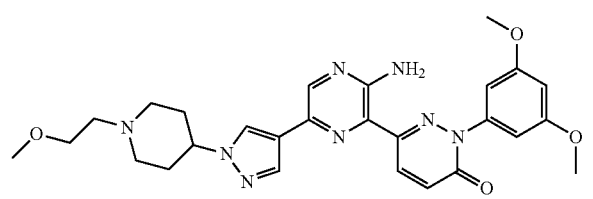

6-(3-amino-6-(1-(1-(2-methoxyethyl)piperidin-4-yl)-1H-pyrazol-4-yl)pyrazin-2-yl)-2-(3,5-dimethoxyphenyl)pyridazin-3 (2H)-one A solution of 6-(3-amino-6-(1-(piperidin-4-yl)-1H-pyrazol-4-yl)pyrazin-2-yl)-2-(3,5-dimethoxyphenyl)pyridazin-3 (2H)-one (Example 31; 10.6 mg, 0.0223 mmol) in DMF (0.5 mL) was treated with 1-bromo-2-methoxyethane (2.5 µL, 0.027 mmol) and K$_2$CO$_{3(s)}$ (6.1 mg, 0.0447 mmol). The resulting mixture was stirred 16 h at ambient temperature, then additional 1-bromo-2-methoxyethane (2.5 µL, 0.027 mmol) and K$_2$CO$_{3(s)}$ (6.1 mg, 0.0447 mmol) were added. The reaction was stirred for an additional period of 24 h at ambient temperature and subsequently diluted with EtOAc (25 mL). The EtOAc solution was washed with water (2×10 mL) and brine (1×10 mL). The organic extracts were dried over anhydrous Na$_2$SO$_{4(s)}$, filtered and concentrated under vacuum. The crude residue was purified by silica chromatography (1-30% DCM-MeOH w/2% NH$_4$OH as the gradient eluent) to afford the title compound (6.1 mg, 51% yield). MS (apci) m/z=533.2 (M+H). $^1$H NMR (400 MHz, DMSO-d$_6$) δ 8.72-8.70 (d, 1H), 8.49 (s, 1H), 8.43 (s, 1H), 8.04 (s, 1H), 7.31 (s, 2H), 7.21-7.18 (d, 1H), 6.86-6.85 (d, 2H), 6.63-6.62 (t, 1H), 4.19-4.12 (m, 1H), 3.79 (s, 6H), 3.47-3.44 (t, 2H), 3.25 (s, 3H), 3.01-2.97 (m, 2H), 2.54-2.51 (m, 2H), 2.19-2.13 (m, 2H), 2.06-1.94 (m, 4H).

Example 34

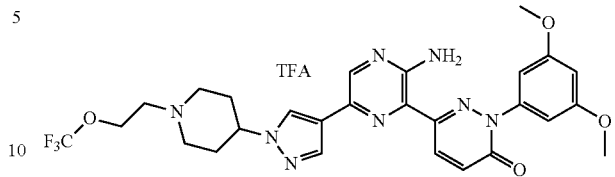

6-(3-amino-6-(1-(1-(2-(trifluoromethoxy)ethyl)piperidin-4-yl)-1H-pyrazol-4-yl)pyrazin-2-yl)-2-(3,5-dimethoxyphenyl)pyridazin-3 (2H)-one 2,2,2-trifluoroacetate salt A solution of 6-(3-amino-6-(1-(piperidin-4-yl)-1H-pyrazol-4-yl)pyrazin-2-yl)-2-(3,5-dimethoxyphenyl)pyridazin-3 (2H)-one (Example 31; 100 mg, 0.211 mmol) in DMSO (843 µL) was treated with 1-bromo-2-(trifluoromethoxy)ethane (36.4 µL, 0.316 mmol) and Cs$_2$CO$_{3(s)}$ (172 mg, 0.527 mmol). The resulting mixture was stirred overnight at ambient temperature then diluted with EtOAc and washed with water (2×) and brine. The organic extracts were dried over anhydrous Na$_2$SO$_{4(s)}$, filtered and concentrated under vacuum. The crude residue was purified by silica chromatography (50-100% EtOAc in Hexanes as the gradient eluent). The material was further purified by C18 reverse phase chromatography (5-95% Acetonitrile in Water with 0.1% TFA as the gradient eluent) to afford the title compound (15 mg, 12% yield). MS (apci) m/z=587.2 (M+H).

Example 35

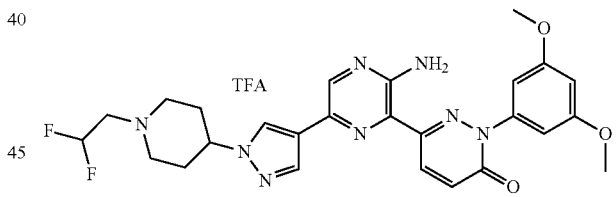

6-(3-amino-6-(1-(1-(2,2-difluoroethyl)piperidin-4-yl)-1H-pyrazol-4-yl)pyrazin-2-yl)-2-(3,5-dimethoxyphenyl)pyridazin-3(2H)-one 2,2,2-trifluoroacetate salt A solution of 6-(3-amino-6-(1-(piperidin-4-yl)-1H-pyrazol-4-yl)pyrazin-2-yl)-2-(3,5-dimethoxyphenyl)pyridazin-3 (2H)-one (Example 31; 100 mg, 0.211 mmol) in DMF (1.05 mL) was treated with DIPEA (110 µL, 0.632 mmol) and 2,2-difluoroethyl trifluoromethanesulfonate (67.7 mg, 0.316 mmol). The resulting mixture was stirred 4 h at ambient temperature then diluted with EtOAc and washed with water and brine. The organic extracts were dried over anhydrous Na$_2$SO$_{4(s)}$, filtered and concentrated under vacuum. The crude residue was purified by silica chromatography (stepwise gradient eluent of 70-100% EtOAc in Hexanes then 0-5% MeOH in EtOAc). The material was further purified by C18 reverse phase chromatography (5-95% Acetonitrile in Water with 0.1% TFA as the gradient eluent) to afford the title compound (11 mg, 10% yield). MS (apci) m/z=539.2 (M+H).

Example 36

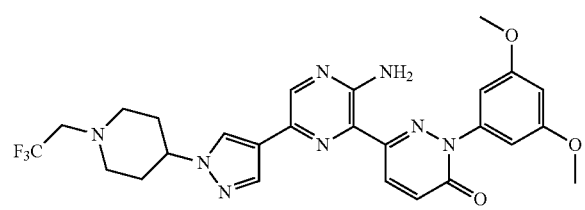 [SMILES: COc1cc(OC)cc(-n2nc(-c3nc(-c4cnn(C5CCN(CC(F)(F)F)CC5)c4)cnc3N)ccc2=O)c1]

6-(3-amino-6-(1-(1-(2,2,2-trifluoroethyl)piperidin-4-yl)-1H-pyrazol-4-yl)pyrazin-2-yl)-2-(3,5-dimethoxyphenyl)pyridazin-3 (2H)-one A solution of 6-(3-amino-6-(1-(piperidin-4-yl)-1H-pyrazol-4-yl)pyrazin-2-yl)-2-(3,5-dimethoxyphenyl)pyridazin-3 (2H)-one (Example 31; 100 mg, 0.211 mmol) in DMF (1.05 mL) was treated with DIPEA (110 µL, 0.632 mmol) and 2,2,2-trifluoroethyl trifluoromethanesulfonate (73.4 mg, 0.316 mmol). The resulting mixture was stirred over the weekend at ambient temperature then diluted with a mixture of EtOAc/water/brine. The organic extracts were washed with water and brine then dried over anhydrous $MgSO_{4(s)}$, filtered and concentrated under vacuum. The crude residue was purified by silica chromatography (50-80% EtOAc in Hexanes as the gradient eluent) to afford the title compound (30.2 mg, 26% yield). MS (apci) m/z=557.2 (M+H).

Example 37

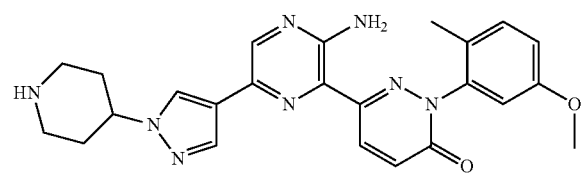 [SMILES: COc1ccc(C)c(-n2nc(-c3nc(-c4cnn(C5CCNCC5)c4)cnc3N)ccc2=O)c1]

6-(3-amino-6-(1-(piperidin-4-yl)-1H-pyrazol-4-yl)pyrazin-2-yl)-2-(5-methoxy-2-methylphenyl)pyridazin-3 (2H)-one Step 1: Preparation of tert-butyl 4-(4-(5-amino-6-(1-(5-methoxy-2-methylphenyl)-6-oxo-1,6-dihydropyridazin-3-yl)pyrazin-2-yl)-1H-pyrazol-1-yl)piperidine-1-carboxylate A suspension of tert-butyl 4-(4-(5-amino-6-bromopyrazin-2-yl)-1H-pyrazol-1-yl)piperidine-1-carboxylate (Intermediate L19; 198.5 mg, 0.4689 mmol), 2-(5-methoxy-2-methylphenyl)-6-(4,4,5,5-tetramethyl-1,3,2-dioxaborolan-2-yl)pyridazin-3(2H)-one (Intermediate R10; 320.9 mg, 0.9379 mmol), $PdCl_2(dppf) \cdot CH_2Cl_2$ (38.58 mg, 0.04689 mmol) and $K_2CO_{3(s)}$ (194.4 mg, 1.407 mmol) in 4:1 dioxane:water (5.0 mL) was sparged with $Ar_{(g)}$, then sealed and stirred 16 h at 100° C. After cooling to ambient temperature, the reaction mixture was diluted with 4:1 DCM:iPrOH (50 mL) and washed with water (2×25 mL). The organic extracts were dried over anhydrous $Na_2SO_{4(s)}$, filtered and concentrated under vacuum. The crude residue was purified by silica chromatography (5-60% DCM-Acetone as the gradient eluent) to afford the title compound which was immediately carried on to step 2. MS (apci) m/z=575.3 (M+H).

Step 2: Preparation of 6-(3-amino-6-(1-(piperidin-4-yl)-1H-pyrazol-4-yl)pyrazin-2-yl)-2-(5-methoxy-2-methylphenyl)pyridazin-3(2H)-one The tert-butyl 4-(4-(5-amino-6-(1-(5-methoxy-2-methylphenyl)-6-oxo-1,6-dihydropyridazin-3-yl)pyrazin-2-yl)-1H-pyrazol-1-yl)piperidine-1-carboxylate was dissolved in 1:1 TFA:DCM (5.0 mL) then stirred 1 h at ambient temperature. The reaction mixture was concentrated under vacuum then purified by C18 reverse phase chromatography (5-95% ACN in $H_2O$ with 0.1% TFA as the gradient eluent) to afford the title compound as a TFA salt. The TFA salt was dissolved in 4:1 DCM:iPrOH (50 mL) and extracted with saturated $NaHCO_{3(aq)}$ (1×25 mL). The organic extracts were dried over anhydrous $Na_2SO_{4(s)}$, filtered and concentrated under vacuum to cleanly afford the title compound (102.0 mg, 47% yield). MS (apci) m/z=459.1 (M+H).

Example 38

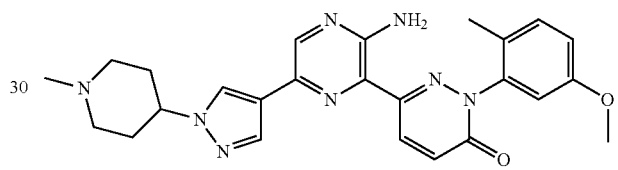

6-(3-amino-6-(1-(1-methylpiperidin-4-yl)-1H-pyrazol-4-yl)pyrazin-2-yl)-2-(5-methoxy-2-methylphenyl)pyridazin-3 (2H)-one A solution of 6-(3-amino-6-(1-(piperidin-4-yl)-1H-pyrazol-4-yl)pyrazin-2-yl)-2-(5-methoxy-2-methylphenyl)pyridazin-3(2H)-one (Example 37; 187.2 mg, 0.3945 mmol) in 1:1 DCM:MeOH (1.5 mL) was treated with formaldehyde (227 µL, 3.02 mmol) and sodium triacetoxyborohydride (128 mg, 0.604 mmol) and stirred 16 h at ambient temperature. The reaction mixture was concentrated under vacuum then purified by C18 reverse phase chromatography (5-95% water-ACN w/0.1% TFA as the gradient eluent). The chromatographic fractions containing the title compound were dissolved in 1:1:1 TFA:ACN:water (6 mL) and stirred for 1 h at ambient temperature then concentrated under vacuum. The residue was diluted with 4:1 DCM:iPrOH (50 mL) and washed with saturated $NaHCO_{3(aq)}$ (1×25 mL). The organic extracts were dried over anhydrous $Na_2SO_{4(s)}$, filtered and concentrated under vacuum to cleanly afford the title compound (55.0 mg, 77% yield). MS (apci) m/z=473.1 (M+H).

Example 39

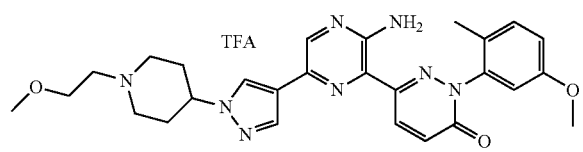

6-(3-amino-6-(1-(1-(2-methoxyethyl)piperidin-4-yl)-1H-pyrazol-4-yl)pyrazin-2-yl)-2-(5-methoxy-2-methylphenyl)pyridazin-3(2H)-one 2,2,2-trifluoroacetate salt A solution of 6-(3-amino-6-(1-(piperidin-4-yl)-1H-pyrazol-4-yl)pyrazin-2-yl)-2-(5-methoxy-2-methylphenyl)pyridazin-3(2H)-one (Example 37; 22.46 mg, 0.04898 mmol) in DMSO (0.1959 mL) was treated with 1-bromo-2-methoxyethane (10.21 mg, 0.07348 mmol) and $K_2CO_{3(s)}$ (27.08 mg, 0.19598 mmol). The resulting mixture was stirred overnight at 50° C., then cooled to ambient temperature. The reaction was diluted with water and extracted with EtOAc. The organic extracts were dried over anhydrous $Na_2SO_{4(s)}$, filtered and concentrated under vacuum. The crude residue was purified by C18 reverse phase chromatography (5-95% Acetonitrile in Water with 0.1% TFA as the gradient eluent) to afford the title compound (6.5 mg, 26% yield). MS (apci) m/z=517.3 (M+H).

Example 40

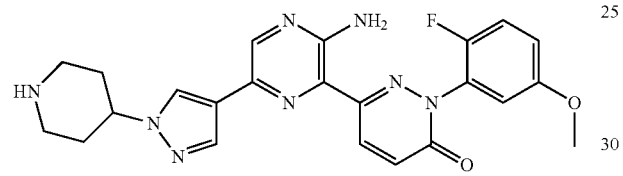

6-(3-amino-6-(1-(piperidin-4-yl)-1H-pyrazol-4-yl)pyrazin-2-yl)-2-(2-fluoro-5-methoxyphenyl)pyridazin-3 (2H)-one Step 1: Preparation of tert-butyl 4-(4-(5-amino-6-(1-(2-fluoro-5-methoxyphenyl)-6-oxo-1,6-dihydropyridazin-3-yl)pyrazin-2-yl)-1H-pyrazol-1-yl)piperidine-1-carboxylate A suspension of tert-butyl 4-(4-(5-amino-6-bromopyrazin-2-yl)-1H-pyrazol-1-yl)piperidine-1-carboxylate (Intermediate L19; 48.06 mg, 0.1135 mmol), 2-(2-fluoro-5-methoxyphenyl)-6-(4,4,5,5-tetramethyl-1,3,2-dioxaborolan-2-yl)pyridazin-3(2H)-one (Intermediate R14; 117.9 mg, 0.1703 mmol), Pd(PPh$_3$)$_4$(13.12 mg, 0.01135 mmol), and 2M $Na_2CO_{3(aq)}$ (170.3 μL, 0.3406 mmol) in dioxane (1135 μL) was sparged with Ar$_{(g)}$, then sealed and stirred overnight at 90° C. After cooling to ambient temperature, the reaction mixture was partitioned between EtOAc and water then the aqueous extracts were washed with EtOAc. The combined organic extracts were dried over anhydrous $Na_2SO_{4(s)}$, filtered and concentrated under vacuum. The resulting crude residue was purified by silica chromatography (0-15% MeOH in EtOAc as the gradient eluent) to afford the title compound (15 mg, 23% yield). MS (apci) m/z=563.3 (M+H).

Step 2: Preparation of 6-(3-amino-6-(1-(piperidin-4-yl)-1H-pyrazol-4-yl)pyrazin-2-yl)-2-(2-fluoro-5-methoxyphenyl)pyridazin-3(2H)-one The tert-butyl 4-(4-(5-amino-6-(1-(2-fluoro-5-methoxyphenyl)-6-oxo-1,6-dihydropyridazin-3-yl)pyrazin-2-yl)-1H-pyrazol-1-yl)piperidine-1-carboxylate (15 mg, 0.027 mmol) was dissolved in 1:1 TFA:DCM (2.0 mL) then stirred overnight at ambient temperature. The reaction mixture was concentrated under vacuum then purified by C18 reverse phase chromatography (5-95% ACN in H$_2$O with 0.1% TFA as the gradient eluent). The chromatographic fractions containing the title compound were combined then neutralized with saturated $NaHCO_{3(aq)}$ and extracted with DCM (3×). The organic extracts were then dried over anhydrous $Na_2SO_{4(s)}$, filtered and concentrated under vacuum to afford the title compound (6.2 mg, 50% yield). MS (apci) m/z=463.2 (M+H).

Example 41

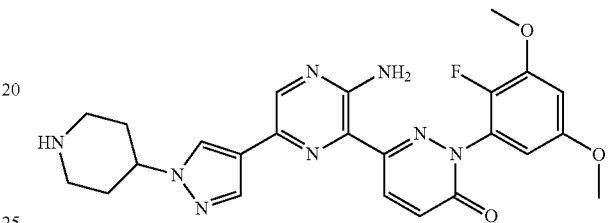

6-(3-amino-6-(1-(piperidin-4-yl)-1H-pyrazol-4-yl)pyrazin-2-yl)-2-(2-fluoro-3,5-dimethoxyphenyl)pyridazin-3 (2H)-one Step 1: Preparation of tert-butyl 4-(4-(5-amino-6-(1-(2-fluoro-3,5-dimethoxyphenyl)-6-oxo-1,6-dihydropyridazin-3-yl)pyrazin-2-yl)-1H-pyrazol-1-yl)piperidine-1-carboxylate A suspension of tert-butyl 4-(4-(5-amino-6-bromopyrazin-2-yl)-1H-pyrazol-1-yl)piperidine-1-carboxylate (Intermediate L19; 69.88 mg, 0.1651 mmol), 2-(2-fluoro-3,5-dimethoxyphenyl)-6-(4,4,5,5-tetramethyl-1,3,2-dioxaborolan-2-yl)pyridazin-3 (2H)-one (Intermediate R13; 124.2 mg, 0.2476 mmol), Pd(PPh$_3$)$_4$(19.08 mg, 0.01651 mmol), and 2M $Na_2CO_{3(aq)}$ (247.6 μL, 0.4952 mmol) in dioxane (1651 μL) was sparged with Ar$_{(g)}$, then sealed and stirred overnight at 90° C. After cooling to ambient temperature, the reaction mixture was partitioned between EtOAc and water then the aqueous extracts were washed with EtOAc. The combined organic extracts were dried over anhydrous $Na_2SO_{4(s)}$, filtered and concentrated under vacuum. The resulting crude residue was purified by silica chromatography (0-15% MeOH in EtOAc as the gradient eluent) to afford the title compound (50 mg, 51% yield). MS (apci) m/z=593.3 (M+H).

Step 2: Preparation of 6-(3-amino-6-(1-(piperidin-4-yl)-1H-pyrazol-4-yl)pyrazin-2-yl)-2-(2-fluoro-3,5-dimethoxyphenyl)pyridazin-3 (2H)-one The tert-butyl 4-(4-(5-amino-6-(1-(2-fluoro-3,5-dimethoxyphenyl)-6-oxo-1,6-dihydropyridazin-3-yl)pyrazin-2-yl)-1H-pyrazol-1-yl)piperidine-1-carboxylate (50 mg, 0.084 mmol) was dissolved in 1:1 TFA:DCM (2.0 mL) then stirred overnight at ambient temperature. The reaction mixture was concentrated under vacuum then purified by C18 reverse phase chromatography (5-95% ACN in H$_2$O as the gradient eluent). The chromatographic fractions containing the title compound were combined then neutralized with saturated NaHCO₃₍aq₎ and extracted with DCM (3×). The organic extracts were then dried over anhydrous Na₂SO₄₍s₎, filtered and concentrated under vacuum to afford the title compound (37.0 mg, 89% yield). MS (apci) m/z=493.2 (M+H).

Example 42

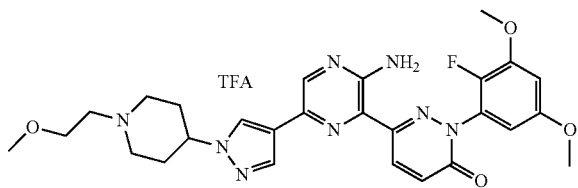

6-(3-amino-6-(1-(1-(2-methoxyethyl)piperidin-4-yl)-1H-pyrazol-4-yl)pyrazin-2-yl)-2-(2-fluoro-3,5-dimethoxyphenyl)pyridazin-3(2H)-one 2,2,2-trifluoroacetate salt A solution of 6-(3-amino-6-(1-(piperidin-4-yl)-1H-pyrazol-4-yl)pyrazin-2-yl)-2-(2-fluoro-3,5-dimethoxyphenyl)pyridazin-3(2H)-one (Example 41; 10 mg, 0.020 mmol) in DMSO (81 µL) was treated with 1-bromo-2-methoxyethane (6.91 µL, 0.0734762 mmol) and K₂CO₃₍s₎ (11 mg, 0.081 mmol). The resulting mixture was stirred 3 h at ambient temperature. The reaction was diluted with water and extracted with DCM. The organic extracts were washed with brine and were dried over anhydrous Na₂SO₄₍s₎, filtered and concentrated under vacuum. The crude residue was purified by C18 reverse phase chromatography (25-75% ACN in water with 0.1% TFA as the gradient eluent) to afford the title compound (4 mg, 36% yield). MS (apci) m/z=551.2 (M+H).

Example 43

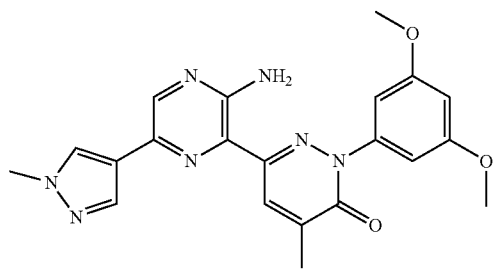

6-(3-amino-6-(1-methyl-1H-pyrazol-4-yl)pyrazin-2-yl)-2-(3,5-dimethoxyphenyl)-4-methylpyridazin-3(2H)-one A solution of 3-bromo-5-(1-methyl-1H-pyrazol-4-yl)pyrazin-2-amine (Intermediate L2; 101.7 mg, 0.4003 mmol) in 4:1 dioxane:water (4.0 mL) was treated with 2-(3,5-dimethoxyphenyl)-4-methyl-6-(4,4,5,5-tetramethyl-1,3,2-dioxaborolan-2-yl)pyridazin-3(2H)-one (Intermediate R18; 260.724 mg, 0.7004 mmol), PdCl₂(dppf)·CH₂Cl₂ (32.93 mg, 0.04003 mmol), K₂CO₃₍s₎ (166.0 mg, 1.201 mmol). The resulting mixture was sparged with Ar₍g₎, then sealed and stirred for 16 h at 100° C. After cooling to ambient temperature, the reaction mixture was diluted with 4:1 DCM:iPrOH (50 mL), and extracted with water (2×25 mL). The organic extracts were dried over anhydrous Na₂SO₄₍s₎, filtered and concentrated under vacuum. The resulting crude residue was purified by silica chromatography (5-75% DCM/Acetone as the gradient eluent). The chromatographic fractions containing the title compound were combined, concentrated under vacuum then triturated with DCM (20 mL). The resulting suspension was filtered and the solids collected were dried under vacuum to cleanly afford the title compound (90.8 mg, 54% yield). MS (apci) m/z=420.1 (M+H). ¹H NMR (400 MHz, DMSO-d₆) δ 8.55-8.54 (d, 1H), 8.46 (s, 1H), 8.32 (s, 1H), 8.07 (s, 1H), 7.30 (s, 2H), 6.84-6.83 (d, 2H), 6.62-6.61 (t, 1H), 3.90 (s, 3H), 3.79 (s, 6H), 2.29 (s, 3H).

Example 44

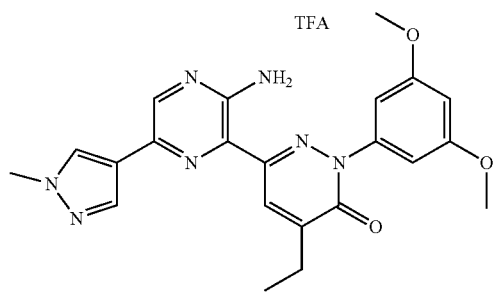

6-(3-amino-6-(1-methyl-1H-pyrazol-4-yl)pyrazin-2-yl)-2-(3,5-dimethoxyphenyl)-4-ethylpyridazin-3(2H)-one 2,2,2-trifluoroacetate salt A suspension of 3-bromo-5-(1-methyl-1H-pyrazol-4-yl)pyrazin-2-amine (Intermediate L2; 0.025 g, 0.098 mmol), 2-(3,5-dimethoxyphenyl)-4-ethyl-6-(4,4,5,5-tetramethyl-1,3,2-dioxaborolan-2-yl)pyridazin-3(2H)-one (Intermediate R26; 0.042 g, 0.11 mmol), Pd(PPh₃)₄ (0.0085 g, 0.0074 mmol) and 2M Na₂CO₃₍aq₎ (0.10 mL, 0.21 mmol) in dioxane (1.0 mL) was sparged with Ar₍g₎, then sealed and stirred for 8 h at 90° C. After cooling to ambient temperature, the reaction mixture was filtered to remove solids. The filtrate was concentrated under vacuum, and the resulting crude residue was purified by C18 reverse phase chromatography (5-95% ACN:water with 0.1% TFA) to afford the title compound as the TFA salt (0.0056 g, 11% yield). MS (apci) m/z=434.1 (M+H).

The following compounds shown in Table 4 were prepared according the method used for the synthesis of Example 44 using 3-bromo-5-(1-methyl-1H-pyrazol-4-yl)pyrazin-2-amine (Intermediate L2) and 2-(3,5-dimethoxyphenyl)-4-alkyl-6-(4,4,5,5-tetramethyl-1,3,2-dioxaborolan-2-yl)pyridazin-3(2H)-one (Intermediates R25, R27). Reaction progression in each was followed by LCMS and reaction time was adjusted as necessary. All compounds were purified using a method similar to that used in Example 44 utilizing the appropriate gradient eluent.

TABLE 4

| Ex # | Structure | Name | MS (apci) m/z = |
|---|---|---|---|
| 45 | 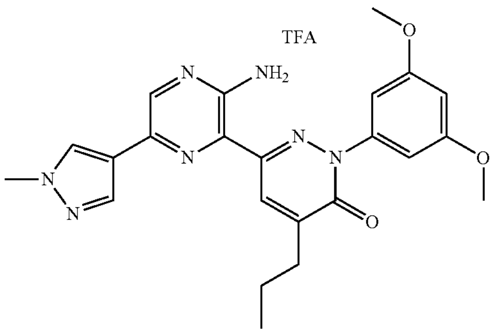 | 6-(3-amino-6-(1-methyl-1H-pyrazol-4-yl)pyrazin-2-yl)-2-(3,5-dimethoxyphenyl)-4-propylpyridazin-3(2H)-one 2,2,2-trifluoroacetate salt | 488.2 (M + H) |
| 46 | 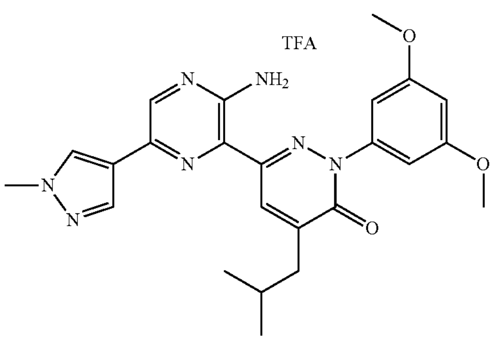 | 6-(3-amino-6-(1-methyl-1H-pyrazol-4-yl)pyrazin-2-yl)-2-(3,5-dimethoxyphenyl)-4-isobutylpyridazin-3(2H)-one 2,2,2-trifluoroacetate salt | 462.2 (M + H) |

Example 47

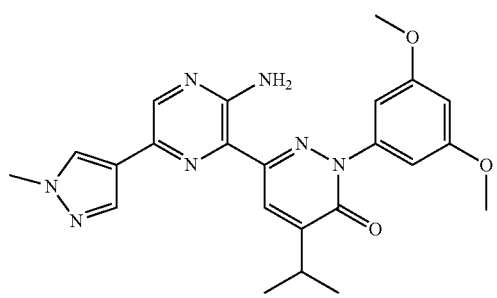

6-(3-amino-6-(1-methyl-1H-pyrazol-4-yl)pyrazin-2-yl)-2-(3,5-dimethoxyphenyl)-4-isopropylpyridazin-3(2H)-one A solution of 3-bromo-5-(1-methyl-1H-pyrazol-4-yl)pyrazin-2-amine (Intermediate L2; 100.0 mg, 0.3936 mmol) in 4:1 dioxane:water (4.0 mL) was treated with 2-(3,5-dimethoxyphenyl)-4-isopropyl-6-(4,4,5,5-tetramethyl-1,3,2-dioxaborolan-2-yl)pyridazin-3(2H)-one (Intermediate R23; 173.3 mg, 0.4329 mmol), $PdCl_2(dppf) \cdot CH_2Cl_2$ (32.93 mg, 0.04003 mmol), $K_2CO_{3(s)}$ (163.2 mg, 1.181 mmol). The resulting mixture was sparged with $Ar_{(g)}$, then sealed and stirred for 16 h at 100° C. After cooling to ambient temperature, the reaction mixture was diluted with 4:1 DCM:iPrOH (50 mL), and extracted with water (2×25 mL). The organic extracts were dried over anhydrous $Na_2SO_{4(s)}$, filtered and concentrated under vacuum. The resulting crude residue was purified by silica chromatography (5-60% DCM/Acetone as the gradient eluent) to cleanly afford the title compound (27.1 mg, 15% yield). MS (apci) m/z=448.1 (M+H). $^1$H NMR (400 MHz, DMSO-$d_6$) δ 8.47 (s, 1H), 8.40 (s, 1H), 8.26 (s, 1H), 8.01 (s, 1H), 7.30 (s, 2H), 6.85-6.84 (d, 2H), 6.62-6.61 (t, 1H), 3.91 (s, 3H), 3.79 (s, 6H), 3.24-3.17 (m, 1H), 1.30-1.29 (d, 6H).

The following compounds shown in Table 5 were prepared according the method used for the synthesis of Example 47 using 3-bromo-5-(1-methyl-1H-pyrazol-4-yl)pyrazin-2-amine (Intermediate L2) and 2-(3,5-dimethoxyphenyl)-4-alkyl-6-(4,4,5,5-tetramethyl-1,3,2-dioxaborolan-2-yl)pyridazin-3(2H)-one (Intermediates R22, R24). Reaction progression in each was followed by LCMS and reaction time was adjusted as necessary. All compounds were purified using a method similar to that used in Example 47 utilizing the appropriate gradient eluent.

TABLE 5

| Ex # | Structure | Name | MS (apci) m/z |
|---|---|---|---|
| 48 | 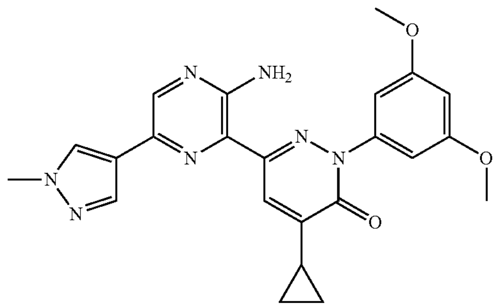 | 6-(3-amino-6-(1-methyl-1H-pyrazol-4-yl)pyrazin-2-yl)-4-cyclopropyl-2-(3,5-dimethoxyphenyl)pyridazin-3(2H)-one | 446.1 (M + H) |
| 49 | 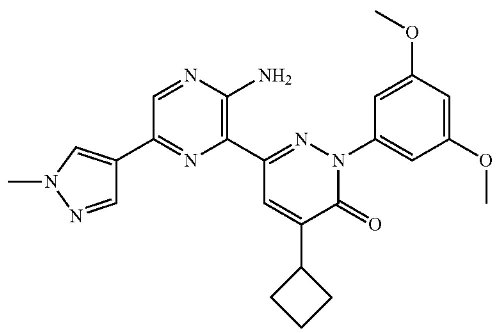 | 6-(3-amino-6-(1-methyl-1H-pyrazol-4-yl)pyrazin-2-yl)-4-cyclobutyl-2-(3,5-dimethoxyphenyl)pyridazin-3(2H)-one | 460.1 (M + H) |

Example 50

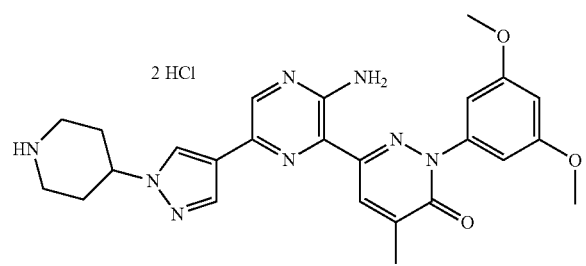 [SMILES: COc1cc(OC)cc(-n2nc(-c3nc(-c4cnn(C5CCNCC5)c4)cnc3N)cc(C)c2=O)c1]

6-(3-amino-6-(1-(piperidin-4-yl)-1H-pyrazol-4-yl)pyrazin-2-yl)-2-(3,5-dimethoxyphenyl)-4-methylpyridazin-3(2H)-one dihydrochloride salt Step 1: Preparation of tert-butyl 4-(4-(5-amino-6-(1-(3,5-dimethoxyphenyl)-5-methyl-6-oxo-1,6-dihydropyridazin-3-yl)pyrazin-2-yl)-1H-pyrazol-1-yl)piperidine-1-carboxylate A mixture of tert-butyl 4-(4-(5-amino-6-bromopyrazin-2-yl)-1H-pyrazol-1-yl)piperidine-1-carboxylate (Intermediate L19; 398 mg, 0.940 mmol), 2-(3,5-dimethoxyphenyl)-4-methyl-6-(4,4,5,5-tetramethyl-1,3,2-dioxaborolan-2-yl)pyridazin-3(2H)-one (Intermediate R18; 350 mg, 0.940 mmol), Pd(PPh$_3$)$_4$(109 mg, 0.0940 mmol), 2M Na$_2$CO$_{3(aq)}$ (1.41 mL, 0.940 mmol) was suspended in dioxane (1.88 mL). The resulting mixture was purged with N$_{2(g)}$ for 6 min, then was sealed and stirred for 16 h at 90° C. After cooling to ambient temperature, the reaction mixture was diluted with DCM (50 mL) and washed with water (2×15 mL). The organic extracts were dried over anhydrous MgSO$_{4(s)}$, filtered and concentrated under vacuum. The crude residue was purified by silica chromatography (1-55% acetone/hexanes as the gradient eluent) to afford the title compound (425 mg, 77% yield). MS (apci) m/z=589.3 (M+H).

Step 2: Preparation of 6-(3-amino-6-(1-(piperidin-4-yl)-1H-pyrazol-4-yl)pyrazin-2-yl)-2-(3,5-dimethoxyphenyl)-4-methylpyridazin-3(2H)-one dihydrochloride salt The tert-butyl 4-(4-(5-amino-6-(1-(3,5-dimethoxyphenyl)-5-methyl-6-oxo-1,6-dihydropyridazin-3-yl)pyrazin-2-yl)-1H-pyrazol-1-yl)piperidine-1-carboxylate (420 mg, 0.713 mmol) was dissolved in TFA (2.0 mL) then stirred 2 h at ambient temperature. The reaction mixture was concentrated under vacuum then dissolved in DCM (2 mL) and treated with 2 N HCl in dioxane (5 mL). The resulting suspension was filtered and the solids were rinsed with ACN and dried under vacuum to afford the title compound (325 mg, 81% yield). MS (apci) m/z=489.2 (M+H). $^1$H NMR (400 MHz, MeOH-d$_4$) δ 8.59 (d, 1H), 8.44 (d, 1H), 8.31 (s, 1H), 8.14 (s, 1H), 6.80 (s, 1H), 6.79 (s, 1H), 6.61 (t, 1H), 4.68-4.61 (m, 1H), 3.82 (s, 6H), 3.6-3.56 (m, 2H), 3.25-3.2 (m, 2H), 2.3 (s, 3H), 2.35-2.32 (m, 4H).

Example 51

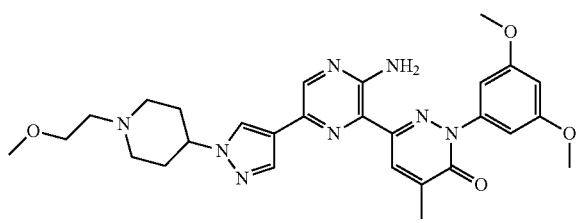

6-(3-amino-6-(1-(1-(2-methoxyethyl)piperidin-4-yl)-1H-pyrazol-4-yl)pyrazin-2-yl)-2-(3,5-dimethoxyphenyl)-4-methylpyridazin-3(2H)-one A solution of 6-(3-amino-6-(1-(piperidin-4-yl)-1H-pyrazol-4-yl)pyrazin-2-yl)-2-(3,5-dimethoxyphenyl)-4-methylpyridazin-3(2H)-one dihydrochloride salt (Example 50; 50 mg, 0.089 mmol) in DMF (1.8 mL) was treated with 1-bromo-2-methoxyethane (10 μL, 0.11 mmol) and $K_2CO_{3(s)}$ (49 mg, 0.36 mmol) under an atmosphere of $N_{2(g)}$. The resulting mixture was stirred overnight at ambient temperature, and then additional 1-bromo-2-methoxyethane (20 μL, 0.21 mmol) and $K_2CO_{3(s)}$ (98 mg, 0.71 mmol) and the reaction was stirred for an additional period of 48 h at ambient temperature. The reaction mixture was diluted with 5% iPrOH/DCM (50 mL) and washed with water (10 mL) diluted. The organic extracts were dried over anhydrous $MgSO_{4(s)}$, filtered and concentrated under vacuum. The crude residue was purified by silica chromatography (2-10% MeOH/DCM as the gradient eluent) to afford the title compound (33 mg, 68% yield). MS (apci) m/z=547.3 (M+H). $^1$H NMR (400 MHz, CDCl3-d) δ 8.44 (d, 1H), 8.25 (s, 1H), 7.91 (d, 2H), 6.79 (d, 2H), 6.51 (t, 1H), 6.48-6.3 (brs, 2H), 4.26-4.18 (m, 1H), 3.81 (s, 6H), 3.53 (t, 2H), 3.3 (s, 3H), 3.15-3.09 (m, 2H), 2.63 (d, 2H), 2.3 (s, 3H), 2.16-2.1 (m, 2H), 1.61-1.57 (m, 2H).

Example 52

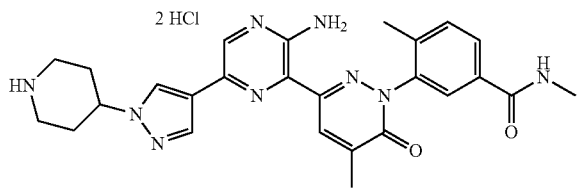 [SMILES: CNC(=O)c1ccc(C)c(-n2nc(-c3nc(-c4cnn(C5CCNCC5)c4)cnc3N)cc(C)c2=O)c1]

3-(3-(3-amino-6-(1-(piperidin-4-yl)-1H-pyrazol-4-yl)pyrazin-2-yl)-5-methyl-6-oxopyridazin-1 (6H)-yl)-N,4-dimethylbenzamide dihydrochloride salt

Step 1: Preparation of tert-butyl 4-(4-(5-amino-6-(1-(5-(methoxycarbonyl)-2-methylphenyl)-5-methyl-6-oxo-1,6-dihydropyridazin-3-yl)pyrazin-2-yl)-1H-pyrazol-1-yl)piperidine-1-carboxylate A mixture of tert-butyl 4-(4-(5-amino-6-bromopyrazin-2-yl)-1H-pyrazol-1-yl)piperidine-1-carboxylate (Intermediate L19; 505 mg, 1.19 mmol), methyl 4-methyl-3-(5-methyl-6-oxo-3-(4,4,5,5-tetramethyl-1,3,2-dioxaborolan-2-yl)pyridazin-1 (6H)-yl)benzoate (Intermediate R19; 550 mg, 1.43 mmol), Pd(PPh$_3$)$_4$(107 mg, 0.119 mmol), 2M Na$_2$CO$_{3(aq)}$ (1.79 mL, 3.58 mmol) was suspended in dioxane (2.39 mL). The resulting mixture was purged with $N_{2(g)}$ for 6 min, then was sealed and stirred overnight at 90° C. After cooling to ambient temperature, the reaction mixture was diluted with 5% iPrOH/DCM (100 mL) and washed with water (2×20 mL) and brine (20 mL). The organic extracts were dried over anhydrous $MgSO_{4(s)}$, filtered and concentrated under vacuum. The crude residue was purified by silica chromatography (with 2-60% acetone/DCM as the gradient eluent) to afford the title compound (782.5 mg, 98% yield). MS (apci) m/z=601.3 (M+H).

Step 2: Preparation of 3-(3-(3-amino-6-(1-(1-(tert-butoxycarbonyl)piperidin-4-yl)-1H-pyrazol-4-yl)pyrazin-2-yl)-5-methyl-6-oxopyridazin-1(6H)-yl)-4-methylbenzoic acid A solution of tert-butyl 4-(4-(5-amino-6-(1-(5-(methoxycarbonyl)-2-methylphenyl)-5-methyl-6-oxo-1,6-dihydropyridazin-3-yl)pyrazin-2-yl)-1H-pyrazol-1-yl)piperidine-1-carboxylate (780 mg, 1.30 mmol) in 4:1 dioxane:MeOH (6.49 mL) was treated with a solution of LiOH•H$_2$O (136 mg, 3.25 mmol) in water (1.30 mL). The resulting mixture was stirred 4 h at ambient temperature then concentrated under vacuum. The resulting aqueous slurry was diluted with water (5 mL) then acidified (pH 2-3) with formic acid. The solid formed was filtered and dried in vacuo to provide the title compound (650 mg, 85% yield). MS (apci) m/z=587.3 (M+H).

Step 3: Preparation of tert-butyl 4-(4-(5-amino-6-(5-methyl-1-(2-methyl-5-(methylcarbamoyl)phenyl)-6-oxo-1,6-dihydropyridazin-3-yl)pyrazin-2-yl)-1H-pyrazol-1-yl)piperidine-1-carboxylate A cold (0° C.) suspension of 3-(3-(3-amino-6-(1-(1-(tert-butoxycarbonyl)piperidin-4-yl)-1H-pyrazol-4-yl)pyrazin-2-yl)-5-methyl-6-oxopyridazin-1(6H)-yl)-4-methylbenzoic acid (650 mg, 1.11 mmol) in DMF (22.2 mL) was treated sequentially with HATU (632 mg, 1.66 mmol), 2M CH$_3$NH$_2$ in THF (1.11 mL, 2.22 mmol) and DIPEA (1.58 mL, 8.86 mmol). The resulting mixture was stirred 15 min at 0° C. then overnight at ambient temperature. The reaction mixture was poured into ice water and extracted with 5% iPrOH/DCM (3×50 mL). The combined organic extracts were dried over anhydrous Na$_2$SO$_{4(s)}$, filtered then concentrated under vacuum. The resulting residue was purified by silica chromatography (5-60% acetone/DCM as the gradient eluent) to afford the title compound (550 mg, 83% yield). MS (apci) m/z=600.3 (M+H).

Step 4: Preparation of 3-(3-(3-amino-6-(1-(piperidin-4-yl)-1H-pyrazol-4-yl)pyrazin-2-yl)-5-methyl-6-oxopyridazin-1 (6H)-yl)-N,4-dimethylbenzamide dihydrochloride salt A ambient temperature solution of tert-butyl 4-(4-(5-amino-6-(5-methyl-1-(2-methyl-5-(methylcarbamoyl)phenyl)-6-oxo-1,6-dihydropyridazin-3-yl)pyrazin-2-yl)-1H-pyrazol-1-yl)piperidine-1-carboxylate (550 mg, 0.917 mmol) in DCM (1 mL) was treated with TFA (2 mL) then stirred 1 h at ambient temperature before concentrating to dryness under vacuum. The resulting residue was dissolved in DCM (2 mL), treated with 4 N HCl in dioxane (2 mL), stirred for 10 min at ambient temperature, and then concentrated to dryness under vacuum. The resulting residue was resuspended in DCM and concentrated to dryness under vacuum twice then dried under high vacuum to afford the title compound (410 mg, 78% yield). MS (apci) m/z=500.2 (M+H).

Example 53

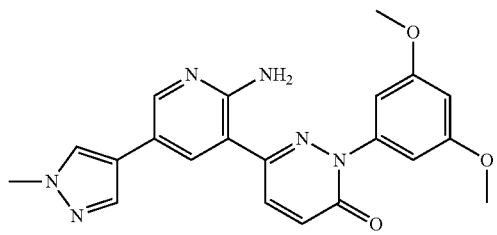

6-(2-amino-5-(1-methyl-1H-pyrazol-4-yl)pyridin-3-yl)-2-(3,5-dimethoxyphenyl)pyridazin-3 (2H)-one A solution of 3-bromo-5-(1-methyl-1H-pyrazol-4-yl)pyrazin-2-amine (Intermediate L20; 204.8 mg, 0.8061 mmol) in 4:1 dioxane:water (7.5 mL) was treated with 2-(3,5-dimethoxyphenyl)-6-(4,4,5,5-tetramethyl-1,3,2-dioxaborolan-2-yl)pyridazin-3 (2H)-one (Intermediate R8; 293.4 mg, 0.8192 mmol), PdCl$_2$(dppf)•CH$_2$Cl$_2$ (61.27 mg, 0.07448 mmol), K$_2$CO$_{3(s)}$ (308.8 mg, 2.234 mmol). The resulting mixture was sparged with Ar$_{(g)}$, then sealed and stirred for 16 h at 100° C. After cooling to ambient temperature, the reaction mixture was diluted with 4:1 DCM:iPrOH (50 mL), and extracted with water (2×25 mL). The organic extracts were dried over anhydrous Na$_2$SO$_{4(s)}$, filtered and concentrated under vacuum. The resulting crude residue was purified by C18 reverse phase chromatography (5-95% water-ACN with 0.1% TFA as the gradient eluent) to afford the title compound as a TFA salt. The TFA salt was dissolved in 4:1 DCM:iPrOH (50 mL) and extracted with saturated NaHCO$_{3(aq)}$ (1×25 mL). The organic extracts were dried over anhydrous Na$_2$SO$_{4(s)}$, filtered and concentrated under vacuum to afford the title compound along with impurities. The resulting residue was subjected to further purification by silica chromatography (40-100% DCM-Acetone as the gradient eluent) to cleanly afford the title compound (40.1 mg, 13% yield). MS (apci) m/z=405.1 (M+H). $^1$H NMR (400 MHz, DMSO-d$_6$) δ 8.32-8.31 (d, 1H), 8.28-8.25 (d, 1H), 8.14-8.12 (m, 2H), 7.89 (s, 1H), 7.20-7.18 (d, 1H), 6.89 (s, 2H), 6.82-6.81 (d, 2H), 6.61-6.60 (t, 1H), 3.85 (s, 3H), 3.78 (s, 6H).

Example 54

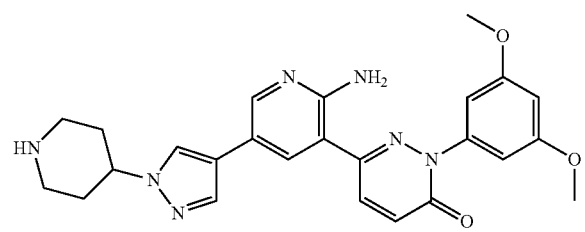

6-(2-amino-5-(1-(piperidin-4-yl)-1H-pyrazol-4-yl)pyridin-3-yl)-2-(3,5-dimethoxyphenyl)pyridazin-3 (2H)-one Step 1: Preparation of tert-butyl 4-(4-(6-amino-5-(1-(3,5-dimethoxyphenyl)-6-oxo-1,6-dihydropyridazin-3-yl)pyridin-3-yl)-1H-pyrazol-1-yl)piperidine-1-carboxylate A solution of tert-butyl 4-(4-(6-amino-5-bromopyridin-3-yl)-1H-pyrazol-1-yl)piperidine-1-carboxylate (Intermediate L21; 622.4 mg, 1.474 mmol) in 4:1 dioxane:water (15 mL) was treated with 2-(3,5-dimethoxyphenyl)-6-(4,4,5,5-tetramethyl-1,3,2-dioxaborolan-2-yl)pyridazin-3 (2H)-one (Intermediate R8; 580.7 mg, 1.621 mmol), PdCl$_2$(dppf)•CH$_2$Cl$_2$ (121.2 mg, 0.1474 mmol) and K$_2$CO$_{3(s)}$ (611.0 mg, 4.421 mmol). The resulting mixture was sparged with Ar$_{(g)}$, then sealed and stirred 16 h at 100° C. After cooling to ambient temperature, the reaction mixture was diluted with 4:1 DCM:iPrOH (250 mL) and washed with water (2×50 mL). The organic extracts were dried over anhydrous Na$_2$SO$_{4(s)}$, filtered and concentrated under vacuum. The crude residue was purified by silica chromatography (5-95% DCM-Acetone as the gradient eluent) to afford the title compound which was immediately carried on to step 2. MS (apci) m/z=574.2 (M+H).

Step 2: Preparation of 6-(2-amino-5-(1-(piperidin-4-yl)-1H-pyrazol-4-yl)pyridin-3-yl)-2-(3,5-dimethoxyphenyl)pyridazin-3 (2H)-one tert-butyl 4-(4-(6-amino-5-(1-(3,5-dimethoxyphenyl)-6-oxo-1,6-dihydropyridazin-3-yl)pyridin-3-yl)-1H-pyrazol-1-yl)piperidine-1-carboxylate was dissolved in 1:1 TFA:DCM (15.0 mL) then stirred 30 min at ambient temperature. The reaction mixture was concentrated under vacuum then purified by C18 reverse phase chromatography (5-95% ACN in H$_2$O with 0.1% TFA as the gradient eluent) to afford the title compound as a TFA salt. The TFA salt was dissolved in 4:1 DCM:iPrOH (50 mL) and extracted with saturated NaHCO$_{3(aq)}$ (1×25 mL). The organic extracts were dried over anhydrous Na$_2$SO$_{4(s)}$, filtered and concentrated under vacuum to cleanly afford the title compound (415.9 mg, 60% yield). MS (apci) m/z=474.1 (M+H).

Example 55

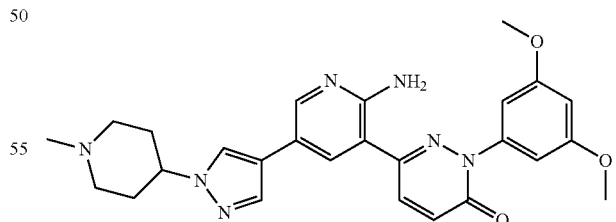

6-(2-amino-5-(1-(1-methylpiperidin-4-yl)-1H-pyrazol-4-yl)pyridin-3-yl)-2-(3,5-dimethoxyphenyl)pyridazin-3 (2H)-one A solution of 6-(2-amino-5-(1-(piperidin-4-yl)-1H-pyrazol-4-yl)pyridin-3-yl)-2-(3,5-dimethoxyphenyl)pyridazin-3 (2H)-one (Example 54; 134.4 mg, 0.2838 mmol) in 1:1

DCM:MeOH (2.0 mL) was treated with formaldehyde (426.5 µL, 5.677 mmol) and sodium triacetoxyborohydride (300.8 mg, 1.419 mmol) and then stirred 60 h at ambient temperature. The reaction mixture was directly purified by silica chromatography (1-30% DCM-MeOH w/2% NH$_4$OH as the gradient eluent). The chromatographic fractions containing the title compound were combined then re-purified using C18 reverse phase chromatography (5-95% water-ACN w/0.1% TFA as the gradient eluent) to afford the title compound as a TFA salt. The TFA salt was dissolved in 4:1 DCM:iPrOH (50 mL) and extracted with saturated NaHCO$_{3(aq)}$ (1×25 mL). The organic extracts were dried over anhydrous Na$_2$SO$_{4(s)}$, filtered and concentrated under vacuum to cleanly afford the title compound (46.9 mg, 34% yield). MS (apci) m/z=488.2 (M+H). $^1$H NMR (400 MHz, DMSO-d$_6$) δ 8.35-8.34 (d, 1H), 8.29 (s, 1H), 8.26 (s, 1H), 8.16-8.15 (d, 1H), 7.91 (s, 1H), 7.21-7.18 (d, 1H), 6.91 (s, 2H), 6.82-6.81 (d, 2H), 6.61-6.60 (t, 1H), 4.13-4.05 (m, 1H), 3.78 (s, 6H), 2.88-2.85 (m, 2H), 2.22 (s, 3H), 2.09-1.91 (m, 6H).

Example 56

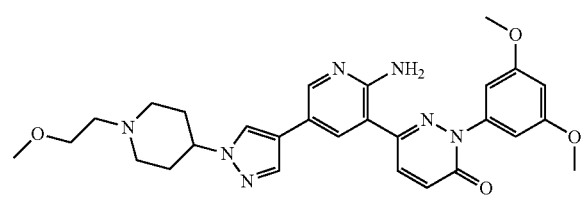

6-(2-amino-5-(1-(1-(2-methoxyethyl)piperidin-4-yl)-1H-pyrazol-4-yl)pyridin-3-yl)-2-(3,5-dimethoxyphenyl)pyridazin-3 (2H)-one A solution of 6-(2-amino-5-(1-(piperidin-4-yl)-1H-pyrazol-4-yl)pyridin-3-yl)-2-(3,5-dimethoxyphenyl)pyridazin-3 (2H)-one (Example 54; 54.1 mg, 0.114 mmol) in DMF (1.2 mL) was treated with 1-bromo-2-methoxyethane (21.5 µL, 0.228 mmol) and K$_2$CO$_{3(s)}$ (63.2 mg, 0.457 mmol). The resulting mixture was stirred 60 h at ambient temperature. The reaction mixture was diluted with EtOAc (25 mL) and washed with water (2×10 mL) and brine (10 mL). The organic extracts were dried over anhydrous Na$_2$SO$_{4(s)}$, filtered and concentrated under vacuum. The crude residue was purified by silica chromatography (1-30% DCM-MeOH w/2% NH$_4$OH as the gradient eluent) to afford the title compound (29.5 mg, 49% yield). MS (apci) m/z=532.2 (M+H).

Example 57

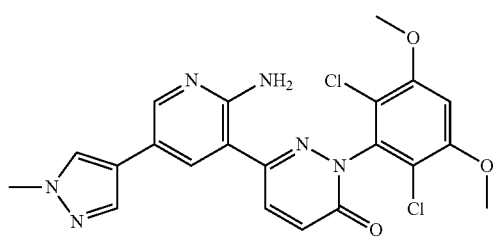

6-(2-amino-5-(1-methyl-1H-pyrazol-4-yl)pyridin-3-yl)-2-(2,6-dichloro-3,5-dimethoxyphenyl)pyridazin-3 (2H)-one A solution of 6-(2-amino-5-bromopyridin-3-yl)-2-(2,6-dichloro-3,5-dimethoxyphenyl)pyridazin-3(2H)-one (Intermediate M2; 14.4 mg, 0.0305 mmol) in 4:1 dioxane:water (1.0 mL) was treated with 1-methyl-4-(4,4,5,5-tetramethyl-1,3,2-dioxaborolan-2-yl)-1H-pyrazole (6.98 mg, 0.0336 mmol), PdCl$_2$(dppf)•CH$_2$Cl$_2$ (2.51 mg, 0.00305 mmol), K$_2$CO$_{3(s)}$ (12.6 mg, 0.0915 mmol). The resulting mixture was sparged with Ar$_{(g)}$, then sealed and stirred for 16 h at 100° C. After cooling to ambient temperature, the reaction mixture was diluted with EtOAc (25 mL), and extracted with water (3×10 mL) and brine (10 mL). The organic extracts were dried over anhydrous Na$_2$SO$_{4(s)}$, filtered and concentrated under vacuum. The resulting crude residue was purified by silica chromatography (5-95% DCM-Acetone as the gradient eluent) to afford the title compound (5.8 mg, 40% yield). MS (apci) m/z=473.0 (M+H). $^1$H NMR (400 MHz, DMSO-d$_6$) δ 8.39-8.37 (d, 1H), 8.34-8.33 (d, 1H), 8.19-8.18 (d, 1H), 8.12 (s, 1H), 7.89 (s, 1H), 7.33-7.30 (d, 1H), 7.12 (s, 1H), 6.72 (s, 2H), 4.01 (s, 6H), 3.85 (s, 3H).

Example 58

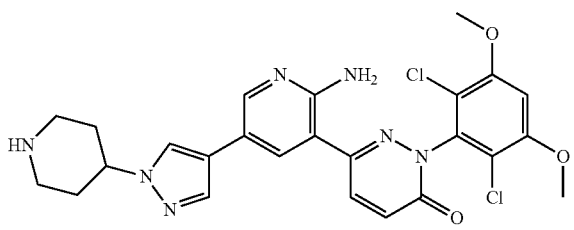 [SMILES: COc1cc(OC)c(Cl)c(-n2nc(-c3cc(-c4cnn(C5CCNCC5)c4)cnc3N)ccc2=O)c1Cl]

6-(2-amino-5-(1-(piperidin-4-yl)-1H-pyrazol-4-yl)pyridin-3-yl)-2-(2,6-dichloro-3,5-dimethoxyphenyl)pyridazin-3 (2H)-one Step 1: Preparation of tert-butyl 4-(4-(6-amino-5-(1-(2,6-dichloro-3,5-dimethoxyphenyl)-6-oxo-1,6-dihydropyridazin-3-yl)pyridin-3-yl)-1H-pyrazol-1-yl)piperidine-1-carboxylate A solution of 6-(2-amino-5-bromopyridin-3-yl)-2-(2,6-dichloro-3,5-dimethoxyphenyl)pyridazin-3(2H)-one (Intermediate M2; 215.0 mg, 0.4554 mmol) in 4:1 dioxane:water (4.6 mL) was treated with tert-Butyl 4-[4-(4,4,5,5-tetramethyl-1,3,2-dioxaborolan-2-yl)pyrazol-1-yl]piperidine-1-carboxylate (180.4 mg, 0.4782 mmol), PdCl$_2$(dppf)•CH$_2$Cl$_2$ (37.46 mg, 0.04554 mmol) and K$_2$CO$_{3(s)}$ (188.8 mg, 1.366 mmol) was sparged with Ar$_{(g)}$, then sealed and stirred 6 h at 90° C. After cooling to ambient temperature, the reaction mixture was diluted with 4:1 DCM:iPrOH (50 mL) and washed with water (2×25 mL). The organic extracts were dried over anhydrous Na$_2$SO$_{4(s)}$, filtered and concentrated under vacuum to afford the title compound in sufficient purity for immediate use in step 2. MS (apci) m/z=646.2 [(M+H)+4], 644.2 [(M+H)+2], 642.2 (M+H) with diCl pattern.

Step 2: Preparation of 6-(2-amino-5-(1-(piperidin-4-yl)-1H-pyrazol-4-yl)pyridin-3-yl)-2-(2,6-dichloro-3,5-dimethoxyphenyl)pyridazin-3(2H)-one The tert-butyl 4-(4-(6-amino-5-(1-(2,6-dichloro-3,5-dimethoxyphenyl)-6-oxo-1,6-dihydropyridazin-3-yl)pyridin-3-yl)pyridin- 3-yl)-1H-pyrazol-1-yl)piperidine-1-carboxylate was dissolved in 1:1 TFA:DCM (3.0 mL) then stirred 1 h at ambient temperature. The reaction mixture was concentrated under vacuum then purified by C18 reverse phase chromatography (2→75% water-ACN with 0.1% TFA as the gradient eluent) to afford the title compound as a TFA salt. The TFA salt was dissolved in 4:1 DCM:iPrOH (50 mL) and extracted with saturated NaHCO$_{3(aq)}$ (1×25 mL). The organic extracts were dried over anhydrous Na$_2$SO$_{4(s)}$, filtered and concentrated under vacuum to cleanly afford the title compound (172.7 mg, 70% yield). MS (apci) m/z=546.1 [(M+H)+4], 544.2 [(M+H)+2], 542.1 (M+H) with diCl pattern.

Example 59

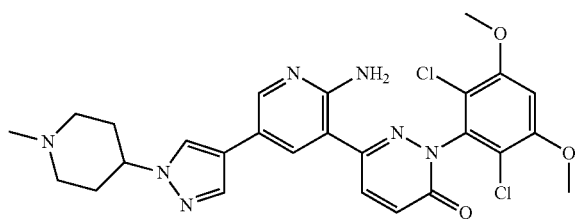

6-(2-amino-5-(1-(1-methylpiperidin-4-yl)-1H-pyrazol-4-yl)pyridin-3-yl)-2-(2,6-dichloro-3,5-dimethoxyphenyl)pyridazin-3 (2H)-one A solution of 6-(2-amino-5-(1-(piperidin-4-yl)-1H-pyrazol-4-yl)pyridin-3-yl)-2-(2,6-dichloro-3,5-dimethoxyphenyl)pyridazin-3(2H)-one (Example 58; 50.0 mg, 0.0922 mmol) in MeOH (1.8 mL) was treated with formaldehyde (139 µL, 1.84 mmol) and stirred 15 min at ambient temperature. The resulting reaction mixture was treated with sodium triacetoxyborohydride (78.1 mg, 0.369 mmol) and stirred 16 h at ambient temperature. The reaction mixture was concentrated under vacuum then purified by C18 reverse phase chromatography (5-95% water-ACN w/0.1% TFA as the gradient eluent) to afford the title compound as a TFA salt. The TFA salt was dissolved in 4:1 DCM:iPrOH (50 mL) and extracted with saturated NaHCO$_{3(aq)}$ (1×25 mL). The organic extracts were dried over anhydrous Na$_2$SO$_{4(s)}$, filtered and concentrated under vacuum to cleanly afford the title compound (24.2 mg, 47% yield). MS (apci) m/z=558.2 [(M+H)+2], 556.2 (M+H) with diCl pattern. H NMR (400 MHz, DMSO-d$_6$) δ 8.39-8.35 (m, 2H), 8.26-8.24 (m, 1H), 8.21-8.20 (m, 1H), 7.91 (s, 1H), 7.33-7.30 (d, 1H), 7.12 (s, 1H), 6.72 (s, 2H), 4.13-4.05 (m, 1H), 4.01 (s, 6H), 2.87-2.84 (m, 2H), 2.21 (s, 3H), 2.09-1.79 (m, 6H).

Example 60

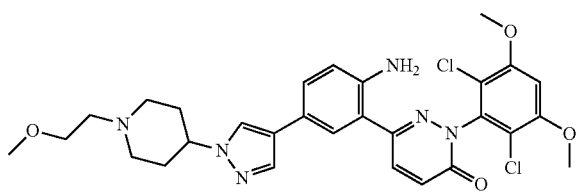

6-(2-amino-5-(1-(1-(2-methoxyethyl)piperidin-4-yl)-1H-pyrazol-4-yl)pyridin-3-yl)-2-(2,6-dichloro-3,5-dimethoxyphenyl)pyridazin-3 (2H)-one A solution of 6-(2-amino-5-(1-(piperidin-4-yl)-1H-pyrazol-4-yl)pyridin-3-yl)-2-(2,6-dichloro-3,5-dimethoxyphenyl)pyridazin-3(2H)-one (Example 58; 17 mg, 0.031 mmol) in DMF (0.31 mL) was treated with 1-bromo-2-methoxyethane (3.8 µL, 0.041 mmol) and K$_2$CO$_{3(s)}$ (6.1 mg, 0.045 mmol). The resulting mixture was stirred overnight at ambient temperature, then filtered through an acrodisc LC 25 mm Syringe filter (with 0.45 m PVDF Membrane) and the filtrate was purified by C18 reverse phase chromatography (5-95% ACN in H$_2$O with 0.1% TFA as the gradient eluent) to afford the title compound as the TFA salt. The chromatographic fractions containing the TFA salt of the title compound were combined then neutralized with 1M NaOH$_{(aq)}$, and extracted with DCM. The organic extracts were dried over anhydrous Na$_2$SO$_{4(s)}$, filtered and concentrated under vacuum. The resulting residue was purified further by silica chromatography (10-90% CHCl$_3$/10% MeOH/1% NH$_4$OH in CHCl$_3$ as the gradient eluent) to afford the title compound (4.0 mg, 21% yield). MS (apci) m/z=600.2 (M+H). H NMR (400 MHz, CD$_3$OD) δ 8.30-8.27 (d, 1H), 8.26 (d, 1H), 8.18 (d, 1H), 8.09 (d, 1H), 8.88-8.85 (m, 2H), 7.26-7.23 (d, 1H), 7.0 (s, 1H), 4.24-4.16 (m, 1H), 4.00 (s, 6H), 3.57-3.54 (t, 3H), 3.34 (s, 3H), 3.15-3.12 (m, 2H), 2.69-2.66 (t, 2H), 2.36-2.29 (m, 2H), 2.14-2.08 (m, 4H).

Example 61

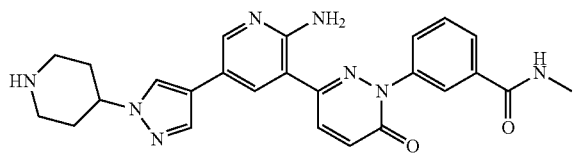 [SMILES: CNC(=O)c1cccc(-n2nc(-c3cc(-c4cnn(C5CCNCC5)c4)cnc3N)ccc2=O)c1]

3-(3-(2-amino-5-(1-(piperidin-4-yl)-1H-pyrazol-4-yl)pyridin-3-yl)-6-oxopyridazin-1 (6H)-yl)-N-methylbenzamide Step 1: Preparation of tert-butyl 4-(4-(6-amino-5-(1-(3-(methylcarbamoyl)phenyl)-6-oxo-1,6-dihydropyridazin-3-yl)pyridin-3-yl)-1H-pyrazol-1-yl)piperidine-1-carboxylate A solution of 3-(3-(2-amino-5-bromopyridin-3-yl)-6-oxopyridazin-1(6H)-yl)-N-methylbenzamide (Intermediate M1; 47.6 mg, 0.119 mmol) in 4:1 dioxane:water (1.2 mL) was treated with tert-Butyl 4-[4-(4,4,5,5-tetramethyl-1,3,2-dioxaborolan-2-yl)pyrazol-1-yl]piperidine-1-carboxylate (49.4 mg, 0.131 mmol), PdCl$_2$(dppf)•CH$_2$Cl$_2$ (9.78 mg, 0.0119 mmol) and K$_2$CO$_{3(s)}$ (49.3 mg, 0.357 mmol). The resulting mixture was sparged with Ar$_{(g)}$, then sealed and stirred 16 h at 100° C. After cooling to ambient temperature, the reaction mixture was diluted with 4:1 DCM:iPrOH (25 mL) and washed with water (2×10 mL). The organic extracts were dried over anhydrous Na$_2$SO$_{4(s)}$, filtered and concentrated under vacuum to afford the title compound which was immediately carried on to step 2. MS (apci) m/z=571.3 (M+H).

Step 2: Preparation of 3-(3-(2-amino-5-(1-(piperidin-4-yl)-1H-pyrazol-4-yl)pyridin-3-yl)-6-oxopyridazin-1(6H)-yl)-N-methylbenzamide tert-Butyl 4-(4-(6-amino-5-(1-(3-(methylcarbamoyl)phenyl)-6-oxo-1,6-dihydropyridazin-3-yl)pyridin-3-yl)-1H-pyrazol-1-yl)piperidine-1-carboxylate was dissolved in 1:1 TFA:DCM (1.2 mL) then stirred 30 min at ambient temperature. The reaction mixture was concentrated under vacuum then purified by C18 reverse phase chromatography (5-95% ACN in H$_2$O with 0.1% TFA as the gradient eluent) to afford the title compound as a TFA salt. The TFA salt was dissolved in 4:1 DCM:iPrOH (50 mL) and extracted with saturated NaHCO$_{3(aq)}$ (1×25 mL). The organic extracts were dried over anhydrous Na$_2$SO$_{4(s)}$, filtered and concentrated under vacuum to cleanly afford the title compound (18.8 mg, 34% yield). MS (apci) m/z=471.2 (M+H).

Example 62

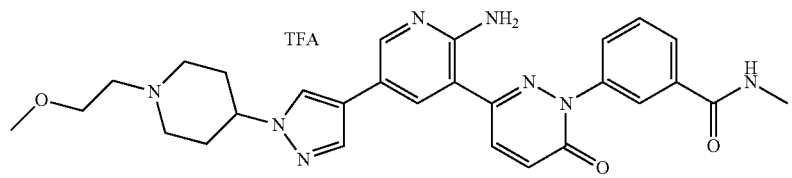

3-(3-(2-amino-5-(1-(1-(2-methoxyethyl)piperidin-4-yl)-1H-pyrazol-4-yl)pyridin-3-yl)-6-oxopyridazin-1(6H)-yl)-N-methylbenzamide 2,2,2-trifluoroacetate salt A mixture of 3-(3-(2-amino-5-(1-(piperidin-4-yl)-1H-pyrazol-4-yl)pyridin-3-yl)-6-oxopyridazin-1(6H)-yl)-N-methylbenzamide (Example 61; 9.88 mg, 0.0210 mmol), 1-bromo-2-methoxyethane (2.17 µL, 0.0231 mmol) and K$_2$CO$_{3(s)}$ (4.35 mg, 0.0315 mmol) in DMSO (0.21 mL) was stirred overnight at ambient temperature. The reaction mixture was diluted with DCM and washed with water and brine. The organic extracts were dried over anhydrous Na$_2$SO$_{4(s)}$, filtered and concentrated in vacuo. The crude residue was purified by C18 reverse phase chromatography (5-95% ACN:water with 0.1% TFA) to afford the title compound (4.8 mg, 37% yield). MS (apci) m/z=444.1 (M+H).

Example 63

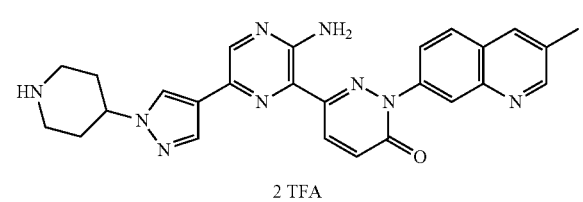 [SMILES: Cc1cnc2cc(-n3nc(-c4nc(-c5cnn(C6CCNCC6)c5)cnc4N)ccc3=O)ccc2c1]

6-(3-amino-6-(1-(piperidin-4-yl)-1H-pyrazol-4-yl)pyrazin-2-yl)-2-(3-methylquinolin-7-yl)pyridazin-3(2H)-one bis(2,2,2-trifluoroacetate)

Step 1: Preparation of tert-butyl 4-(4-(5-amino-6-(1-(3-methylquinolin-7-yl)-6-oxo-1,6-dihydropyridazin-3-yl)pyrazin-2-yl)-1H-pyrazol-1-yl)piperidine-1-carboxylate A suspension of tert-butyl 4-(4-(5-amino-6-bromopyrazin-2-yl)-1H-pyrazol-1-yl)piperidine-1-carboxylate (Intermediate L19; 25.640 mg, 0.060570 mmol), 2-(3-methylquinolin-7-yl)-6-(4,4,5,5-tetramethyl-1,3,2-dioxaborolan-2-yl)pyridazin-3(2H)-one (Intermediate R$^{30}$; 33 mg, 0.1 mmol), Na$_2$CO$_3$ (90.855 µL, 0.18171 mmol), and Pd(PPh$_3$)$_4$(7.0 mg, 0.006 mmol) in dioxane (605.70 µL, 0.060570 mmol) was sparged with Ar(g), then sealed and stirred 16 h at 90° C. After cooling to ambient temperature, the reaction mixture was partitioned between EtOAc and water. The organic extracts were washed with brine, dried over anhydrous Na$_2$SO$_{4(s)}$, filtered and concentrated. The residue was purified using silica gel chromatography 0-15% MeOH in EtOAc to afford the title compound (12 mg, 0.02 mmol, 34.2% yield). MS (apci) m/z=580.3 (M+H).

Step 2: Preparation of 6-(3-amino-6-(1-(piperidin-4-yl)-1H-pyrazol-4-yl)pyrazin-2-yl)-2-(3-methylquinolin-7-yl)pyridazin-3(2H)-one bis(2,2,2-trifluoroacetate)

tert-butyl 4-(4-(5-amino-6-(1-(3-methylquinolin-7-yl)-6-oxo-1,6-dihydropyridazin-3-yl)pyrazin-2-yl)-1H-pyrazol-1-yl)piperidine-1-carboxylate (12 mg, 0.021 mmol) was dissolved in 1:1 TFA/DCM (2.0 mL) and stirred at ambient temperature for 6 h. The reaction mixture was concentrated under vacuum, and then treated with 2 mL MeOH. The mixture was concentrated under vacuum to afford the title compound as the TFA salt (9.1 mg, 0.019 mmol, 92% yield) MS (apci) m/z=480.2 (M+H).

Example 64

6-(3-amino-6-(1-(1-(2-methoxyethyl)piperidin-4-yl)-1H-pyrazol-4-yl)pyrazin-2-yl)-2-(3-methylquinolin-7-yl)pyridazin-3 (2H)-one A solution 6-(3-amino-6-(1-(piperidin-4-yl)-1H-pyrazol-4-yl)pyrazin-2-yl)-2-(3-methylquinolin-7-yl)pyridazin-3 (2H)-one bis(2,2,2-trifluoroacetate) (Example 63; 8 mg, 0.02 mmol) in DMSO (556 µL) was treated with K$_2$CO$_{3(s)}$ (4.6 mg, 0.03 mmol). The mixture was cooled to 0° C. in an ice water bath, and 1-bromo-2-methoxyethane (2 L, 0.02 mmol) was added. The resulting mixture was warmed to ambient temperature and stirred for 50 h. The reaction was diluted with water and extracted with DCM. The organic extracts were washed with brine, dried over anhydrous Na$_2$SO$_{4(s)}$, filtered and concentrated under vacuum. The crude residue was purified by silica gel chromatography (0-100% Acetone in DCM as the gradient eluent followed by 10% MeOH in DCM) to afford the title compound (1.8 mg, 20% yield). MS (apci) m/z=538.2 (M+H).

Example 65

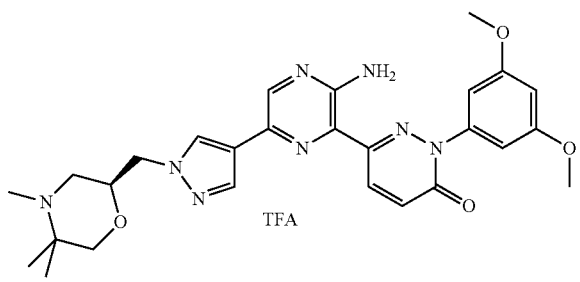

(S)-6-(3-amino-6-(1-((4,5,5-trimethylmorpholin-2-yl)methyl)-1H-pyrazol-4-yl)pyrazin-2-yl)-2-(3,5-dimethoxyphenyl)pyridazin-3 (2H)-one 2,2,2-trifluoroacetate A solution of (S)-6-(3-amino-6-(1-((5,5-dimethylmorpholin-2-yl)methyl)-1H-pyrazol-4-yl)pyrazin-2-yl)-2-(3,5-dimethoxyphenyl)pyridazin-3(2H)-one (29 mg, 0.0559 mmol) (Example 27; 29 mg, 0.06 mmol) in MeOH (0.5 mL) was treated with formaldehyde (12.6 µL, 0.168 mmol) and stirred for 15 min at ambient temperature. The resulting reaction mixture was treated with sodium triacetoxyborohydride (35.6 mg, 0.168 mmol) and stirred 30 minutes at ambient temperature. The reaction mixture was concentrated under vacuum and then purified by C18 reverse phase chromatography (5-95% water-ACN w/0.1% TFA as the gradient eluent) to afford the title compound as a TFA salt (22 mg, 74% yield). MS (apci) m/z=533.2 (M+H).

Example 66

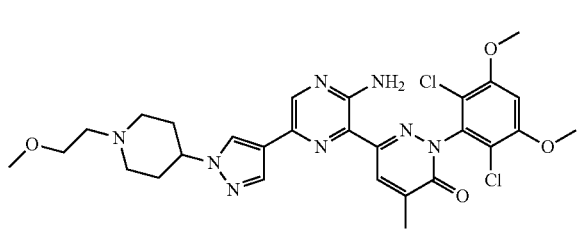

6-(3-amino-6-(1-(1-(2-methoxyethyl)piperidin-4-yl)-1H-pyrazol-4-yl)pyrazin-2-yl)-2-(2,6-dichloro-3,5-dimethoxyphenyl)-4-methylpyridazin-3(2H)-one Step 1: A mixture of tert-butyl 4-(4-(5-amino-6-bromopyrazin-2-yl)-1H-pyrazol-1-yl)piperidine-1-carboxylate (Intermediate L19; 0.225 g, 0.532 mmol), 2-(2,6-dichloro-3,5-dimethoxyphenyl)-4-methyl-6-(4,4,5,5-tetramethyl-1,3,2-dioxaborolan-2-yl)pyridazin-3 (2H)-one (Intermediate R16; 0.234 g, 0.532 mmol), Pd(PPh$_3$)$_4$(0.0461 g, 0.0399 mmol) and 2 M solution of Na$_2$CO$_3$ (0.558 mL, 1.12 mmol) in dioxane (3 mL) was stirred at 90° C. for 8 hours. The mixture was then filtered through filter paper and the filtrate was concentrated. The residue was purified on a silica column using Hexanes:EtOAc (10-90%) to give tert-butyl 4-(4-(5-amino-6-(1-(2,6-dichloro-3,5-dimethoxyphenyl)-5-methyl-6-oxo-1,6-dihydropyridazin-3-yl)pyrazin-2-yl)-1H-pyrazol-1-yl)piperidine-1-carboxylate (0.213 g, 0.324 mmol, 60.9% yield). MS (apci) m/z=657.2 (M+H).

Step 2: A mixture of tert-butyl 4-(4-(5-amino-6-(1-(2,6-dichloro-3,5-dimethoxyphenyl)-5-methyl-6-oxo-1,6-dihydropyridazin-3-yl)pyrazin-2-yl)-1H-pyrazol-1-yl)piperidine-1-carboxylate (0.213 g, 0.324 mmol) in TFA (1.5 ml) and DCM (1.62 ml) was stirred at room temperature for 30 min and then concentrated. The residue was partitioned between DCM and aqueous saturated Na$_2$CO$_3$. The combined organic extracts were washed with brine, dried over Na$_2$SO$_4$ and concentrated to give 6-(3-amino-6-(1-(piperidin-4-yl)-1H-pyrazol-4-yl)pyrazin-2-yl)-2-(2,6-dichloro-3,5-dimethoxyphenyl)-4-methylpyridazin-3(2H)-one (0.157 g, 0.282 mmol, 86.9% yield). MS (apci) m/z=557.2 (M+H).

Step 3: 1-bromo-2-methoxyethane (0.009365 ml, 0.09965 mmol) was added to 6-(3-amino-6-(1-(piperidin-4-yl)-1H-pyrazol-4-yl)pyrazin-2-yl)-2-(2,6-dichloro-3,5-dimethoxyphenyl)-4-methylpyridazin-3(2H)-one (0.0505 g, 0.09059 mmol) and K$_2$CO$_3$ (0.03756 g, 0.2718 mmol) in DMF (0.9059 ml) at room temperature. The reaction mixture was stirred for 3 days. The mixture was taken up in DCM and extracted with water. The combined organic extracts were washed with water and brine, dried over Na$_2$SO$_4$, filtered and concentrated. The residue was purified by C18 reverse phase chromatography (5-95% ACN:water with 0.1% TFA). The isolated product was taken up in DCM and washed with aqueous saturated Na$_2$CO$_3$ and brine, dried over Na$_2$SO$_4$, filtered and concentrated to provide 6-(3-amino-6-(1-(1-(2-methoxyethyl)piperidin-4-yl)-1H-pyrazol-4-yl)pyrazin-2-yl)-2-(2,6-dichloro-3,5-dimethoxyphenyl)-4-methylpyridazin-3(2H)-one (0.0145 g, 0.02356 mmol, 26.00% yield). MS (apci) m/z=615.2 (M+H).

Example 67

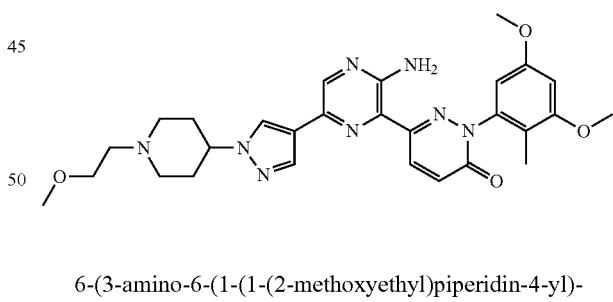

6-(3-amino-6-(1-(1-(2-methoxyethyl)piperidin-4-yl)-1H-pyrazol-4-yl)pyrazin-2-yl)-2-(3,5-dimethoxy-2-methylphenyl)pyridazin-3(2H)-one Step 1: To a solution of 6-chloro-2-(3,5-dimethoxyphenyl)pyridazin-3(2H)-one (0.505 g, 1.89 mmol) in acetonitrile (18.9 mL, 1.89 mmol) was added 1-bromopyrrolidine-2,5-dione (0.337 g, 1.89 mmol) at 0° C. The reaction mixture was warmed to ambient temperature after 10 minutes and stirred for 2.5 hours. The mixture was partitioned between EtOAc and water. The combined organic phases were washed with water and brine, dried over Na$_2$SO$_4$, filtered and concentrated in vacuo. The residue was purified by flash chromatography (10-90% EtOAc in hexanes) to yield 2-(2- bromo-3,5-dimethoxyphenyl)-6-chloropyridazin-3(2H)-one (0.611 g, 1.77 mmol, 93.4% yield). MS (apci) m/z=346.9 [(M+H)+2], 344.9 (M+H) with Br pattern.

Step 2: To a solution of 2-(2-bromo-3,5-dimethoxyphenyl)-6-chloropyridazin-3(2H)-one (0.308 g, 0.891 mmol) in THF (5.94 ml, 0.891 mmol) was added methylzinc(II) chloride (0.446 mL, 0.891 mmol) and the mixture was sparged with Ar for 15 min. Bis(tri-t-butylphosphine) Pd(0) (0.0455 g, 0.0891 mmol) was added and the reaction mixture was heated to 60° C. under $N_2$ for 3 hours. The mixture was concentrated in vacuo and the concentrate was suspended in DCM, washed with water and brine, dried over $Na_2SO_4$, filtered and concentrated in vacuo. The residue was purified by flash chromatography (10-90% EtOAc in hexanes) to yield 6-chloro-2-(3,5-dimethoxy-2-methylphenyl)pyridazin-3 (2H)-one (0.109 g, 0.388 mmol, 43.6% yield). MS (apci) m/z=281.0 (M+H).

Step 3: To a solution of 6-chloro-2-(3,5-dimethoxy-2-methylphenyl)pyridazin-3(2H)-one (0.031 g, 0.11 mmol) and 4,4,4',4',5,5,5',5'-octamethyl-2,2'-bi(1,3,2-dioxaborolane) (0.042 g, 0.17 mmol) in 1,4-dioxane (1.1 mL, 0.11 mmol) was added potassium acetate (0.033 g, 0.33 mmol) and the mixture was sparged with Ar for 5 mins. 2-(Dicyclohexylphosphino)-2,4,6-Triisopropylbiphenyl (0.0079 g, 0.017 mmol) and Palladium(II) acetate (0.0025 g, 0.011 mmol) were then added sequentially and the reaction mixture was sparged with Ar. The reaction vessel was sealed and the reaction mixture was heated to 100° C. for 1 hr. The mixture was partitioned between DCM and water. The combined organic extracts were washed with water and brine, dried over $Na_2SO_4$, filtered and concentrated in vacuo to provide 2-(3,5-dimethoxy-2-methylphenyl)-6-(4,4,5,5-tetramethyl-1,3,2-dioxaborolan-2-yl)pyridazin-3(2H)-one (0.041 g, 0.11 mmol, assumed quantitative yield).

Step 4: To a solution of 3-bromo-5-(1-(1-(2-methoxyethyl)piperidin-4-yl)-1H-pyrazol-4-yl)pyrazin-2-amine (Intermediate L22; 0.034 g, 0.089 mmol) and 2-(3,5-dimethoxy-2-methylphenyl)-6-(4,4,5,5-tetramethyl-1,3,2-dioxaborolan-2-yl)pyridazin-3(2H)-one (0.040 g, 0.11 mmol) in 1,4-dioxane (0.89 mL, 0.089 mmol) was added sodium carbonate (0.13 mL, 0.27 mmol) and the reaction mixture was sparged with Ar for 5 mins. Tetrakis(triphenylphosphine)Pd(0) (0.0082 g, 0.0071 mmol) was added and the reaction mixture was sparged with Ar. The mixture was sealed and heated to 100° C. for 2 hours with stirring. The mixture was cooled to ambient temperature and purified by reverse phase chromatography (5-95% ACN:water with 0.1% TFA) to provide the title compound (0.020 g, 0.037 mmol, 41% yield) as a yellow powder. MS (apci) m/z=547.3 (M+H).

Example 68

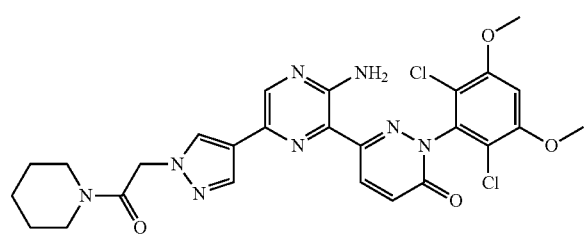 [SMILES: COc1cc(OC)c(Cl)c(-n2nc(-c3nc(-c4cnn(CC(=O)N5CCCCC5)c4)cnc3N)ccc2=O)c1Cl]

6-(3-amino-6-(1-(2-oxo-2-(piperidin-1-yl)ethyl)-1H-pyrazol-4-yl)pyrazin-2-yl)-2-(2,6-dichloro-3,5-dimethoxyphenyl)pyridazin-3(2H)-one To a solution of 6-(3-amino-6-bromopyrazin-2-yl)-2-(2,6-dichloro-3,5-dimethoxyphenyl)pyridazin-3(2H)-one (Intermediate M3; 0.025 g, 0.053 mmol) in 1,4-dioxane (0.53 mL, 0.053 mmol) was added sodium carbonate (0.079 mL, 0.16 mmol) and 1-(piperidin-1-yl)-2-(4-(4,4,5,5-tetramethyl-1,3,2-dioxaborolan-2-yl)-1H-pyrazol-1-yl)ethanone (0.020 g, 0.063 mmol) and the reaction mixture was sparged with Ar for 5 mins. Tetrakis(triphenylphosphine)palladium (0) (0.0049 g, 0.0042 mmol) was added and the reaction mixture was sparged with Ar. The reaction was sealed, heated to 100° C. and stirred for 2.5 hrs. The reaction was cooled to ambient temperature and purified by reverse phase chromatography (5-95% ACN:water with 0.1% TFA) to provide the title compound (0.020 g, 0.037 mmol, 41% yield) as a yellow powder. MS (apci) m/z=589.2 [(M+H)+4], 587.2 [(M+H)+2], 585.1 (M+H) with di Cl pattern.

Example 69

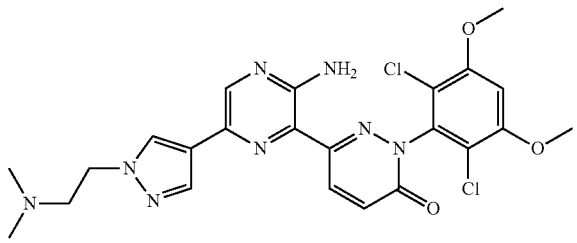

6-(3-amino-6-(1-(2-(dimethylamino)ethyl)-1H-pyrazol-4-yl)pyrazin-2-yl)-2-(2,6-dichloro-3,5-dimethoxyphenyl)pyridazin-3 (2H)-one To a solution of 6-(3-amino-6-bromopyrazin-2-yl)-2-(2,6-dichloro-3,5-dimethoxyphenyl)pyridazin-3(2H)-one (Intermediate M3; 0.026 g, 0.055 mmol) in 1,4-dioxane (0.55 mL, 0.053 mmol) was added sodium carbonate (0.079 mL, 0.16 mmol) and N,N-dimethyl-2-(4-(4,4,5,5-tetramethyl-1,3,2-dioxaborolan-2-yl)-1H-pyrazol-1-yl)ethanamine (0.019 g, 0.071 mmol) and the reaction mixture was sparged with Ar for 5 mins. Tetrakis(triphenylphosphine)Palladium(0) (0.0051 g, 0.0044 mmol) was added and the reaction mixture was sparged with Ar. The reaction was sealed, heated to 100° C. and stirred for 2.5 hrs. The mixture was cooled to ambient temperature and purified by flash chromatography (1-9% MeOH in DCM) to yield the title compound (0.018 g, 0.034 mmol, 62% yield) as a yellow powder. MS (apci) m/z=535.1 [(M+H)+4], 533.1 [(M+H)+2], 531.2 (M+H) with di Cl pattern. $^1$H NMR (DMSO) δ 8.71 (d, 1H), 8.48 (s, 1H), 8.32 (d, 1H), 8.00 (d, 1H), 7.30 (d, 1H), 7.10 (s, 1H), 7.03 (br s, 2H, NH$_2$), 4.20 (t, 2H), 3.99 (s, 6H), 2.66 (t, 2H), 2.15 (s, 6H).

The following compounds shown in Table 6 were prepared according the method used for the synthesis of Example 69 using 6-(3-amino-6-bromopyrazin-2-yl)-2-(2,6-dichloro-3,5-dimethoxyphenyl)pyridazin-3(2H)-one (Intermediate M3; 0.026 g, 0.055 mmol). Reaction progression in each was followed by LCMS and reaction time was adjusted as necessary. All compounds were purified using a method similar to that used in either Example 68 or Example 69 utilizing the appropriate gradient eluent.

TABLE 6

| Ex. # | Structure | Name | MS (apci) m/z |
|---|---|---|---|
| 70 | 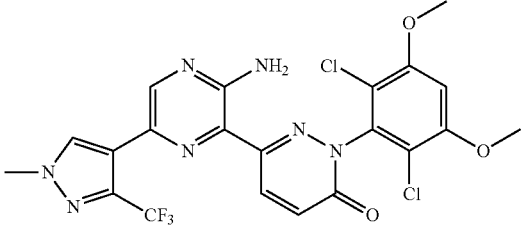 | 6-(3-amino-6-(1-methyl-3-(trifluoromethyl)-1H-pyrazol-4-yl)pyrazin-2-yl)-2-(2,6-dichloro-3,5-dimethoxyphenyl)pyridazin-3(2H)-one | 542.1 (M + H) |
| 71 | 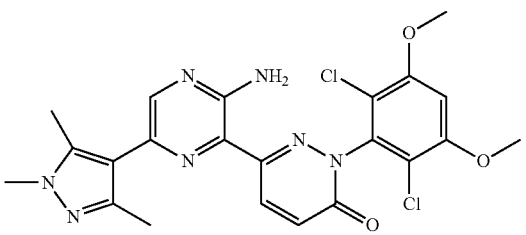 | 6-(3-amino-6-(1,3,5-trimethyl-1H-pyrazol-4-yl)pyrazin-2-yl)-2-(2,6-dichloro-3,5-dimethoxyphenyl)pyridazin-3(2H)-one | 502.1 (M + H) |
| 72 | 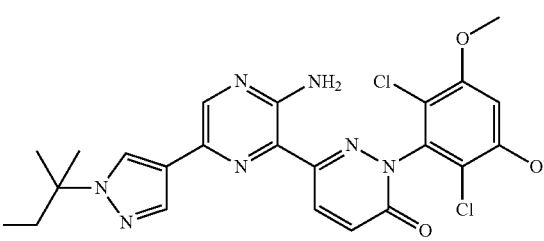 | 6-(3-amino-6-(1-(1-hydroxy-2-methylpropan-2-yl)-1H-pyrazol-4-yl)pyrazin-2-yl)-2-(2,6-dichloro-3,5-dimethoxyphenyl)pyridazin-3(2H)-one | 532.1 (M + H) |
| 73 | 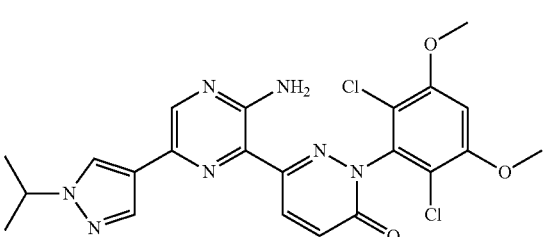 | 6-(3-amino-6-(1-isopropyl-1H-pyrazol-4-yl)pyrazin-2-yl)-2-(2,6-dichloro-3,5-dimethoxyphenyl)pyridazin-3(2H)-one | 502.1 (M + H) |
| 74 | 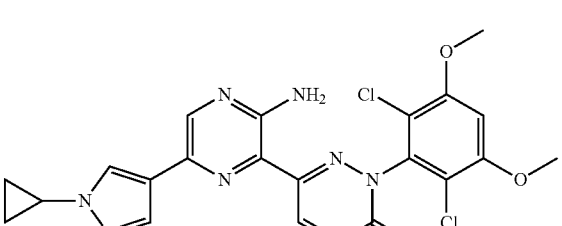 | 6-(3-amino-6-(1-cyclopropyl-1H-pyrazol-4-yl)pyrazin-2-yl)-2-(2,6-dichloro-3,5-dimethoxyphenyl)pyridazin-3(2H)-one | 500.1 (M + H) |
| 75 | 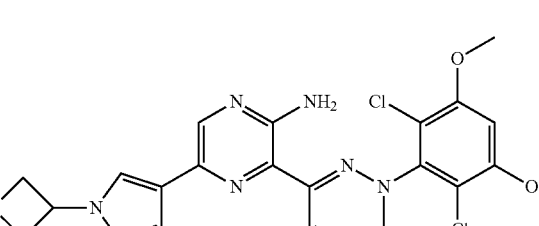 | 6-(3-amino-6-(1-(azetidin-3-yl)-1H-pyrazol-4-yl)pyrazin-2-yl)-2-(2,6-dichloro-3,5-dimethoxyphenyl)pyridazin-3(2H)-one | 515.1 (M + H) |

Example 76

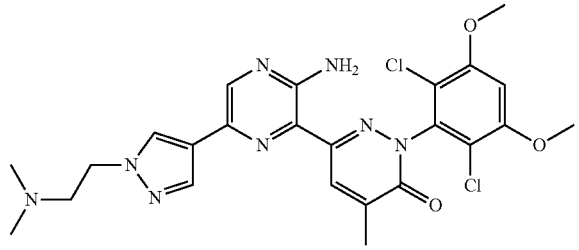

6-(3-amino-6-(1-(2-(dimethylamino)ethyl)-1H-pyrazol-4-yl)pyrazin-2-yl)-2-(2,6-dichloro-3,5-dimethoxyphenyl)-4-methylpyridazin-3 (2H)-one To a solution of 6-(3-amino-6-bromopyrazin-2-yl)-2-(2,6-dichloro-3,5-dimethoxyphenyl)-4-methylpyridazin-3 (2H)-one (Intermediate M4; 0.069 g, 0.14 mmol) in 1,4-dioxane (1.42 ml, 0.142 mmol) was added sodium carbonate (0.21 mL, 0.43 mmol) and N,N-dimethyl-2-(4-(4,4,5,5-tetramethyl-1,3,2-dioxaborolan-2-yl)-1H-pyrazol-1-yl)ethanamine (0.0488 g, 0.184 mmol) and the reaction mixture was sparged with Ar for 5 mins. Tetrakis(Triphenylphosphine)Palladium(0) (0.0131 g, 0.0113 mmol) was added and the reaction mixture was sparged with Ar. The reaction was sealed, heated to 100° C. and stirred for 2 hrs. The mixture was cooled to ambient temperature and purified by flash chromatography (1-9% MeOH in DCM) to yield the title compound (0.0256 g, 0.0469 mmol, 33.1% yield) as a yellow powder. MS (apci) m/z=549.1 [(M+H)+4], 547.1 [(M+H)+2], 545.2 (M+H) with di Cl pattern. $^1$H NMR (CDCl$_3$) δ 8.48 (m, 1H), 8.27 (s, 1H), 7.96 (d, 1H), 7.94 (d, 1H), 6.71 (s, 1H), 6.20 (br s, 2H, NH$_2$), 4.30 (t, 2H), 3.99 (s, 6H), 2.83 (t, 2H), 2.41 (d, 3H), 2.31 (s, 6H).

Example 77

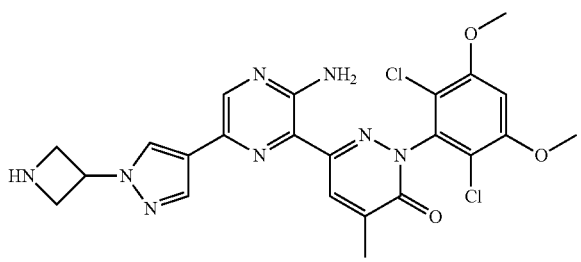 [SMILES: COc1cc(OC)c(Cl)c(-n2nc(-c3nc(-c4cnn(C5CNC5)c4)cnc3N)cc(C)c2=O)c1Cl]

6-(3-amino-6-(1-(azetidin-3-yl)-1H-pyrazol-4-yl)pyrazin-2-yl)-2-(2,6-dichloro-3,5-dimethoxyphenyl)-4-methylpyridazin-3 (2H)-one Step 1: To a solution of 6-(3-amino-6-bromopyrazin-2-yl)-2-(2,6-dichloro-3,5-dimethoxyphenyl)-4-methyl-pyridazin-3(2H)-one (Intermediate M4; 0.120 g, 0.246 mmol) in 1,4-dioxane (2.46 ml, 0.246 mmol) was added sodium carbonate (0.370 mL, 0.739 mmol) and tert-butyl 3-(4-(4,4,5,5-tetramethyl-1,3,2-dioxaborolan-2-yl)-1H-pyrazol-1-yl)azetidine-1-carboxylate (0.103 g, 0.296 mmol) and the reaction mixture was sparged with Ar. tetrakis(triphenylphosphine)palladium(0) (0.0228 g, 0.0197 mmol) was added and the reaction mixture was sparged with Ar. The reaction was sealed, heated to 100° C. and stirred for 2 hrs. The mixture was cooled to ambient temperature and purified by flash chromatography (1-5% MeOH in DCM) to yield the title compound (0.0256 g, 0.0469 mmol, 33.1% yield) as a yellow powder. MS (apci) m/z=633.2 [(M+H)+4], 631.2 [(M+H)+2], 629.2 (M+H) with di Cl pattern.

Step 2: 2,2,2-Trifluoroacetic acid (1.0 ml, 0.10 mmol) was added to a solution of tert-butyl 3-(4-(5-amino-6-(1-(2,6-dichloro-3,5-dimethoxyphenyl)-5-methyl-6-oxo-1,6-dihydropyridazin-3-yl)pyrazin-2-yl)-1H-pyrazol-1-yl)azetidine-1-carboxylate (0.065 g, 0.10 mmol) in dichloromethane (1.0 mL, 0.10 mmol) at ambient temperature for 3.5 hrs. The mixture was partitioned between DCM and aqueous saturated Na$_2$CO$_3$. The combined organic extracts were washed with brine and concentrated to provide the title compound (0.045 g, 0.085 mmol, 82% yield) as a yellow solid. MS (apci) m/z=533.1 [(M+H)+4], 531.1 [(M+H)+2], 529.2 (M+H) with di Cl pattern.

Example 78

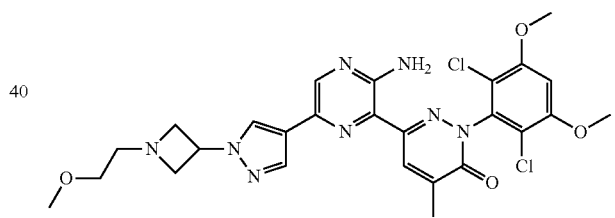

6-(3-amino-6-(1-(1-(2-methoxyethyl)azetidin-3-yl)-1H-pyrazol-4-yl)pyrazin-2-yl)-2-(2,6-dichloro-3,5-dimethoxyphenyl)-4-methylpyridazin-3(2H)-one 1-Bromo-2-methoxyethane (0.002915 mL, 0.03138 mmol) was added to a vial containing 6-(3-amino-6-(1-(azetidin-3-yl)-1H-pyrazol-4-yl)pyrazin-2-yl)-2-(2,6-dichloro-3,5-dimethoxyphenyl)-4-methylpyridazin-3(2H)-one (Example 77; 0.0151 g, 0.02852 mmol) and potassium carbonate (0.005913 g, 0.04279 mmol) in DMF (0.5705 mL, 0.02852 mmol) at ambient temperature. The mixture was stirred in sealed vial for 48 hrs. The mixture was partitioned between DCM and water. The combined organic extracts were washed with water and brine, dried over Na$_2$SO$_4$, and concentrated in vacuo. The residue was purified by reverse phase chromatography (5-95% ACN:water with 0.1% TFA) to yield the title compound (0.0051 g, 0.008681 mmol, 30.44% yield) as a yellow solid. MS (apci) m/z=591.1 [(M+H)+4], 589.1 [(M+H)+2], 587.1 (M+H) with di Cl pattern.

Example 79

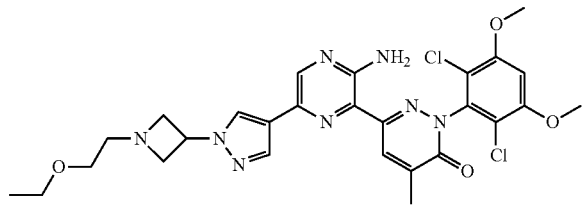 [SMILES: CCOCCN1CC(n2cc(-c3cnc(N)c(-c4cc(C)c(=O)n(-c5c(Cl)c(OC)cc(OC)c5Cl)n4)n3)cn2)C1]

6-(3-amino-6-(1-(1-(2-ethoxyethyl)azetidin-3-yl)-1H-pyrazol-4-yl)pyrazin-2-yl)-2-(2,6-dichloro-3,5-dimethoxyphenyl)-4-methylpyridazin-3(2H)-one 1-Bromo-2-ethoxyethane (0.003632 mL, 0.03221 mmol) was added to a vial containing 6-(3-amino-6-(1-(azetidin-3-yl)-1H-pyrazol-4-yl)pyrazin-2-yl)-2-(2,6-dichloro-3,5-dimethoxyphenyl)-4-methylpyridazin-3(2H)-one (Example 77; 0.0155 g, 0.02928 mmol) and potassium carbonate (0.006070 g, 0.04392 mmol) in DMF (0.9760 mL, 0.02928 mmol) at ambient temperature. The reaction stirred in a sealed vial for 15 hrs. The mixture was partitioned between DCM and water. The combined organics were washed with water and brine, dried over $Na_2SO_4$, and concentrated in vacuo. The mixture was purified by reverse phase chromatography (5-95% ACN:water with 0.1% TFA) to yield the title compound (0.0042 g, 0.006983 mmol, 23.85% yield) as a yellow solid. MS (apci) m/z=605.2 [(M+H)+4], 603.2 [(M+H)+2], 601.2 (M+H) with di Cl pattern.

Example 80

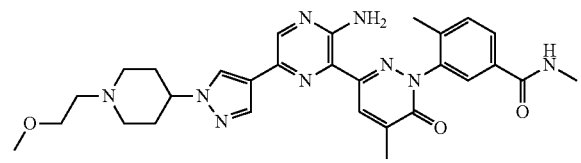

3-(3-(3-amino-6-(1-(1-(2-methoxyethyl)piperidin-4-yl)-1H-pyrazol-4-yl)pyrazin-2-yl)-5-methyl-6-oxopyridazin-1(6H)-yl)-N,4-dimethylbenzamide To a solution of the 3-(3-(3-amino-6-(1-(piperidin-4-yl)-1H-pyrazol-4-yl)pyrazin-2-yl)-5-methyl-6-oxopyridazin-1(6H)-yl)-N,4-dimethylbenzamide dihydrochloride (50 mg, 0.087 mmol) in N,N-dimethylformamide (1747 µL, 0.087 mmol) at 0° C. under a nitrogen atmosphere was sequentially added $K_2CO_3$ (49 mg, 0.35 mmol) and 1-bromo-2-methoxyethane (10 µL, 0.11 mmol). The mixture was stirred at RT overnight. The resulting mixture was diluted with 5% IPA/DCM (50 mL) and washed with water (10 mL). The organic layer was separated, dried ($MgSO_4$), filtered and concentrated in vacuo. The residue was purified by flash chromatography on silica gel (Redi Sep 24 g) eluting with 2-20% MeOH/DCM with 2% $NH_4OH$ to provide 3-(3-(3-amino-6-(1-(1-(2-methoxyethyl)piperidin-4-yl)-1H-pyrazol-4-yl)pyrazin-2-yl)-5-methyl-6-oxopyridazin-1(6H)-yl)-N,4-dimethylbenzamide (25 mg, 51% yield) as a solid. LCMS (APCI+) m/z 558.2 (M+1), Retention time=1.751 min.

Example 81

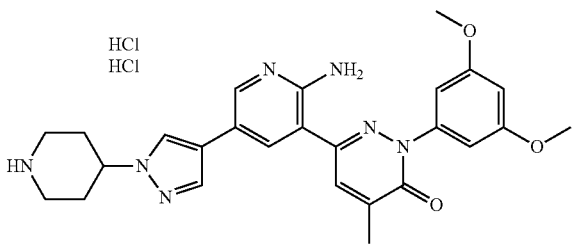 [SMILES: COc1cc(OC)cc(-n2nc(-c3cc(-c4cnn(C5CCNCC5)c4)cnc3N)cc(C)c2=O)c1 ; "HClHCl"]

6-(2-amino-5-(1-(piperidin-4-yl)-1H-pyrazol-4-yl)pyridin-3-yl)-2-(3,5-dimethoxyphenyl)-4-methylpyridazin-3 (2H)-one dihydrochloride Step 1: A glass pressure tube was charged with Intermediate R18 [crude 2-(3,5-dimethoxyphenyl)-4-methyl-6-(4,4,5,5-tetramethyl-1,3,2-dioxaborolan-2-yl)pyridazin-3 (2H)-one] (660 mg, 1.77 mmol), Intermediate L21 [tert-butyl 4-(4-(6-amino-5-bromopyridin-3-yl)-1H-pyrazol-1-yl)piperidine-1-carboxylate] (749 mg, 1.77 mmol), $Pd(Ph_3P)_4$ (205 mg, 0.177 mmol), sodium carbonate 2M in water (2660 µL, 5.32 mmol) and 1,4-dioxane (3546 µL, 1.77 mmol). The mixture was purged with $N_2$ for 6 minutes. The tube was sealed with a Teflon screw cap and heated at 90° C. with vigorous stirring for 16 hours. The mixture was cooled to RT, diluted with DCM (100 mL) and washed with water. The organic phase was separated, dried ($MgSO_4$), filtered and concentrated in vacuo. The residue was purified by flash chromatography on silica gel (Redi Sep 40 g) eluting with 1-55% acetone/hexanes (20 CV) to provide tert-butyl 4-(4-(6-amino-5-(1-(3,5-dimethoxyphenyl)-5-methyl-6-oxo-1,6-dihydropyridazin-3-yl)pyridin-3-yl)-1H-pyrazol-1-yl)piperidine-1-carboxylate (780 mg, 75% yield) as a solid. LCMS (APC1+) m/z 588.2 (M+1), retention time=2.528 min.

Step 2: Neat TFA (3 mL) was added to the tert-butyl 4-(4-(6-amino-5-(1-(3,5-dimethoxyphenyl)-5-methyl-6-oxo-1,6-dihydropyridazin-3-yl)pyridin-3-yl)-1H-pyrazol-1-yl)piperidine-1-carboxylate (600 mg, 1.02 mmol). The mixture was stirred at RT for 1 hour. The TFA was removed in vacuo and the residue was treated with 4N HCl in dioxane (5 mL). The mixture was stirred at RT for 15 minutes and the solvent was removed in vacuo. The residue was evaporated from $CH_3CN$ and dried under high vacuum to provide 6-(2-amino-5-(1-(piperidin-4-yl)-1H-pyrazol-4-yl)pyridin-3-yl)-2-(3,5-dimethoxyphenyl)-4-methylpyridazin-3 (2H)-one dihydrochloride (425 mg, 74.3% yield) as a solid. LCMS (APCI+) m/z 488.2 (M+1); Retention time=2.261 min.

Example 82

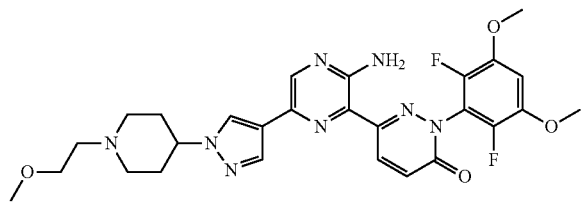

6-(3-amino-6-(1-(1-(2-methoxyethyl)piperidin-4-yl)-
1H-pyrazol-4-yl)pyrazin-2-yl)-2-(2,6-difluoro-3,5-
dimethoxyphenyl)pyridazin-3 (2H)-one Step 1: A mixture of Intermediate L19 (228 mg, 0.538 mmol), Intermediate $R^{29}$ (212 mg, 0.538 mmol), $K_2CO_3$ (2M, 807 μL, 1.61 mmol) and $Pd(Ph_3P)_4$ (31.1 mg, 0.027 mmol) in dioxane (2.7 mL, 0.54 mmol) was sparged with nitrogen and heated at 80° C. for 3 h. The reaction mixture was partitioned between ethyl acetate and water. The aqueous layer was extracted with EtOAc. The combined organic layers were dried and concentrated. The residue was purified by flash chromatography eluting with a hexanes/EtOAc gradient (0-100%) to provide tert-butyl 4-(4-(5-amino-6-(1-(2,6-difluoro-3,5-dimethoxyphenyl)-6-oxo-1,6-dihydropyridazin-3-yl)pyrazin-2-yl)-1H-pyrazol-1-yl)piperidine-1-carboxylate. LCMS (APCI+) m/z 611.2 (M+1); Retention time=3.35 min.

Step 2: tert-butyl 4-(4-(5-amino-6-(1-(2,6-difluoro-3,5-dimethoxyphenyl)-6-oxo-1,6-dihydropyridazin-3-yl)pyrazin-2-yl)-1H-pyrazol-1-yl)piperidine-1-carboxylate was stirred in a solution of 1:1 DCM/TFA (10 mL) for 1 h. The mixture was concentrated at 50° C. The residue was diluted with MeOH (5 mL) and 6N HCl/iPrOH (5 mL) was added. The mixture was concentrated to provide 6-(3-amino-6-(1-(piperidin-4-yl)-1H-pyrazol-4-yl)pyrazin-2-yl)-2-(2,6-difluoro-3,5-dimethoxyphenyl)pyridazin-3(2H)-one hydrochloride salt as a white solid. LCMS (APCI+) m/z 511.2 (M+1); Retention time=2.35 min.

Step 3: To a suspension of 6-(3-amino-6-(1-(piperidin-4-yl)-1H-pyrazol-4-yl)pyrazin-2-yl)-2-(2,6-difluoro-3,5-dimethoxyphenyl)pyridazin-3(2H)-one hydrochloride salt (31.8 mg, 0.062 mmol) and $K_2CO_3$ (43.0 mg, 0.312 mmol) in DMF (1246 μL, 0.062 mmol) was added 2-bromoethyl methyl ether (7.01 μL, 0.075 mmol) and the resulting mixture was stirred at RT for 1 d. The crude reaction mixture was loaded onto a silica column equilibrated with hexanes and eluted with hexanes>DCM>20% MeOH/DCM to provide the title compound (18 mg, 0.031 mmol, 50.8%). LCMS (APCI+) m/z=569.2; retention time 2.40 min.

Example 83

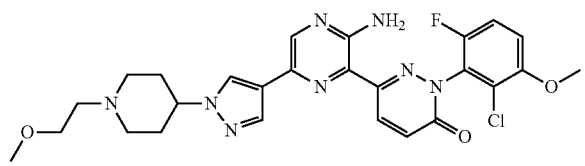

6-(3-amino-6-(1-(1-(2-methoxyethyl)piperidin-4-yl)-
1H-pyrazol-4-yl)pyrazin-2-yl)-2-(2-chloro-6-fluoro-
3-methoxyphenyl)pyridazin-3 (2H)-one Step 1: A mixture of Intermediate L19 (262 mg, 0.620 mmol), Intermediate $R^{28}$ (236 mg, 0.620 mmol), $K_2CO_3$ (2 M, 930 μL, 1.86 mmol) and $Pd(Ph_3P)_4$ (35.8 mg, 0.031 mmol) in dioxane (3.1 mL, 0.62 mmol) was sparged with nitrogen and heated at 80° C. for 3 h. The reaction was partitioned between ethyl acetate and water. The combined organic layers were dried over $Na_2SO_4$, filtered and concentrated. The residue was purified by flash chromatography eluting with a hexane/Ethyl acetate gradient of 0-100% to provide tert-butyl 4-(4-(5-amino-6-(1-(2-chloro-6-fluoro-3-methoxyphenyl)-6-oxo-1,6-dihydropyridazin-3-yl)pyrazin-2-yl)-1H-pyrazol-1-yl)piperidine-1-carboxylate. LCMS (APCI+) m/z=597.2 (100%), 599.2 (40%); retention time 3.38 min.

Step 2: tert-butyl 4-(4-(5-amino-6-(1-(2-chloro-6-fluoro-3-methoxyphenyl)-6-oxo-1,6-dihydropyridazin-3-yl)pyrazin-2-yl)-1H-pyrazol-1-yl)piperidine-1-carboxylate was treated with 1:1 DCM/TFA (20 mL) for 1 h. The solution was concentrated and 5 mL of 6N HCl/iPrOH and 5 mL of MeOH was added. The mixture was stirred for 1 h to form a white slurry and the suspension was concentrated. LCMS (APCI+) m/z=497.0 (100%), 499.0 (40%); retention time 2.33 min.

Step 3: To a suspension of 6-(3-amino-6-(1-(piperidin-4-yl)-1H-pyrazol-4-yl)pyrazin-2-yl)-2-(2-chloro-6-fluoro-3-methoxyphenyl)pyridazin-3(2H)-one (25.3 mg, 0.051 mmol) and $K_2CO_3$ (35.2 mg, 0.255 mmol) in DMF (1.0 ml, 0.051 mmol) was added 2-bromoethyl methyl ether (5.74 μl, 0.06 mmol) and the resulting mixture was stirred at RT for 1d. The crude reaction mixture was loaded onto a silica column equilibrated with hexanes and eluted with hexanes>DCM>20% MeOH/DCM to provide the title compound (12 mg, 0.021 mmol, 42%). LCMS (APCI+) m/z=555.2; retention time 2.388.

Biological Activity

Example A

Enzyme Assay

FGFR1, 2 and 3 kinase activity was measured by the Invitrogen LanthaScreen™ Assay technology which directly measures the amount of substrate phosphorylation by TR-FRET using a fluorescein-labeled peptide and Europium-labeled antibody.

To measure FGFR1 kinase activity, 200 pM His-tagged recombinant human FGFR1 catalytic domain (amino acids 308-731) (Life Technologies Cat. No. PR4660A) was incubated with 100 nM Alexa Fluor® 647-Poly-GT Peptide Substrate (Life Technologies Cat. No. PV5836) and ATP in the presence of $Mg^{++}$, along with test compound in a buffer consisting of 250 mM HEPES, 25 mM $MgCl_2$, 0.05% TritonX-100, pH 7.5, and 2% DMSO. Compounds were typically prepared in a threefold serial dilution in DMSO and added to the assay to give the appropriate final concentration. After 20 minutes incubation at 22° C., an equal volume of 2 nM LanthaScreen® Eu-PY20 Antibody (Life Technologies Cat. No. PV5691) and EDTA were added to quench the kinase reaction and start the detection reaction. After an additional 60 minute incubation at 22° C., the reaction was measured using a PerkinElmer EnVision multimode plate reader via TR-FRET dual wavelength detection, and the percent of control (POC) calculated using a ratiometric emission factor. 100 POC is determined using no test compound and 0 POC is determined using no enzyme. The POC values were fit to a 4 parameter logistic curve and the $IC_{50}$ value is point where the curve crosses 50 POC.

To measure FGFR2 kinase activity: 200 pM His-tagged recombinant human FGFR2 cytoplasmic domain (amino acids 403-822), (Life Technologies Cat. No. PR5332A); 20 minutes incubation at 22° C., 60 minute detection incubation at 22° C.

To measure FGFR3 kinase activity: 750 pM N-terminal GST-HIS6 fusion protein with a 3C cleavage site recombinant human FGFR3 (amino acids R397-T806) (ProQinase Cat. No. 1068-0000-1); 10 minutes incubation at 22° C., 60 minute detection incubation at 22° C.

The averaged $IC_{50}$ values for the compounds tested in this assay are provided in Table F.

TABLE F $IC_{50}$'s of compounds tested in the assay of Example A

| Ex. # | FGFR1 Enz FRET IC50 (nM) [AVERAGE] | FGFR2 Enz FRET IC50 (nM) [AVERAGE] | FGFR3 Enz FRET IC50 (nM) [AVERAGE] |
|---|---|---|---|
| 1 | 18.1 | 3.4 | 4.3 |
| 2 | 259.6 | 60.4 | 69.1 |
| 3 | 4749.7 | 1963.4 | 4121.7 |
| 4 | 15.4 | 2.8 | 2.4 |
| 5 | 17.0 | 3.2 | 2.9 |
| 6 | 22.2 | 6.4 | 11.2 |
| 7 | 14.5 | 6.5 | 10.7 |
| 8 | N/A | 120.0 | 176.7 |
| 9 | N/A | 1055.6 | 4251.3 |
| 10 | N/A | 214.7 | 293.0 |
| 11 | 143.2 | 23.7 | 22.6 |
| 12 | 838.2 | 150.6 | 191.5 |
| 13 | 316.3 | 64.3 | 15.1 |
| 14 | 6.3 | 1.6 | 1.7 |
| 15 | 17.4 | 3.7 | 7.0 |
| 16 | 22.8 | 5.6 | 10.6 |
| 17 | 79.2 | 10.2 | 3.8 |
| 18 | 47.7 | 8.5 | 8.7 |
| 19 | 15.1 | 2.8 | 2.2 |
| 20 | 399.9 | 39.8 | 61.5 |
| 21 | 39.1 | 7.5 | 4.9 |
| 22 | 192.5 | 21.1 | 6.7 |
| 23 | 3.8 | 5.5 | 2.8 |
| 24 | 15.0 | 1.8 | 4.0 |
| 25 | 51.1 | 6.6 | 11.8 |
| 26 | 8.6 | 2.2 | 4.3 |
| 27 | 19.0 | 1.9 | 8.2 |
| 28 | 17.0 | 2.3 | 4.7 |
| 29 | 22.0 | 3.7 | 7.1 |
| 30 | 14.1 | 2.9 | 6.5 |
| 31 | 7.7 | 1.4 | 3.9 |
| 32 | 9.2 | 1.3 | 1.8 |
| 33 | 11.6 | 1.8 | 4.5 |
| 34 | 38.4 | 3.7 | 13.4 |
| 35 | 15.4 | 3.2 | 4.8 |
| 36 | 62.8 | 6.2 | 21.3 |
| 37 | 56.0 | 19.2 | 23.5 |
| 38 | 91.5 | 16.8 | 21.1 |
| 39 | 141.8 | 9.4 | 28.6 |
| 40 | 49.7 | 2.9 | 10.2 |
| 41 | 3.0 | 0.8 | 3.2 |
| 42 | 6.3 | 1.4 | 8.6 |
| 43 | 7.0 | 1.6 | 1.7 |
| 44 | 7.1 | 1.4 | 6.2 |
| 45 | 1561.6 | 825.7 | 1086.6 |
| 46 | 3101.2 | 1231.5 | 3604.1 |
| 47 | 5.6 | 1.6 | 1.5 |
| 48 | 3.1 | 1.0 | 1.4 |
| 49 | 6.0 | 1.3 | 2.1 |
| 50 | 3.5 | 0.9 | 1.8 |
| 51 | 4.0 | 0.6 | 1.0 |
| 52 | 26.8 | 5.0 | 42.5 |
| 53 | 193.4 | 72.3 | 35.6 |
| 54 | 29.6 | 10.9 | 10.1 |
| 55 | 31.4 | 6.3 | 19.9 |
| 56 | 43.3 | 7.5 | 5.7 |
| 57 | 13.8 | 5.8 | 6.2 |
| 58 | 4.4 | 2.4 | 0.7 |
| 59 | 5.0 | 6.6 | 10.6 |
| 60 | 11.6 | 1.5 | 10.3 |
| 61 | 98.2 | 24.1 | 13.7 |
| 62 | 231.3 | 31.2 | 166.2 |
| 63 | 14.0 | 16.0 | 53.5 |
| 64 | 61.4 | 42.1 | 213.7 |
| 65 | 8.9 | 2.9 | 35.0 |
| 66 | 5.6 | 7.8 | 3.9 |
| 67 | 9.1 | 6.5 | 13.3 |
| 68 | 9.8 | 11.1 | 6.4 |
| 69 | 7.2 | 9.6 | 9.6 |
| 70 | 30.9 | 54.4 | 30.8 |
| 71 | 26.5 | 38.8 | 45.1 |
| 72 | 7.3 | 9.3 | 5.2 |
| 73 | 7.2 | 10.6 | 6.0 |
| 74 | 5.8 | 9.5 | 6.1 |
| 75 | 8.0 | 11.3 | 10.2 |
| 76 | 10.6 | 3.85 | 7.1 |
| 77 | 16.1 | 6.2 | 12.4 |
| 78 | 9.8 | 3.7 | 6.9 |
| 79 | 17.3 | 6.3 | 10.7 |
| 80 | 57.0 | 16.3 | 50.6 |
| 81 | 3.6 | 1.1 | 11.4 |
| 82 | 2.4 | 3.1 | 2.2 |
| 83 | 6.9 | 16.6 | 26.5 |

N/A = Not available

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is claimed is:

1. A compound of the general Formula I:

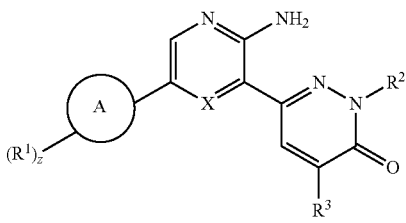

and pharmaceutically acceptable salts thereof, wherein:

X is N or CH;

Ring A is a 5-membered heteroaryl ring having 1-2 ring nitrogen atoms;

z is 1, 2 or 3;

each $R^1$ is independently selected from the group consisting of:
(a) hydrogen;
(b) C1-C6 alkyl optionally substituted with 1-3 fluoros,
(c) hydroxy(C1-C6 alkyl)- optionally substituted with 1-3 fluoros,
(d) dihydroxy(C1-C6 alkyl)- optionally substituted with 1-3 fluoros,
(e) cyano(C1-C6 alkyl)-,
(f) $R^aR^bN$(C1-C6 alkyl)-,
(g) (C1-C3 alkoxy)C1-C6 alkyl- optionally substituted with 1-3 fluoros,
(h) (C3-C6 cycloalkyl)(CH$_2$)$_n$— where n is 0-3 and said cycloalkyl is optionally substituted with CN, OH, $R^aR^bN$—, (1-3C)alkyl, or (1-3C)alkoxy;
(i) hetCyc$^1$(CH$_2$)$_m$— where m is 0-3,
(j) hetCyc$^2$(CH$_2$)$_p$— where p is 0 or 1,
(k) hetAr$^1$(CH$_2$)$_q$— where q is 1 or 2,
(l) halogen, and
(m) hetCyc$^1$C(=O)CH$_2$—;

hetCyc$^1$ is a 4-7 membered saturated heterocyclic ring having 1-2 ring heteroatoms independently selected from N and O, wherein said heterocyclic ring is optionally substituted with one or more substituents independently selected from the group consisting of fluoro, HO, C1-C6 alkyl (optionally substituted with 1-3 fluoros), (C1-C6 alkoxy)C1-C6 alkyl- (optionally substituted with 1-3 fluoros), (C3-C6 cycloalkoxy)C1-C6 alkyl-, hydroxy(C1-C6 alkyl)-, $R^cR^dN$- and (C1-C6 alkyl)C(=O)—;

hetCyc$^2$ is a 7-10 membered heterospirocyclic ring having 1-2 ring heteroatoms independently selected from N and O, wherein said heterospirocyclic ring is optionally substituted with one or more substituents independently selected from the group consisting of C1-C6 alkyl (optionally substituted with 1-3 fluoros), (C1-C6 alkoxy)C1-C6 alkyl- (optionally substituted with 1-3 fluoros), (C3-C6 cycloalkoxy)C1-C6 alkyl-, hydroxy (C1-C6 alkyl)-, $R^cR^dN$- and (C1-C6 alkyl)C(=O)—;

hetAr$^1$ is a 6-membered heteroaryl ring having 1-2 ring nitrogen atoms, wherein said ring is optionally substituted with one or more substituents independently selected from C1-C6 alkyl and halogen;

$R^2$ is AO or hetAr$^2$;

Ar$^1$ is phenyl substituted with one or more groups independently selected from halogen, cyano, C1-C3 alkyl, C1-C3 alkoxy, (C1-C3 alkyl)NHC(=O)—, (C1-C3 alkyl)C(=O)NH—, (cyclopropyl)C(=O)NH— and (cyclopropyl)NHC(=O)—, wherein each of said C1-C3 alkyl and C1-C3 alkoxy portions is optionally substituted with 1-3 fluoros;

hetAr$^2$ is a 6-10 membered heteroaryl ring having 1-2 ring nitrogen atoms, wherein said ring is optionally substituted with one or more groups independently selected from halogen, C1-C3 alkyl, C1-C3 alkoxy, (C1-C3 alkyl)NHC(=O)—, (C1-C3 alkyl)C(=O)NH—, (C3-C4 cycloalkyl)C(=O)NH- and (C3-C4 cycloalkyl)NHC(=O)—, wherein each of said C1-C3 alkyl and C1-C3 alkoxy portions is optionally substituted with 1-3 fluoros;

$R^3$ is H, C1-C4 alkyl or (C3-C4)cycloalkyl; and $R^a$, $R^b$, $R^c$ and $R^d$ are independently hydrogen or C1-C6 alkyl optionally substituted with F, OH or C1-C6 alkoxy.

2. A compound according to claim 1, wherein X is N.

3. A compound according to claim 1, wherein X is CH.

4. A compound according to claim 1, wherein $R^2$ is Ar$^1$.

5. A compound according to claim 1, wherein $R^2$ is hetAr$^2$.

6. A compound according to claim 1, wherein Ring A is pyrazolyl.

7. A compound according to claim 1, wherein $R^3$ is hydrogen.

8. A compound according to claim 1, wherein $R^3$ is C1-C4 alkyl.

9. A compound according to claim 1, wherein $R^3$ is (C3-C4)cycloalkyl.

10. A compound according to claim 1, wherein each occurrence of $R^1$ is hydrogen.

11. A compound according to claim 1, wherein each occurrence of $R^1$ is C1-C6 alkyl optionally substituted with 1-3 fluoros.

12. A compound according to claim 1, wherein each occurrence of $R^1$ is hydroxy(C1-C6 alkyl)- optionally substituted with 1-3 fluoros.

13. A compound according to claim 1, wherein each occurrence of $R^1$ is dihydroxy(C1-C6 alkyl)- optionally substituted with 1-3 fluoros.

14. A compound according to claim 1, wherein each occurrence of $R^1$ is cyano(C1-C6 alkyl)-.

15. A compound according to claim 1, wherein each occurrence of $R^1$ is $R^a R^b N$(C1-C6 alkyl)-, where $R^a$ and $R^b$ are independently hydrogen or C1-C6 alkyl optionally substituted with F, OH or C1-C6 alkoxy.

16. A compound according to claim 1, wherein each occurrence of $R^1$ is (C1-C3 alkoxy)C1-C6 alkyl- optionally substituted with 1-3 fluoros.

17. A compound according to claim 1, wherein each occurrence of $R^1$ is (C3-C6 cycloalkyl)$(CH_2)_n$— where n is 0-3 and said cycloalkyl is optionally substituted with CN, OH, $R^a R^b N$—, (1-3C)alkyl or (1-3C)alkoxy.

18. A compound according to claim 1, wherein each occurrence of $R^1$ is $hetCyc^1(CH_2)_m$—, where m is 0-3, and $hetCyc^1$ is a 4-7 membered saturated heterocyclic ring having 1-2 ring heteroatoms independently selected from N and O, wherein said heterocyclic ring is optionally substituted with one or more substituents independently selected from the group consisting of fluoro, HO, C1-C6 alkyl (optionally substituted with 1-3 fluoros), (C1-C6 alkoxy) C1-C6 alkyl- (optionally substituted with 1-3 fluoros), (C3-C6 cycloalkoxy)C1-C6 alkyl-, hydroxy(C1-C6 alkyl)-, $R^c R^d N$- and (C1-C6 alkyl)C(=O)—.

19. A compound according to claim 1, wherein each occurrence of $R^1$ is $hetCyc^2(CH_2)_p$— where p is 0 or 1, and $hetCyc^2$ is a 7-10 membered heterospirocyclic ring having 1-2 ring heteroatoms independently selected from N and O, wherein said heterospirocyclic ring is optionally substituted with one or more substituents independently selected from the group consisting of C1-C6 alkyl (optionally substituted with 1-3 fluoros), (C1-C6 alkoxy)C1-C6 alkyl- (optionally substituted with 1-3 fluoros), (C3-C6 cycloalkoxy)C1-C6 alkyl-, hydroxy(C1-C6 alkyl)-, $R^c R^d N$- and (C1-C6 alkyl) C(=O)—.

20. A compound according to claim 1, wherein each occurrence of $R^1$ is $hetAr^1(CH_2)_q$— where q is 1 or 2 and $hetAr^1$ is a 6-membered heteroaryl ring having 1-2 ring nitrogen atoms, wherein said ring is optionally substituted with one or more substituents independently selected from C1-C6 alkyl and halogen.

21. A compound according to claim 1, wherein each occurrence of $R^1$ is halogen.

22. A compound according to claim 1, wherein each occurrence of $R^1$ is $hetCyc^1C(=O)CH_2$—.

23. A compound according to claim 10, wherein z is 2 or 3.

24. A compound according to claim 1, wherein z is 1.

25. A compound of claim 1, wherein the compound is selected from the group consisting:

| Example # | Structure | Name |
|---|---|---|
| 1 | 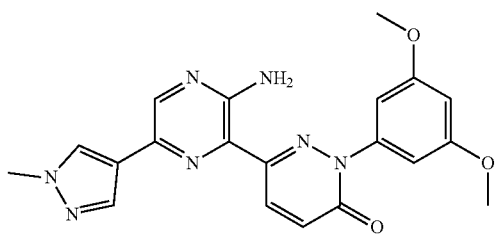 | 6-(3-amino-6-(1-methyl-1H-pyrazol-4-yl)pyrazin-2-yl)-2-(3,5-dimethoxyphenyl)pyridazin-3(2H)-one |
| 2 | 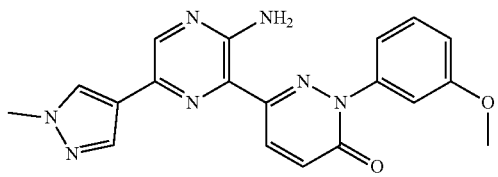 | 6-(3-amino-6-(1-methyl-1H-pyrazol-4-yl)pyrazin-2-yl)-2-(3-methoxyphenyl)pyridazin-3(2H)-one |
| 3 | 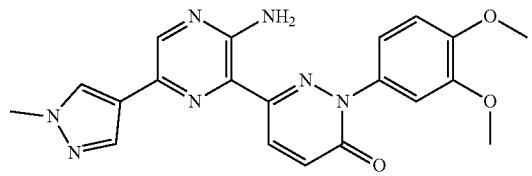 | 6-(3-amino-6-(1-methyl-1H-pyrazol-4-yl)pyrazin-2-yl)-2-(3,4-dimethoxyphenyl)pyridazin-3(2H)-one |

-continued

| Example # | Structure | Name |
|---|---|---|
| 4 | 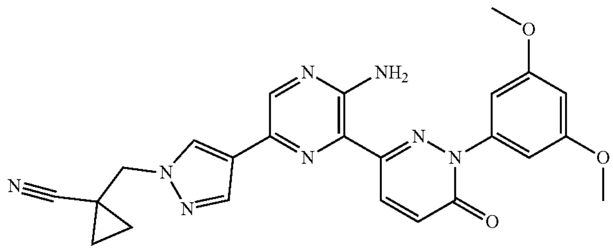 [SMILES: COc1cc(OC)cc(-n2nc(-c3nc(-c4cnn(CC5(C#N)CC5)c4)cnc3N)ccc2=O)c1] | 1-((4-(5-amino-6-(1-(3,5-dimethoxyphenyl)-6-oxo-1,6-dihydropyridazin-3-yl)pyrazin-2-yl)-1H-pyrazol-1-yl)methyl)cyclopropane-1-carbonitrile |
| 5 | 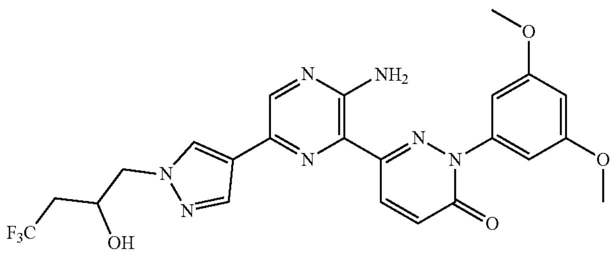 [SMILES: COc1cc(OC)cc(-n2nc(-c3nc(-c4cnn(CC(O)CC(F)(F)F)c4)cnc3N)ccc2=O)c1] | 6-(3-amino-6-(1-(4,4,4-trifluoro-2-hydroxybutyl)-1H-pyrazol-4-yl)pyrazin-2-yl)-2-(3,5-dimethoxyphenyl)pyridazin-3(2H)-one |
| 6 | 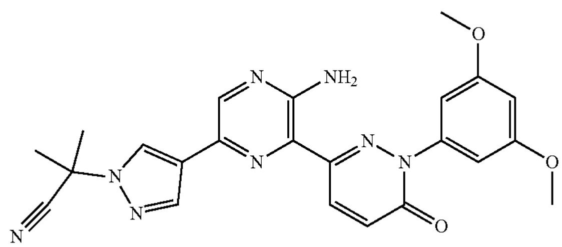 [SMILES: COc1cc(OC)cc(-n2nc(-c3nc(-c4cnn(C(C)(C)C#N)c4)cnc3N)ccc2=O)c1] | 2-(4-(5-amino-6-(1-(3,5-dimethoxyphenyl)-6-oxo-1,6-dihydropyridazin-3-yl)pyrazin-2-yl)-1H-pyrazol-1-yl)-2-methylpropanenitrile |
| 7 | 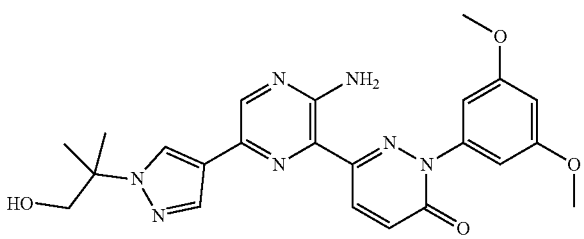 [SMILES: COc1cc(OC)cc(-n2nc(-c3nc(-c4cnn(C(C)(C)CO)c4)cnc3N)ccc2=O)c1] | 6-(3-amino-6-(1-(1-hydroxy-2-methylpropan-2-yl)-1H-pyrazol-4-yl)pyrazin-2-yl)-2-(3,5-dimethoxyphenyl)pyridazin-3(2H)-one |
| 8 | 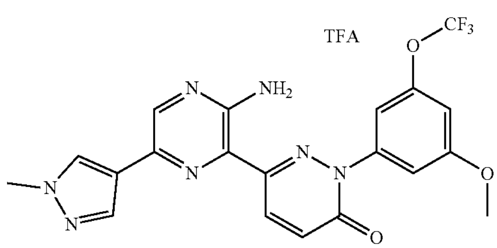 | 6-(3-amino-6-(1-methyl-1H-pyrazol-4-yl)pyrazin-2-yl)-2-(3-methoxy-5-(trifluoromethoxy)phenyl)pyridazin-3(2H)-one 2,2,2-trifluoroacetate salt |
| 9 | 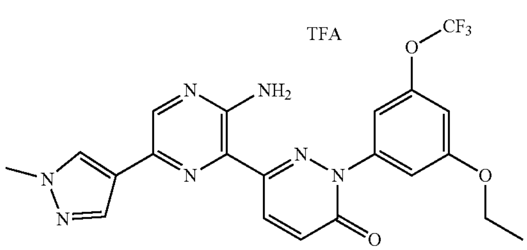 [SMILES: CCOc1cc(OC(F)(F)F)cc(-n2nc(-c3nc(-c4cnn(C)c4)cnc3N)ccc2=O)c1] | 6-(3-amino-6-(1-methyl-1H-pyrazol-4-yl)pyrazin-2-yl)-2-(3-ethoxy-5-(trifluoromethoxy)phenyl)pyridazin-3(2H)-one 2,2,2-trifluoroacetate salt |

-continued

| Example # | Structure | Name |
|---|---|---|
| 10 | TFA | 6-(3-amino-6-(1-methyl-1H-pyrazol-4-yl)pyrazin-2-yl)-2-(3-methoxy-5-(trifluoromethyl)phenyl)pyridazin-3(2H)-one 2,2,2-trifluoroacetate salt |
| 11 | TFA | 6-(3-amino-6-(1-methyl-1H-pyrazol-4-yl)pyrazin-2-yl)-2-(2-chloro-3-methoxyphenyl)pyridazin-3(2H)-one 2,2,2-trifluoroacetate salt |
| 12 | TFA | 6-(3-amino-6-(1-methyl-1H-pyrazol-4-yl)pyrazin-2-yl)-2-(o-tolyl)pyridazin-3(2H)-one 2,2,2-trifluoroacetate salt |
| 13 | TFA | 3-(3-(3-amino-6-(1-methyl-1H-pyrazol-4-yl)pyrazin-2-yl)-6-oxopyridazin-1(6H)-yl)-5-methoxybenzonitrile 2,2,2-trifluoroacetate salt |
| 14 | TFA | 6-(3-amino-6-(1-methyl-1H-pyrazol-4-yl)pyrazin-2-yl)-2-(2-chloro-3,5-dimethoxyphenyl)pyridazin-3(2H)-one (2,2,2-trifluoroacetate) salt |
| 15 | TFA | 6-(3-amino-6-(1-isopropyl-1H-pyrazol-4-yl)pyrazin-2-yl)-2-(3,5-dimethoxyphenyl)pyridazin-3(2H)-one 2,2,2-trifluoroacetate |

-continued

| Example # | Structure | Name |
|---|---|---|
| 16 | 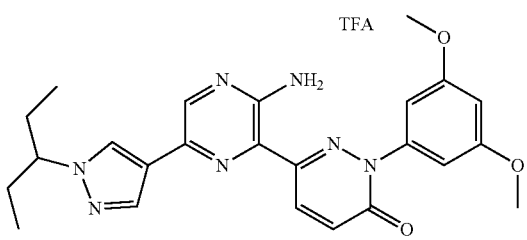 [SMILES: CCC(CC)n1cc(-c2cnc(N)c(-c3ccc(=O)n(-c4cc(OC)cc(OC)c4)n3)n2)cn1] | 6-(3-amino-6-(1-(pentan-3-yl)-1H-pyrazol-4-yl)pyrazin-2-yl)-2-(3,5-dimethoxyphenyl)pyridazin-3(2H)-one 2,2,2-trifluoroacetate salt |
| 17 | 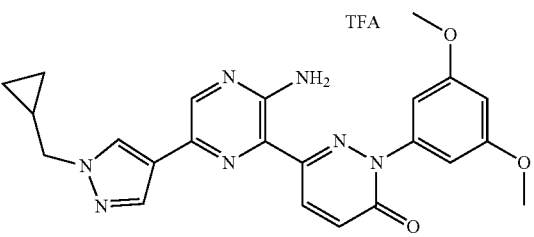 [SMILES: COc1cc(OC)cc(-n2nc(-c3nc(-c4cnn(CC5CC5)c4)cnc3N)ccc2=O)c1] | 6-(3-amino-6-(1-(cyclopropylmethyl)-1H-pyrazol-4-yl)pyrazin-2-yl)-2-(3,5-dimethoxyphenyl)pyridazin-3(2H)-one 2,2,2-trifluoroacetate salt |
| 18 | 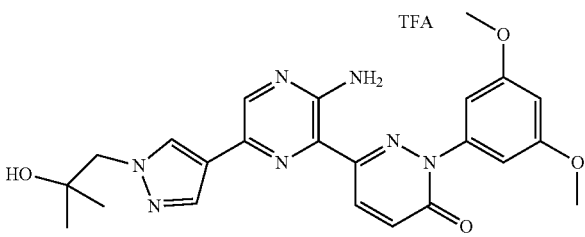 [SMILES: COc1cc(OC)cc(-n2nc(-c3nc(-c4cnn(CC(C)(C)O)c4)cnc3N)ccc2=O)c1] | 6-(3-amino-6-(1-(2-hydroxy-2-methylpropyl)-1H-pyrazol-4-yl)pyrazin-2-yl)-2-(3,5-dimethoxyphenyl)pyridazin-3(2H)-one 2,2,2-trifluoroacetate salt |
| 19 | 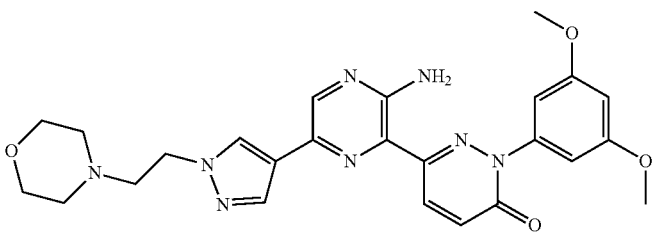 [SMILES: COc1cc(OC)cc(-n2nc(-c3nc(-c4cnn(CCN5CCOCC5)c4)cnc3N)ccc2=O)c1] | 6-(3-amino-6-(1-(2-morpholinoethyl)-1H-pyrazol-4-yl)pyrazin-2-yl)-2-(3,5-dimethoxyphenyl)pyridazin-3(2H)-one |
| 20 | 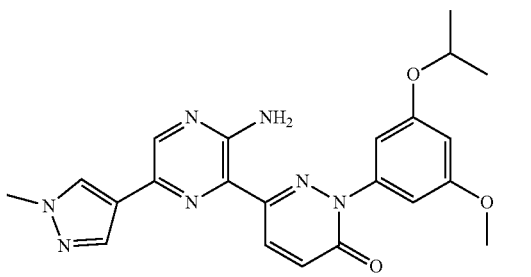 [SMILES: COc1cc(OC(C)C)cc(-n2nc(-c3nc(-c4cnn(C)c4)cnc3N)ccc2=O)c1] | 6-(3-amino-6-(1-methyl-1H-pyrazol-4-yl)pyrazin-2-yl)-2-(3-isopropoxy-5-methoxyphenyl)pyridazin-3(2H)-one |
| 21 | 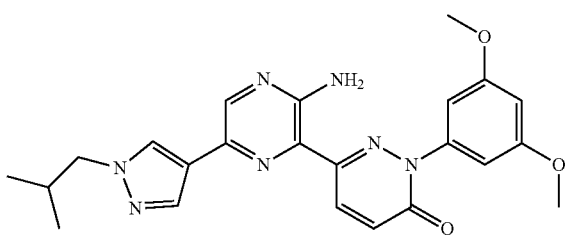 [SMILES: COc1cc(OC)cc(-n2nc(-c3nc(-c4cnn(CC(C)C)c4)cnc3N)ccc2=O)c1] | 6-(3-amino-6-(1-isobutyl-1H-pyrazol-4-yl)pyrazin-2-yl)-2-(3,5-dimethoxyphenyl)pyridazin-3(2H)-one |

-continued

| Example # | Structure | Name |
|---|---|---|
| 22 | 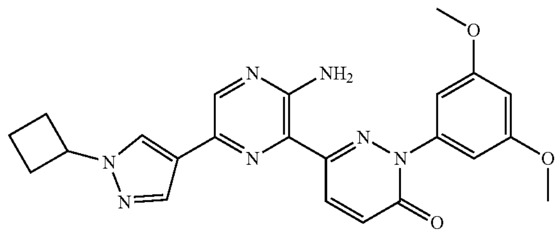 [SMILES: COc1cc(OC)cc(-n2nc(-c3nc(-c4cnn(C5CCC5)c4)cnc3N)ccc2=O)c1] | 6-(3-amino-6-(1-cyclobutyl-1H-pyrazol-4-yl)pyrazin-2-yl)-2-(3,5-dimethoxyphenyl)pyridazin-3(2H)-one |
| 23 | 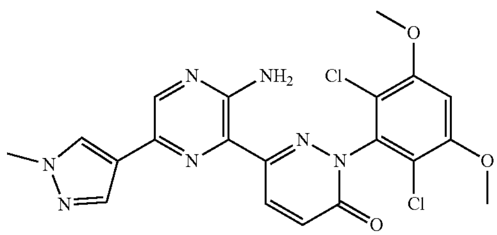 | 6-(3-amino-6-(1-methyl-1H-pyrazol-4-yl)pyrazin-2-yl)-2-(2,6-dichloro-3,5-dimethoxyphenyl)pyridazin-3(2H)-one |
| 24 | 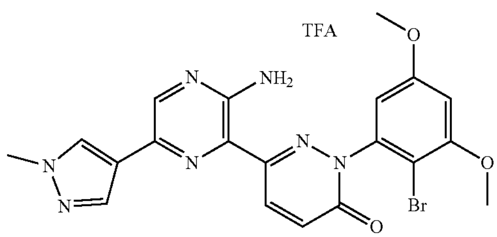 | 6-(3-amino-6-(1-methyl-1H-pyrazol-4-yl)pyrazin-2-yl)-2-(2-bromo-3,5-dimethoxyphenyl)pyridazin-3(2H)-one 2,2,2-trifluoroacetate salt |
| 25 | 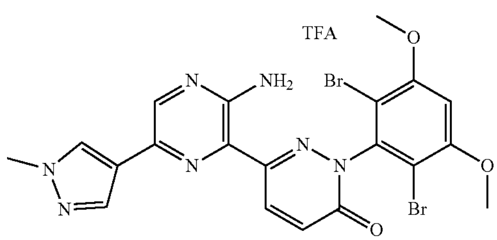 | 6-(3-amino-6-(1-methyl-1H-pyrazol-4-yl)pyrazin-2-yl)-2-(2,6-dibromo-3,5-dimethoxyphenyl)pyridazin-3(2H)-one 2,2,2-trifluoroacetate salt |
| 26 | 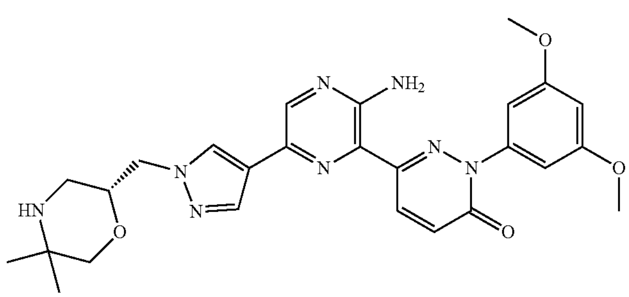 | (R)-6-(3-amino-6-(1-((5,5-dimethylmorpholin-2-yl)methyl)-1H-pyrazol-4-yl)pyrazin-2-yl)-2-(3,5-dimethoxyphenyl)pyridazin-3(2H)-one |
| 27 | 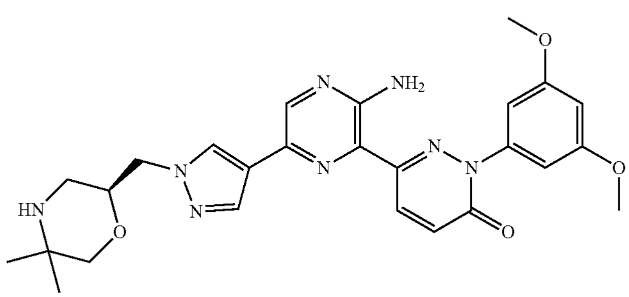 | (S)-6-(3-amino-6-(1-((5,5-dimethylmorpholin-2-yl)methyl)-1H-pyrazol-4-yl)pyrazin-2-yl)-2-(3,5-dimethoxyphenyl)pyridazin-3(2H)-one |

| Example # | Structure | Name |
|---|---|---|
| 28 | 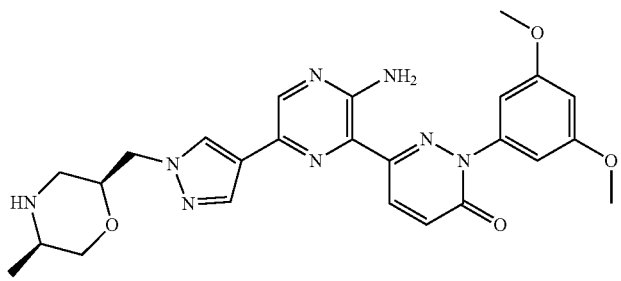 | 6-(3-amino-6-(1-(((2S,5R)-5-methylmorpholin-2-yl)methyl)-1H-pyrazol-4-yl)pyrazin-2-yl)-2-(3,5-dimethoxyphenyl)pyridazin-3(2H)-one |
| 29 | 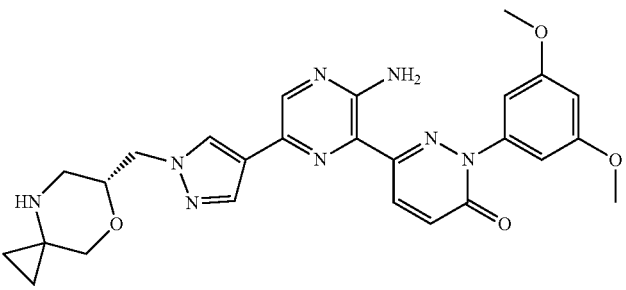 [SMILES: COc1cc(OC)cc(-n2nc(-c3nc(-c4cnn(C[C@H]5CNC6(CC6)CO5)c4)cnc3N)ccc2=O)c1] | (R)-6-(6-(1-((7-oxa-4-azaspiro[2.5]octan-6-yl)methyl)-1H-pyrazol-4-yl)-3-aminopyrazin-2-yl)-2-(3,5-dimethoxyphenyl)pyridazin-3(2H)-one |
| 30 | 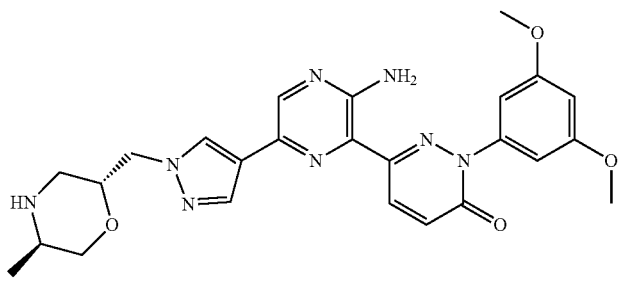 | 6-(3-amino-6-(1-(((2R,5R)-5-methylmorpholin-2-yl)methyl)-1H-pyrazol-4-yl)pyrazin-2-yl)-2-(3,5-dimethoxyphenyl)pyridazin-3(2H)-one |
| 31 | 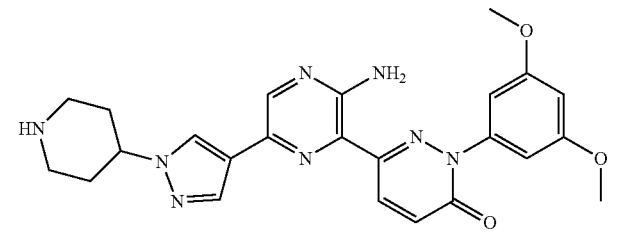 [SMILES: COc1cc(OC)cc(-n2nc(-c3nc(-c4cnn(C5CCNCC5)c4)cnc3N)ccc2=O)c1] | 6-(3-amino-6-(1-(piperidin-4-yl)-1H-pyrazol-4-yl)pyrazin-2-yl)-2-(3,5-dimethoxyphenyl)pyridazin-3(2H)-one |
| 32 | 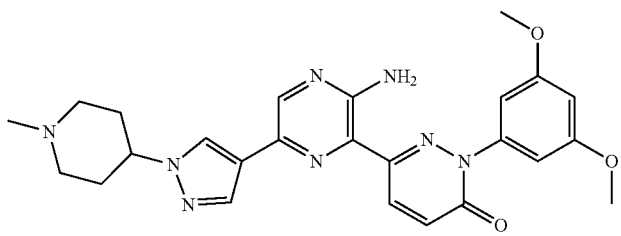 | 6-(3-amino-6-(1-(1-methylpiperidin-4-yl)-1H-pyrazol-4-yl)pyrazin-2-yl)-2-(3,5-dimethoxyphenyl)pyridazin-3(2H)-one |

| Example # | Structure | Name |
|---|---|---|
| 33 | 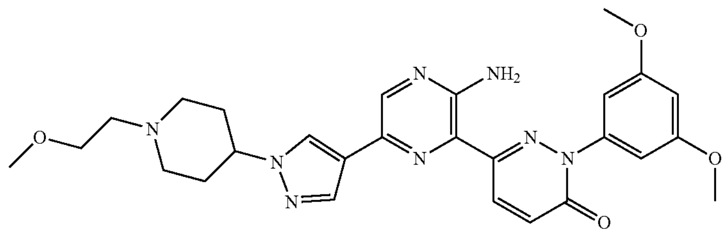 | 6-(3-amino-6-(1-(1-(2-methoxyethyl)piperidin-4-yl)-1H-pyrazol-4-yl)pyrazin-2-yl)-2-(3,5-dimethoxyphenyl)pyridazin-3(2H)-one |
| 34 | 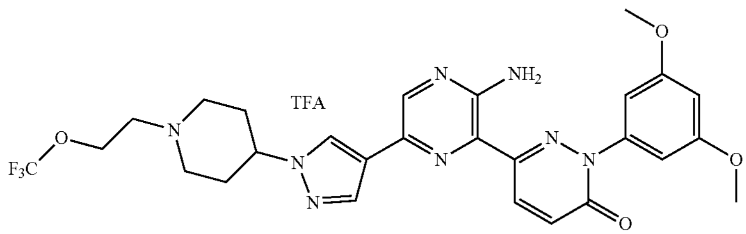 [SMILES: COc1cc(OC)cc(-n2nc(-c3nc(-c4cnn(C5CCN(CCOC(F)(F)F)CC5)c4)cnc3N)ccc2=O)c1] | 6-(3-amino-6-(1-(1-(2-(trifluoromethoxy)ethyl)piperidin-4-yl)-1H-pyrazol-4-yl)pyrazin-2-yl)-2-(3,5-dimethoxyphenyl)pyridazin-3(2H)-one 2,2,2-trifluoroacetate salt |
| 35 | 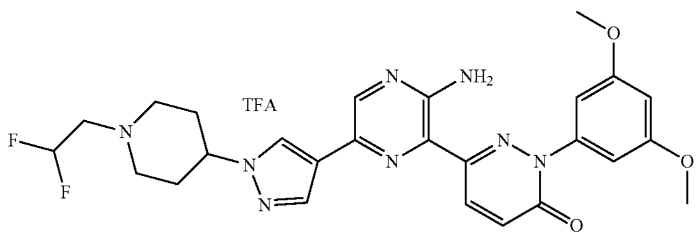 [SMILES: COc1cc(OC)cc(-n2nc(-c3nc(-c4cnn(C5CCN(CC(F)F)CC5)c4)cnc3N)ccc2=O)c1] | 6-(3-amino-6-(1-(1-(2,2-difluoroethyl)piperidin-4-yl)-1H-pyrazol-4-yl)pyrazin-2-yl)-2-(3,5-dimethoxyphenyl)pyridazin-3(2H)-one 2,2,2-trifluoroacetate salt |
| 36 | 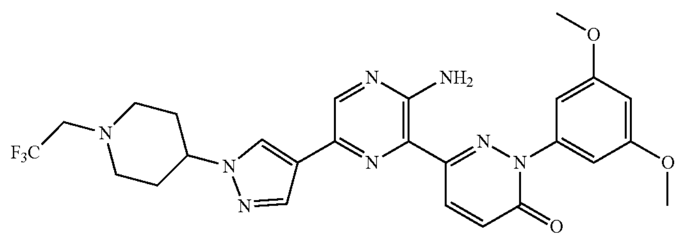 [SMILES: COc1cc(OC)cc(-n2nc(-c3nc(-c4cnn(C5CCN(CC(F)(F)F)CC5)c4)cnc3N)ccc2=O)c1] | 6-(3-amino-6-(1-(1-(2,2,2-trifluoroethyl)piperidin-4-yl)-1H-pyrazol-4-yl)pyrazin-2-yl)-2-(3,5-dimethoxyphenyl)pyridazin-3(2H)-one |
| 37 | 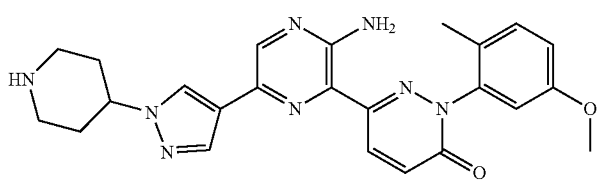 [SMILES: COc1ccc(C)c(-n2nc(-c3nc(-c4cnn(C5CCNCC5)c4)cnc3N)ccc2=O)c1] | 6-(3-amino-6-(1-(piperidin-4-yl)-1H-pyrazol-4-yl)pyrazin-2-yl)-2-(5-methoxy-2-methylphenyl)pyridazin-3(2H)-one |
| 38 | 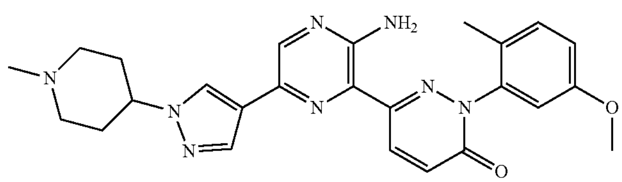 | 6-(3-amino-6-(1-(1-methylpiperidin-4-yl)-1H-pyrazol-4-yl)pyrazin-2-yl)-2-(5-methoxy-2-methylphenyl)pyridazin-3(2H)-one |
| 39 | 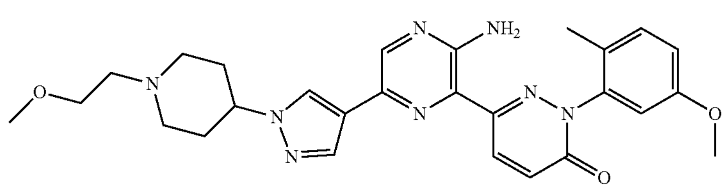 | 6-(3-amino-6-(1-(1-(2-methoxyethyl)piperidin-4-yl)-1H-pyrazol-4-yl)pyrazin-2-yl)-2-(5-methoxy-2-methylphenyl)pyridazin-3(2H)-one 2,2,2-trifluoroacetate salt |

| Example # | Structure | Name |
|---|---|---|
| 40 | 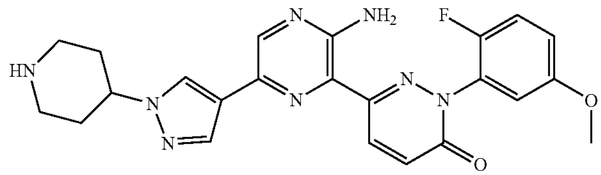 [SMILES: COc1ccc(F)c(-n2nc(-c3nc(-c4cnn(C5CCNCC5)c4)cnc3N)ccc2=O)c1] | 6-(3-amino-6-(1-(piperidin-4-yl)-1H-pyrazol-4-yl)pyrazin-2-yl)-2-(2-fluoro-5-methoxyphenyl)pyridazin-3(2H)-one |
| 41 | 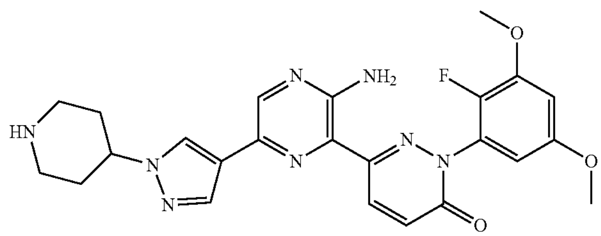 [SMILES: COc1cc(OC)c(F)c(-n2nc(-c3nc(-c4cnn(C5CCNCC5)c4)cnc3N)ccc2=O)c1] | 6-(3-amino-6-(1-(piperidin-4-yl)-1H-pyrazol-4-yl)pyrazin-2-yl)-2-(2-fluoro-3,5-dimethoxyphenyl)pyridazin-3(2H)-one |
| 42 | 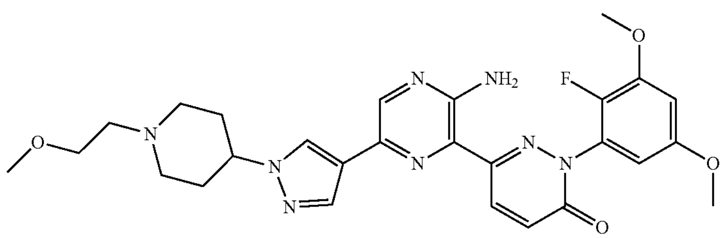 | 6-(3-amino-6-(1-(1-(2-methoxyethyl)piperidin-4-yl)-1H-pyrazol-4-yl)pyrazin-2-yl)-2-(2-fluoro-3,5-dimethoxyphenyl)pyridazin-3(2H)-one 2,2,2-trifluoroacetate salt |
| 43 | 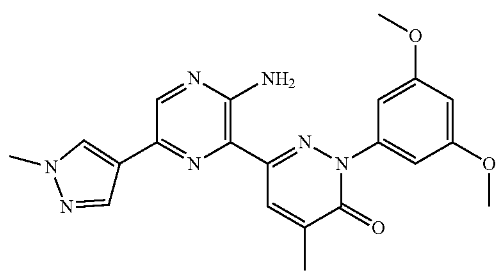 | 6-(3-amino-6-(1-methyl-1H-pyrazol-4-yl)pyrazin-2-yl)-2-(3,5-dimethoxyphenyl)-4-methylpyridazin-3(2H)-one |
| 44 | 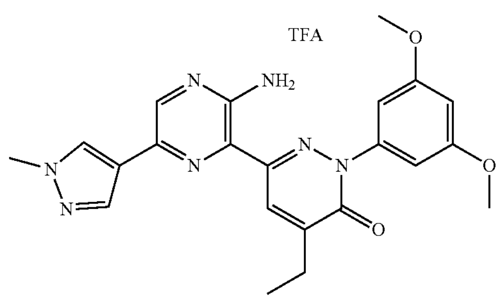 | 6-(3-amino-6-(1-methyl-1H-pyrazol-4-yl)pyrazin-2-yl)-2-(3,5-dimethoxyphenyl)-4-ethylpyridazin-3(2H)-one 2,2,2-trifluoroacetate salt |
| 45 | 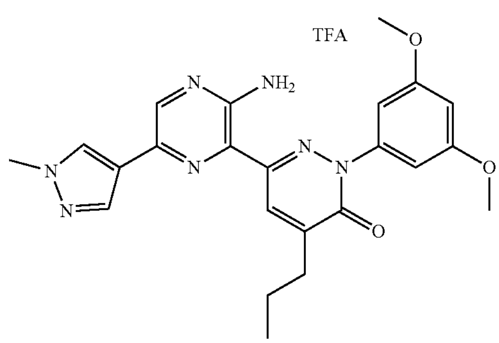 | 6-(3-amino-6-(1-methyl-1H-pyrazol-4-yl)pyrazin-2-yl)-2-(3,5-dimethoxyphenyl)-4-propylpyridazin-3(2H)-one 2,2,2-trifluoroacetate salt |

| Example # | Structure | Name |
|---|---|---|
| 46 | 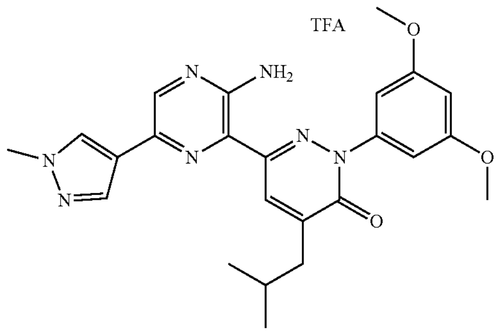 | 6-(3-amino-6-(1-methyl-1H-pyrazol-4-yl)pyrazin-2-yl)-2-(3,5-dimethoxyphenyl)-4-isobutylpyridazin-3(2H)-one 2,2,2-trifluoroacetate salt |
| 47 | 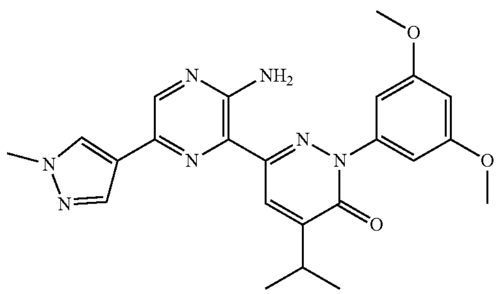 | 6-(3-amino-6-(1-methyl-1H-pyrazol-4-yl)pyrazin-2-yl)-2-(3,5-dimethoxyphenyl)-4-isopropylpyridazin-3(2H)-one |
| 48 | 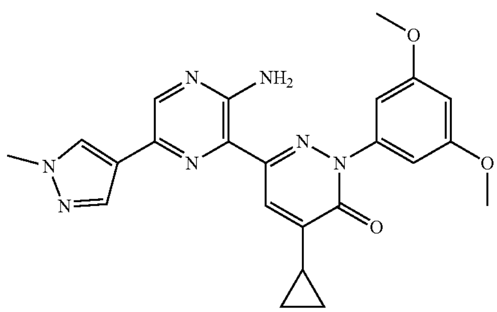 | 6-(3-amino-6-(1-methyl-1H-pyrazol-4-yl)pyrazin-2-yl)-4-cyclopropyl-2-(3,5-dimethoxyphenyl)pyridazin-3(2H)-one |
| 49 | 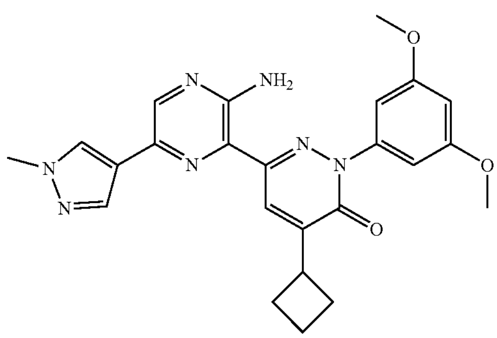 | 6-(3-amino-6-(1-methyl-1H-pyrazol-4-yl)pyrazin-2-yl)-4-cyclobutyl-2-(3,5-dimethoxyphenyl)pyridazin-3(2H)-one |
| 50 | 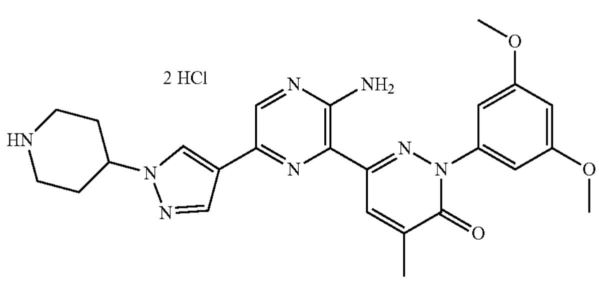 [SMILES: COc1cc(OC)cc(-n2nc(-c3nc(-c4cnn(C5CCNCC5)c4)cnc3N)cc(C)c2=O)c1] | 6-(3-amino-6-(1-(piperidin-4-yl)-1H-pyrazol-4-yl)pyrazin-2-yl)-2-(3,5-dimethoxyphenyl)-4-methylpyridazin-3(2H)-one dihydrochloride salt |

-continued

| Example # | Structure | Name |
|---|---|---|
| 51 | 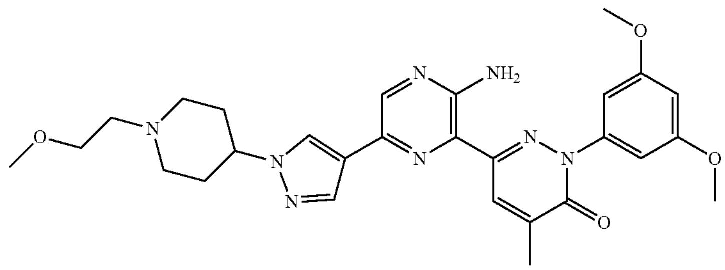 | 6-(3-amino-6-(1-(1-(2-methoxyethyl)piperidin-4-yl)-1H-pyrazol-4-yl)pyrazin-2-yl)-2-(3,5-dimethoxyphenyl)-4-methylpyridazin-3(2H)-one |
| 52 | 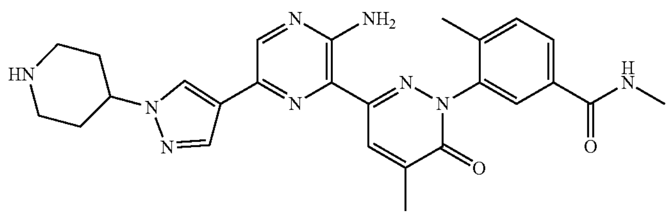 [SMILES: CNC(=O)c1ccc(C)c(-n2nc(-c3nc(-c4cnn(C5CCNCC5)c4)cnc3N)cc(C)c2=O)c1] | 3-(3-(3-amino-6-(1-(piperidin-4-yl)-1H-pyrazol-4-yl)pyrazin-2-yl)-5-methyl-6-oxopyridazin-1(6H)-yl)-N,4-dimethylbenzamide dihydrochloride salt |
| 53 | 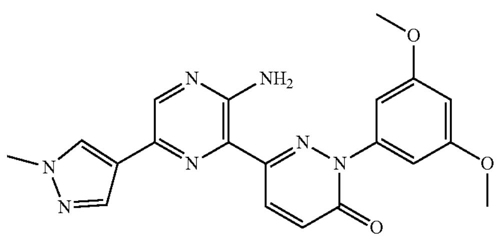 | 6-(2-amino-5-(1-methyl-1H-pyrazol-4-yl)pyridin-3-yl)-2-(3,5-dimethoxyphenyl)pyridazin-3(2H)-one |
| 54 | 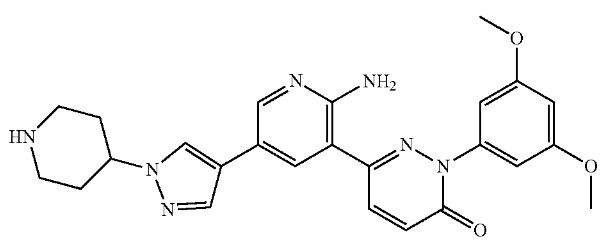 [SMILES: COc1cc(OC)cc(-n2nc(-c3cc(-c4cnn(C5CCNCC5)c4)cnc3N)ccc2=O)c1] | 6-(2-amino-5-(1-(piperidin-4-yl)-1H-pyrazol-4-yl)pyridin-3-yl)-2-(3,5-dimethoxyphenyl)pyridazin-3(2H)-one |
| 55 | 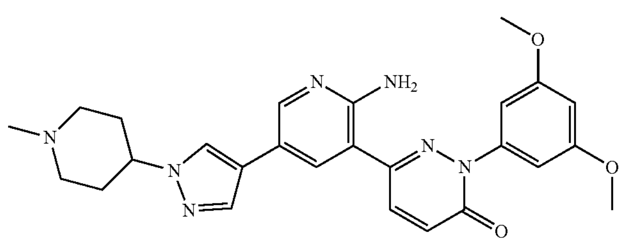 | 6-(2-amino-5-(1-(1-methylpiperidin-4-yl)-1H-pyrazol-4-yl)pyridin-3-yl)-2-(3,5-dimethoxyphenyl)pyridazin-3(2H)-one |
| 56 | 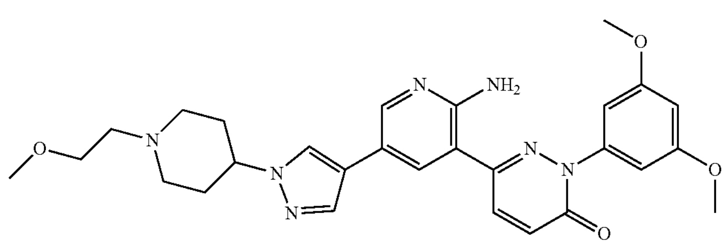 | 6-(2-amino-5-(1-(1-(2-methoxyethyl)piperidin-4-yl)-1H-pyrazol-4-yl)pyridin-3-yl)-2-(3,5-dimethoxyphenyl)pyridazin-3(2H)-one |

-continued

| Example # | Structure | Name |
|---|---|---|
| 57 | 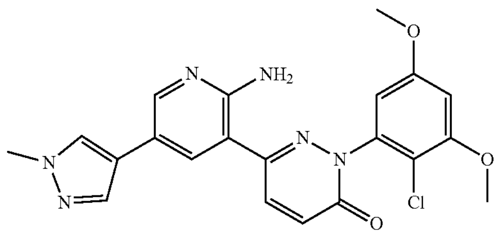 | 6-(2-amino-5-(1-methyl-1H-pyrazol-4-yl)pyridin-3-yl)-2-(2,6-dichloro-3,5-dimethoxyphenyl)pyridazin-3(2H)-one |
| 58 | 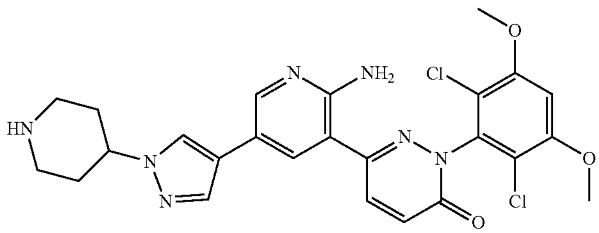 [SMILES: COc1cc(OC)c(Cl)c(-n2nc(-c3cc(-c4cnn(C5CCNCC5)c4)cnc3N)ccc2=O)c1Cl] | 6-(2-amino-5-(1-(piperidin-4-yl)-1H-pyrazol-4-yl)pyridin-3-yl)-2-(2,6-dichloro-3,5-dimethoxyphenyl)pyridazin-3(2H)-one |
| 59 | 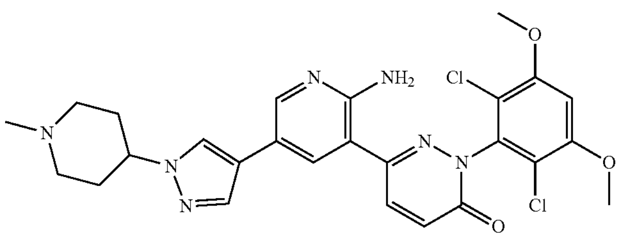 | 6-(2-amino-5-(1-(1-methylpiperidin-4-yl)-1H-pyrazol-4-yl)pyridin-3-yl)-2-(2,6-dichloro-3,5-dimethoxyphenyl)pyridazin-3(2H)-one |
| 60 | 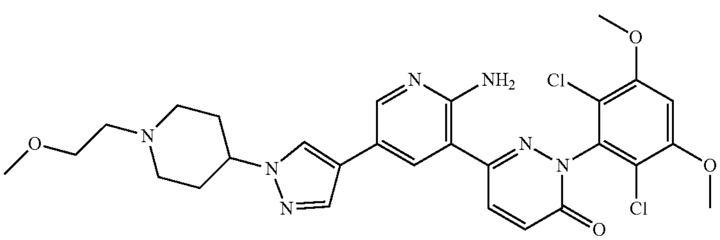 | 6-(2-amino-5-(1-(1-(2-methoxyethyl)piperidin-4-yl)-1H-pyrazol-4-yl)pyridin-3-yl)-2-(2,6-dichloro-3,5-dimethoxyphenyl)pyridazin-3(2H)-one |
| 61 | 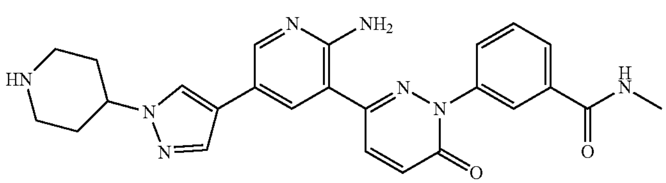 [SMILES: CNC(=O)c1cccc(-n2nc(-c3cc(-c4cnn(C5CCNCC5)c4)cnc3N)ccc2=O)c1] | 3-(3-(2-amino-5-(1-(piperidin-4-yl)-1H-pyrazol-4-yl)pyridin-3-yl)-6-oxopyridazin-1(6H)-yl)-N-methylbenzamide |
| 62 | 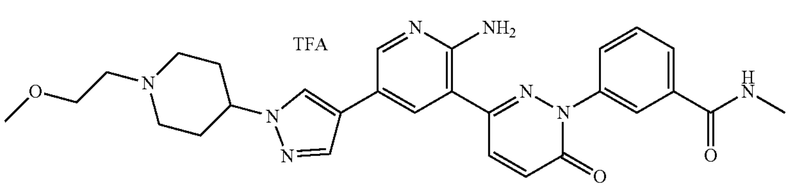 | 3-(3-(2-amino-5-(1-(1-(2-methoxyethyl)piperidin-4-yl)-1H-pyrazol-4-yl)pyridin-3-yl)-6-oxopyridazin-1(6H)-yl)-N-methylbenzamide 2,2,2-trifluoroacetate salt |
| 63 | 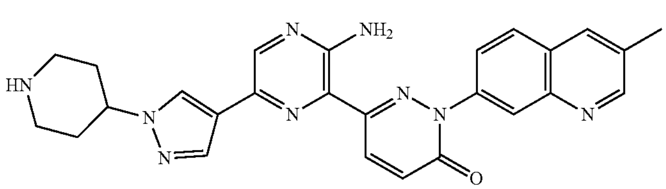 [SMILES: Cc1cnc2cc(-n3nc(-c4nc(-c5cnn(C6CCNCC6)c5)cnc4N)ccc3=O)ccc2c1] | 6-(3-amino-6-(1-(piperidin-4-yl)-1H-pyrazol-4-yl)pyrazin-2-yl)-2-(3-methylquinolin-7-yl)pyridazin-3(2H)-one bis(2,2,2-trifluoroacetate) |

| Example # | Structure | Name |
|---|---|---|
| 64 | 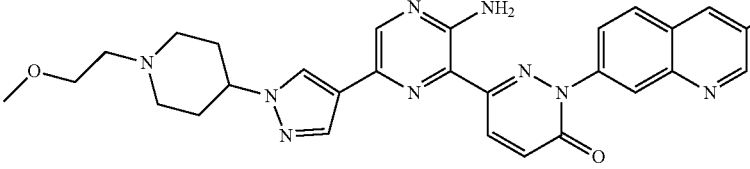 | 6-(3-amino-6-(1-(1-(2-methoxyethyl)piperidin-4-yl)-1H-pyrazol-4-yl)pyrazin-2-yl)-2-(3-methylquinolin-7-yl)pyridazin-3(2H)-one |
| 65 | 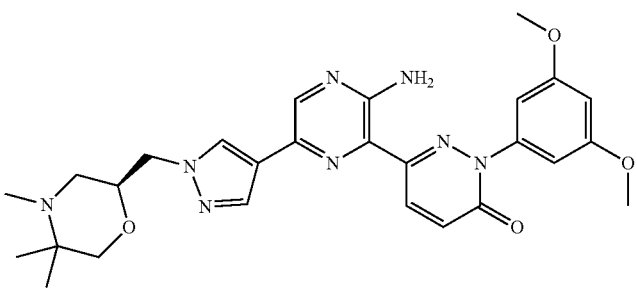 | (S)-6-(3-amino-6-(1-((4,5,5-trimethylmorpholin-2-yl)methyl)-1H-pyrazol-4-yl)pyrazin-2-yl)-2-(3,5-dimethoxyphenyl)pyridazin-3(2H)-one 2,2,2-trifluoroacetate |
| 66 | 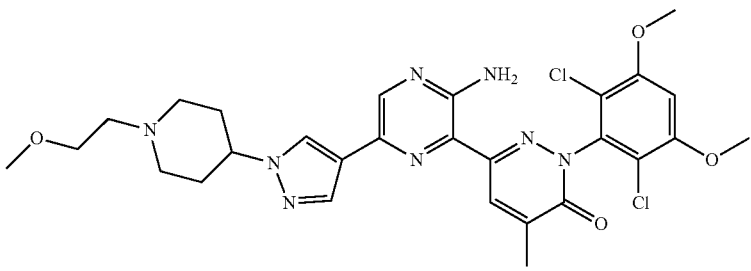 | 6-(3-amino-6-(1-(1-(2-methoxyethyl)piperidin-4-yl)-1H-pyrazol-4-yl)pyrazin-2-yl)-2-(2,6-dichloro-3,5-dimethoxyphenyl)-4-methylpyridazin-3(2H)-one |
| 67 | 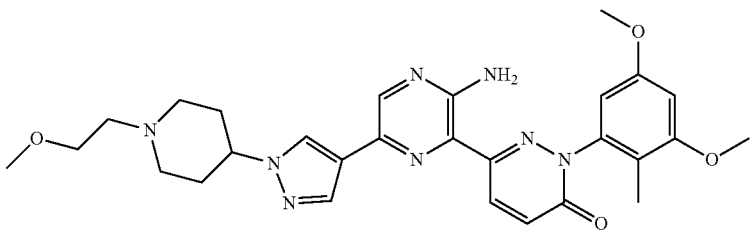 | 6-(3-amino-6-(1-(1-(2-methoxyethyl)piperidin-4-yl)-1H-pyrazol-4-yl)pyrazin-2-yl)-2-(3,5-dimethoxy-2-methylphenyl)pyridazin-3(2H)-one |
| 68 | 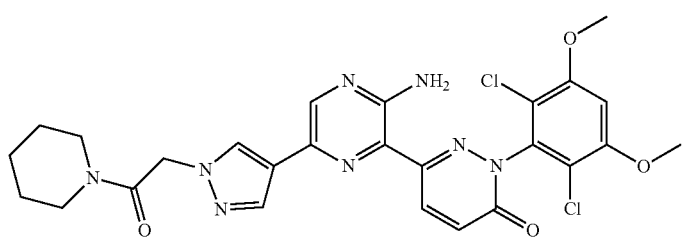 [SMILES: COc1cc(OC)c(Cl)c(-n2nc(-c3nc(-c4cnn(CC(=O)N5CCCCC5)c4)cnc3N)ccc2=O)c1Cl] | 6-(3-amino-6-(1-(2-oxo-2-(piperidin-1-yl)ethyl)-1H-pyrazol-4-yl)pyrazin-2-yl)-2-(2,6-dichloro-3,5-dimethoxyphenyl)pyridazin-3(2H)-one |
| 69 | 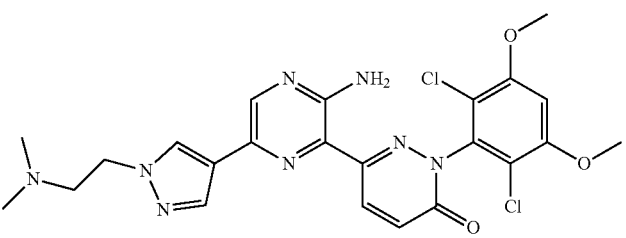 | 6-(3-amino-6-(1-(2-(dimethylamino)ethyl)-1H-pyrazol-4-yl)pyrazin-2-yl)-2-(2,6-dichloro-3,5-dimethoxyphenyl)pyridazin-3(2H)-one |

-continued

| Example # | Structure | Name |
|---|---|---|
| 70 | 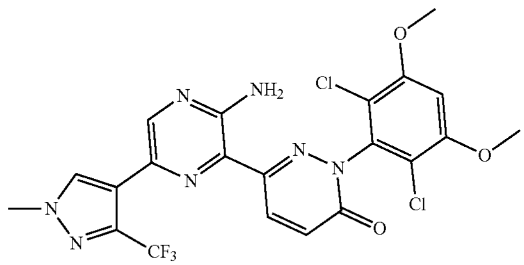 | 6-(3-amino-6-(1-methyl-3-(trifluoromethyl)-1H-pyrazol-4-yl)pyrazin-2-yl)-2-(2,6-dichloro-3,5-dimethoxyphenyl)pyridazin-3(2H)-one |
| 71 | 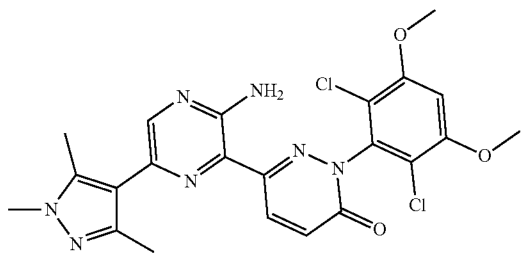 | 6-(3-amino-6-(1,3,5-trimethyl-1H-pyrazol-4-yl)pyrazin-2-yl)-2-(2,6-dichloro-3,5-dimethoxyphenyl)pyridazin-3(2H)-one |
| 72 | 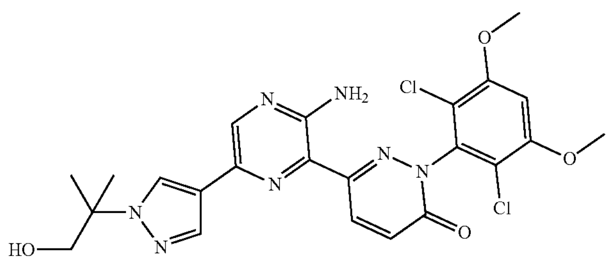 [SMILES: COc1cc(OC)c(Cl)c(-n2nc(-c3nc(-c4cnn(C(C)(C)CO)c4)cnc3N)ccc2=O)c1Cl] | 6-(3-amino-6-(1-(1-hydroxy-2-methylpropan-2-yl)-1H-pyrazol-4-yl)pyrazin-2-yl)-2-(2,6-dichloro-3,5-dimethoxyphenyl)pyridazin-3(2H)-one |
| 73 | 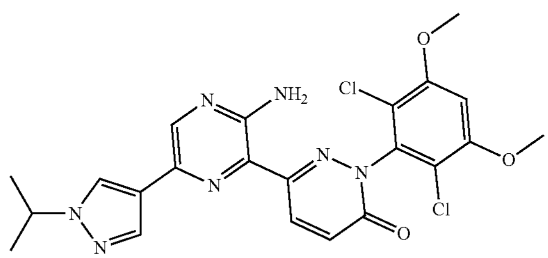 [SMILES: COc1cc(OC)c(Cl)c(-n2nc(-c3nc(-c4cnn(C(C)C)c4)cnc3N)ccc2=O)c1Cl] | 6-(3-amino-6-(1-isopropyl-1H-pyrazol-4-yl)pyrazin-2-yl)-2-(2,6-dichloro-3,5-dimethoxyphenyl)pyridazin-3(2H)-one |
| 74 | 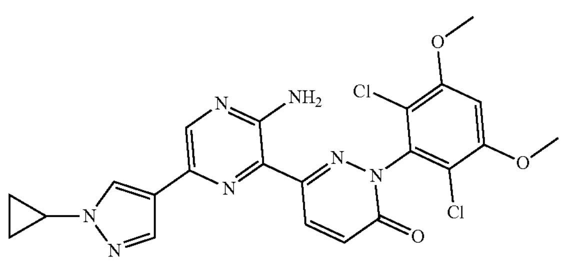 [SMILES: COc1cc(OC)c(Cl)c(-n2nc(-c3nc(-c4cnn(C5CC5)c4)cnc3N)ccc2=O)c1Cl] | 6-(3-amino-6-(1-cyclopropyl-1H-pyrazol-4-yl)pyrazin-2-yl)-2-(2,6-dichloro-3,5-dimethoxyphenyl)pyridazin-3(2H)-one |
| 75 | 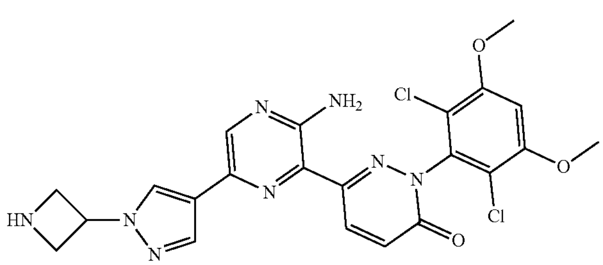 [SMILES: COc1cc(OC)c(Cl)c(-n2nc(-c3nc(-c4cnn(C5CNC5)c4)cnc3N)ccc2=O)c1Cl] | 6-(3-amino-6-(1-(azetidin-3-yl)-1H-pyrazol-4-yl)pyrazin-2-yl)-2-(2,6-dichloro-3,5-dimethoxyphenyl)pyridazin-3(2H)-one |

-continued

| Example # | Structure | Name |
|---|---|---|
| 76 | 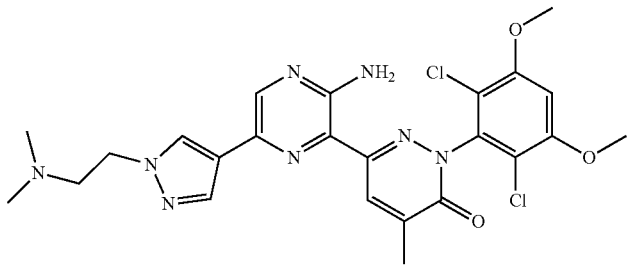 | 6-(3-amino-6-(1-(2-(dimethylamino)ethyl)-1H-pyrazol-4-yl)pyrazin-2-yl)-2-(2,6-dichloro-3,5-dimethoxyphenyl)-4-methylpyridazin-3(2H)-one |
| 77 | 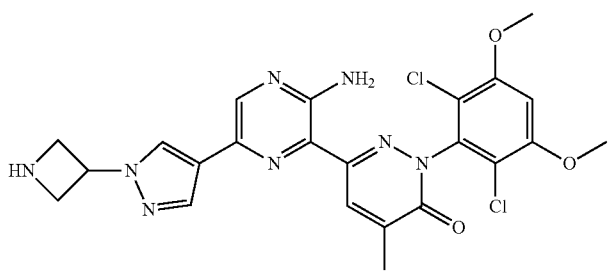 [SMILES: COc1cc(OC)c(Cl)c(-n2nc(-c3nc(-c4cnn(C5CNC5)c4)cnc3N)cc(C)c2=O)c1Cl] | 6-(3-amino-6-(1-(azetidin-3-yl)-1H-pyrazol-4-yl)pyrazin-2-yl)-2-(2,6-dichloro-3,5-dimethoxyphenyl)-4-methylpyridazin-3(2H)-one |
| 78 | 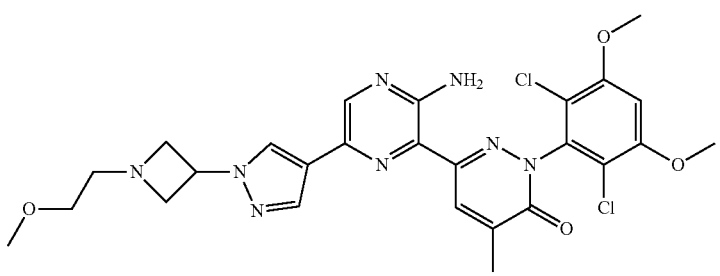 | 6-(3-amino-6-(1-(1-(2-methoxyethyl)azetidin-3-yl)-1H-pyrazol-4-yl)pyrazin-2-yl)-2-(2,6-dichloro-3,5-dimethoxyphenyl)-4-methylpyridazin-3(2H)-one |
| 79 | 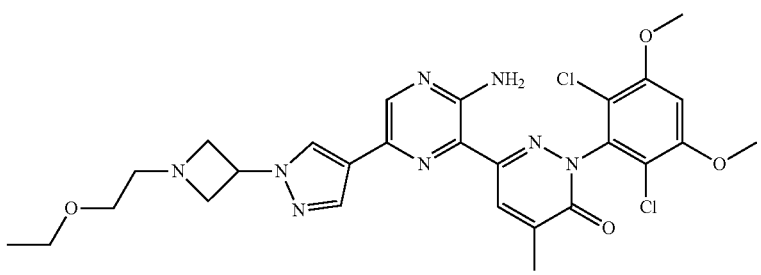 [SMILES: CCOCCN1CC(n2cc(-c3cnc(N)c(-c4cc(C)c(=O)n(-c5c(Cl)c(OC)cc(OC)c5Cl)n4)n3)cn2)C1] | 6-(3-amino-6-(1-(1-(2-ethoxyethyl)azetidin-3-yl)-1H-pyrazol-4-yl)pyrazin-2-yl)-2-(2,6-dichloro-3,5-dimethoxyphenyl)-4-methylpyridazin-3(2H)-one |
| 80 | 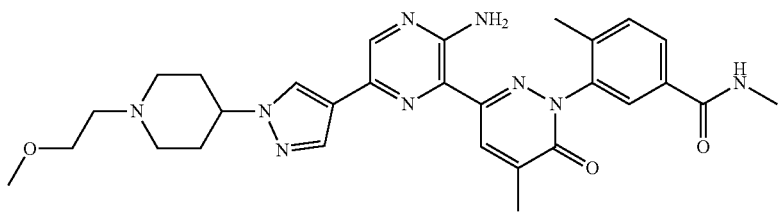 | 3-(3-(3-amino-6-(1-(1-(2-methoxyethyl)piperidin-4-yl)-1H-pyrazol-4-yl)pyrazin-2-yl)-5-methyl-6-oxopyridazin-1(6H)-yl)-N,4-dimethylbenzamide |

| Example # | Structure | Name |
|---|---|---|
| 81 | 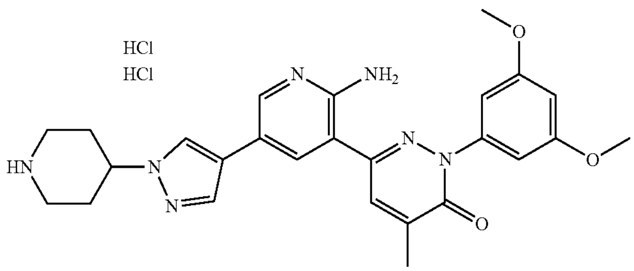 [SMILES: COc1cc(OC)cc(-n2nc(-c3cc(-c4cnn(C5CCNCC5)c4)cnc3N)cc(C)c2=O)c1 ; Cl ; Cl] | 6-(2-amino-5-(1-(piperidin-4-yl)-1H-pyrazol-4-yl)pyridin-3-yl)-2-(3,5-dimethoxyphenyl)-4-methylpyridazin-3(2H)-one dihydrochloride |
| 82 | 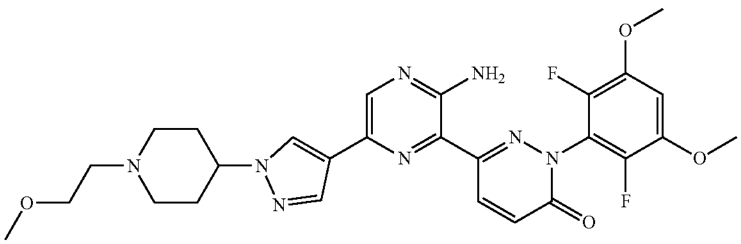 | 6-(3-amino-6-(1-(1-(2-methoxyethyl)piperidin-4-yl)-1H-pyrazol-4-yl)pyrazin-2-yl)-2-(2,6-difluoro-3,5-dimethoxyphenyl)pyridazin-3(2H)-one |
| 83 | | 6-(3-amino-6-(1-(1-(2-methoxyethyl)piperidin-4-yl)-1H-pyrazol-4-yl)pyrazin-2-yl)-2-(2-chloro-6-fluoro-3-methoxyphenyl)pyridazin-3(2H)-one | or a pharmaceutically acceptable salt thereof.

26. A pharmaceutical composition, comprising a compound according to claim 1, or a pharmaceutically acceptable salt or solvate thereof, and a pharmaceutically acceptable carrier or excipient.

27. A process for the preparation of a compound of Formula 1 or a pharmaceutically acceptable salt thereof according to claim 1, comprising:

(a) reacting a compound having the formula 5:

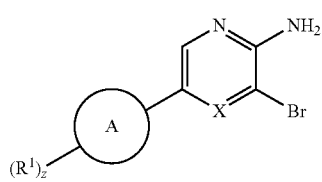

5 where X, $R^1$, Ring A and z are as defined for Formula I, with a compound having the formula 4:

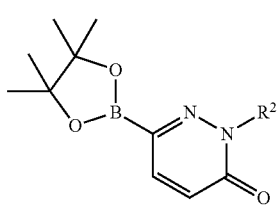

4 where $R^2$ is as defined for Formula I, in the presence of a palladium (II) catalyst and an inorganic base; or (b) for a compound of Formula I where X, $R^2$ and $R^3$ are as defined in claim 1, z is 1 and $R^1$ is a piperidine substituted with C1-C6 alkyl (optionally substituted with 1-3 fluoros), (C1-C3 alkoxy)C1-C6 alkyl (optionally substituted with 1-3 fluoros) or hydroxy(C1-C6 alkyl), reacting a compound having the formula 9A:

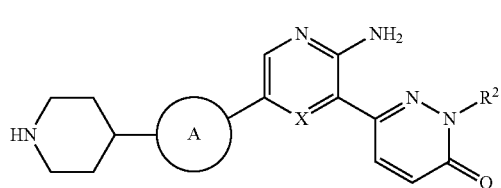

9A where X, $R^2$ and Ring A are as defined in claim 1, with a compound having the formula $R^x$-Y, where $R^x$ is C1-C6 alkyl (optionally substituted with 1-3 fluoros), (C1-C3 alkoxy)C1-C6 alkyl (optionally substituted with 1-3 fluoros) or hydroxy(C1-C6 alkyl), and Y is a leaving group, under standard alkylation reaction conditions; and removing any protecting groups if present and optionally forming a pharmaceutically acceptable salt.

* * * * *

SEQUENCE LISTING

<160> NUMBER OF SEQ ID NOS: 8

<210> SEQ ID NO 1
<211> LENGTH: 822
<212> TYPE: PRT

-continued

```
<213> ORGANISM: Homo sapiens

<400> SEQUENCE: 1

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365

Met Thr Ser Pro Leu Tyr Leu Glu Ile Ile Ile Tyr Cys Thr Gly Ala
    370                 375                 380

Phe Leu Ile Ser Cys Met Val Gly Ser Val Ile Val Tyr Lys Met Lys
385                 390                 395                 400
```

```
Ser Gly Thr Lys Lys Ser Asp Phe His Ser Gln Met Ala Val His Lys
            405                 410                 415
Leu Ala Lys Ser Ile Pro Leu Arg Arg Gln Val Thr Val Ser Ala Asp
            420                 425                 430
Ser Ser Ala Ser Met Asn Ser Gly Val Leu Leu Val Arg Pro Ser Arg
            435                 440                 445
Leu Ser Ser Ser Gly Thr Pro Met Leu Ala Gly Val Ser Glu Tyr Glu
            450                 455                 460
Leu Pro Glu Asp Pro Arg Trp Glu Leu Pro Arg Asp Arg Leu Val Leu
465                 470                 475                 480
Gly Lys Pro Leu Gly Glu Gly Cys Phe Gly Gln Val Val Leu Ala Glu
            485                 490                 495
Ala Ile Gly Leu Asp Lys Asp Lys Pro Asn Arg Val Thr Lys Val Ala
            500                 505                 510
Val Lys Met Leu Lys Ser Asp Ala Thr Glu Lys Asp Leu Ser Asp Leu
            515                 520                 525
Ile Ser Glu Met Glu Met Met Lys Met Ile Gly Lys His Lys Asn Ile
            530                 535                 540
Ile Asn Leu Leu Gly Ala Cys Thr Gln Asp Gly Pro Leu Tyr Val Ile
545                 550                 555                 560
Val Glu Tyr Ala Ser Lys Gly Asn Leu Arg Glu Tyr Leu Gln Ala Arg
            565                 570                 575
Arg Pro Pro Gly Leu Glu Tyr Cys Tyr Asn Pro Ser His Asn Pro Glu
            580                 585                 590
Glu Gln Leu Ser Ser Lys Asp Leu Val Ser Cys Ala Tyr Gln Val Ala
            595                 600                 605
Arg Gly Met Glu Tyr Leu Ala Ser Lys Lys Cys Ile His Arg Asp Leu
            610                 615                 620
Ala Ala Arg Asn Val Leu Val Thr Glu Asp Asn Val Met Lys Ile Ala
625                 630                 635                 640
Asp Phe Gly Leu Ala Arg Asp Ile His His Ile Asp Tyr Tyr Lys Lys
            645                 650                 655
Thr Thr Asn Gly Arg Leu Pro Val Lys Trp Met Ala Pro Glu Ala Leu
            660                 665                 670
Phe Asp Arg Ile Tyr Thr His Gln Ser Asp Val Trp Ser Phe Gly Val
            675                 680                 685
Leu Leu Trp Glu Ile Phe Thr Leu Gly Gly Ser Pro Tyr Pro Gly Val
            690                 695                 700
Pro Val Glu Glu Leu Phe Lys Leu Leu Lys Glu Gly His Arg Met Asp
705                 710                 715                 720
Lys Pro Ser Asn Cys Thr Asn Glu Leu Tyr Met Met Met Arg Asp Cys
            725                 730                 735
Trp His Ala Val Pro Ser Gln Arg Pro Thr Phe Lys Gln Leu Val Glu
            740                 745                 750
Asp Leu Asp Arg Ile Val Ala Leu Thr Ser Asn Gln Glu Tyr Leu Asp
            755                 760                 765
Leu Ser Met Pro Leu Asp Gln Tyr Ser Pro Ser Phe Pro Asp Thr Arg
            770                 775                 780
Ser Ser Thr Cys Ser Ser Gly Glu Asp Ser Val Phe Ser His Glu Pro
785                 790                 795                 800
Leu Pro Glu Glu Pro Cys Leu Pro Arg His Pro Ala Gln Leu Ala Asn
            805                 810                 815
Gly Gly Leu Lys Arg Arg
```

820

<210> SEQ ID NO 2
<211> LENGTH: 820
<212> TYPE: PRT
<213> ORGANISM: Homo sapiens

<400> SEQUENCE: 2

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
        275                 280                 285

Lys His Ile Glu Val Asn Gly Ser Lys Ile Gly Pro Asp Asn Leu Pro
    290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
            340                 345                 350

Trp Leu Thr Val Leu Glu Ala Leu Glu Glu Arg Pro Ala Val Met Thr
        355                 360                 365
```

```
Ser Pro Leu Tyr Leu Glu Ile Ile Tyr Cys Thr Gly Ala Phe Leu
370                 375                 380

Ile Ser Cys Met Val Gly Ser Val Ile Val Tyr Lys Met Lys Ser Gly
385                 390                 395                 400

Thr Lys Lys Ser Asp Phe His Ser Gln Met Ala Val His Lys Leu Ala
                405                 410                 415

Lys Ser Ile Pro Leu Arg Arg Gln Val Thr Val Ser Ala Asp Ser Ser
                420                 425                 430

Ala Ser Met Asn Ser Gly Val Leu Leu Val Arg Pro Ser Arg Leu Ser
            435                 440                 445

Ser Ser Gly Thr Pro Met Leu Ala Gly Val Ser Glu Tyr Glu Leu Pro
450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
                485                 490                 495

Gly Leu Asp Lys Asp Lys Pro Asn Arg Val Thr Lys Val Ala Val Lys
                500                 505                 510

Met Leu Lys Ser Asp Ala Thr Glu Lys Asp Leu Ser Asp Leu Ile Ser
                515                 520                 525

Glu Met Glu Met Met Lys Met Ile Gly Lys His Lys Asn Ile Ile Asn
530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
                565                 570                 575

Pro Gly Leu Glu Tyr Cys Tyr Asn Pro Ser His Asn Pro Glu Glu Gln
                580                 585                 590

Leu Ser Ser Lys Asp Leu Val Ser Cys Ala Tyr Gln Val Ala Arg Gly
                595                 600                 605

Met Glu Tyr Leu Ala Ser Lys Lys Cys Ile His Arg Asp Leu Ala Ala
610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
                645                 650                 655

Asn Gly Arg Leu Pro Val Lys Trp Met Ala Pro Glu Ala Leu Phe Asp
                660                 665                 670

Arg Ile Tyr Thr His Gln Ser Asp Val Trp Ser Phe Gly Val Leu Leu
                675                 680                 685

Trp Glu Ile Phe Thr Leu Gly Gly Ser Pro Tyr Pro Gly Val Pro Val
690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
                740                 745                 750

Asp Arg Ile Val Ala Leu Thr Ser Asn Gln Glu Tyr Leu Asp Leu Ser
                755                 760                 765

Met Pro Leu Asp Gln Tyr Ser Pro Ser Phe Pro Asp Thr Arg Ser Ser
                770                 775                 780

Thr Cys Ser Ser Gly Glu Asp Ser Val Phe Ser His Glu Pro Leu Pro
```

```
                    785                 790                 795                 800
                Glu Glu Pro Cys Leu Pro Arg His Pro Ala Gln Leu Ala Asn Gly Gly
                                    805                 810                 815

Leu Lys Arg Arg
                            820

<210> SEQ ID NO 3
<211> LENGTH: 821
<212> TYPE: PRT
<213> ORGANISM: Homo sapiens

<400> SEQUENCE: 3

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
        50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335
```

```
Ala Gly Glu Tyr Thr Cys Leu Ala Gly Asn Ser Ile Gly Ile Ser Phe
                340                 345                 350

His Ser Ala Trp Leu Thr Val Leu Pro Ala Pro Gly Arg Glu Lys Glu
            355                 360                 365

Ile Thr Ala Ser Pro Asp Tyr Leu Glu Ile Ala Ile Tyr Cys Ile Gly
        370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
            420                 425                 430

Glu Ser Ser Ser Ser Met Asn Ser Asn Thr Pro Leu Val Arg Ile Thr
        435                 440                 445

Thr Arg Leu Ser Ser Thr Ala Asp Thr Pro Met Leu Ala Gly Val Ser
    450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
        515                 520                 525

Ser Asp Leu Val Ser Glu Met Glu Met Met Lys Met Ile Gly Lys His
    530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
        595                 600                 605

Gln Leu Ala Arg Gly Met Glu Tyr Leu Ala Ser Gln Lys Cys Ile His
    610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
        675                 680                 685

Phe Gly Val Leu Met Trp Glu Ile Phe Thr Leu Gly Gly Ser Pro Tyr
    690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
```

```
              755                 760                 765
Tyr Leu Asp Leu Ser Gln Pro Leu Glu Gln Tyr Ser Pro Ser Tyr Pro
770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 4
<211> LENGTH: 822
<212> TYPE: PRT
<213> ORGANISM: Homo sapiens

<400> SEQUENCE: 4

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
        290                 295                 300
```

```
Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
            325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
            355                 360                 365

Glu Ile Thr Ala Ser Pro Asp Tyr Leu Glu Ile Ala Ile Tyr Cys Ile
            370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
            405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
            435                 440                 445

Thr Thr Arg Leu Ser Ser Thr Ala Asp Thr Pro Met Leu Ala Gly Val
            450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
            485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
            515                 520                 525

Leu Ser Asp Leu Val Ser Glu Met Glu Met Met Lys Met Ile Gly Lys
            530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
            565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
            595                 600                 605

Tyr Gln Leu Ala Arg Gly Met Glu Tyr Leu Ala Ser Gln Lys Cys Ile
            610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
            645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
            675                 680                 685

Ser Phe Gly Val Leu Met Trp Glu Ile Phe Thr Leu Gly Gly Ser Pro
            690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
```

```
                        725                 730                 735
Met Arg Asp Cys Trp His Ala Val Pro Ser Gln Arg Pro Thr Phe Lys
                740                 745                 750

Gln Leu Val Glu Asp Leu Asp Arg Ile Leu Thr Leu Thr Thr Asn Glu
            755                 760                 765

Glu Tyr Leu Asp Leu Ser Gln Pro Leu Glu Gln Tyr Ser Pro Ser Tyr
770             775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
                805                 810                 815

Asn Gly Ser Val Lys Thr
                820

<210> SEQ ID NO 5
<211> LENGTH: 806
<212> TYPE: PRT
<213> ORGANISM: Homo sapien

<400> SEQUENCE: 5

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270
```

-continued

Phe His Cys Lys Val Tyr Ser Asp Ala Gln Pro His Ile Gln Trp Leu
            275                 280                 285
Lys His Val Glu Val Asn Gly Ser Lys Val Gly Pro Asp Gly Thr Pro
        290                 295                 300
Tyr Val Thr Val Leu Lys Thr Ala Gly Ala Asn Thr Thr Asp Lys Glu
305                 310                 315                 320
Leu Glu Val Leu Ser Leu His Asn Val Thr Phe Glu Asp Ala Gly Glu
                325                 330                 335
Tyr Thr Cys Leu Ala Gly Asn Ser Ile Gly Phe Ser His His Ser Ala
            340                 345                 350
Trp Leu Val Val Leu Pro Ala Glu Glu Glu Leu Val Glu Ala Asp Glu
        355                 360                 365
Ala Gly Ser Val Tyr Ala Gly Ile Leu Ser Tyr Gly Val Gly Phe Phe
370                 375                 380
Leu Phe Ile Leu Val Val Ala Ala Val Thr Leu Cys Arg Leu Arg Ser
385                 390                 395                 400
Pro Pro Lys Lys Gly Leu Gly Ser Pro Thr Val His Lys Ile Ser Arg
                405                 410                 415
Phe Pro Leu Lys Arg Gln Val Ser Leu Glu Ser Asn Ala Ser Met Ser
            420                 425                 430
Ser Asn Thr Pro Leu Val Arg Ile Ala Arg Leu Ser Ser Gly Glu Gly
        435                 440                 445
Pro Thr Leu Ala Asn Val Ser Glu Leu Glu Leu Pro Ala Asp Pro Lys
    450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
                485                 490                 495
Asp Arg Ala Ala Lys Pro Val Thr Val Ala Val Lys Met Leu Lys Asp
            500                 505                 510
Asp Ala Thr Asp Lys Asp Leu Ser Asp Leu Val Ser Glu Met Glu Met
        515                 520                 525
Met Lys Met Ile Gly Lys His Lys Asn Ile Ile Asn Leu Leu Gly Ala
    530                 535                 540
Cys Thr Gln Gly Gly Pro Leu Tyr Val Leu Val Glu Tyr Ala Ala Lys
545                 550                 555                 560
Gly Asn Leu Arg Glu Phe Leu Arg Ala Arg Arg Pro Pro Gly Leu Asp
                565                 570                 575
Tyr Ser Phe Asp Thr Cys Lys Pro Pro Glu Glu Gln Leu Thr Phe Lys
            580                 585                 590
Asp Leu Val Ser Cys Ala Tyr Gln Val Ala Arg Gly Met Glu Tyr Leu
        595                 600                 605
Ala Ser Gln Lys Cys Ile His Arg Asp Leu Ala Ala Arg Asn Val Leu
    610                 615                 620
Val Thr Glu Asp Asn Val Met Lys Ile Ala Asp Phe Gly Leu Ala Arg
625                 630                 635                 640
Asp Val His Asn Leu Asp Tyr Tyr Lys Lys Thr Thr Asn Gly Arg Leu
                645                 650                 655
Pro Val Lys Trp Met Ala Pro Glu Ala Leu Phe Asp Arg Val Tyr Thr
            660                 665                 670
His Gln Ser Asp Val Trp Ser Phe Gly Val Leu Leu Trp Glu Ile Phe
        675                 680                 685
Thr Leu Gly Gly Ser Pro Tyr Pro Gly Ile Pro Val Glu Glu Leu Phe

```
                    690                 695                 700
Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gly Gln Asp Thr Pro Ser Ser Ser Ser Ser Gly
    770                 775                 780

Asp Asp Ser Val Phe Ala His Asp Leu Leu Pro Ala Pro Pro Ser
785                 790                 795                 800

Ser Gly Gly Ser Arg Thr
                805

<210> SEQ ID NO 6
<211> LENGTH: 808
<212> TYPE: PRT
<213> ORGANISM: Homo sapiens

<400> SEQUENCE: 6

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255
```

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
            340                 345                 350

Leu Ser Val His Gly Pro Arg Ala Ala Glu Glu Glu Leu Val Glu Ala
        355                 360                 365

Asp Glu Ala Gly Ser Val Tyr Ala Gly Ile Leu Ser Tyr Gly Val Gly
    370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
        435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
            500                 505                 510

Lys Asp Asp Ala Thr Asp Lys Asp Leu Ser Asp Leu Val Ser Glu Met
        515                 520                 525

Glu Met Met Lys Met Ile Gly Lys His Lys Asn Ile Ile Asn Leu Leu
    530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
        595                 600                 605

Tyr Leu Ala Ser Gln Lys Cys Ile His Arg Asp Leu Ala Ala Arg Asn
    610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu

```
                675                 680                 685
Ile Phe Thr Leu Gly Gly Ser Pro Tyr Pro Gly Ile Pro Val Glu Glu
690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
            740                 745                 750

Val Leu Thr Val Thr Ser Thr Asp Glu Tyr Leu Asp Leu Ser Ala Pro
        755                 760                 765

Phe Glu Gln Tyr Ser Pro Gly Gly Gln Asp Thr Pro Ser Ser Ser Ser
770                 775                 780

Ser Gly Asp Asp Ser Val Phe Ala His Asp Leu Leu Pro Pro Ala Pro
785                 790                 795                 800

Pro Ser Ser Gly Gly Ser Arg Thr
                805

<210> SEQ ID NO 7
<211> LENGTH: 802
<212> TYPE: PRT
<213> ORGANISM: Homo sapiens

<400> SEQUENCE: 7

Met Arg Leu Leu Leu Ala Leu Gly Val Leu Leu Ser Val Pro Gly
1               5                   10                  15

Pro Pro Val Leu Ser Leu Glu Ala Ser Glu Glu Val Glu Leu Glu Pro
                20                  25                  30

Cys Leu Ala Pro Ser Leu Glu Gln Gln Glu Gln Glu Leu Thr Val Ala
            35                  40                  45

Leu Gly Gln Pro Val Arg Leu Cys Cys Gly Arg Ala Glu Arg Gly Gly
        50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
210                 215                 220

Leu Val Glu Asn Ala Val Gly Ser Ile Arg Tyr Asn Tyr Leu Leu Asp
225                 230                 235                 240
```

-continued

Val Leu Glu Arg Ser Pro His Arg Pro Ile Leu Gln Ala Gly Leu Pro
            245                 250                 255

Ala Asn Thr Thr Ala Val Val Gly Ser Asp Val Glu Leu Leu Cys Lys
        260                 265                 270

Val Tyr Ser Asp Ala Gln Pro His Ile Gln Trp Leu Lys His Ile Val
    275                 280                 285

Ile Asn Gly Ser Ser Phe Gly Ala Asp Gly Phe Pro Tyr Val Gln Val
    290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Glu Glu Asp Pro Thr Trp Thr Ala Ala Ala Pro Glu Ala Arg Tyr Thr
        355                 360                 365

Asp Ile Ile Leu Tyr Ala Ser Gly Ser Leu Ala Leu Ala Val Leu Leu
    370                 375                 380

Leu Leu Ala Gly Leu Tyr Arg Gly Gln Ala Leu His Gly Arg His Pro
385                 390                 395                 400

Arg Pro Pro Ala Thr Val Gln Lys Leu Ser Arg Phe Pro Leu Ala Arg
                405                 410                 415

Gln Phe Ser Leu Glu Ser Gly Ser Ser Gly Lys Ser Ser Ser Ser Leu
            420                 425                 430

Val Arg Gly Val Arg Leu Ser Ser Ser Gly Pro Ala Leu Leu Ala Gly
        435                 440                 445

Leu Val Ser Leu Asp Leu Pro Leu Asp Pro Leu Trp Glu Phe Pro Arg
    450                 455                 460

Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
                485                 490                 495

Ala Ser Thr Val Ala Val Lys Met Leu Lys Asp Asn Ala Ser Asp Lys
            500                 505                 510

Asp Leu Ala Asp Leu Val Ser Glu Met Glu Val Met Lys Leu Ile Gly
        515                 520                 525

Arg His Lys Asn Ile Ile Asn Leu Leu Gly Val Cys Thr Gln Glu Gly
    530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Val Leu Val Ser Cys
            580                 585                 590

Ala Tyr Gln Val Ala Arg Gly Met Gln Tyr Leu Glu Ser Arg Lys Cys
        595                 600                 605

Ile His Arg Asp Leu Ala Ala Arg Asn Val Leu Val Thr Glu Asp Asn
    610                 615                 620

Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val

```
                        660                 665                 670
Trp Ser Phe Gly Ile Leu Leu Trp Glu Ile Phe Thr Leu Gly Gly Ser
            675                 680                 685
Pro Tyr Pro Gly Ile Pro Val Glu Glu Leu Phe Ser Leu Leu Arg Glu
        690                 695                 700
Gly His Arg Met Asp Arg Pro His Cys Pro Glu Leu Tyr Gly
705                 710                 715                 720
Leu Met Arg Glu Cys Trp His Ala Ala Pro Ser Gln Arg Pro Thr Phe
                    725                 730                 735
Lys Gln Leu Val Glu Ala Leu Asp Lys Val Leu Leu Ala Val Ser Glu
                740                 745                 750
Glu Tyr Leu Asp Leu Arg Leu Thr Phe Gly Pro Tyr Ser Pro Ser Gly
            755                 760                 765
Gly Asp Ala Ser Ser Thr Cys Ser Ser Ser Asp Ser Val Phe Ser His
        770                 775                 780
Asp Pro Leu Pro Leu Gly Ser Ser Ser Phe Pro Phe Gly Ser Gly Val
785                 790                 795                 800
Gln Thr

<210> SEQ ID NO 8
<211> LENGTH: 762
<212> TYPE: PRT
<213> ORGANISM: Homo sapiens

<400> SEQUENCE: 8

Met Arg Leu Leu Leu Ala Leu Leu Gly Val Leu Leu Ser Val Pro Gly
1               5                   10                  15
Pro Pro Val Leu Ser Leu Glu Ala Ser Glu Glu Val Glu Leu Glu Pro
            20                  25                  30
Cys Leu Ala Pro Ser Leu Glu Gln Gln Glu Gln Glu Leu Thr Val Ala
        35                  40                  45
Leu Gly Gln Pro Val Arg Leu Cys Cys Gly Arg Ala Glu Arg Gly Gly
    50                  55                  60
His Trp Tyr Lys Glu Gly Ser Arg Leu Ala Pro Ala Gly Arg Val Arg
65                  70                  75                  80
Gly Trp Arg Gly Arg Leu Glu Ile Ala Ser Phe Leu Pro Glu Asp Ala
                85                  90                  95
Gly Arg Tyr Leu Cys Leu Ala Arg Gly Ser Met Ile Val Leu Gln Asn
            100                 105                 110
Leu Thr Leu Ile Thr Gly Asp Ser Leu Thr Ser Ser Asn Asp Asp Glu
        115                 120                 125
Asp Pro Lys Ser His Arg Asp Pro Ser Asn Arg His Ser Tyr Pro Gln
    130                 135                 140
Gln Ala Pro Tyr Trp Thr His Pro Gln Arg Met Glu Lys Lys Leu His
145                 150                 155                 160
Ala Val Pro Ala Gly Asn Thr Val Lys Phe Arg Cys Pro Ala Ala Gly
                165                 170                 175
Asn Pro Thr Pro Thr Ile Arg Trp Leu Lys Asp Gly Gln Ala Phe His
            180                 185                 190
Gly Glu Asn Arg Ile Gly Gly Ile Arg Leu Arg His Gln His Trp Ser
        195                 200                 205
Leu Val Met Glu Ser Val Val Pro Ser Asp Arg Gly Thr Tyr Thr Cys
    210                 215                 220
Leu Val Glu Asn Ala Val Gly Ser Ile Arg Tyr Asn Tyr Leu Leu Asp
```

```
            225                 230                 235                 240
    Val Leu Glu Arg Ser Pro His Arg Pro Ile Leu Gln Ala Gly Leu Pro
                        245                 250                 255
    Ala Asn Thr Thr Ala Val Val Gly Ser Asp Val Glu Leu Leu Cys Lys
                        260                 265                 270
    Val Tyr Ser Asp Ala Gln Pro His Ile Gln Trp Leu Lys His Ile Val
                        275                 280                 285
    Ile Asn Gly Ser Ser Phe Gly Ala Asp Gly Phe Pro Tyr Val Gln Val
                        290                 295                 300
    Leu Lys Thr Ala Asp Ile Asn Ser Ser Glu Val Glu Val Leu Tyr Leu
    305                 310                 315                 320
    Arg Asn Val Ser Ala Glu Asp Ala Gly Glu Tyr Thr Cys Leu Ala Gly
                        325                 330                 335
    Asn Ser Ile Gly Leu Ser Tyr Gln Ser Ala Trp Leu Thr Val Leu Pro
                        340                 345                 350
    Gly Thr Gly Arg Ile Pro His Leu Thr Cys Asp Ser Leu Thr Pro Ala
                        355                 360                 365
    Gly Arg Thr Lys Ser Pro Thr Leu Gln Phe Ser Leu Glu Ser Gly Ser
                        370                 375                 380
    Ser Gly Lys Ser Ser Ser Ser Leu Val Arg Gly Val Arg Leu Ser Ser
    385                 390                 395                 400
    Ser Gly Pro Ala Leu Leu Ala Gly Leu Val Ser Leu Asp Leu Pro Leu
                        405                 410                 415
    Asp Pro Leu Trp Glu Phe Pro Arg Asp Arg Leu Val Leu Gly Lys Pro
                        420                 425                 430
    Leu Gly Glu Gly Cys Phe Gly Gln Val Val Arg Ala Glu Ala Phe Gly
                        435                 440                 445
    Met Asp Pro Ala Arg Pro Asp Gln Ala Ser Thr Val Ala Val Lys Met
                        450                 455                 460
    Leu Lys Asp Asn Ala Ser Asp Lys Asp Leu Ala Asp Leu Val Ser Glu
    465                 470                 475                 480
    Met Glu Val Met Lys Leu Ile Gly Arg His Lys Asn Ile Ile Asn Leu
                        485                 490                 495
    Leu Gly Val Cys Thr Gln Glu Gly Pro Leu Tyr Val Ile Val Glu Cys
                        500                 505                 510
    Ala Ala Lys Gly Asn Leu Arg Glu Phe Leu Arg Ala Arg Arg Pro Pro
                        515                 520                 525
    Gly Pro Asp Leu Ser Pro Asp Gly Pro Arg Ser Ser Glu Gly Pro Leu
                        530                 535                 540
    Ser Phe Pro Val Leu Val Ser Cys Ala Tyr Gln Val Ala Arg Gly Met
    545                 550                 555                 560
    Gln Tyr Leu Glu Ser Arg Lys Cys Ile His Arg Asp Leu Ala Ala Arg
                        565                 570                 575
    Asn Val Leu Val Thr Glu Asp Asn Val Met Lys Ile Ala Asp Phe Gly
                        580                 585                 590
    Leu Ala Arg Gly Val His His Ile Asp Tyr Tyr Lys Lys Thr Ser Asn
                        595                 600                 605
    Gly Arg Leu Pro Val Lys Trp Met Ala Pro Glu Ala Leu Phe Asp Arg
                        610                 615                 620
    Val Tyr Thr His Gln Ser Asp Val Trp Ser Phe Gly Ile Leu Leu Trp
    625                 630                 635                 640
    Glu Ile Phe Thr Leu Gly Gly Ser Pro Tyr Pro Gly Ile Pro Val Glu
                        645                 650                 655
```

```
Glu Leu Phe Ser Leu Leu Arg Glu Gly His Arg Met Asp Arg Pro Pro
            660             665             670

His Cys Pro Pro Glu Leu Tyr Gly Leu Met Arg Glu Cys Trp His Ala
        675             680             685

Ala Pro Ser Gln Arg Pro Thr Phe Lys Gln Leu Val Glu Ala Leu Asp
    690             695             700

Lys Val Leu Leu Ala Val Ser Glu Glu Tyr Leu Asp Leu Arg Leu Thr
705             710             715             720

Phe Gly Pro Tyr Ser Pro Ser Gly Gly Asp Ala Ser Ser Thr Cys Ser
                725             730             735

Ser Ser Asp Ser Val Phe Ser His Asp Pro Leu Pro Leu Gly Ser Ser
            740             745             750

Ser Phe Pro Phe Gly Ser Gly Val Gln Thr
        755             760
```